United States Patent
Li et al.

(10) Patent No.: US 12,193,327 B2
(45) Date of Patent: *Jan. 7, 2025

(54) DONOR-ACCEPTOR TYPE THERMALLY ACTIVATED DELAYED FLUORESCENT MATERIALS BASED ON IMIDAZO[1,2-F]PHENANTHRIDINE AND ANALOGUES

(71) Applicant: Arizona Board of Regents on behalf of Arizona State University, Scottsdale, AZ (US)

(72) Inventors: Jian Li, Tempe, AZ (US); Zhi-Qiang Zhu, Mesa, AZ (US)

(73) Assignee: Arizona Board of Regents on behalf Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,067

(22) Filed: Sep. 1, 2022

(65) Prior Publication Data

US 2023/0068759 A1    Mar. 2, 2023

Related U.S. Application Data

(63) Continuation of application No. 16/834,193, filed on Mar. 30, 2020, now Pat. No. 11,450,816, which is a continuation of application No. 15/984,157, filed on May 18, 2018, now Pat. No. 10,615,349.

(60) Provisional application No. 62/508,518, filed on May 19, 2017.

(51) Int. Cl.
| | |
|---|---|
| C07D 471/14 | (2006.01) |
| C07D 471/20 | (2006.01) |
| C07D 471/22 | (2006.01) |
| C07D 491/147 | (2006.01) |
| C07D 491/22 | (2006.01) |
| C07D 495/14 | (2006.01) |
| C07D 495/22 | (2006.01) |
| C09K 11/06 | (2006.01) |
| H10K 85/60 | (2023.01) |
| H10K 50/11 | (2023.01) |

(52) U.S. Cl.
CPC ....... *H10K 85/6572* (2023.02); *C07D 471/14* (2013.01); *C07D 471/20* (2013.01); *C07D 471/22* (2013.01); *C07D 491/147* (2013.01); *C07D 491/22* (2013.01); *C07D 495/14* (2013.01); *C07D 495/22* (2013.01); *C09K 11/06* (2013.01); *H10K 85/657* (2023.02); *C09K 2211/1018* (2013.01); *H10K 50/11* (2023.02)

(58) Field of Classification Search
CPC .. C07D 471/14; C07D 495/22; C07D 471/20; C07D 491/147; C07D 491/22; C07D 471/22; C07D 495/14; H01L 51/0072; H01L 51/0071
USPC ........................................................ 544/230
See application file for complete search history.

(56) References Cited

U.S. PATENT DOCUMENTS

| | | |
|---|---|---|
| 4,769,292 A | 9/1988 | Tang |
| 5,707,745 A | 1/1998 | Forrest |
| 5,844,363 A | 12/1998 | Gu |
| 6,303,238 B1 | 10/2001 | Thompson |
| 7,279,704 B2 | 10/2007 | Walters |
| 8,106,199 B2 | 1/2012 | Jabbour |
| 8,389,725 B2 | 3/2013 | Li |
| 8,669,364 B2 | 3/2014 | Li |
| 8,816,080 B2 | 8/2014 | Li |
| 8,846,940 B2 | 9/2014 | Li |
| 8,927,713 B2 | 1/2015 | Li |
| 8,946,417 B2 | 2/2015 | Li |
| 9,012,599 B2 | 4/2015 | Stoessel |
| 9,076,974 B2 | 7/2015 | Li |
| 9,082,989 B2 | 7/2015 | Li |
| 9,203,039 B2 | 12/2015 | Li |
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,502,671 B2 | 11/2016 | Li |
| 9,550,801 B2 | 1/2017 | Li |
| 9,598,449 B2 | 3/2017 | Li |
| 9,617,291 B2 | 4/2017 | Li |
| 9,673,409 B2 | 6/2017 | Li |
| 9,698,359 B2 | 7/2017 | Li |
| 9,711,739 B2 | 7/2017 | Li |

(Continued)

FOREIGN PATENT DOCUMENTS

| | | |
|---|---|---|
| CN | 108148088 A | 6/2018 |
| CN | 108794539 A | 11/2018 |

(Continued)

OTHER PUBLICATIONS

Machine Translation of KR20160067034A (Year: 2016). Baldo et al., "Very High-Efficiency Green Organic Light-Emitting Devices Based on Electrophosphorescence", Appl Phys Lett, 75(3):4-6 (1999).
Baldo et al., "Highly Efficient Phosphorescent Emission from Organic Electroluminescent Devices," Nature, vol. 395, Sep. 10, 1998, pp. 151-154.
STN Abstract of KR 2013043460 A (Year: 2013).

(Continued)

*Primary Examiner* — Kahsay Habte
(74) *Attorney, Agent, or Firm* — Riverside Law LLP

(57) ABSTRACT

Donor-acceptor type thermally activated delayed fluorescent emitters based on imidazo[1,2-F]phenanthridine and analogues for full color displays and lighting applications.

9 Claims, 1 Drawing Sheet

(56) References Cited

U.S. PATENT DOCUMENTS

| | | | |
|---|---|---|---|
| 9,711,741 B2 | 7/2017 | Li | |
| 9,711,742 B2 | 7/2017 | Li | |
| 9,755,163 B2 | 9/2017 | Li | |
| 9,818,959 B2 | 11/2017 | Li | |
| 9,865,825 B2 | 1/2018 | Li | |
| 9,879,039 B2 | 1/2018 | Li | |
| 9,882,150 B2 | 1/2018 | Li | |
| 9,899,614 B2 | 2/2018 | Li | |
| 9,920,242 B2 | 3/2018 | Li | |
| 9,923,155 B2 | 3/2018 | Li | |
| 9,941,479 B2 | 4/2018 | Li | |
| 9,947,881 B2 | 4/2018 | Li | |
| 9,985,224 B2 | 5/2018 | Li | |
| 10,020,455 B2 | 7/2018 | Li | |
| 10,033,003 B2 | 7/2018 | Li | |
| 10,056,564 B2 | 8/2018 | Li | |
| 10,056,567 B2 | 8/2018 | Li | |
| 10,158,091 B2 | 12/2018 | Li | |
| 10,177,323 B2 | 1/2019 | Li | |
| 10,211,411 B2 | 2/2019 | Li | |
| 10,211,414 B2 | 2/2019 | Li | |
| 10,263,197 B2 | 4/2019 | Li | |
| 10,294,417 B2 | 5/2019 | Li | |
| 10,392,387 B2 | 8/2019 | Li | |
| 10,411,202 B2 | 9/2019 | Li | |
| 10,414,785 B2 | 9/2019 | Li | |
| 10,516,117 B2 | 12/2019 | Li | |
| 10,566,553 B2 | 2/2020 | Li | |
| 10,566,554 B2 | 2/2020 | Li | |
| 10,615,349 B2 * | 4/2020 | Li | C07D 471/20 |
| 10,622,571 B2 | 4/2020 | Li | |
| 10,727,422 B2 | 7/2020 | Li | |
| 10,745,615 B2 | 8/2020 | Li | |
| 10,790,457 B2 | 9/2020 | Li | |
| 10,793,546 B2 | 10/2020 | Li | |
| 10,804,476 B2 | 10/2020 | Li | |
| 10,822,363 B2 | 11/2020 | Li | |
| 10,836,785 B2 | 11/2020 | Li | |
| 10,851,106 B2 | 12/2020 | Li | |
| 10,886,478 B2 | 1/2021 | Li | |
| 10,930,865 B2 | 2/2021 | Li | |
| 10,937,976 B2 | 3/2021 | Li | |
| 10,944,064 B2 | 3/2021 | Li | |
| 10,964,897 B2 | 3/2021 | Li | |
| 10,991,897 B2 | 4/2021 | Li | |
| 10,995,108 B2 | 5/2021 | Li | |
| 11,011,712 B2 | 5/2021 | Li | |
| 11,063,228 B2 | 7/2021 | Li | |
| 11,101,435 B2 | 8/2021 | Li | |
| 11,114,626 B2 | 9/2021 | Li | |
| 11,121,328 B2 | 9/2021 | Li | |
| 11,145,830 B2 | 10/2021 | Li | |
| 11,450,816 B2 * | 9/2022 | Li | C07D 471/20 |
| 2005/0139810 A1 | 6/2005 | Kuehl | |
| 2007/0160905 A1 | 7/2007 | Morishita | |
| 2007/0252140 A1 | 11/2007 | Limmert | |
| 2008/0269491 A1 | 10/2008 | Jabbour | |
| 2009/0136779 A1 | 5/2009 | Cheng | |
| 2009/0167167 A1 | 7/2009 | Aoyama | |
| 2010/0288362 A1 | 11/2010 | Hatwar | |
| 2011/0028723 A1 | 2/2011 | Li | |
| 2011/0066763 A1 | 3/2011 | Minot | |
| 2011/0301351 A1 | 12/2011 | Li | |
| 2012/0095232 A1 | 4/2012 | Li | |
| 2012/0108806 A1 | 5/2012 | Li | |
| 2012/0146012 A1 | 6/2012 | Limmert | |
| 2012/0202997 A1 | 8/2012 | Parham | |
| 2012/0215001 A1 | 8/2012 | Li | |
| 2012/0264938 A1 | 10/2012 | Li | |
| 2012/0302753 A1 | 11/2012 | Li | |
| 2013/0137870 A1 | 5/2013 | Li | |
| 2013/0203996 A1 | 8/2013 | Li | |
| 2013/0237706 A1 | 9/2013 | Li | |
| 2014/0066628 A1 | 3/2014 | Li | |
| 2014/0073798 A1 | 3/2014 | Li | |
| 2014/0114072 A1 | 4/2014 | Li | |
| 2014/0147996 A1 | 5/2014 | Vogt | |
| 2014/0148594 A1 | 5/2014 | Li | |
| 2014/0249310 A1 | 9/2014 | Li | |
| 2014/0330019 A1 | 11/2014 | Li | |
| 2014/0364605 A1 | 12/2014 | Li | |
| 2015/0008419 A1 | 1/2015 | Li | |
| 2015/0018558 A1 | 1/2015 | Li | |
| 2015/0060804 A1 | 3/2015 | Kanitz | |
| 2015/0105556 A1 | 4/2015 | Li | |
| 2015/0123047 A1 | 5/2015 | Maltenberger | |
| 2015/0162552 A1 | 6/2015 | Li | |
| 2015/0194616 A1 | 7/2015 | Li | |
| 2015/0207086 A1 | 7/2015 | Li | |
| 2015/0228914 A1 | 8/2015 | Li | |
| 2015/0274762 A1 | 10/2015 | Li | |
| 2015/0287938 A1 | 10/2015 | Li | |
| 2015/0311456 A1 | 10/2015 | Li | |
| 2015/0318500 A1 | 11/2015 | Li | |
| 2015/0349279 A1 | 12/2015 | Li | |
| 2016/0028028 A1 | 1/2016 | Li | |
| 2016/0028029 A1 | 1/2016 | Li | |
| 2016/0043331 A1 | 2/2016 | Li | |
| 2016/0133861 A1 | 5/2016 | Li | |
| 2016/0133862 A1 | 5/2016 | Li | |
| 2016/0190473 A1 | 6/2016 | Kim | |
| 2016/0190474 A1 | 6/2016 | Kim | |
| 2016/0194344 A1 | 7/2016 | Li | |
| 2016/0197291 A1 | 7/2016 | Li | |
| 2016/0285015 A1 | 9/2016 | Li | |
| 2016/0359120 A1 | 12/2016 | Li | |
| 2016/0359125 A1 | 12/2016 | Li | |
| 2017/0005278 A1 | 1/2017 | Li | |
| 2017/0012224 A1 | 1/2017 | Li | |
| 2017/0040555 A1 | 2/2017 | Li | |
| 2017/0047533 A1 | 2/2017 | Li | |
| 2017/0066792 A1 | 3/2017 | Li | |
| 2017/0069855 A1 | 3/2017 | Li | |
| 2017/0077420 A1 | 3/2017 | Li | |
| 2017/0125708 A1 | 5/2017 | Li | |
| 2017/0267923 A1 | 9/2017 | Li | |
| 2017/0271611 A1 | 9/2017 | Li | |
| 2017/0301871 A1 | 10/2017 | Li | |
| 2017/0305881 A1 | 10/2017 | Li | |
| 2017/0331056 A1 | 11/2017 | Li | |
| 2017/0342098 A1 | 11/2017 | Li | |
| 2017/0373260 A1 | 12/2017 | Li | |
| 2018/0006246 A1 | 1/2018 | Li | |
| 2018/0053904 A1 | 2/2018 | Li | |
| 2018/0130960 A1 | 5/2018 | Li | |
| 2018/0138428 A1 | 5/2018 | Li | |
| 2018/0148464 A1 | 5/2018 | Li | |
| 2018/0159051 A1 | 6/2018 | Li | |
| 2018/0166655 A1 | 6/2018 | Li | |
| 2018/0175329 A1 | 6/2018 | Li | |
| 2018/0194790 A1 | 7/2018 | Li | |
| 2018/0219161 A1 | 8/2018 | Li | |
| 2018/0226592 A1 | 8/2018 | Li | |
| 2018/0226593 A1 | 8/2018 | Li | |
| 2018/0277777 A1 | 9/2018 | Li | |
| 2018/0301641 A1 | 10/2018 | Li | |
| 2018/0312750 A1 | 11/2018 | Li | |
| 2018/0331307 A1 | 11/2018 | Li | |
| 2018/0334459 A1 | 11/2018 | Li | |
| 2018/0337345 A1 | 11/2018 | Li | |
| 2018/0337349 A1 | 11/2018 | Li | |
| 2018/0337350 A1 | 11/2018 | Li | |
| 2019/0013485 A1 | 1/2019 | Li | |
| 2019/0067602 A1 | 2/2019 | Li | |
| 2019/0109288 A1 | 4/2019 | Li | |
| 2019/0194536 A1 | 6/2019 | Li | |
| 2019/0259963 A1 | 8/2019 | Li | |
| 2019/0276485 A1 | 9/2019 | Li | |
| 2019/0312217 A1 | 10/2019 | Li | |
| 2019/0367546 A1 | 12/2019 | Li | |
| 2019/0389893 A1 | 12/2019 | Li | |
| 2020/0006678 A1 | 1/2020 | Li | |
| 2020/0071330 A1 | 3/2020 | Li | |
| 2020/0075868 A1 | 3/2020 | Li | |

(56) References Cited

U.S. PATENT DOCUMENTS

| | | |
|---|---|---|
| 2020/0119288 A1 | 4/2020 | Li |
| 2020/0152891 A1 | 5/2020 | Li |
| 2020/0227656 A1 | 7/2020 | Li |
| 2020/0227660 A1 | 7/2020 | Li |
| 2020/0239505 A1 | 7/2020 | Li |
| 2020/0243776 A1 | 7/2020 | Li |
| 2020/0287153 A1 | 9/2020 | Li |
| 2020/0332185 A1 | 10/2020 | Li |
| 2020/0373505 A1 | 11/2020 | Li |
| 2020/0403167 A1 | 12/2020 | Li |
| 2021/0024526 A1 | 1/2021 | Li |
| 2021/0024559 A1 | 1/2021 | Li |
| 2021/0047296 A1 | 2/2021 | Li |
| 2021/0091316 A1 | 3/2021 | Li |
| 2021/0104687 A1 | 4/2021 | Li |
| 2021/0111355 A1 | 4/2021 | Li |
| 2021/0126208 A1 | 4/2021 | Li |
| 2021/0193936 A1 | 6/2021 | Li |
| 2021/0193947 A1 | 6/2021 | Li |
| 2021/0217973 A1 | 7/2021 | Li |
| 2021/0230198 A1 | 7/2021 | Li |
| 2021/0261589 A1 | 8/2021 | Li |
| 2021/0273182 A1 | 9/2021 | Li |

FOREIGN PATENT DOCUMENTS

| | | | |
|---|---|---|---|
| CN | 108948044 A | | 12/2018 |
| CN | 110713482 A | | 1/2020 |
| EP | 1617493 | | 1/2006 |
| EP | 1968131 | | 9/2008 |
| EP | 2020694 | | 2/2009 |
| EP | 2684932 | | 1/2014 |
| KR | 20110066763 | | 6/2011 |
| KR | 20130043460 A | | 4/2013 |
| KR | 20140027030 | | 3/2014 |
| KR | 20140065357 A | * | 5/2014 |
| KR | 20160067034 A | | 6/2016 |
| WO | 2000070655 | | 11/2000 |
| WO | 2006081780 | | 8/2006 |
| WO | 2009003455 | | 1/2009 |
| WO | 2009008277 | | 1/2009 |
| WO | 2009011327 | | 1/2009 |
| WO | 2009086209 | | 7/2009 |
| WO | 2009111299 | | 9/2009 |
| WO | 2010050778 | | 5/2010 |
| WO | 2010105141 | | 9/2010 |
| WO | 2010118026 A2 | | 10/2010 |
| WO | 2011137429 A2 | | 11/2011 |
| WO | 2011137431 A2 | | 11/2011 |
| WO | 2012074909 | | 6/2012 |
| WO | 2012112853 A1 | | 8/2012 |
| WO | 2012142387 | | 10/2012 |
| WO | 2012162488 A1 | | 11/2012 |
| WO | 2013130483 A1 | | 9/2013 |
| WO | 2014009310 | | 1/2014 |
| WO | 2014031977 | | 2/2014 |
| WO | 2014047616 A1 | | 3/2014 |
| WO | 2014109814 | | 7/2014 |
| WO | 2015027060 A1 | | 2/2015 |
| WO | 2015099507 | | 7/2015 |
| WO | 2015131158 | | 9/2015 |
| WO | 2016025921 | | 2/2016 |
| WO | 2016029137 | | 2/2016 |
| WO | 2016029186 | | 2/2016 |
| WO | 2016197019 | | 12/2016 |
| WO | 2018071697 | | 4/2018 |
| WO | 2018140765 | | 8/2018 |
| WO | 2019079505 | | 4/2019 |
| WO | 2019079508 | | 4/2019 |
| WO | 2019079509 | | 4/2019 |
| WO | 2019236541 | | 12/2019 |
| WO | 2020018476 | | 1/2020 |

OTHER PUBLICATIONS

Joyama et al., "Highly efficient organic light-emitting diodes from delayed fluorescence" Nature, 492:234-238, (2012).

Yan, et al., "Palladium-catalyzed tandem N—H/C—H arylation: regioselective synthesis of N-heterocycle-fused phenanthridines as versatile blue-emitting luminophores," Organic & Biomolecular Chemistry, 11(45), 2013, 7966-7977.

Su "Pyridine-Containing Bipolar Host Materials for Highly Efficient Blue Phosphorescent OLEDs" Chem. Mater. 2008, 20, 1691-1693 1691.

Bunz "Large N-Heteroacenes: New Tricks for Very Old Dogs?" Angew. Chem. Int. Ed. 2013, 52, 3810-3821.

Kader Azaindolo[3,2, 1-jk]carbazoles New Building Blocks for Functional Organic Materials Chem. Eur. J. 2019, 25, 4412-4425.

Kotwica "Azaacenes Based Electroactive Materials: Preparation, Structure, Electrochemistry, Spectroscopy and Applications—A Critical Review" Materials 2021, 14, 5155.

Miao "Ten Years of N-Heteropentacenes as Semiconductors for Organic Thin-Film Transistors" Adv. Mater. 2014, 26, 5541-5549.

Richards "Putting the 'N' in ACENE: Pyrazinacenes and their structural relatives" Org. Biomol. Chem., 2011, 9, 5005.

Bachowska, B. Monatshefte fuer Chemie, 126(2), 1995, 227-231.

\* cited by examiner

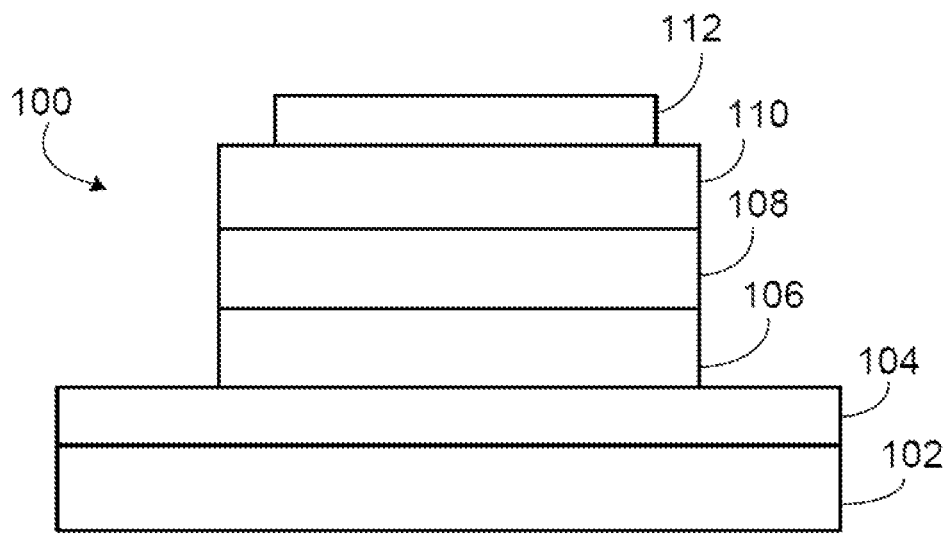

DONOR-ACCEPTOR TYPE THERMALLY ACTIVATED DELAYED FLUORESCENT MATERIALS BASED ON IMIDAZO[1,2-F]PHENANTHRIDINE AND ANALOGUES

CROSS-REFERENCE TO RELATED APPLICATION

The present application is a continuation of U.S. patent application Ser. No. 16/834,193, filed Mar. 30, 2020, now allowed, which is a continuation of U.S. patent application Ser. No. 15/984,157, filed May 18, 2018, now U.S. Pat. No. 10,615,349, which claims the benefit of U.S. Provisional Patent Application No. 62/508,518, filed May 19, 2017, all of which applications are incorporated herein by reference in their entireties.

TECHNICAL FIELD

This invention relates to donor-acceptor type thermally activated delayed fluorescent materials based on imidazo[1,2-F]phenanthridine and analogues for full color displays and lighting applications.

BACKGROUND

Compounds capable of absorbing or emitting light can be used in a variety of optical and electro-optical devices, including photo-absorbing devices (e.g., solar- and photo-sensitive devices), photo-emitting devices, organic light-emitting diodes (OLEDs), and devices capable of photo-absorption and photo-emission. Much research has been devoted to the discovery and optimization of organic and organometallic materials for use in optical and electro-optical devices. Metal complexes can be used for many applications, such as emitters for OLEDs. Despite advances in research devoted to optical and electro-optical materials, many currently available materials exhibit a number of disadvantages, including poor processing ability, inefficient emission or absorption, and insufficient stability.

SUMMARY

General Formulas I-IV include donor-acceptor type thermally activated delayed fluorescent materials based on imidazol[1,2-f]phenanthridine and analogues for organic light emitting diodes (OLEDS) suitable for full color displays and lighting applications.

General Formula I

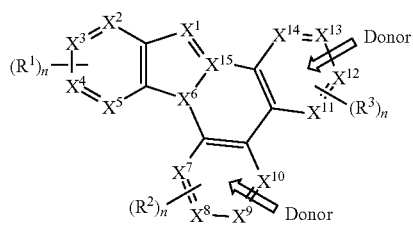

General Formula II

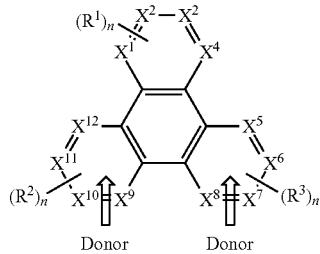

General Formula III

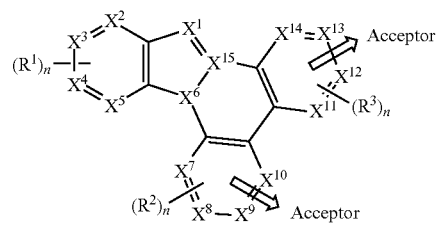

General Formula IV

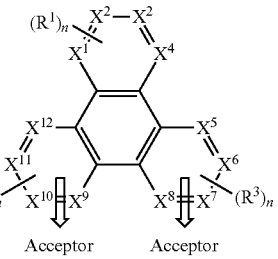

In General Formulas I-IV:

$R^1$, $R^2$, and $R^3$ each independently represents hydrogen, cyanide, halogen, hydroxy, amino, nitro, thiol, or substituted or unsubstituted $C_1$-$C_4$ alkyl, alkoxy, or aryl, and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ each independently represents substituted or unsubstituted C, N, Si, O, or S, valency permitting, and each n is independently an integer as permitted by valence.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 depicts a cross-sectional view of an organic light emitting device.

DETAILED DESCRIPTION

General Formulas I-IV include donor-acceptor type thermally activated delayed fluorescent materials based on imidazo[1,2-f]phenanthridine and analogues for organic light emitting diodes (OLEDS) suitable for full color displays and lighting applications.

General Formula I

General Formula II

General Formula III

General Formula IV

In General Formulas I-IV:
R¹, R², and R³ each independently represents hydrogen, cyanide, halogen, hydroxy, amino, nitro, thiol, or substituted or unsubstituted $C_1$-$C_4$ alkyl, alkoxy, or aryl, and $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, and $X^{15}$ each independently represents substituted or unsubstituted C, N, Si, O, or S, valency permitting, and each n is independently an integer as permitted by valence.

Implementations of General Formulas I-IV are shown below.

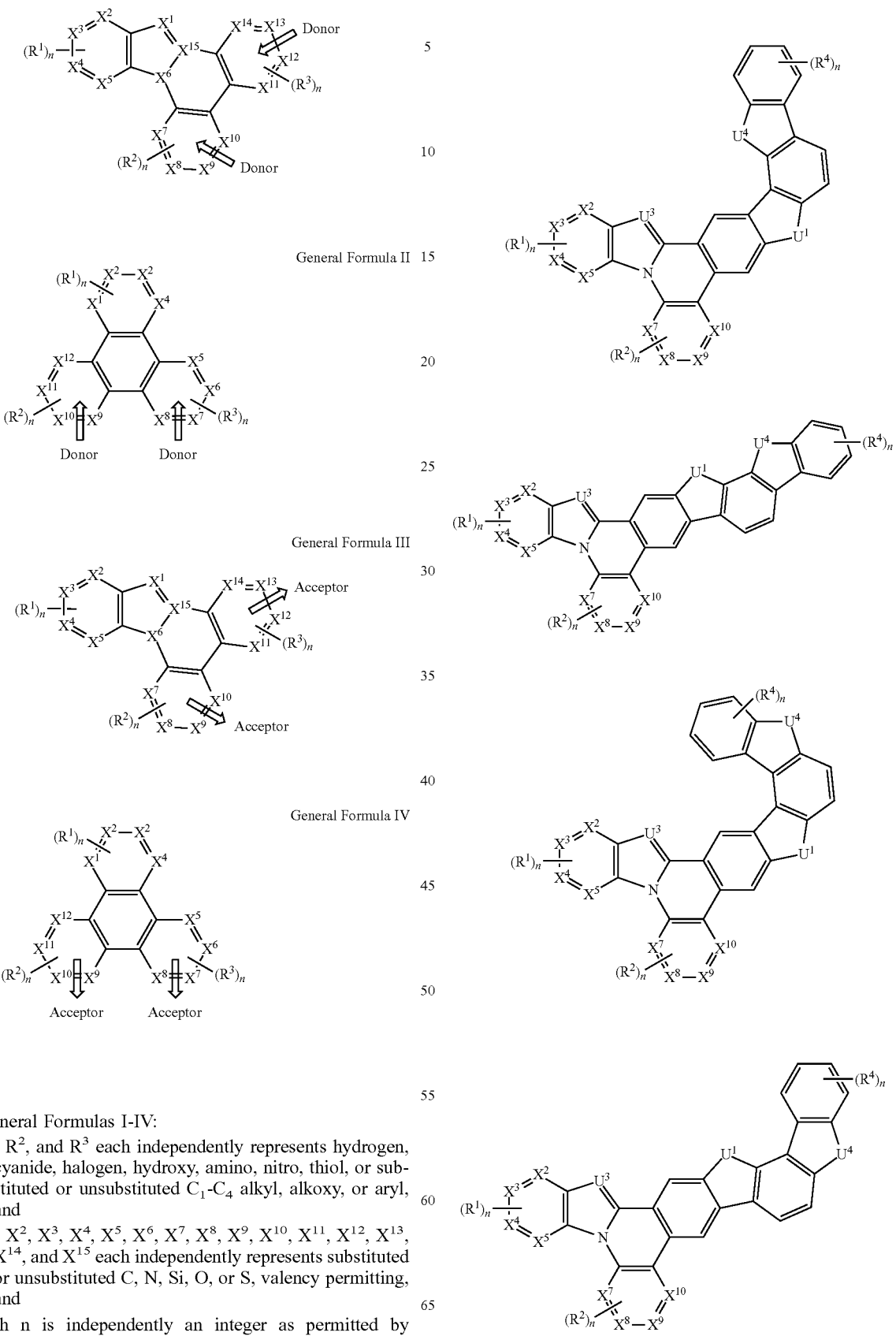

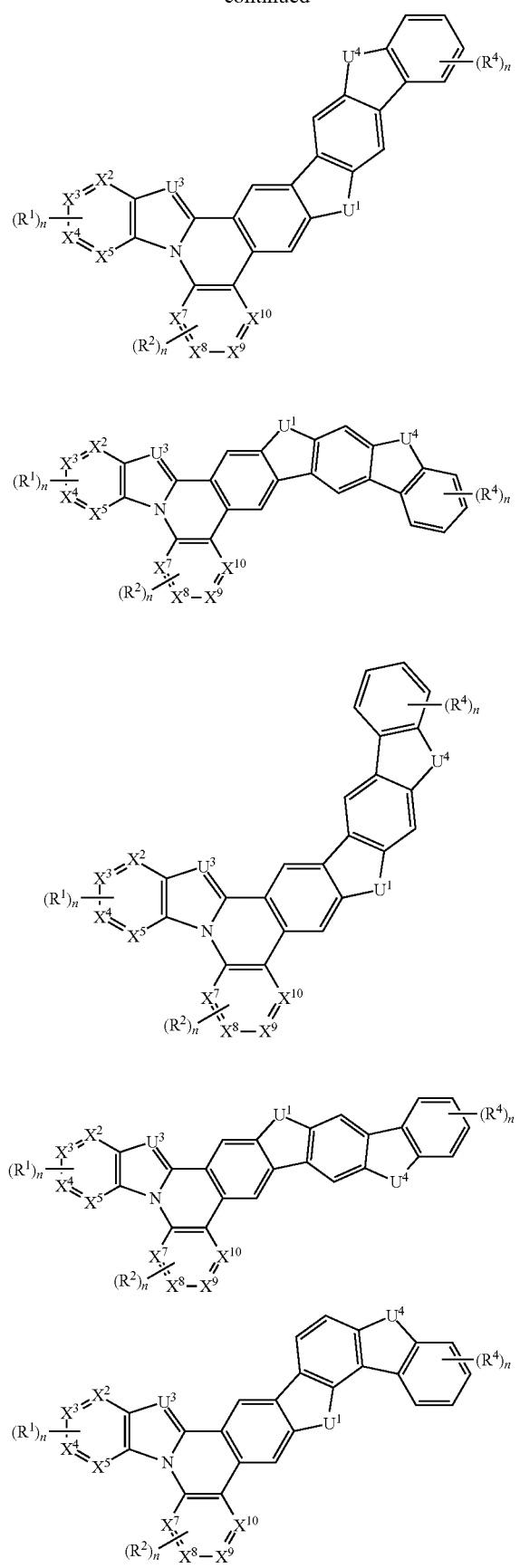
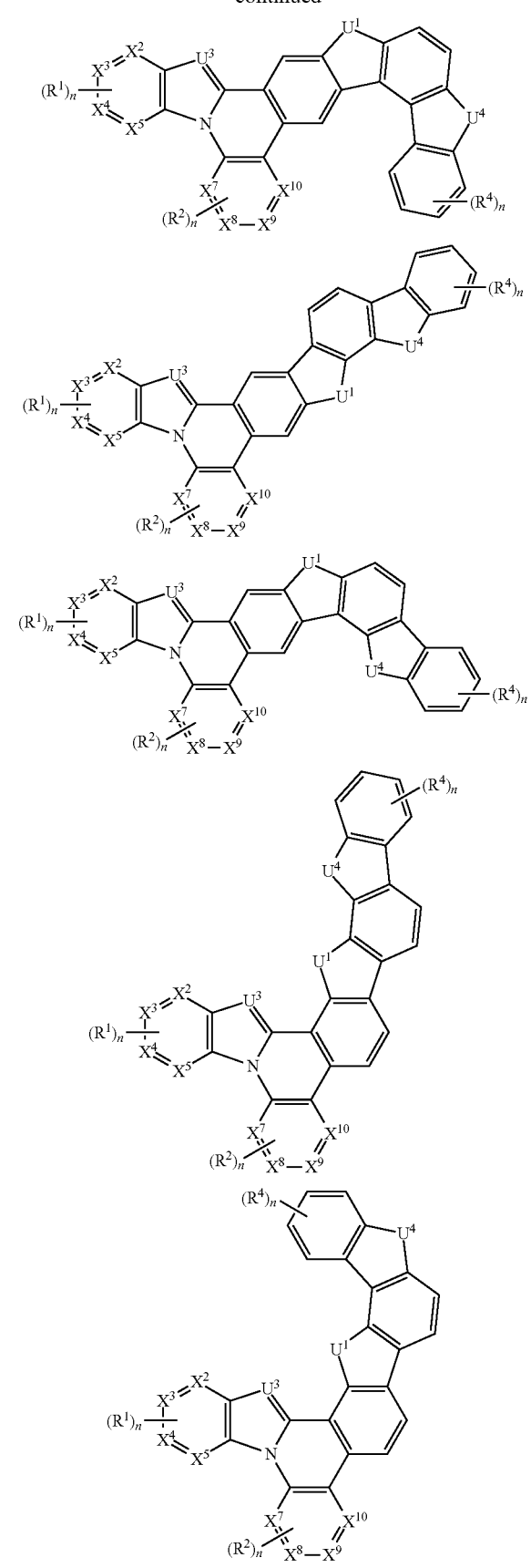

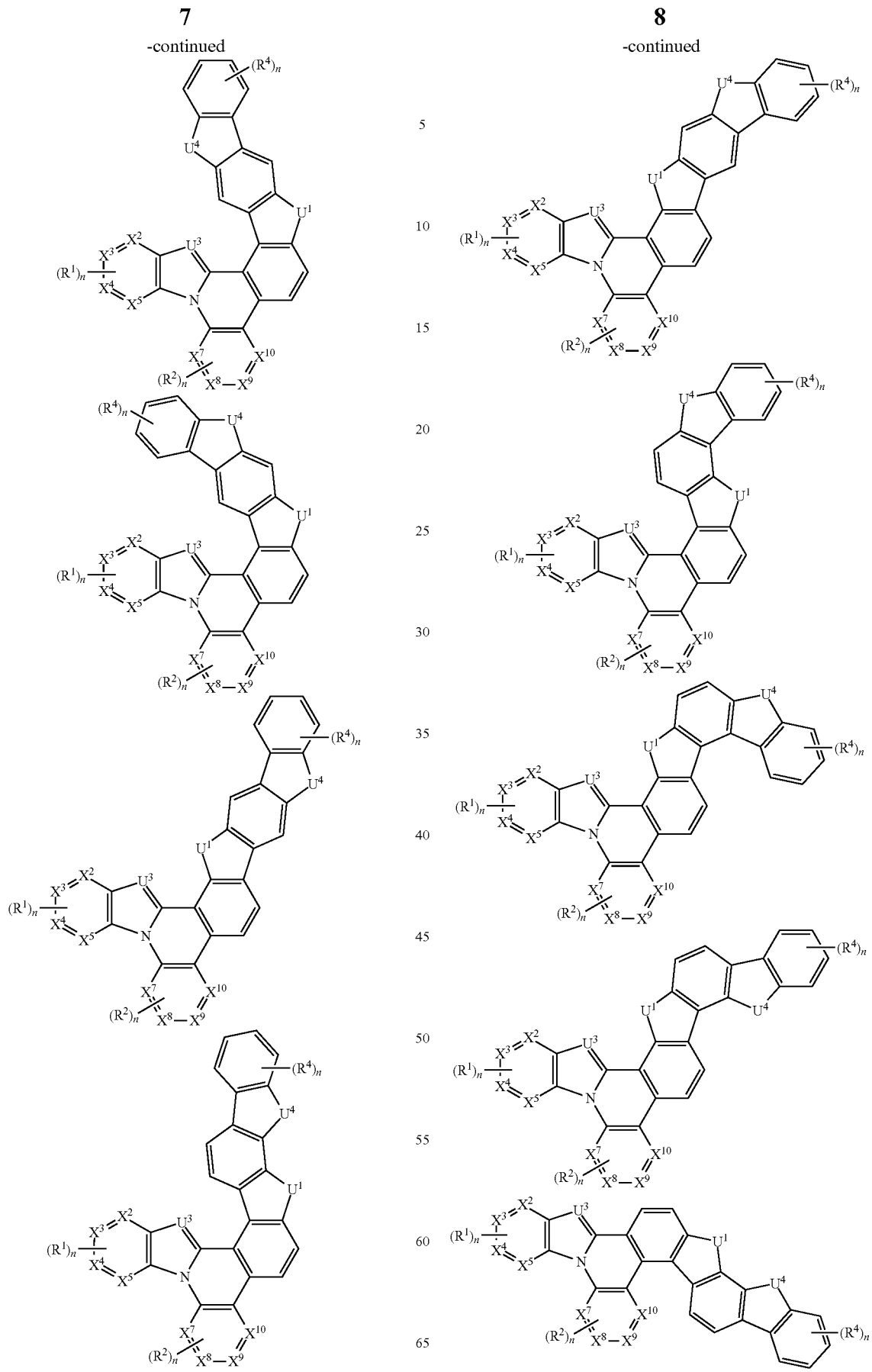

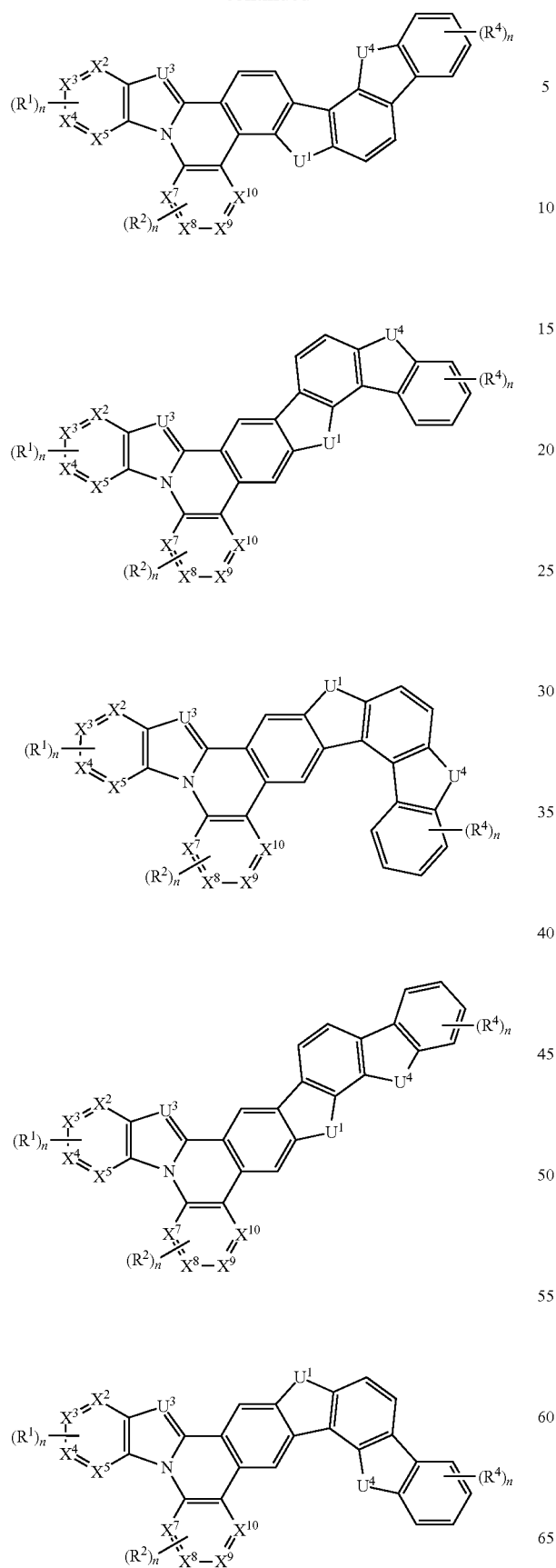
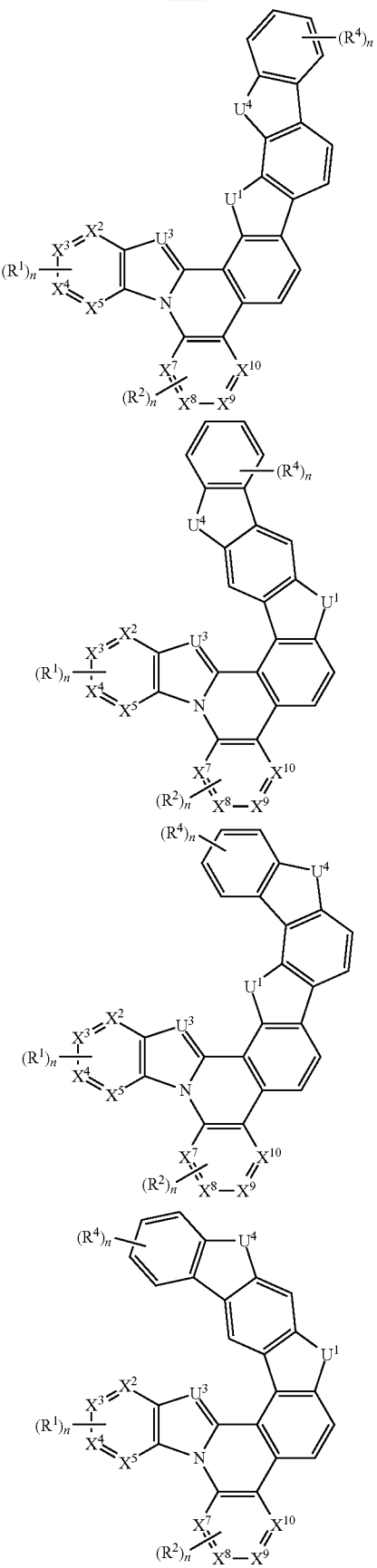

-continued
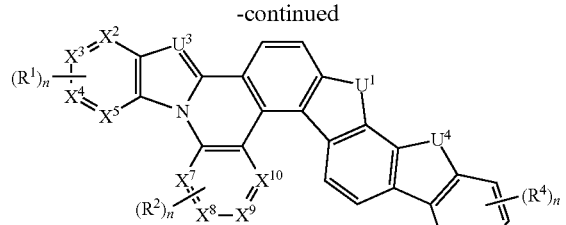
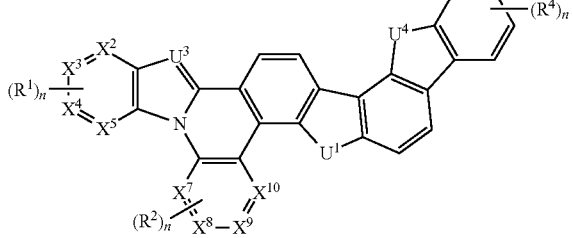
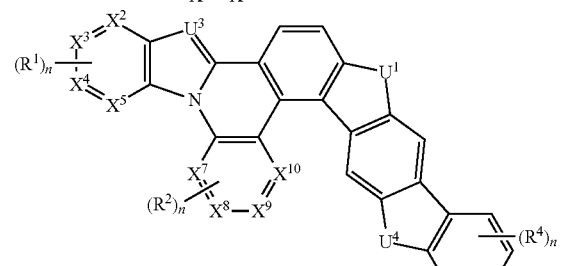
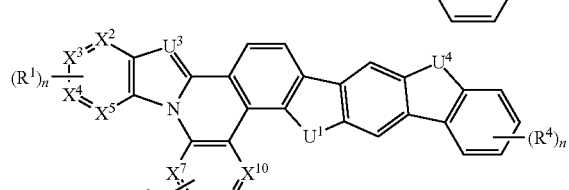
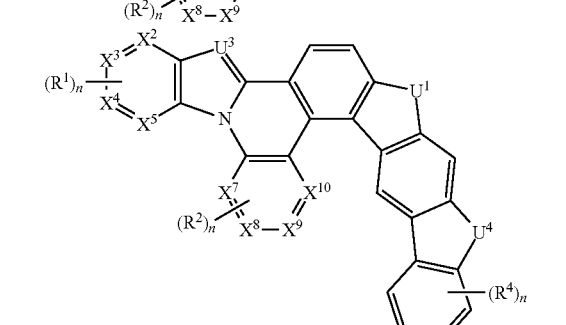
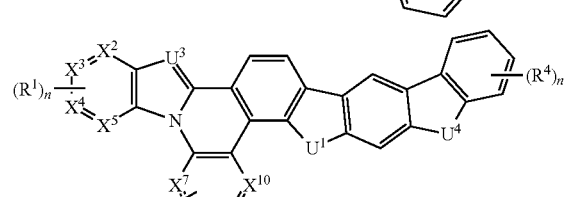
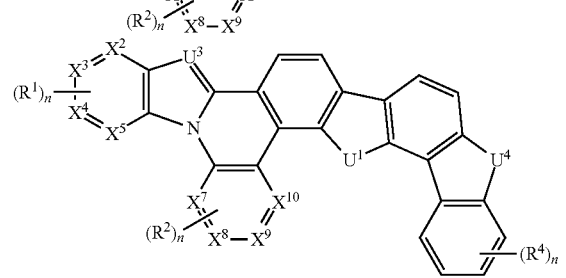
-continued
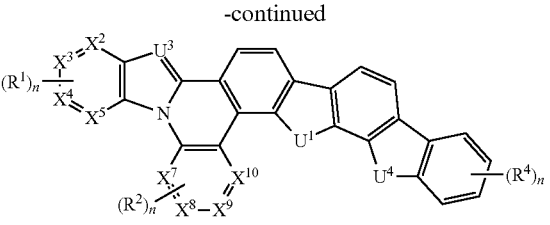
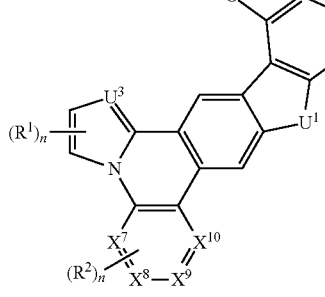
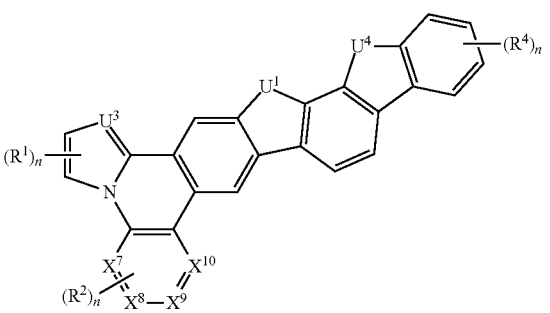
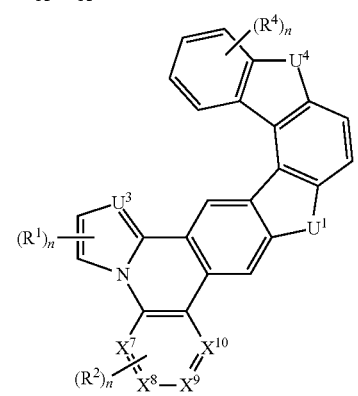
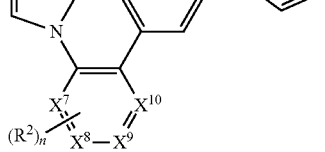

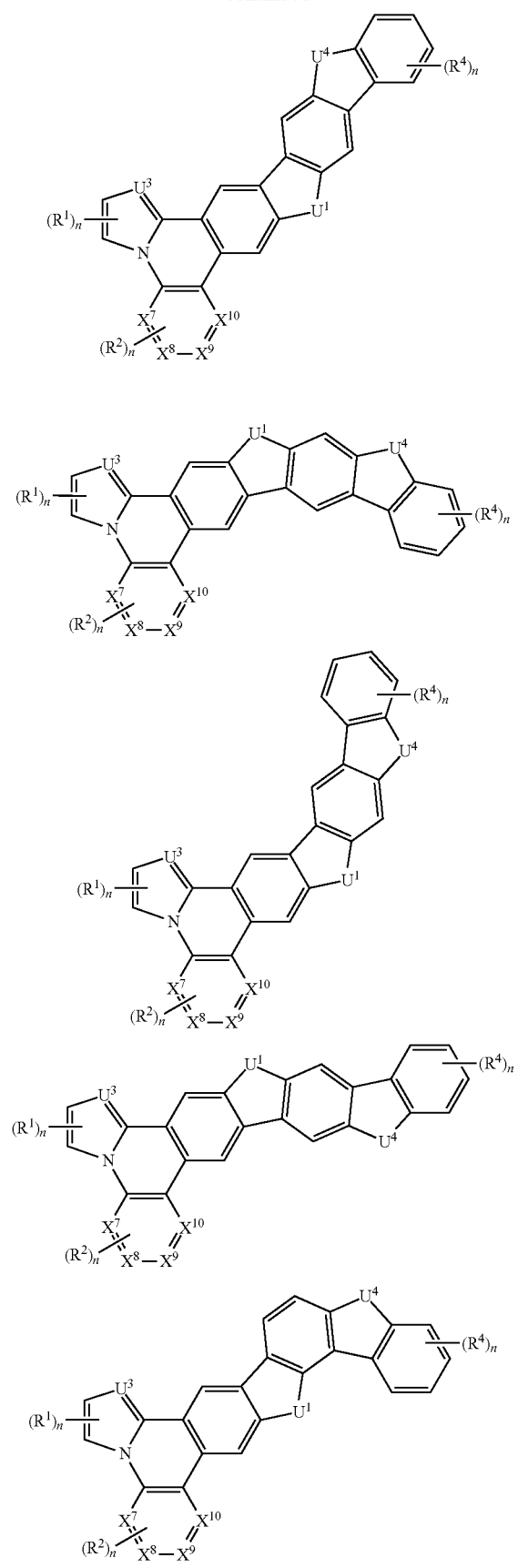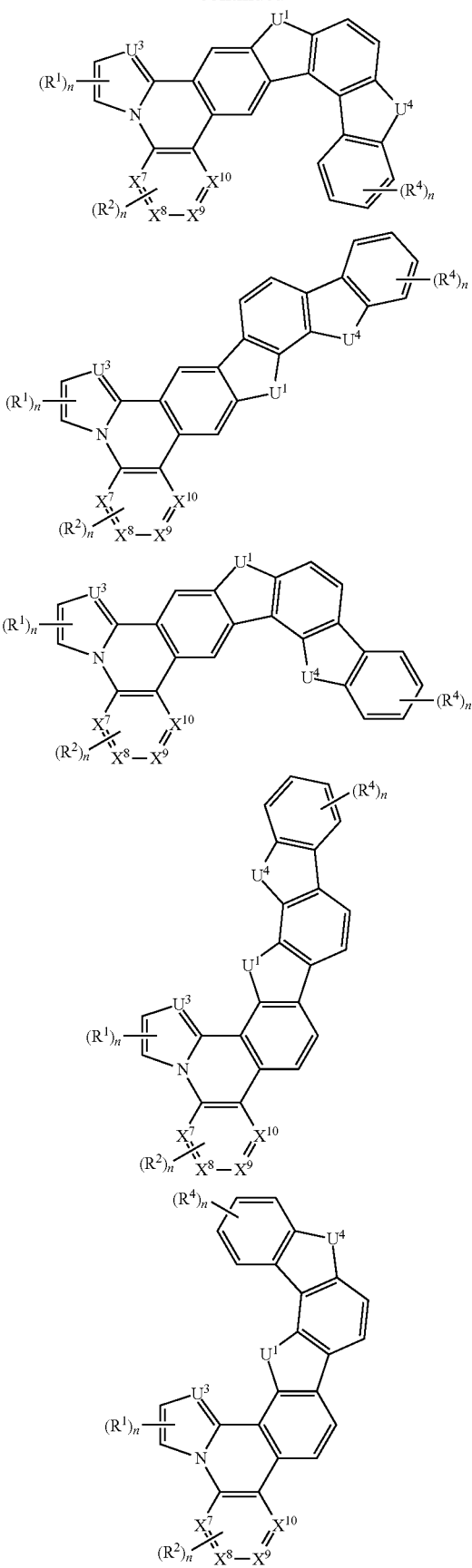

-continued
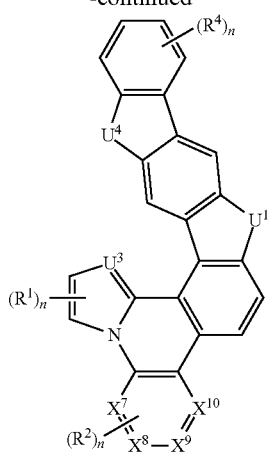
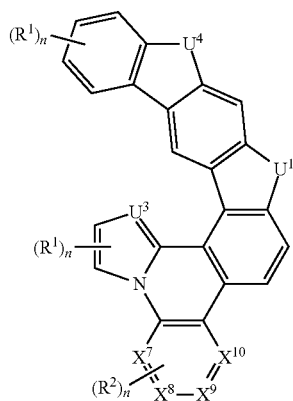
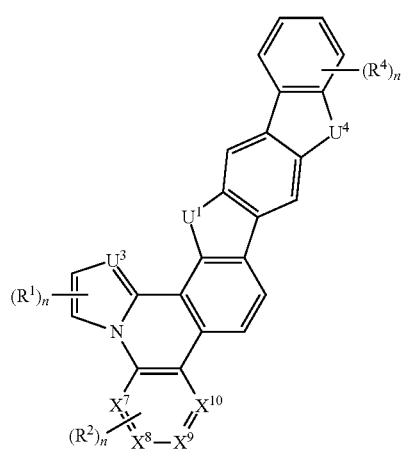
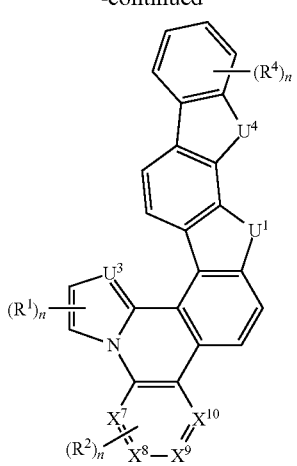
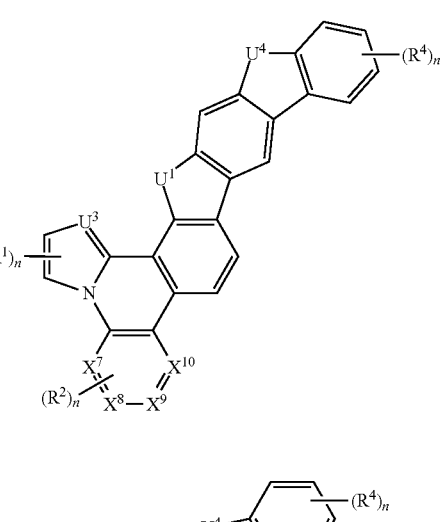
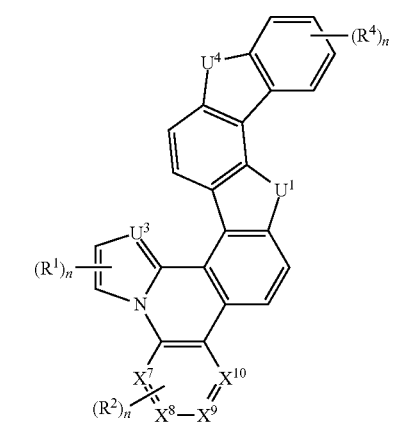
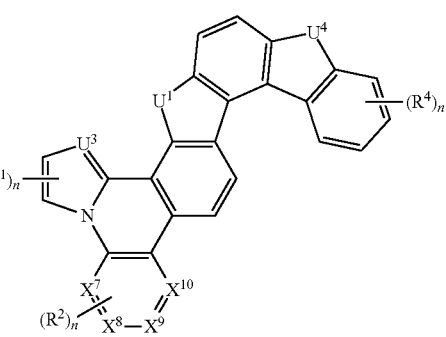

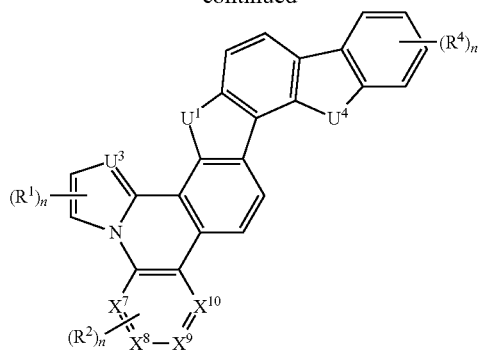
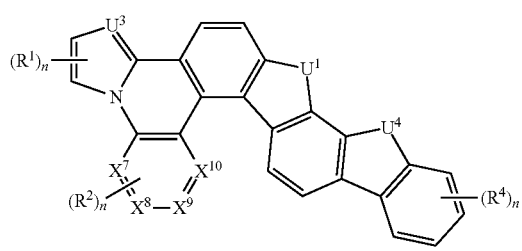
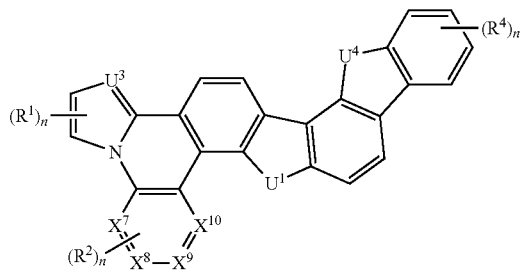
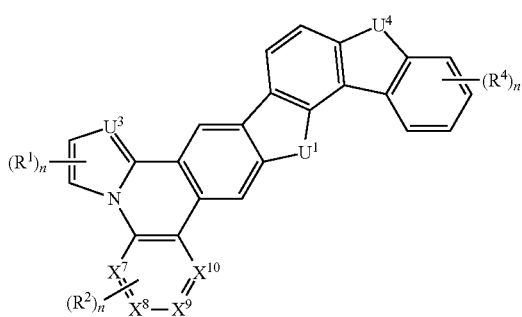
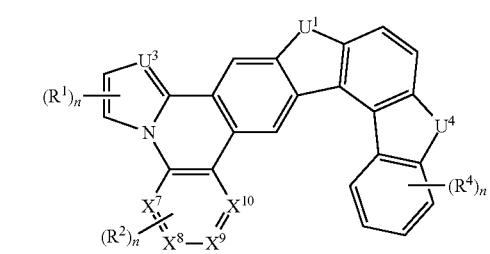
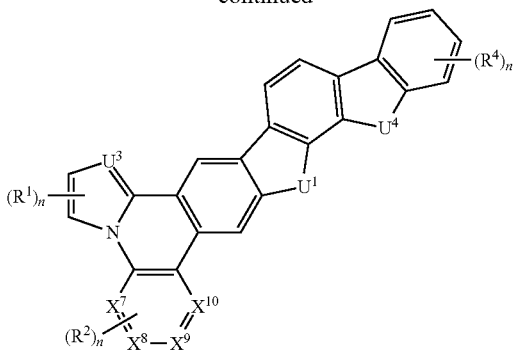
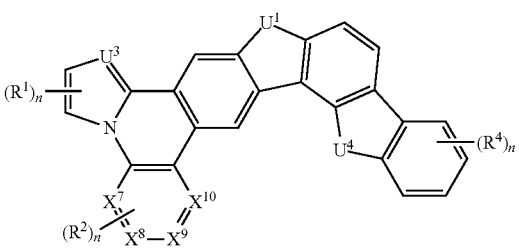
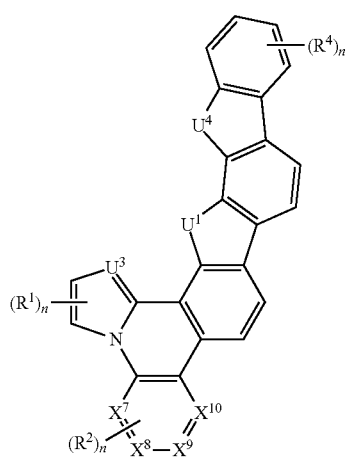
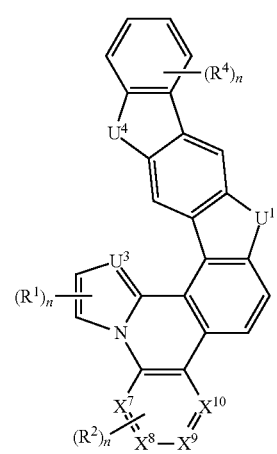

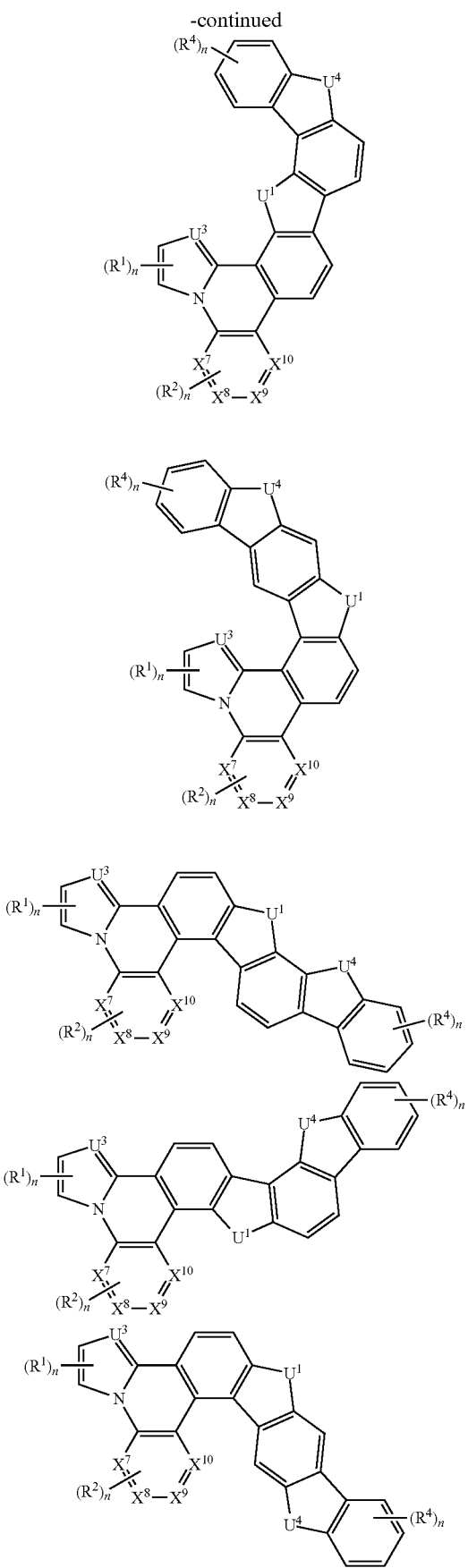
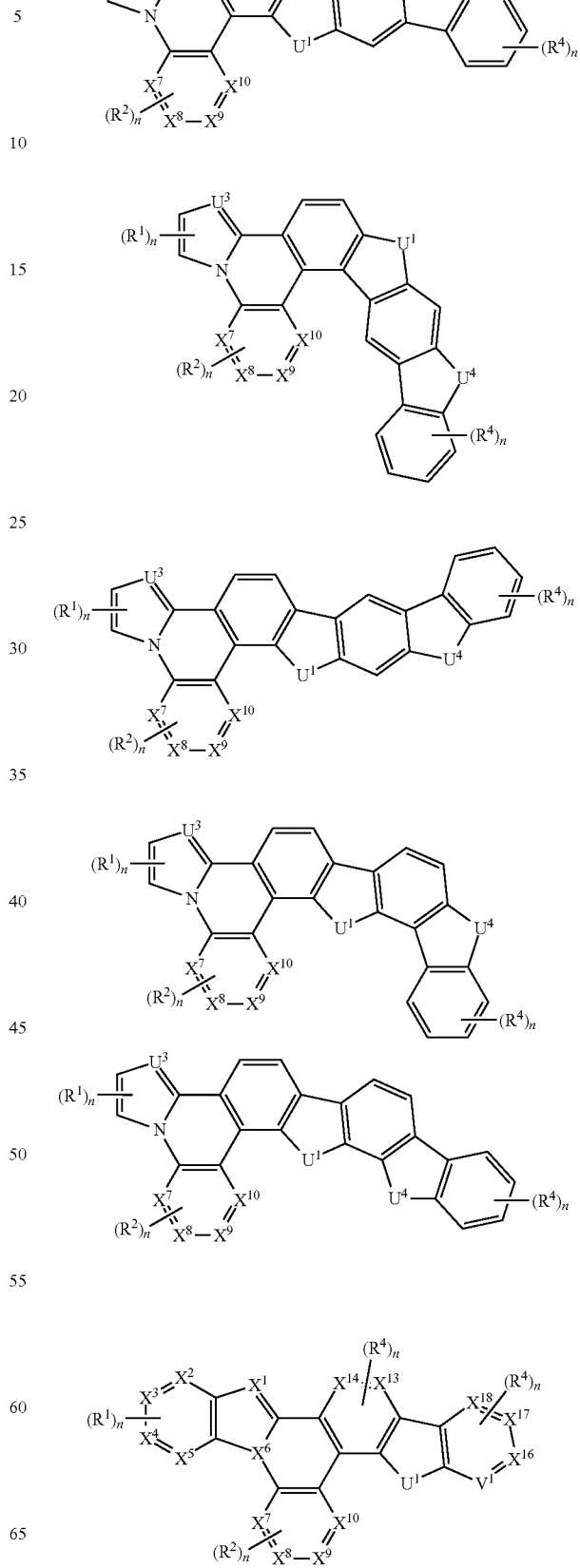

-continued
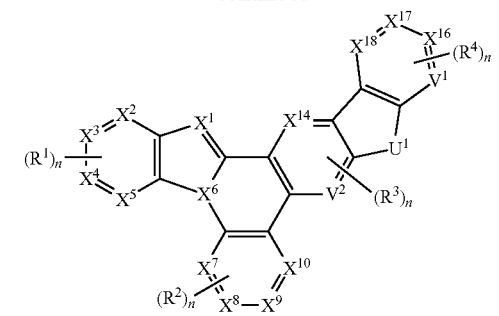
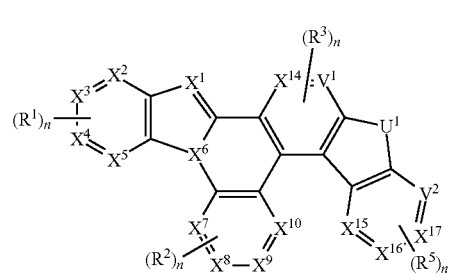
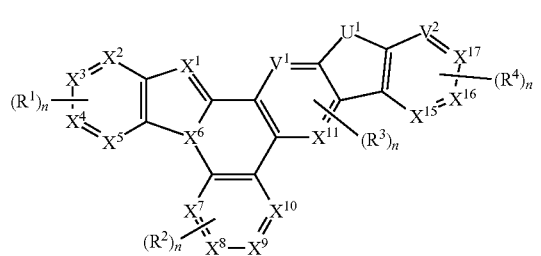
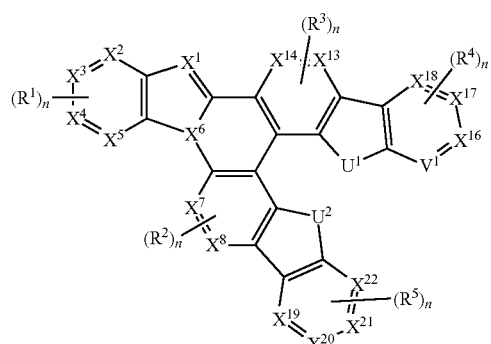
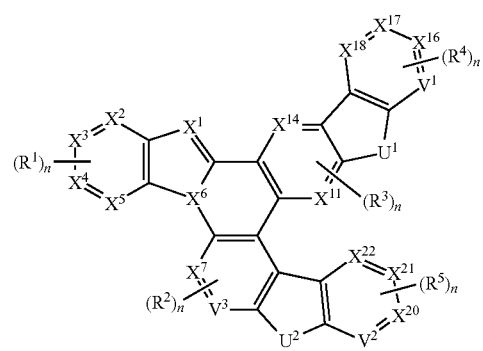
-continued
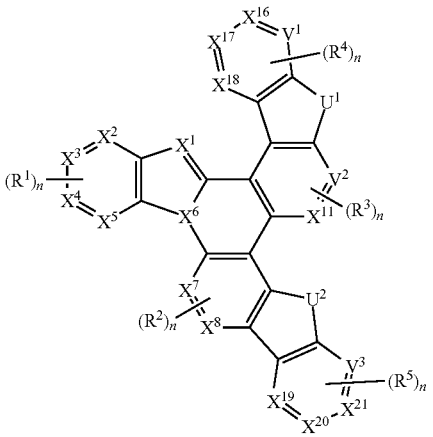
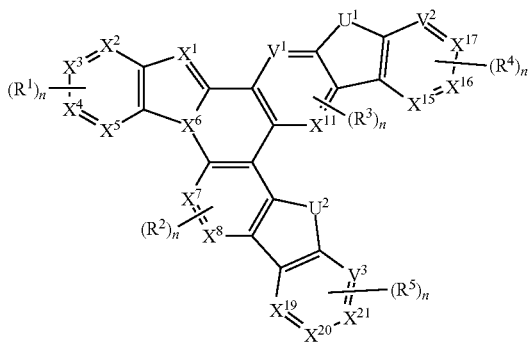
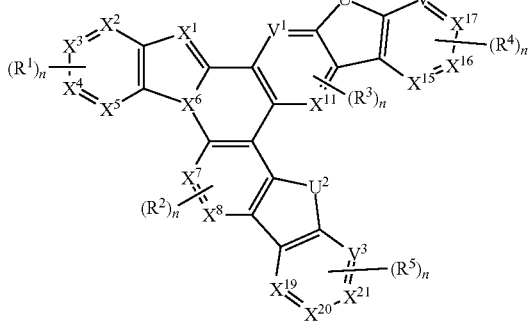
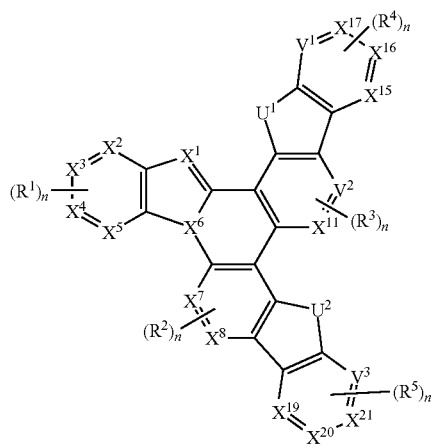
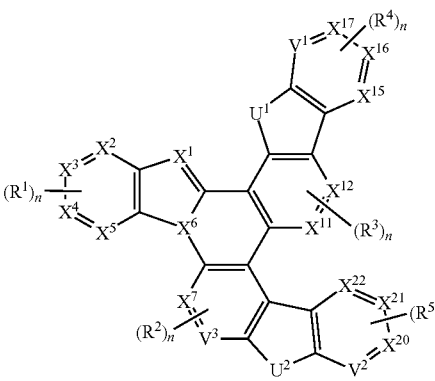

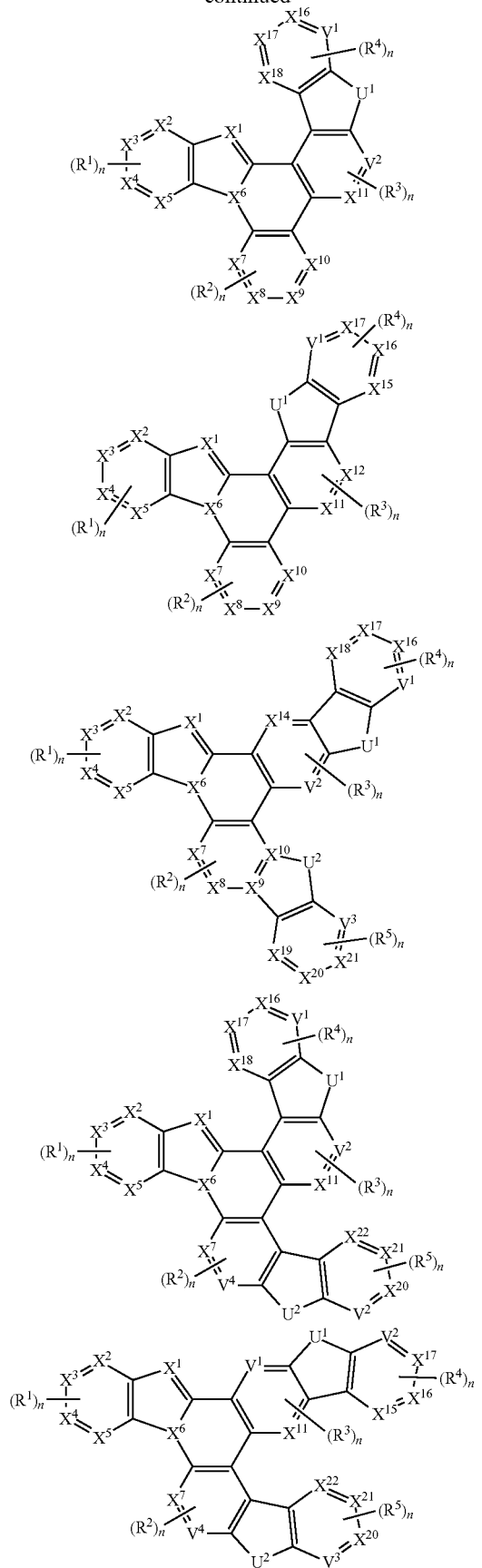
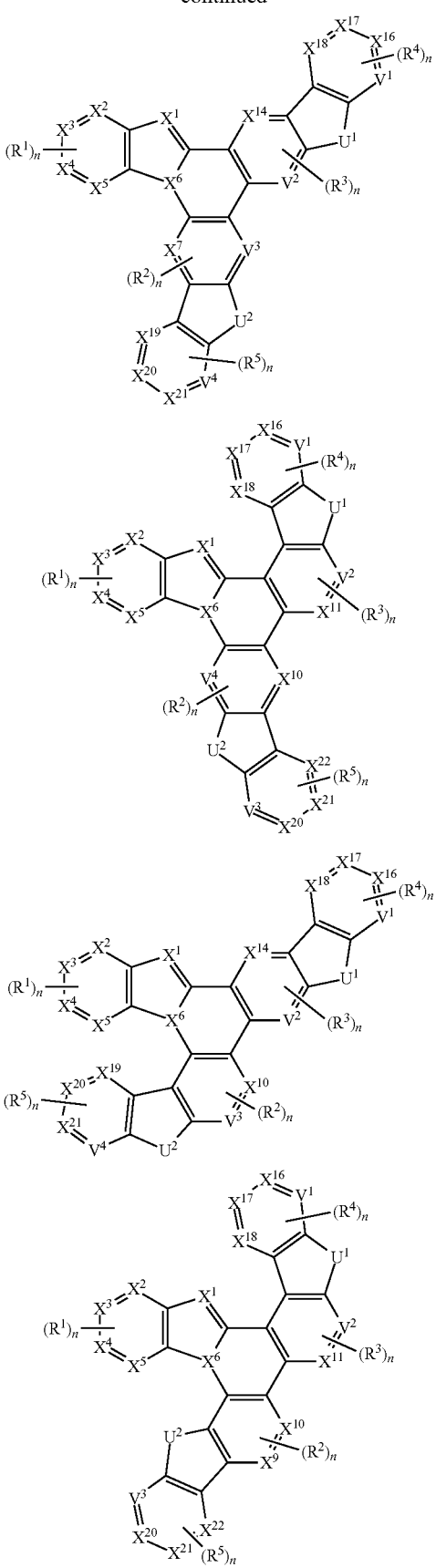

-continued
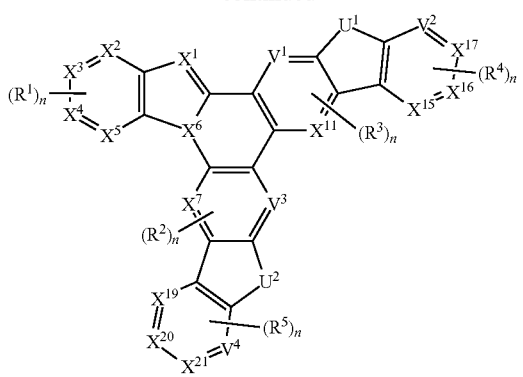
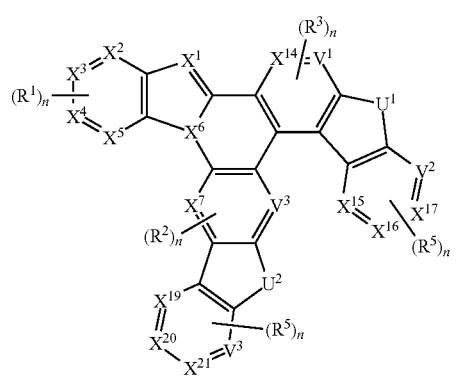
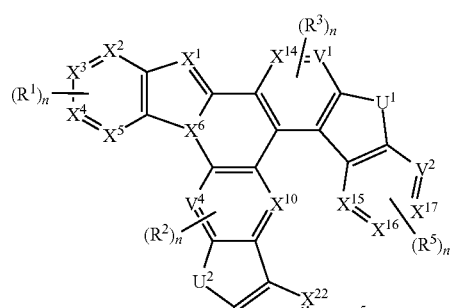
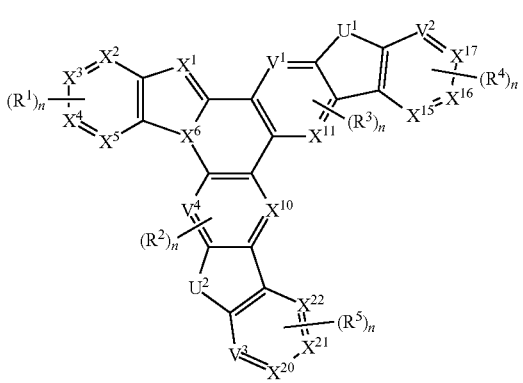
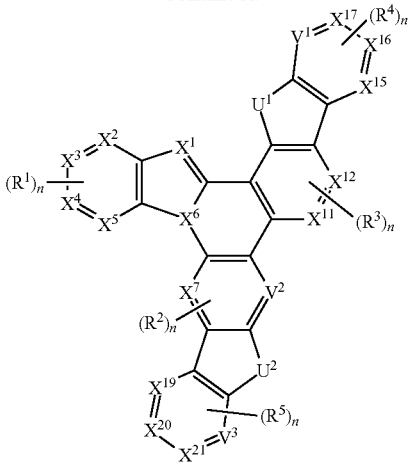
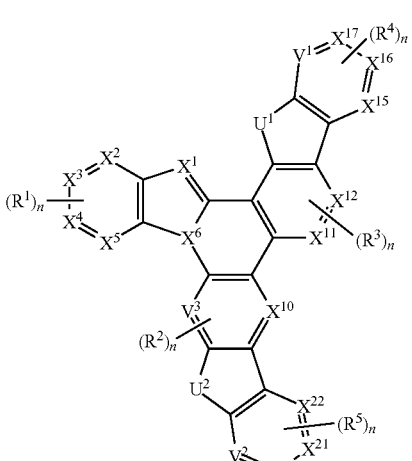
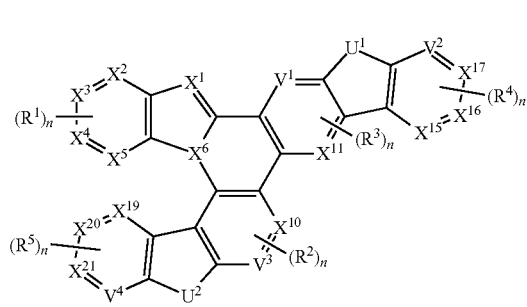
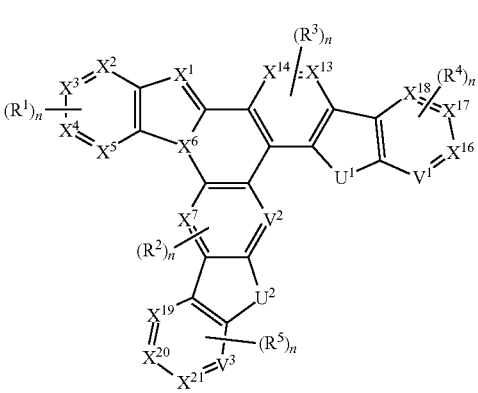

-continued
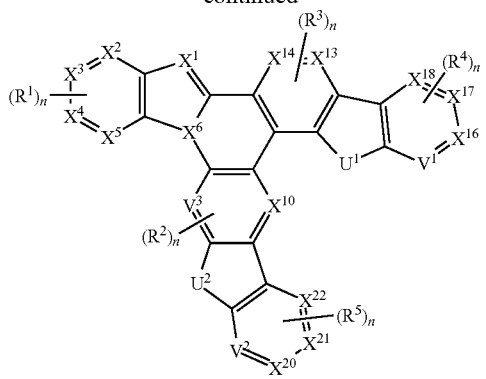
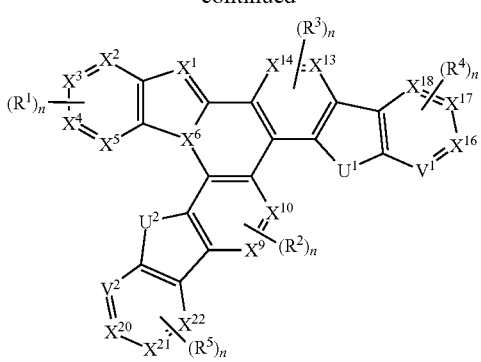
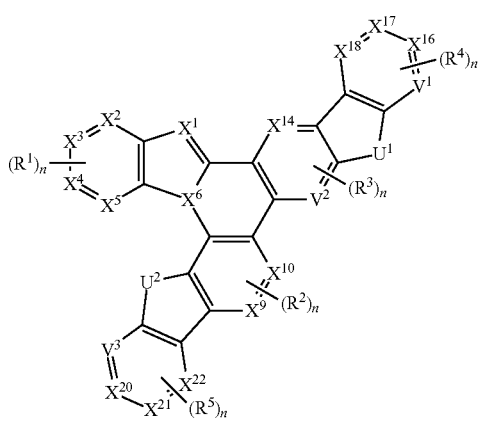
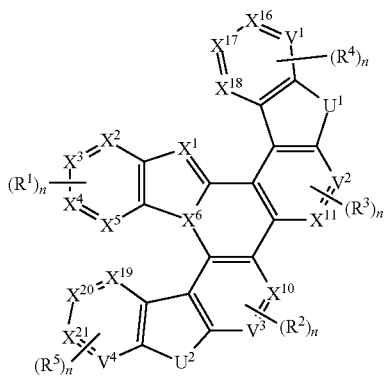
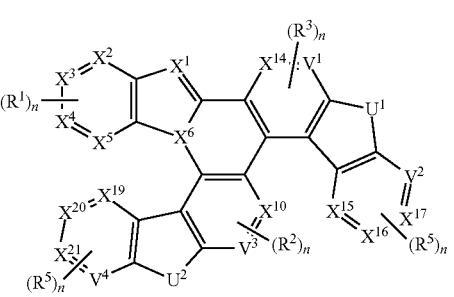

-continued
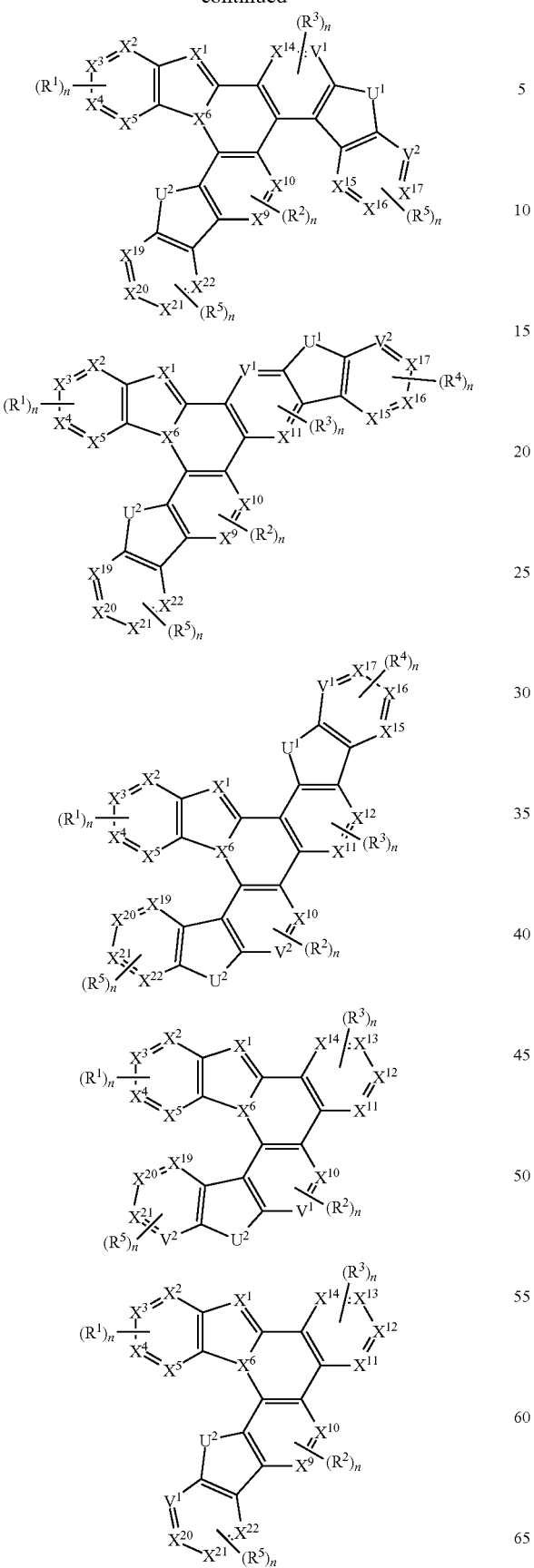
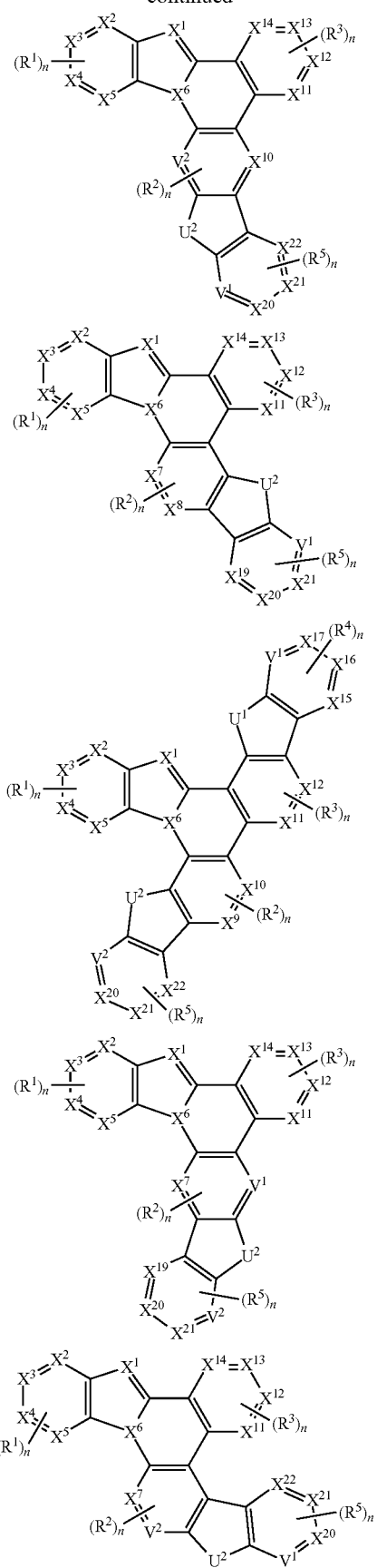

-continued
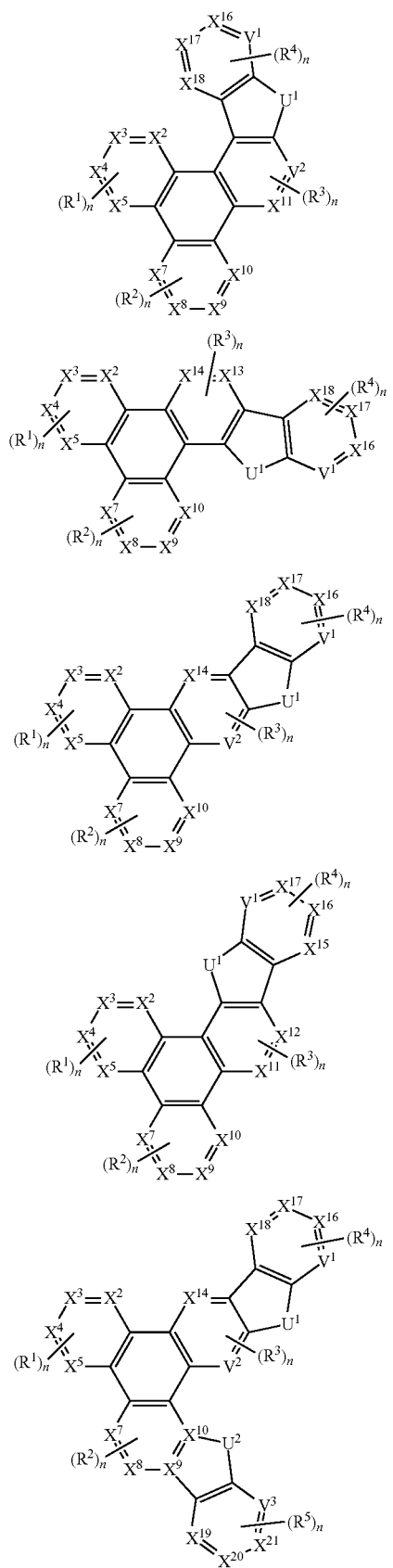
-continued
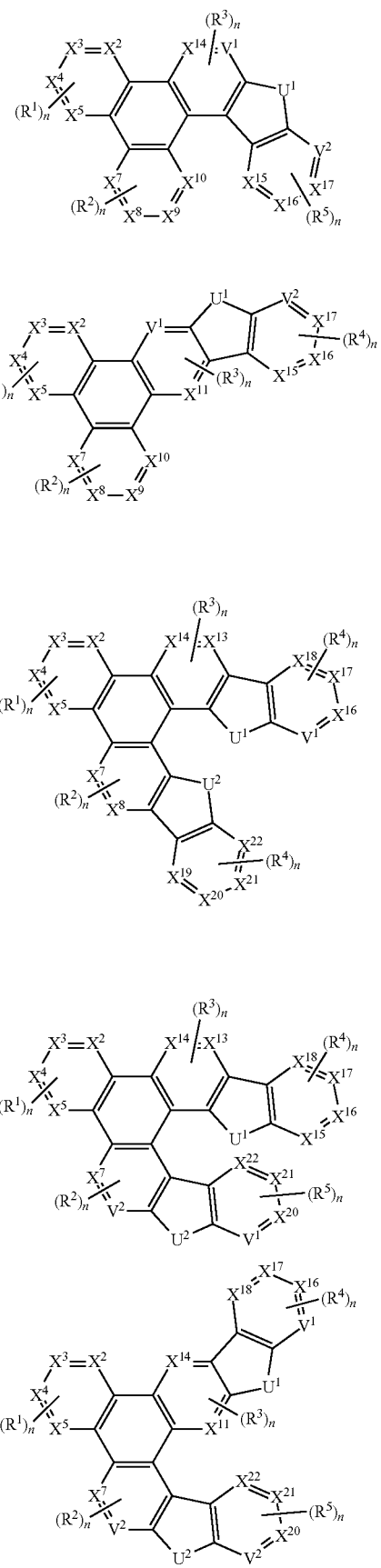

33
-continued
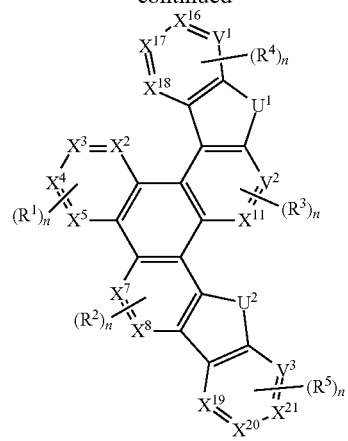
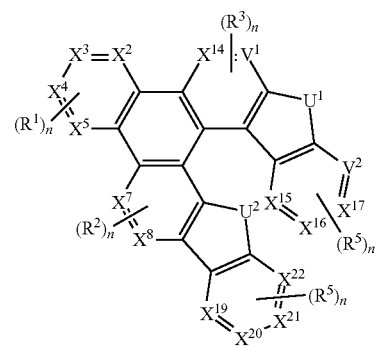
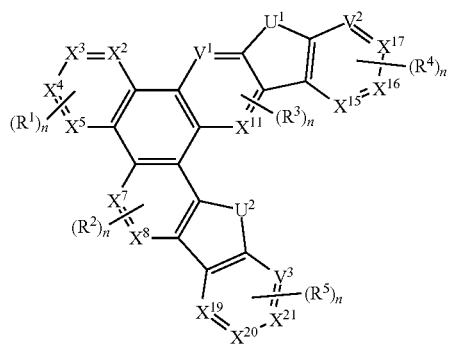
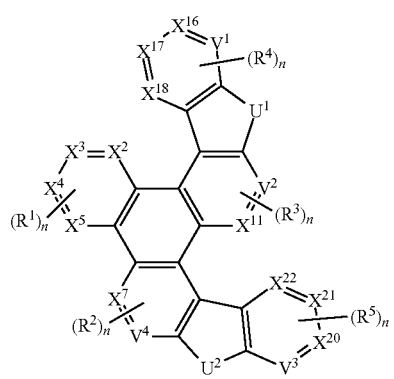
34
-continued
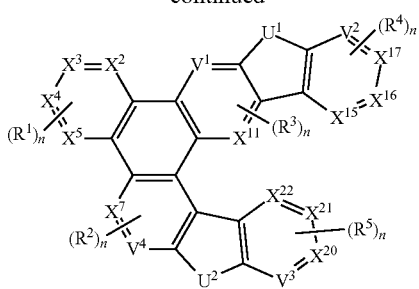
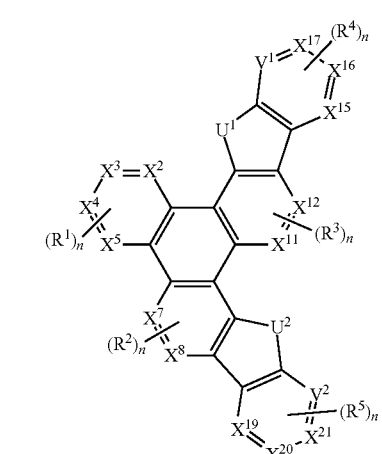
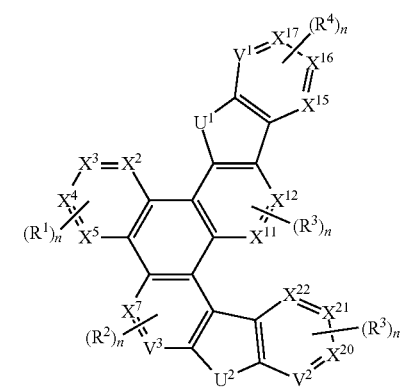
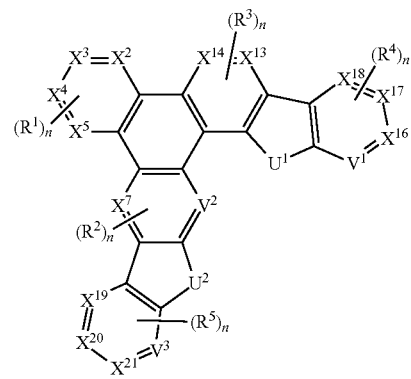

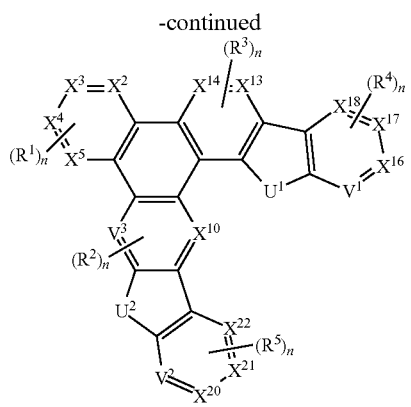
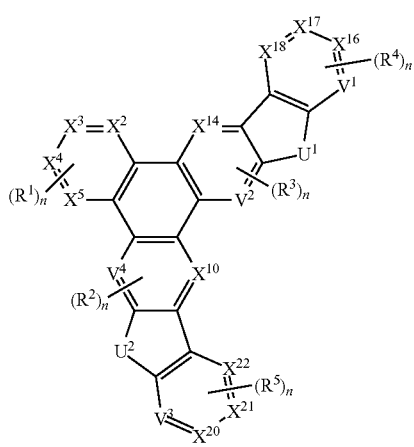
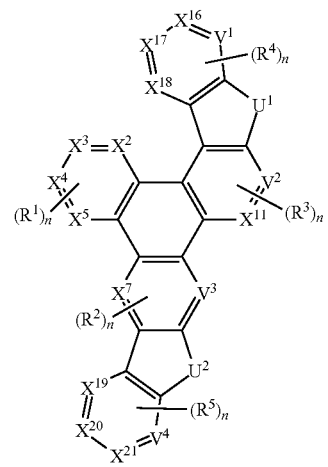
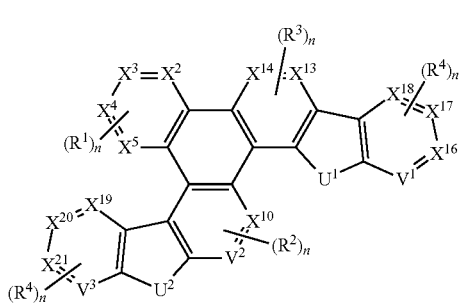
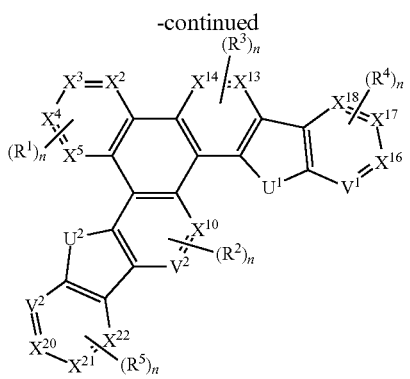
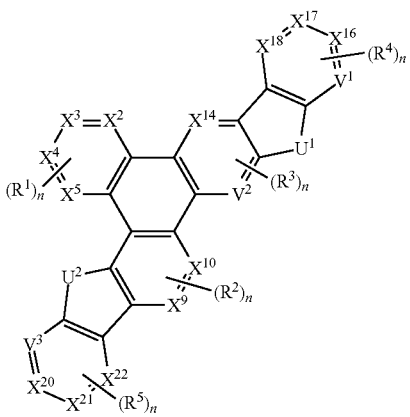
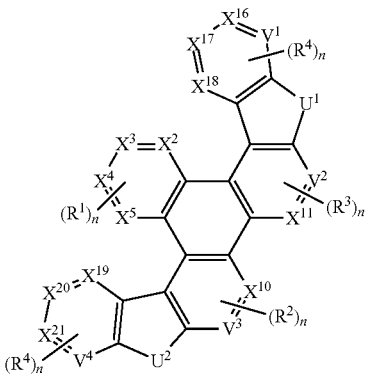
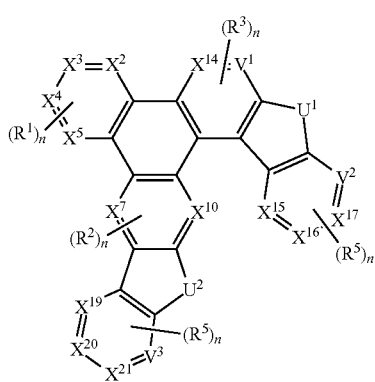

-continued
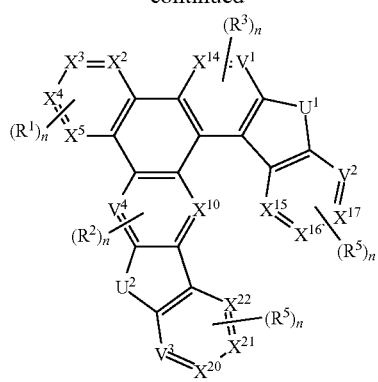
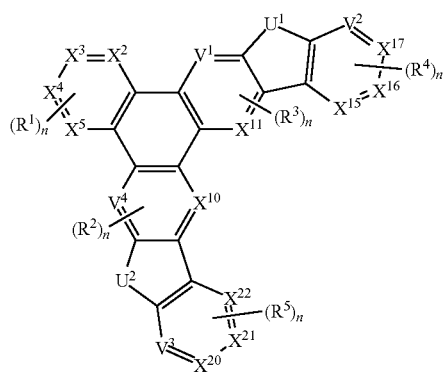
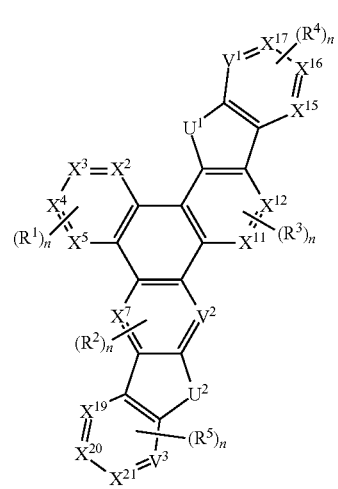
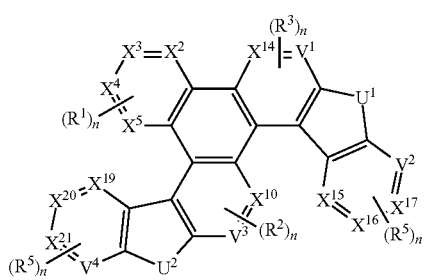
-continued
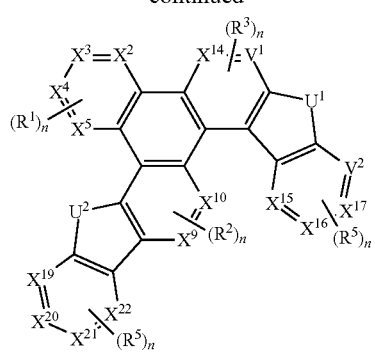
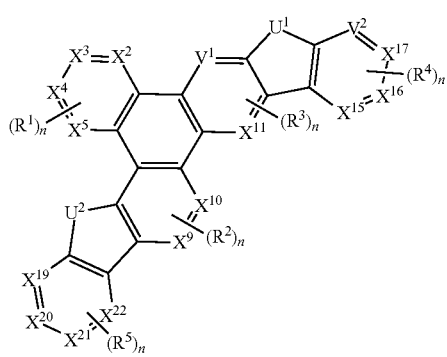
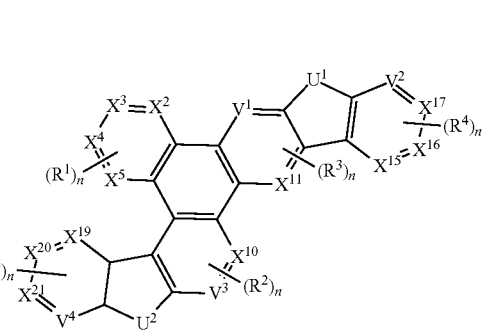
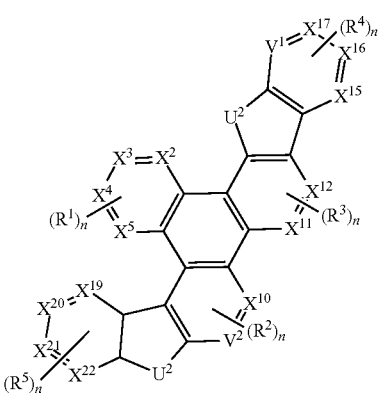

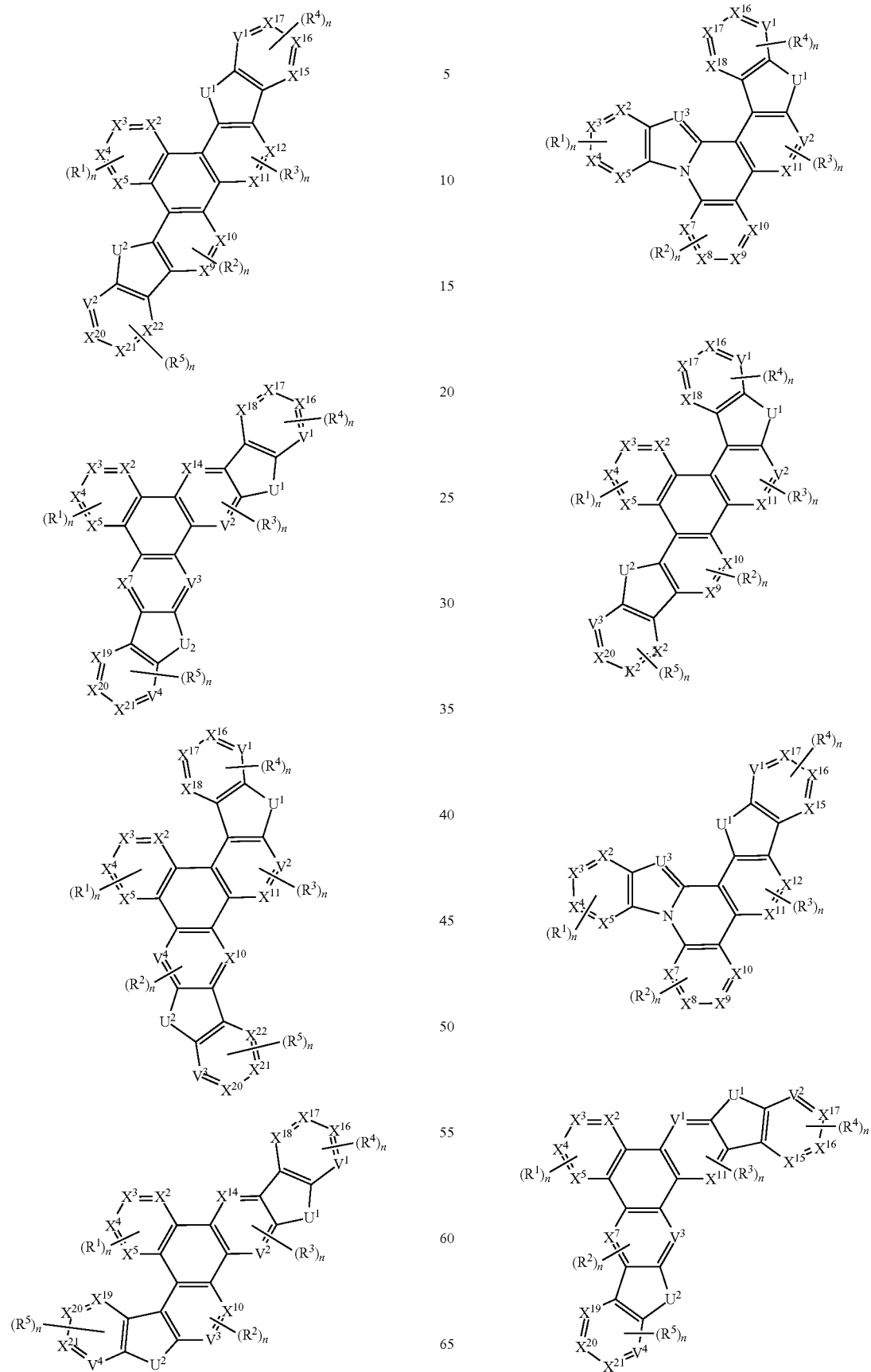

-continued
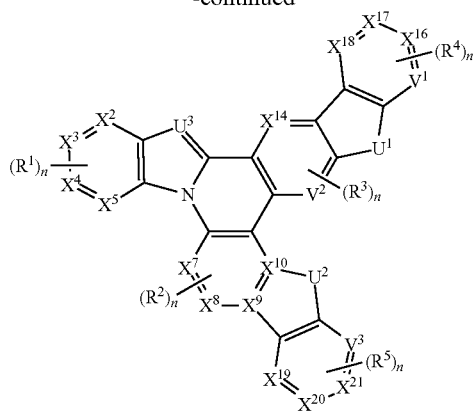
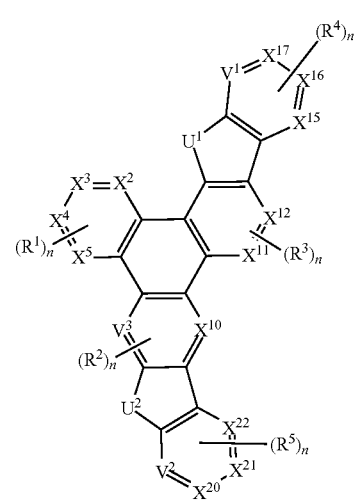
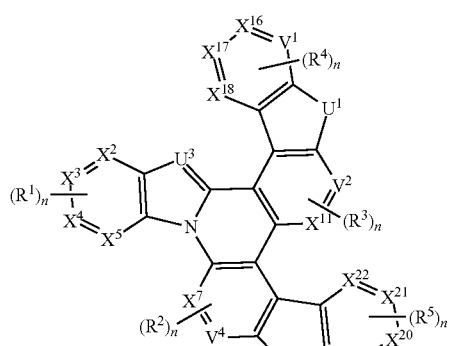
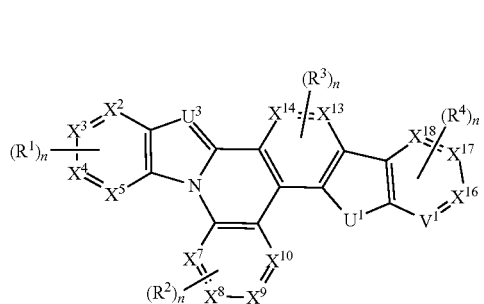
-continued
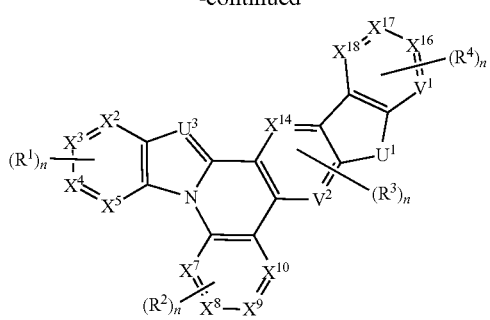
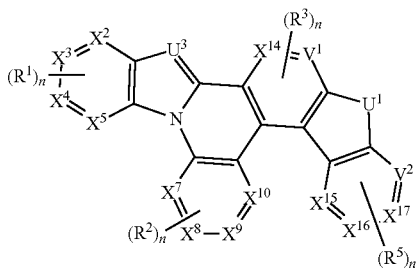
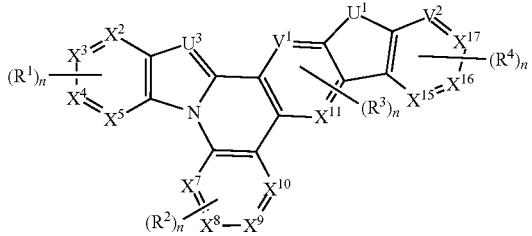
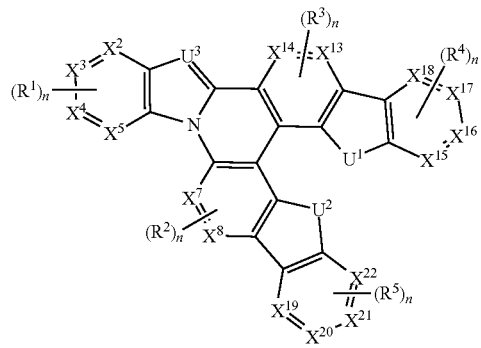
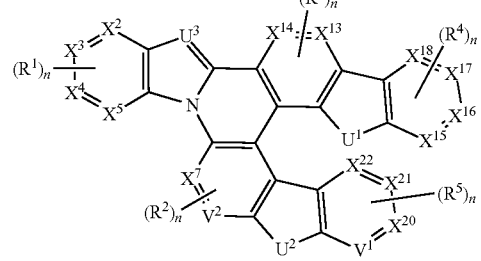

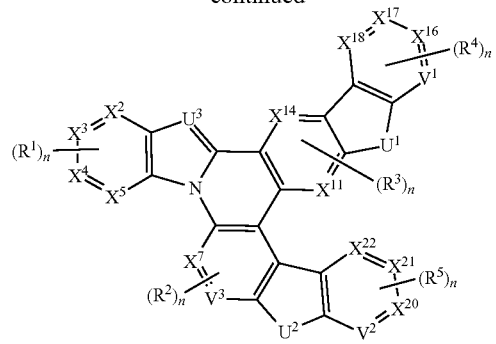

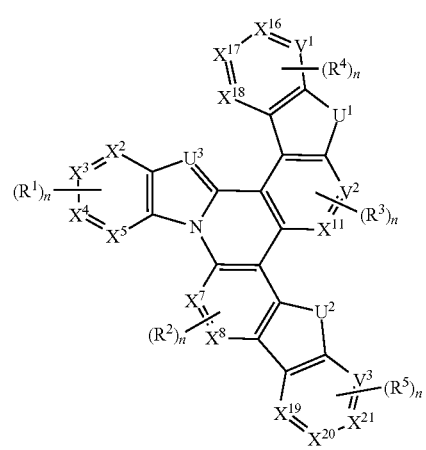
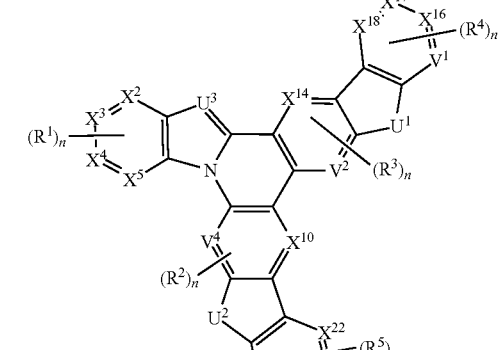
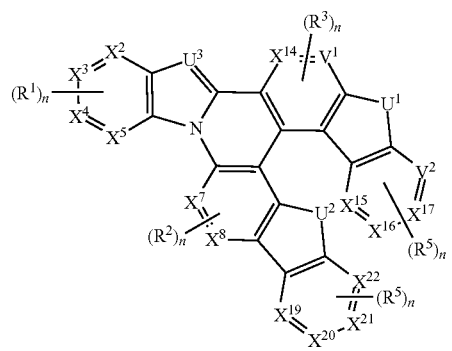
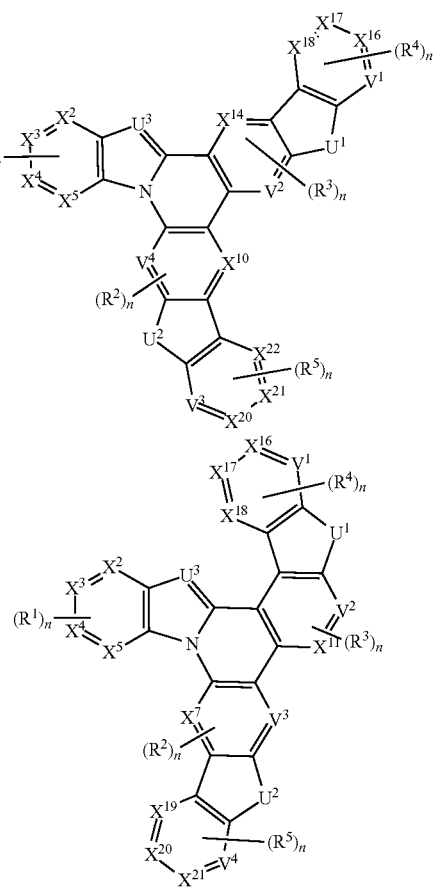
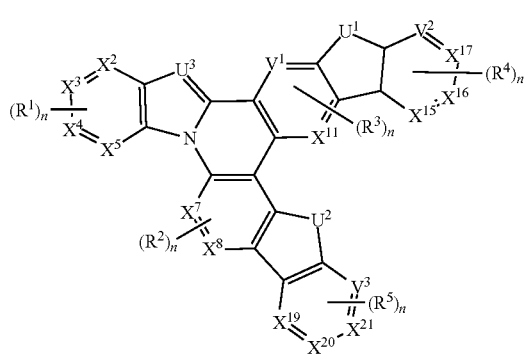

-continued
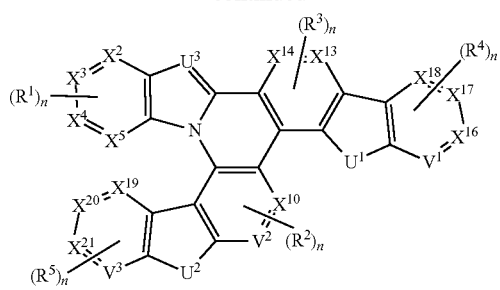
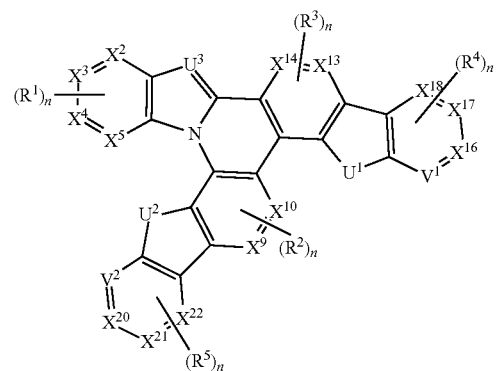
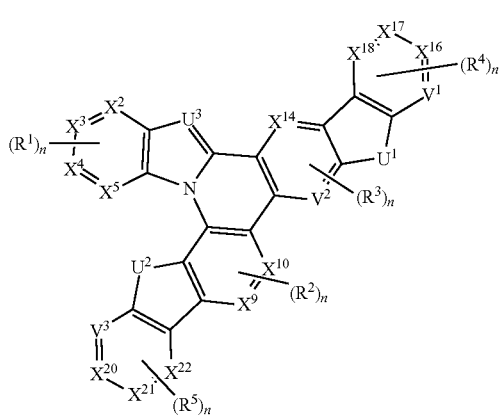
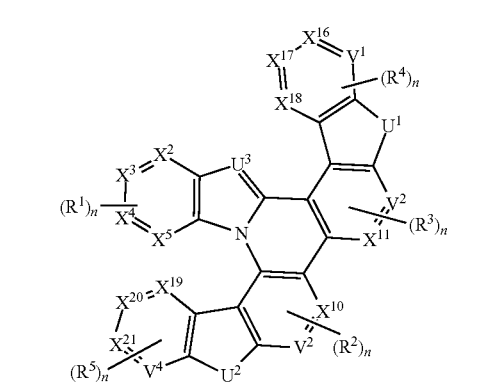
-continued
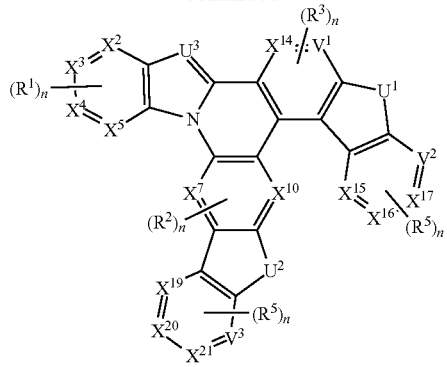
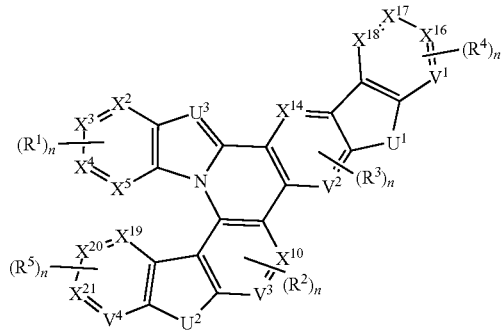
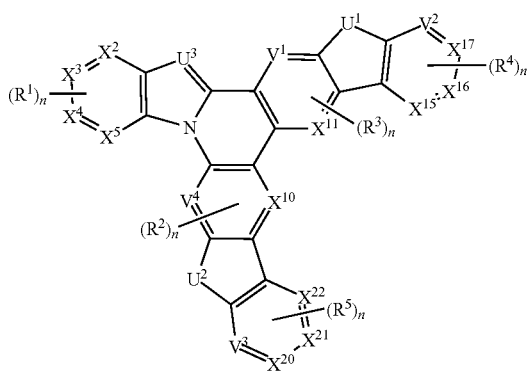
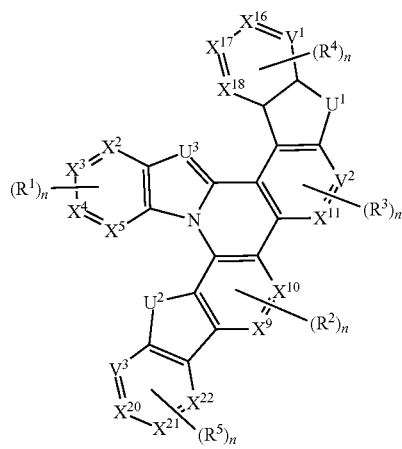

-continued
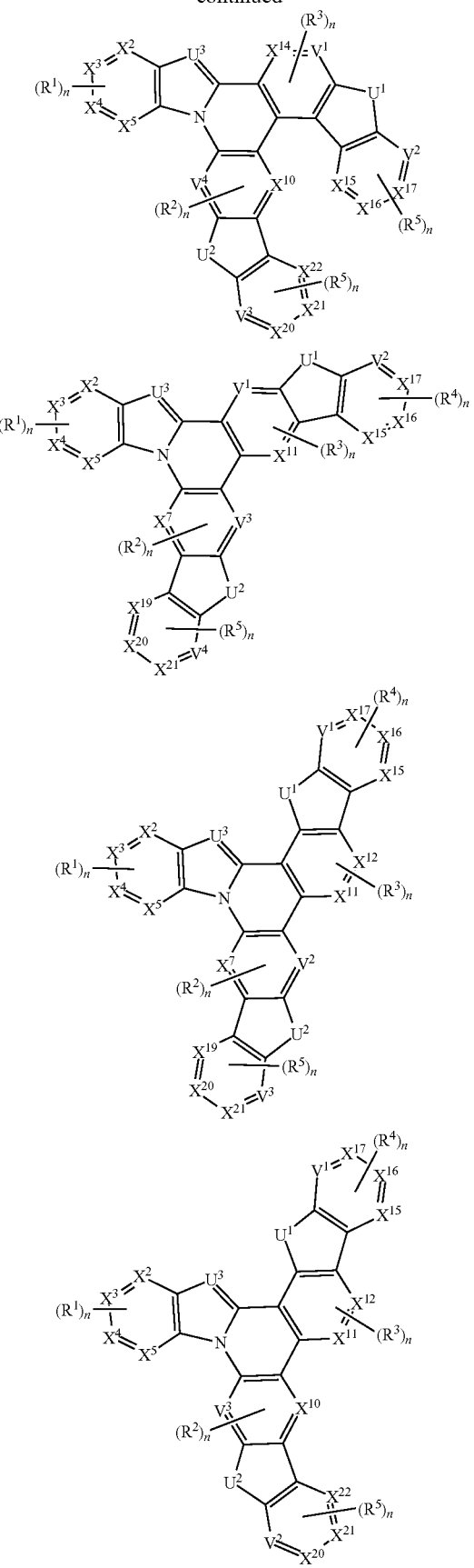
-continued
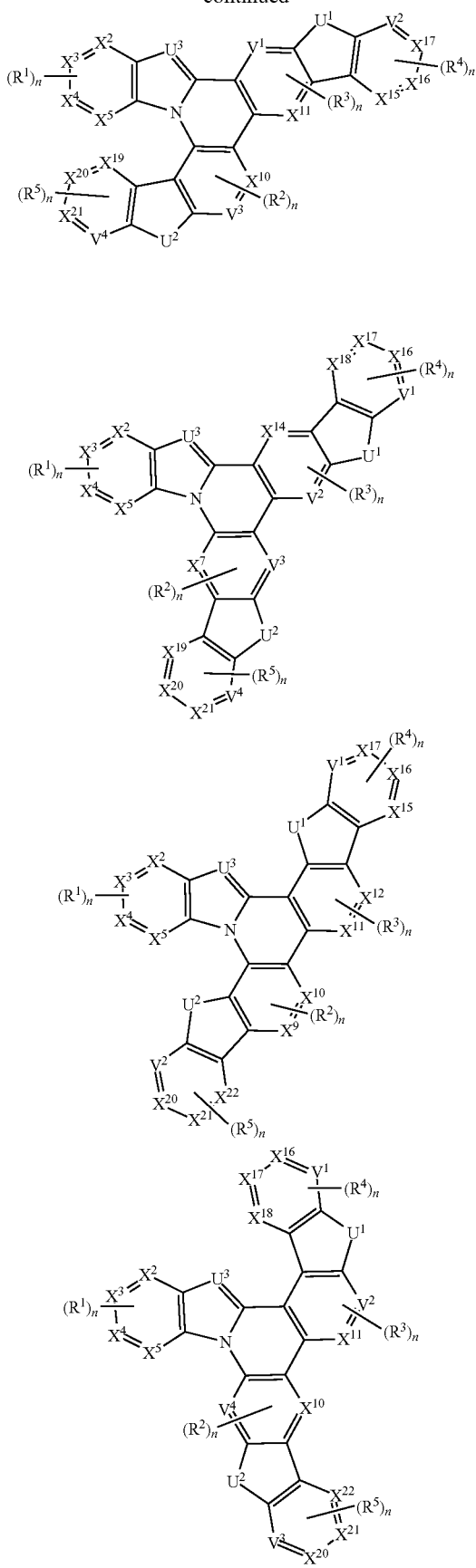

-continued
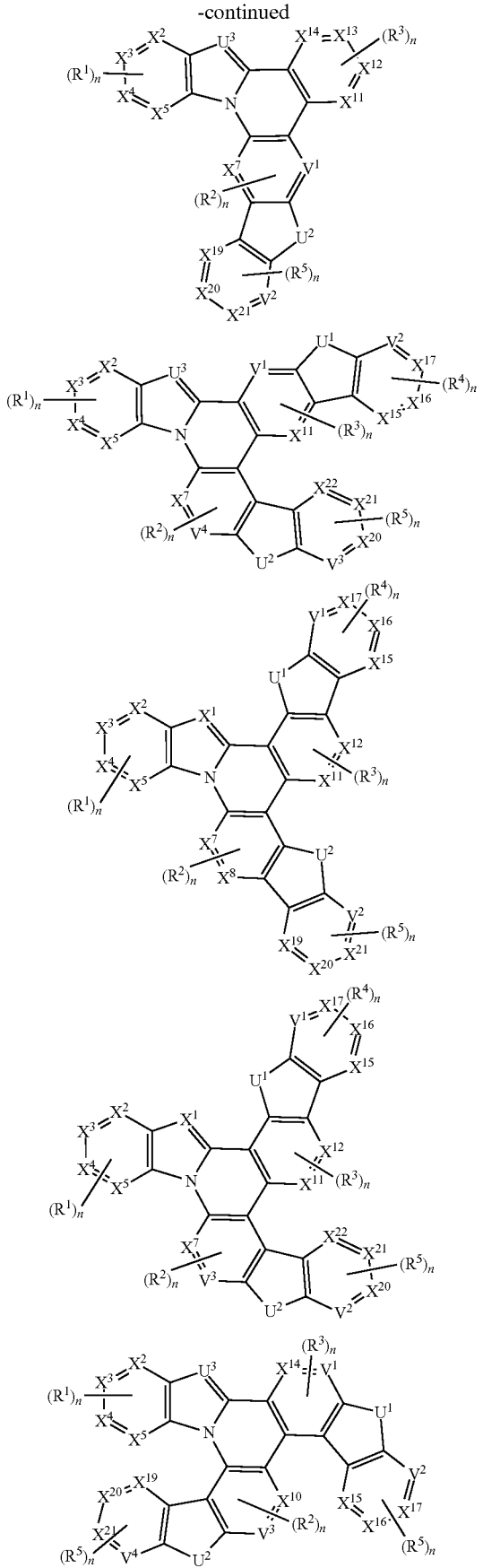
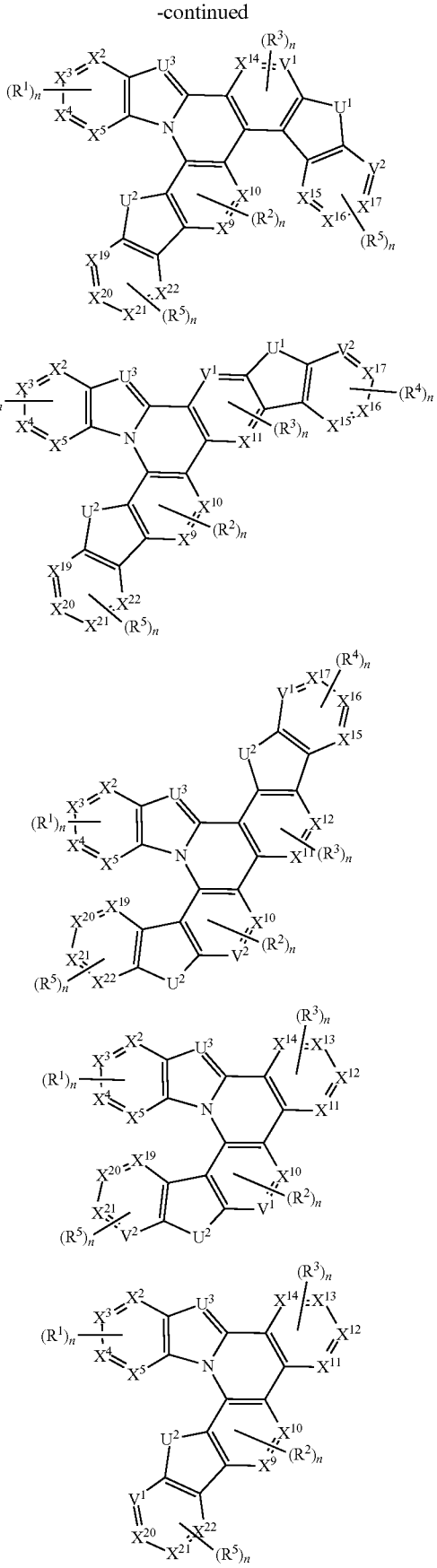

51
-continued
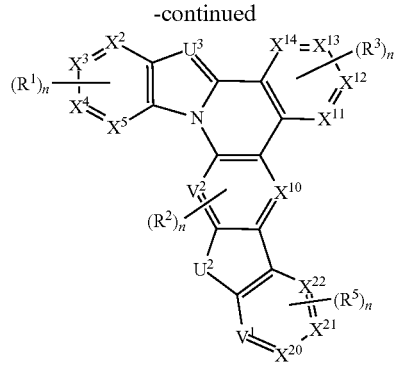
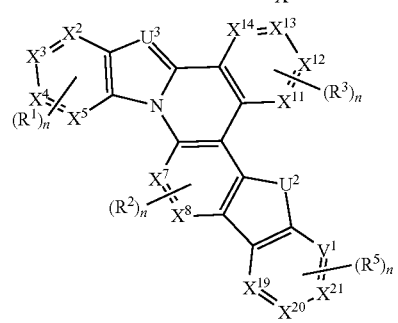
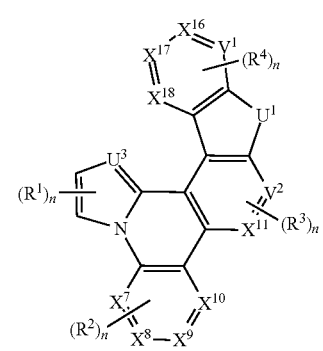
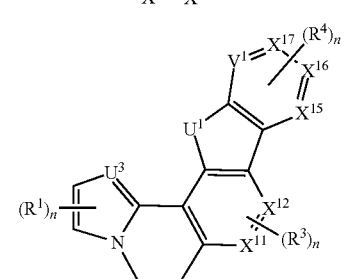
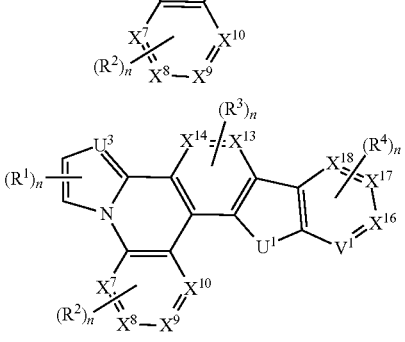
52
-continued
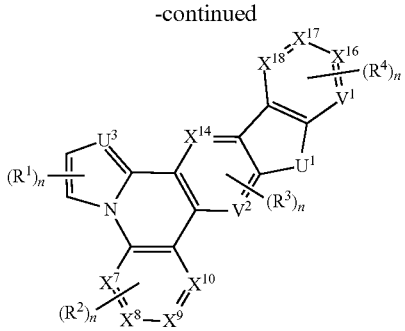
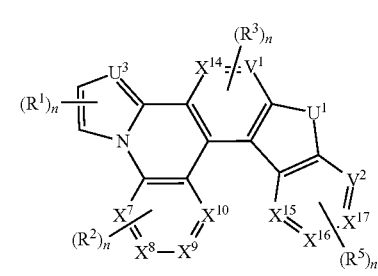
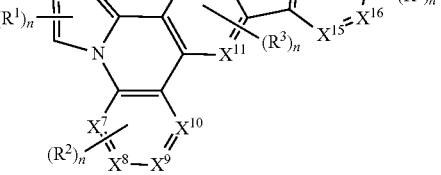
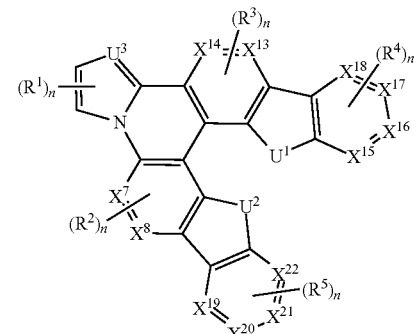
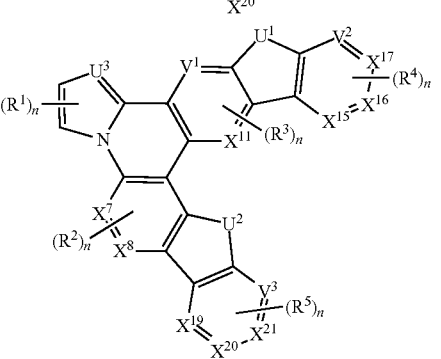

-continued
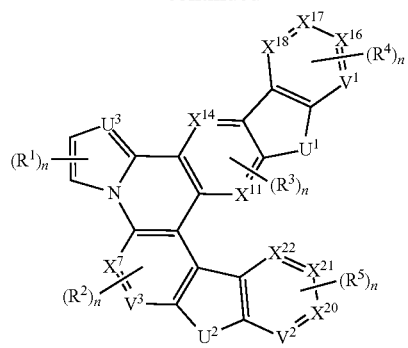
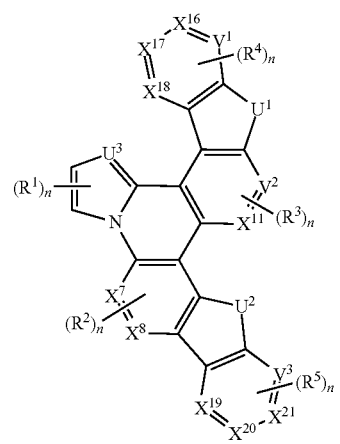
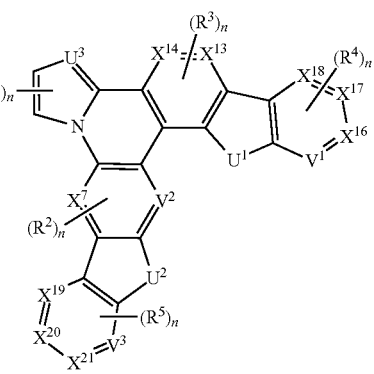
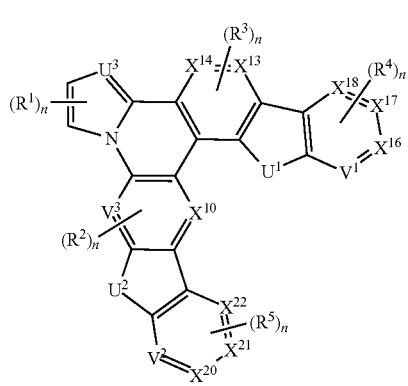
-continued
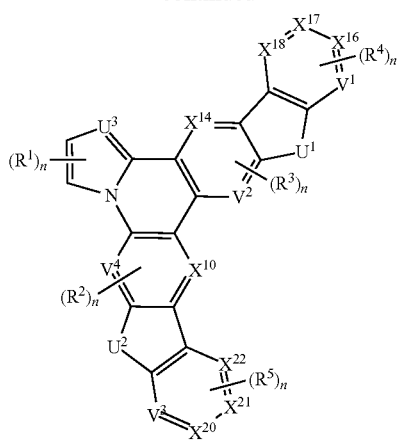
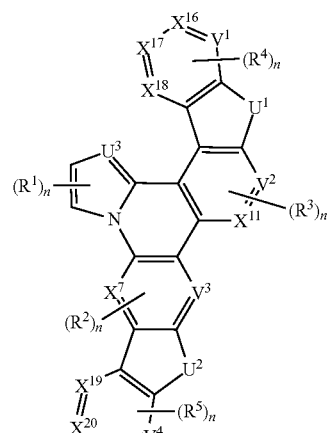
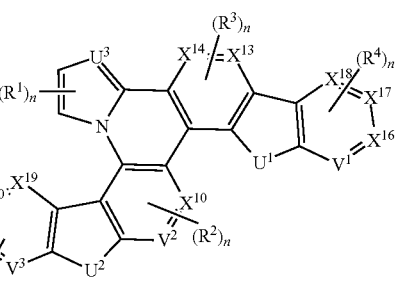
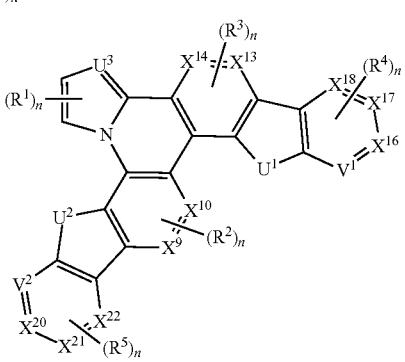

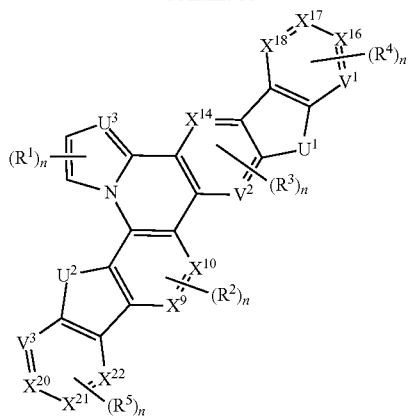
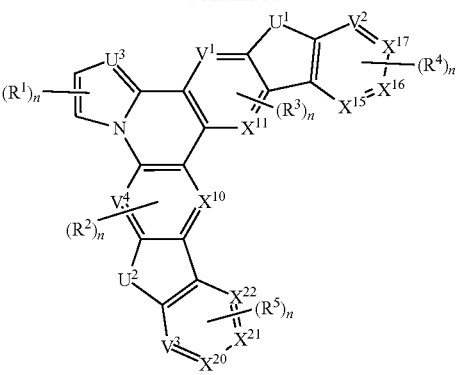
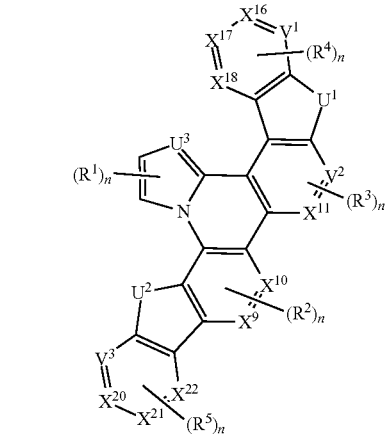
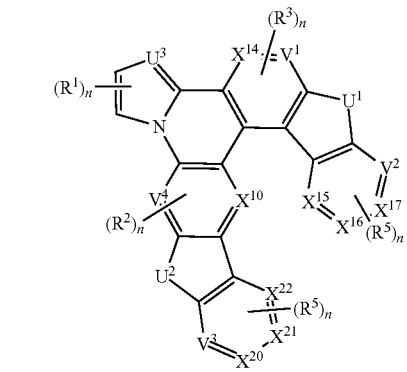
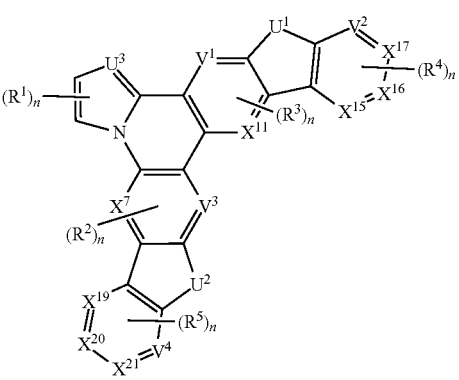

-continued
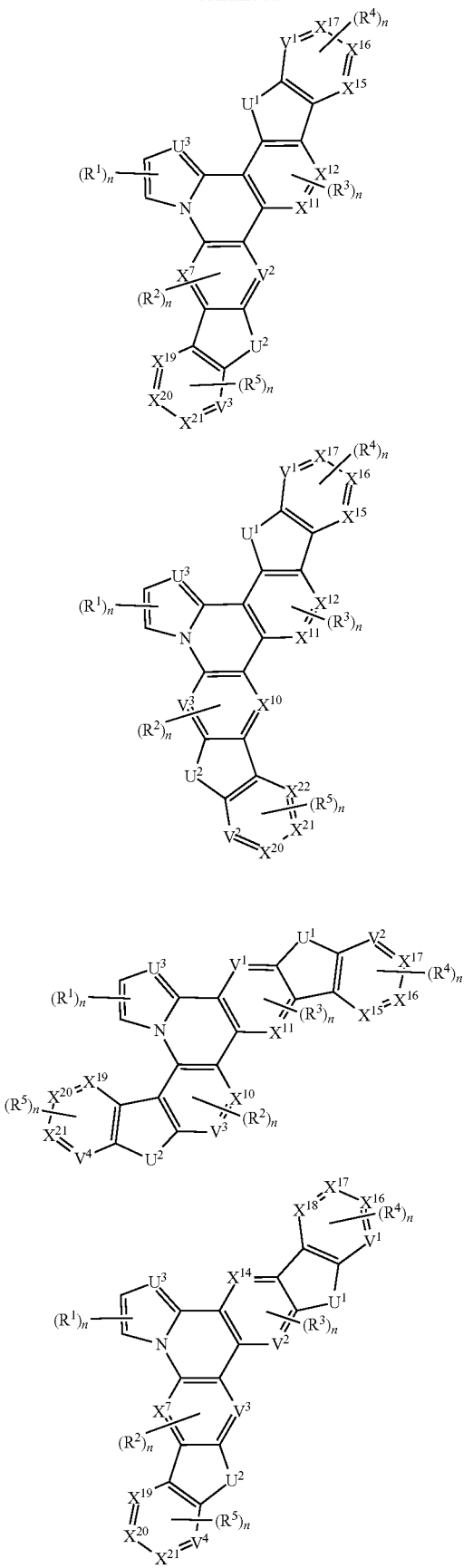
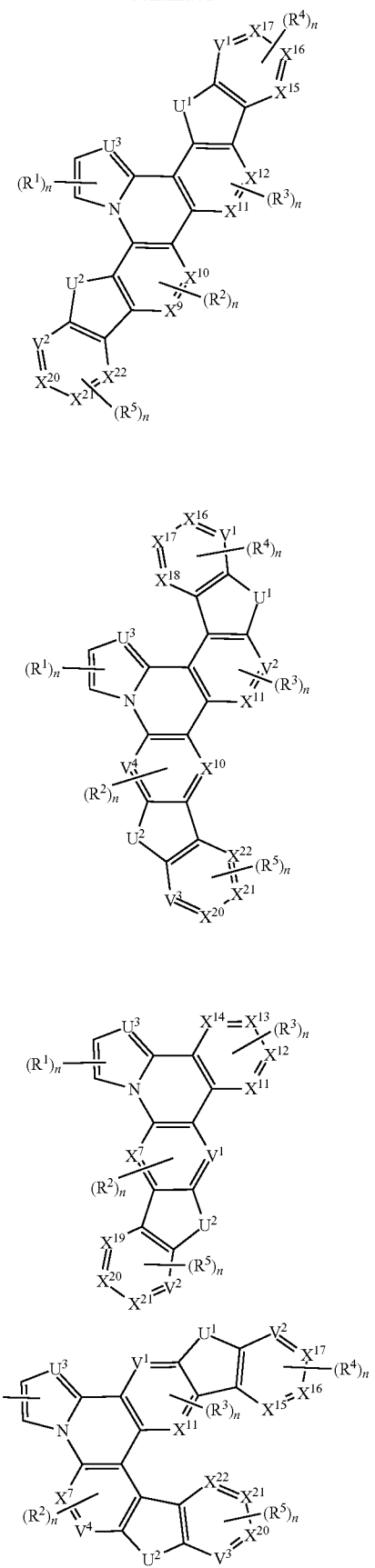

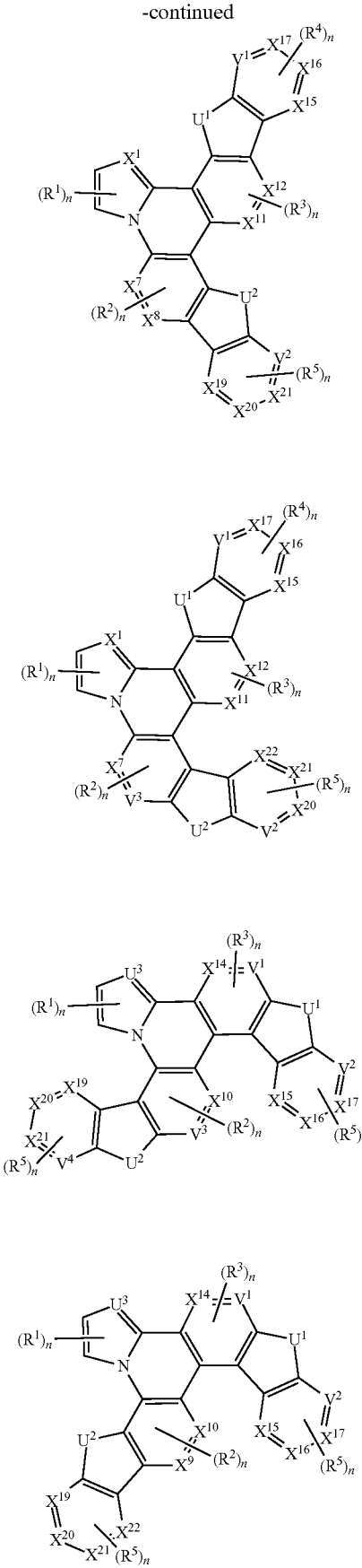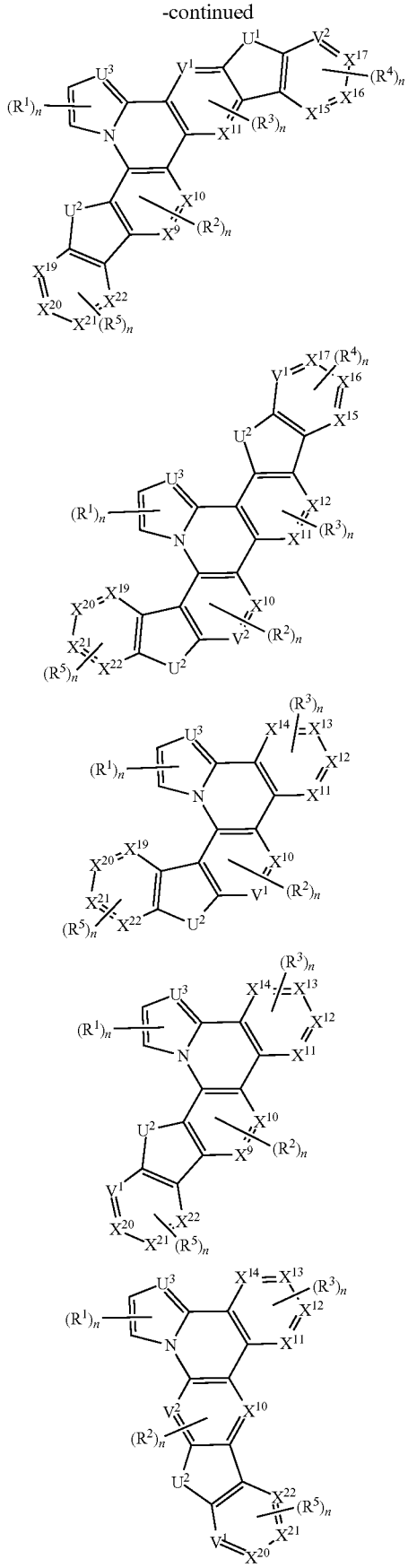

-continued
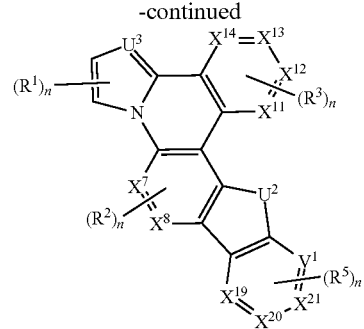
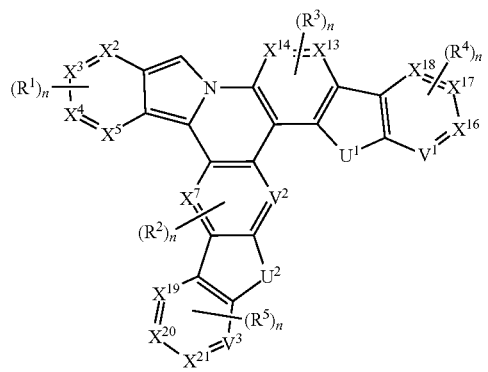
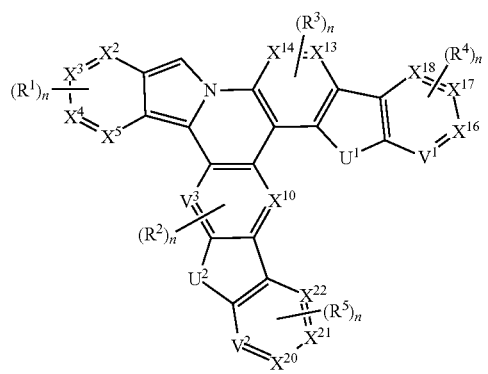
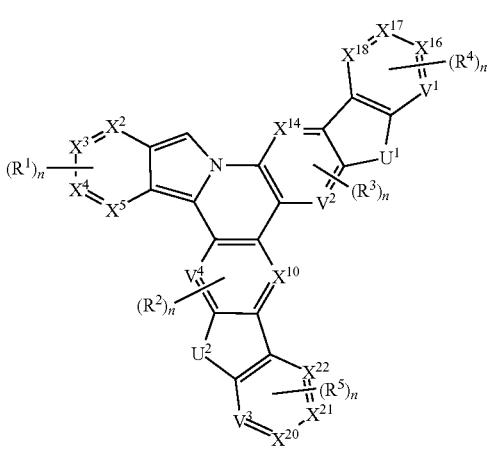
-continued
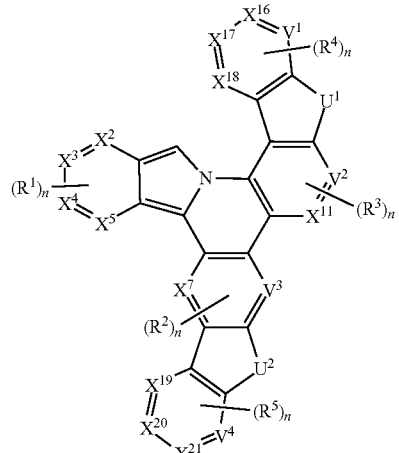
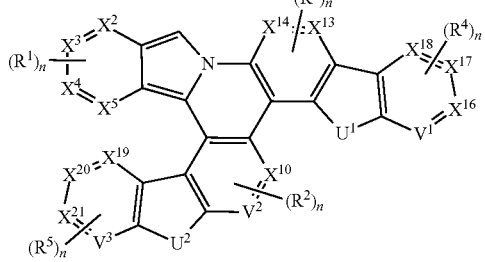
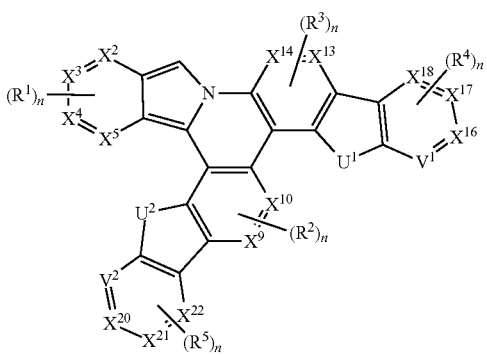
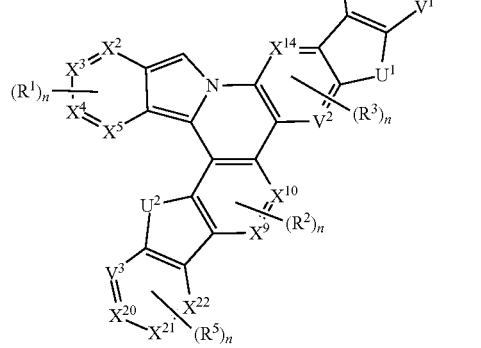

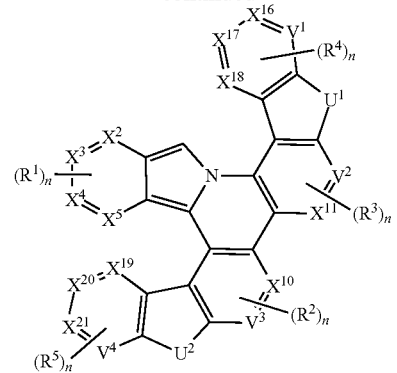
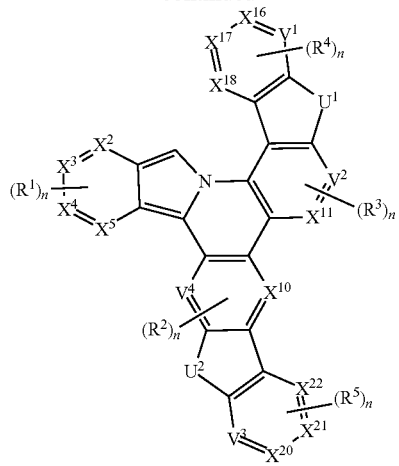
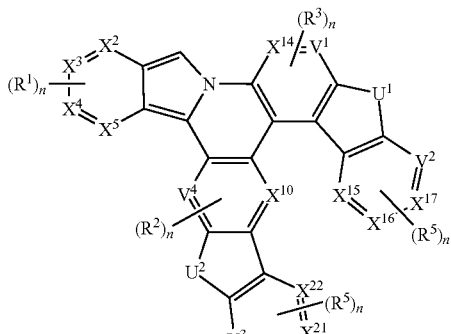
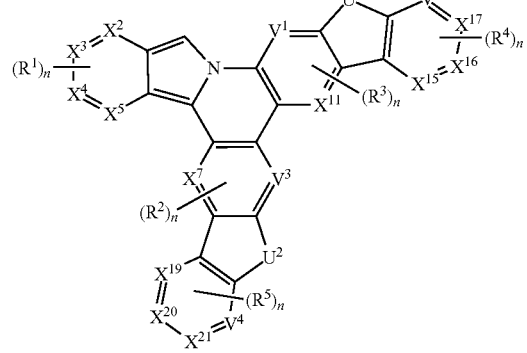
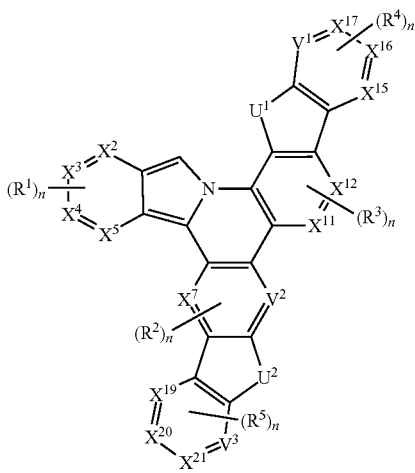

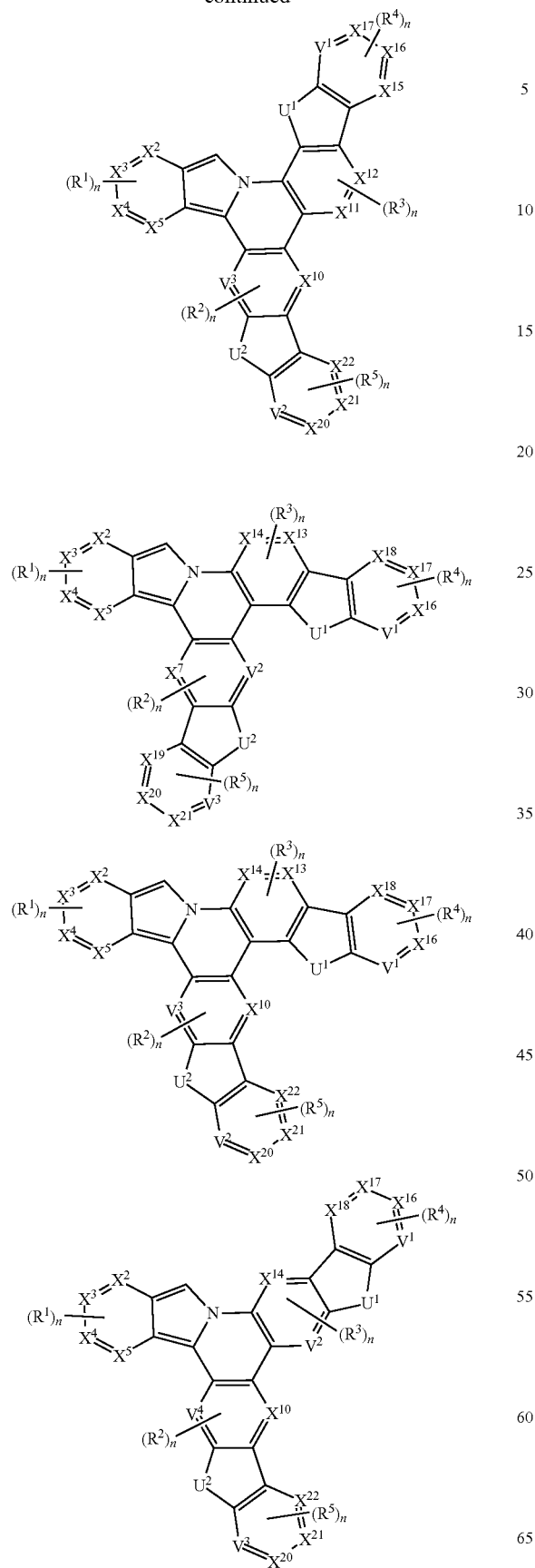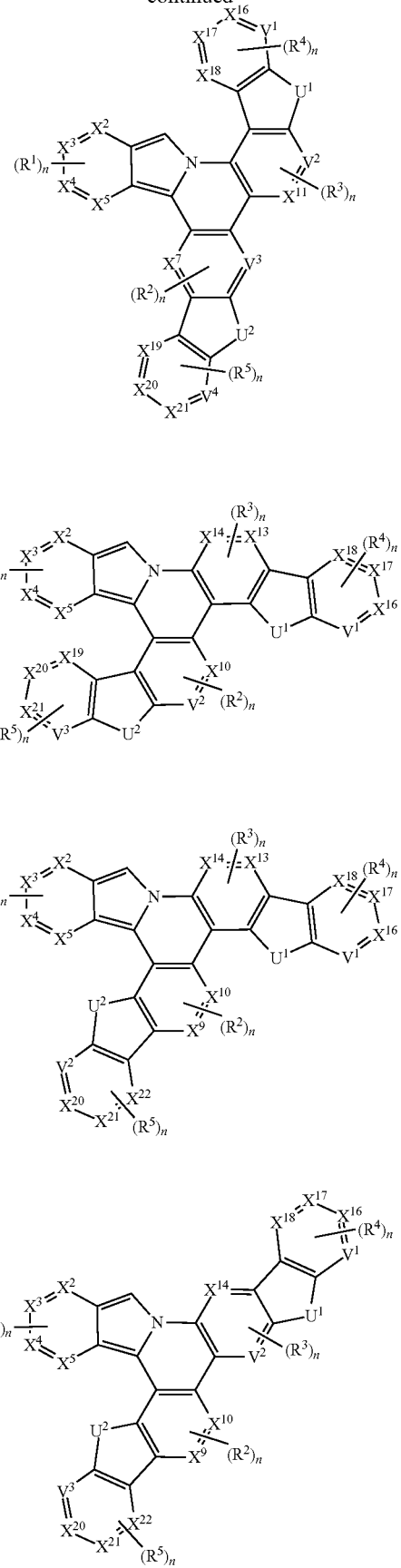

-continued
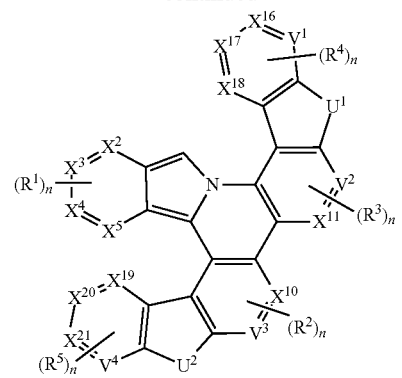
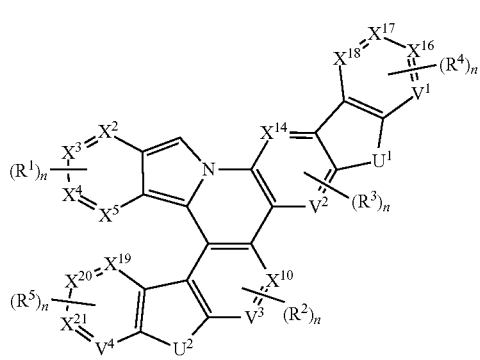
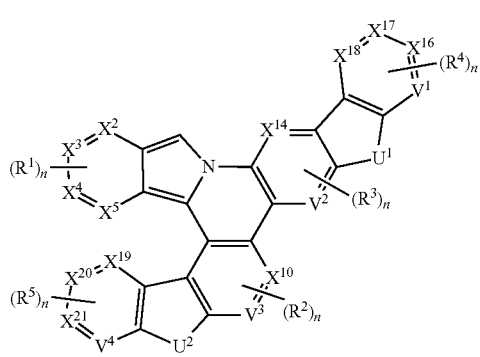
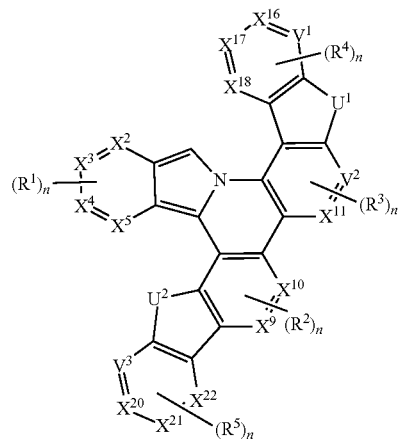
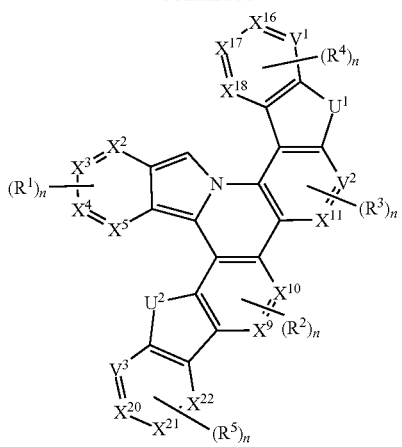
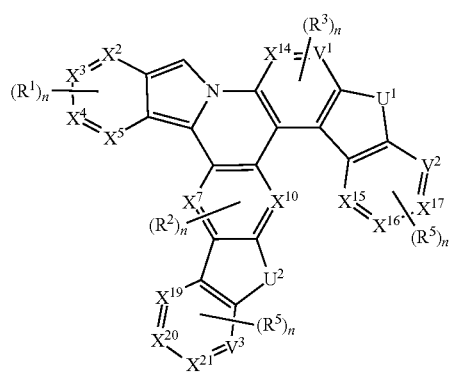
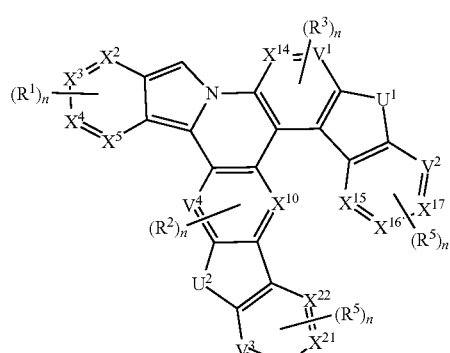
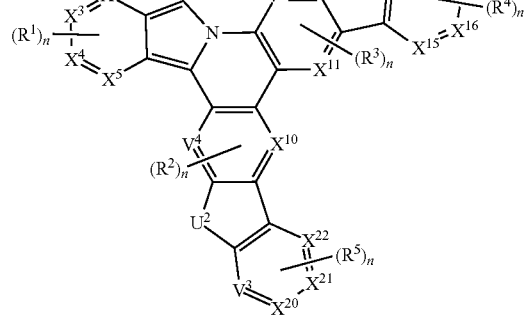

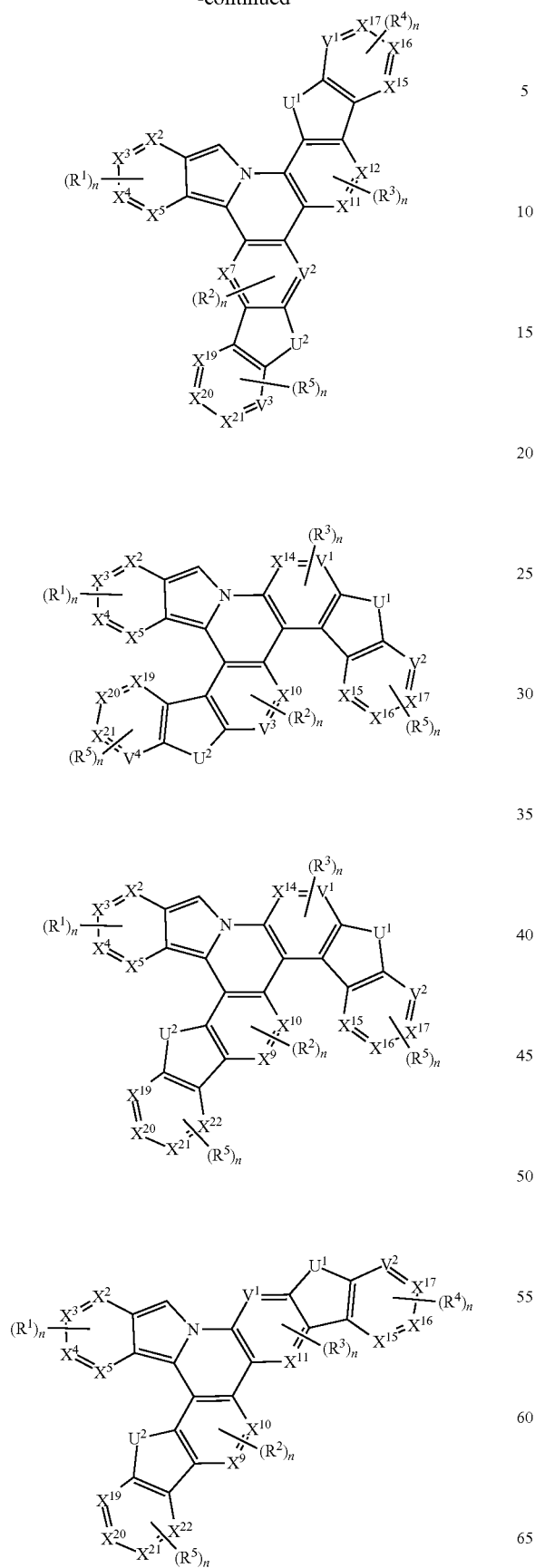
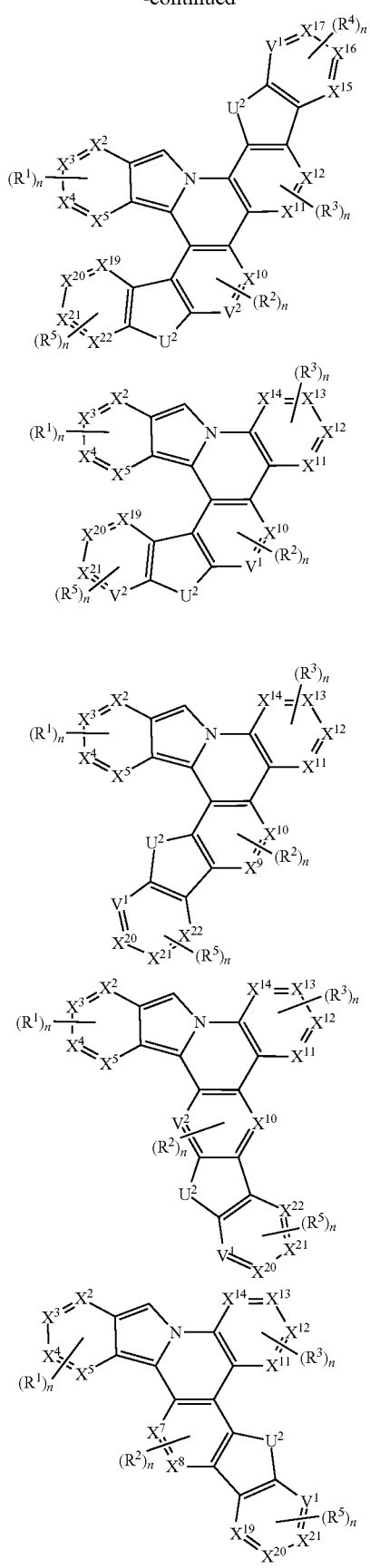

-continued
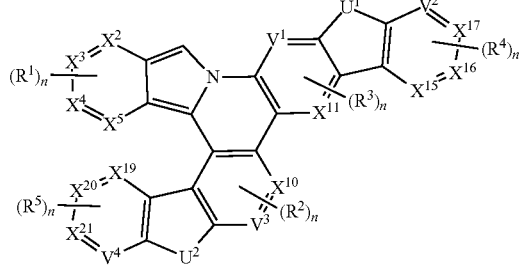
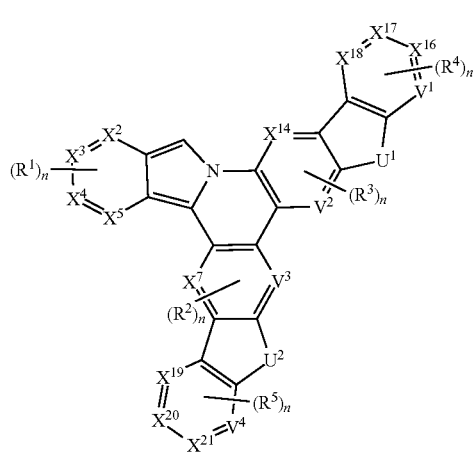
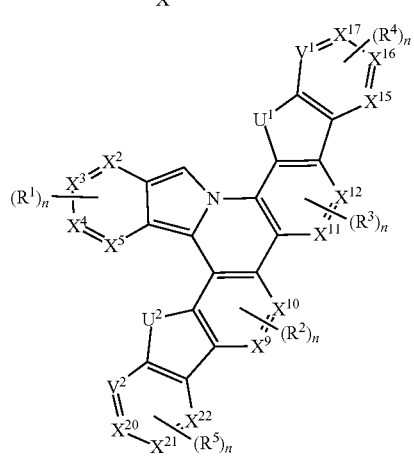
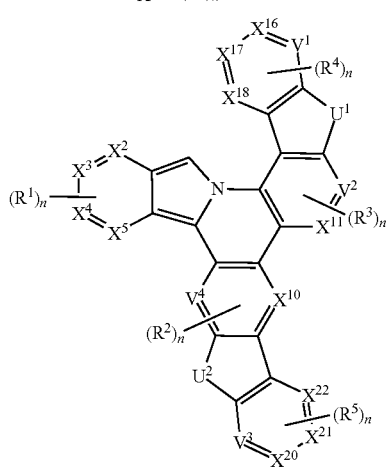
-continued
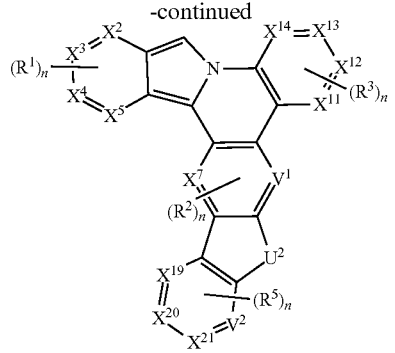
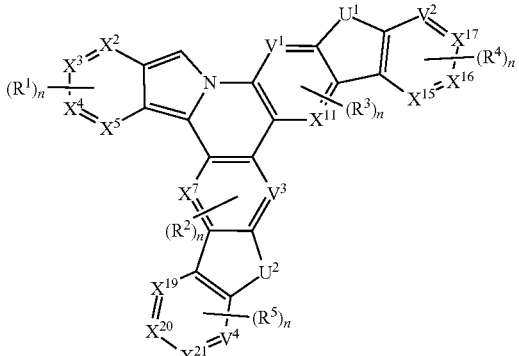
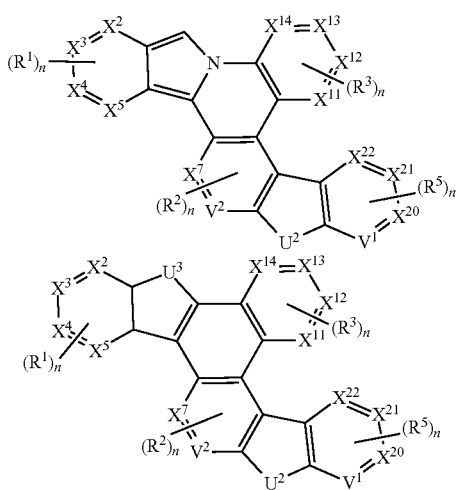
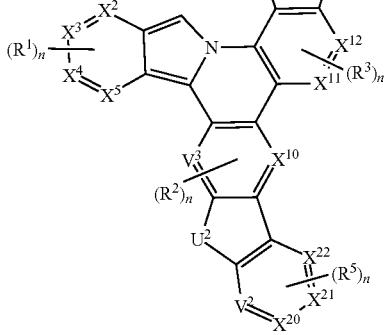

In these implementations of General Formulas I-IV, $R^1$, $R^2$, $R^3$, $R^4$, and $R^5$ each independently represents hydrogen, cyanide, halogen, hydroxy, amino, nitro, thiol, or substituted or unsubstituted $C_1$-$C_4$ alkyl, alkoxy, or aryl, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, and $X^{22}$ each independently represents substituted or unsubstituted C, N, Si, O, or S, valency permitting.

$V^1$, $V^2$, $V^3$, and $V^4$ each independently represents substituted or unsubstituted C or N, valency permitting.

$U^1$ and $U^2$ each independently represents O, S, CRR', SIRR', or NAr*, where R and R' each independently represents hydrogen, cyanide, halogen, hydroxy, amino, nitro, thiol, or optionally substituted $C_1$-$C_4$ alkyl, alkoxy, or aryl, and Ar* represents a substituted phenyl, pyridyl, naphthyl, pyrimidyl, pyridazinyl, pyrazinyl, pyrazolyl, imidazolyl, oxazolyl, or thiazolyl ring, and Ar* is optionally covalently bonded to $V^1$, $V^2$, $V^3$, or $V^4$ to form one or more 5-membered or 6-membered rings, $U^3$ and $U^4$ each independently represents CR, SiR, or N, where R represents optionally substituted $C_1$-$C_4$ alkyl, alkoxy, aryl or heteroaryl, and each n is independently an integer as permitted by valence.

Compounds of General Formulas I-IV are shown below.

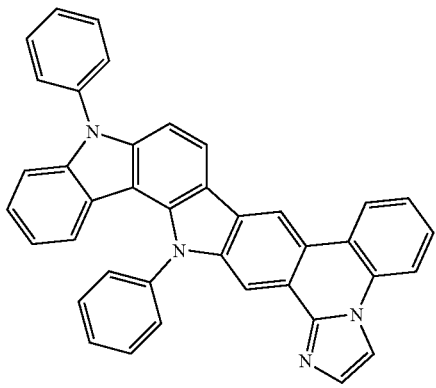

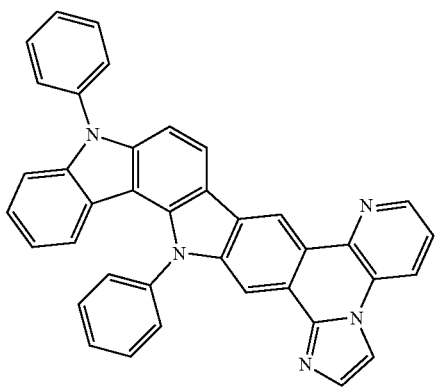

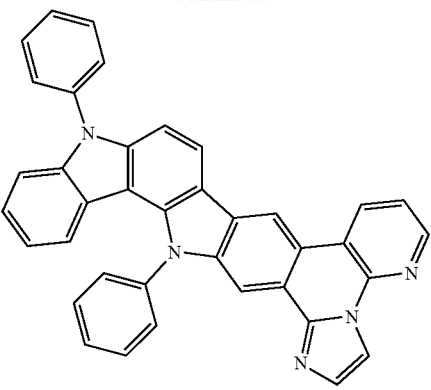

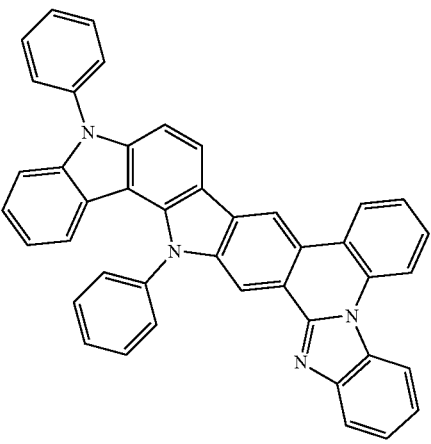

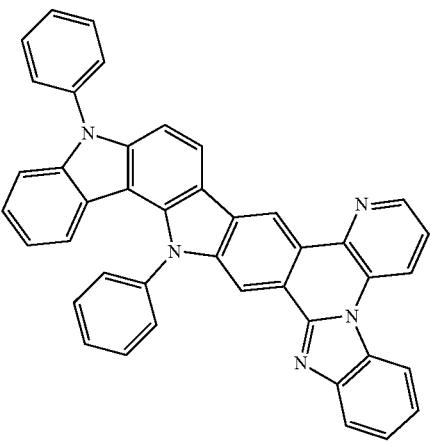

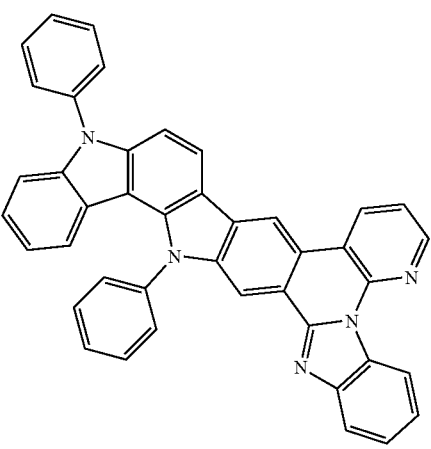

-continued

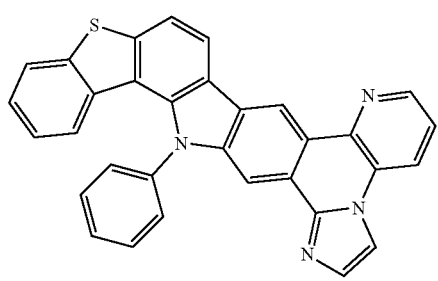
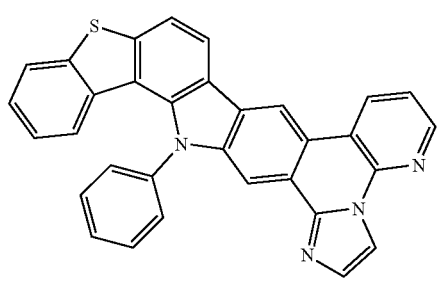
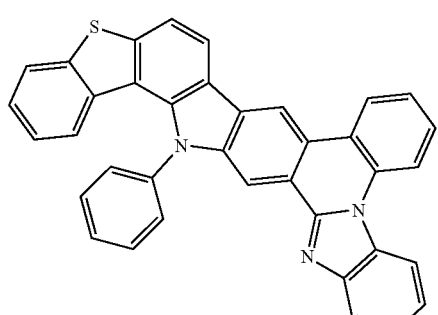
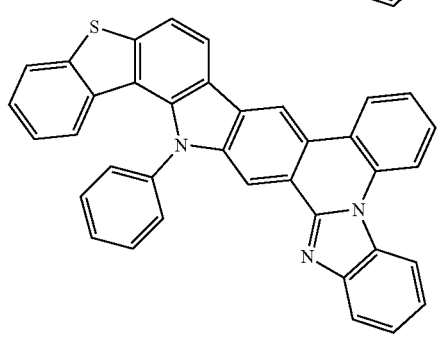
-continued
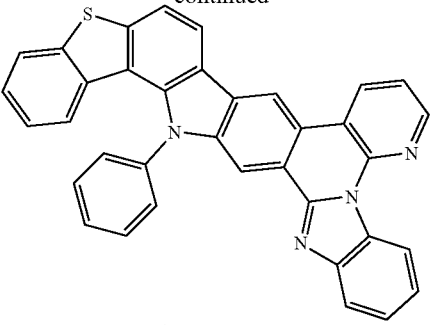
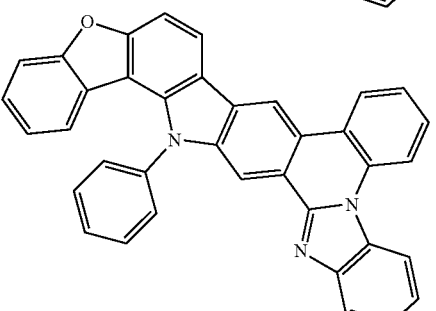
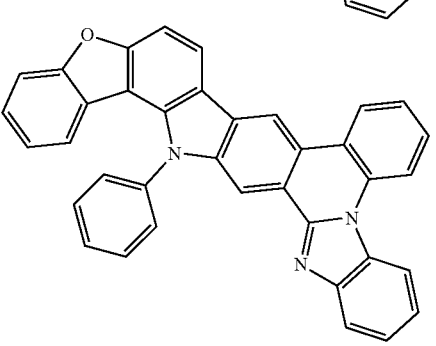
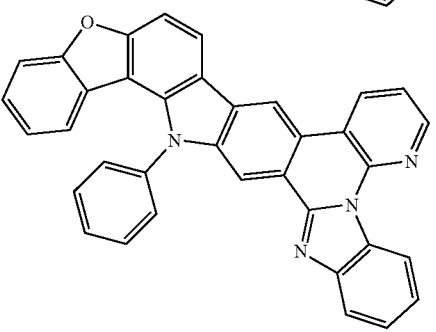
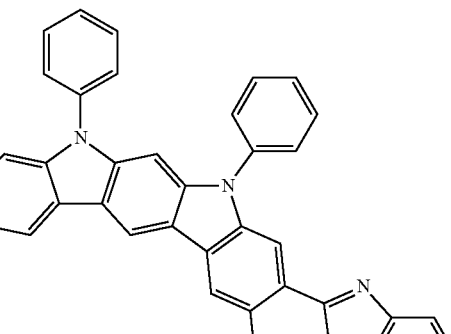

77
-continued
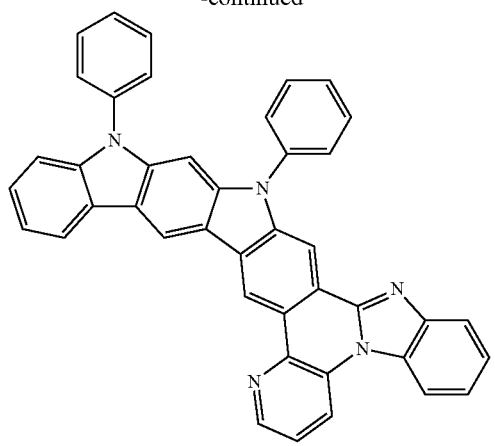
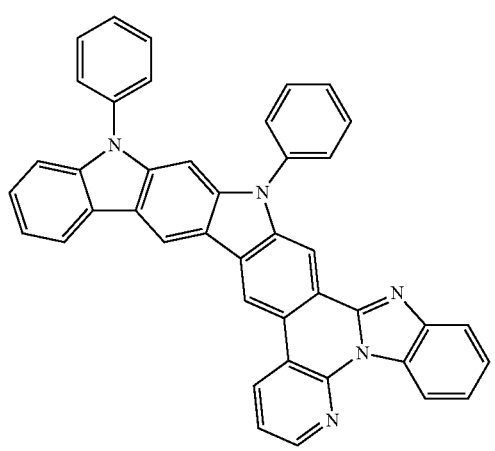
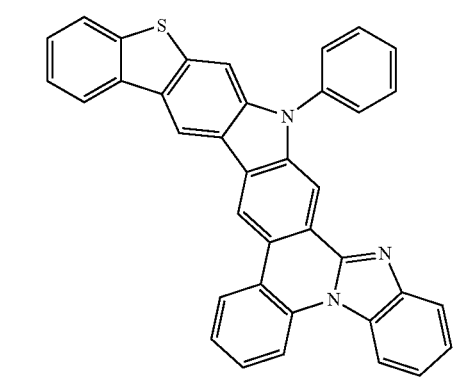
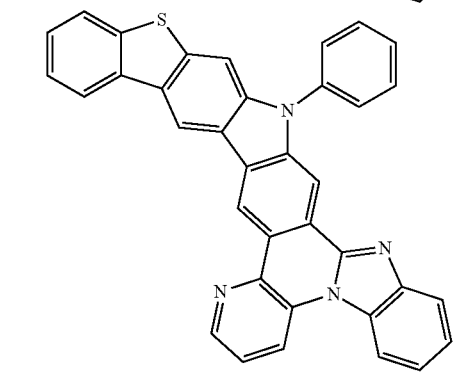
78
-continued
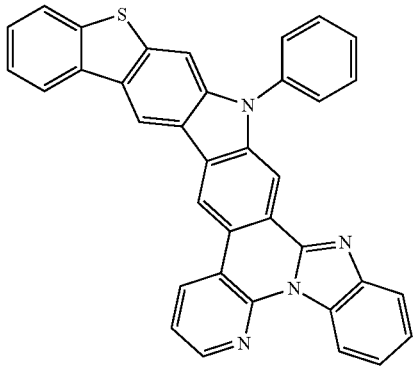
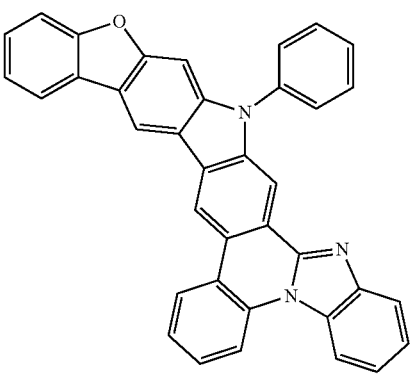
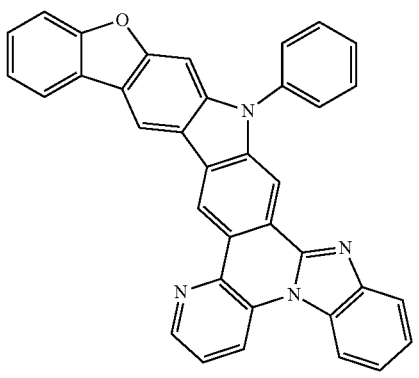
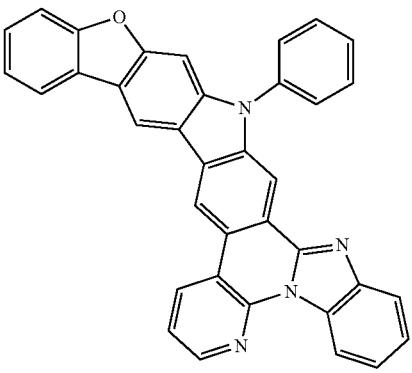

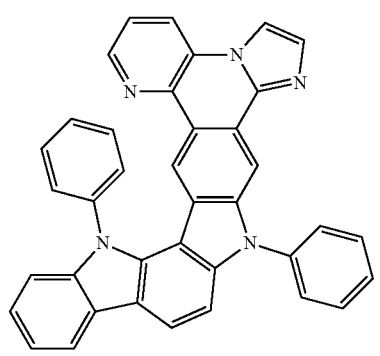
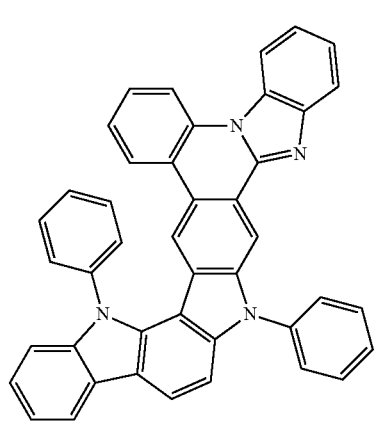
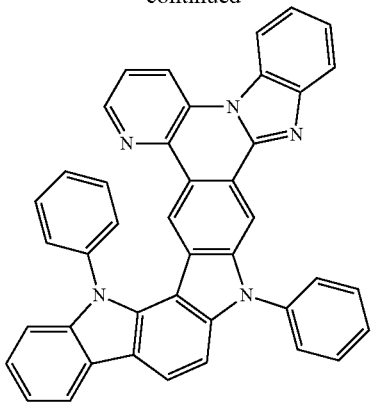
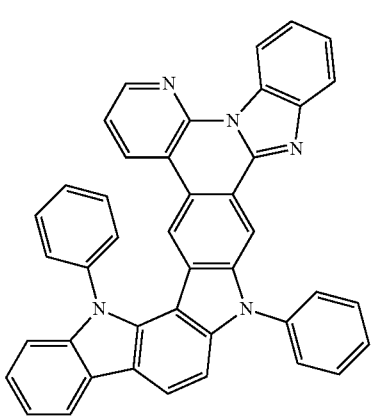
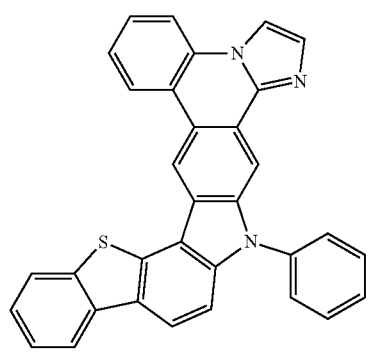
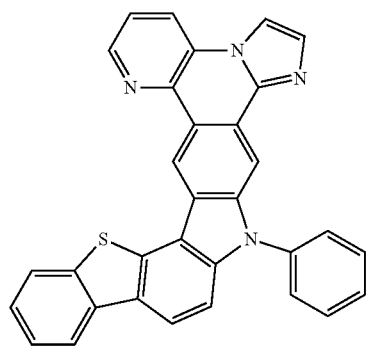

81
-continued
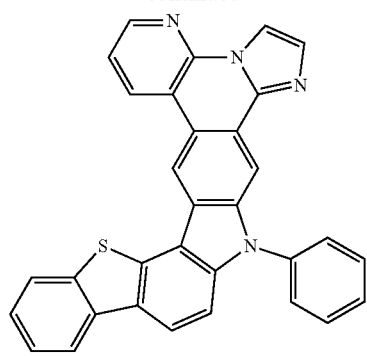
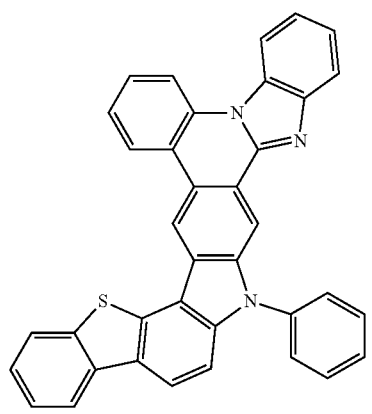
82
-continued
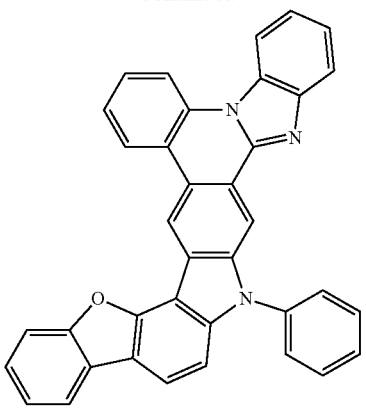
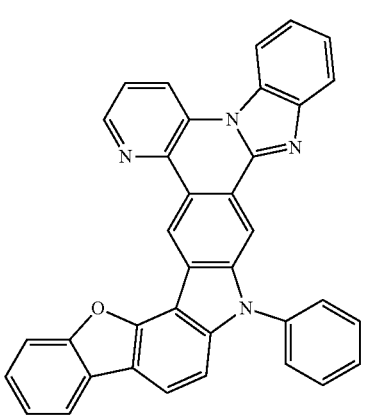
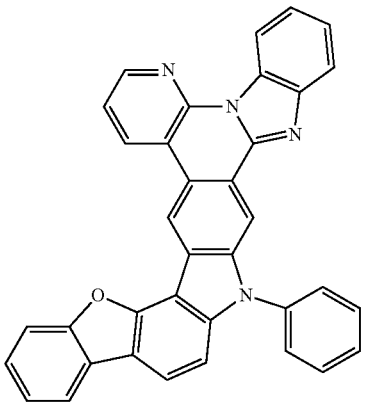
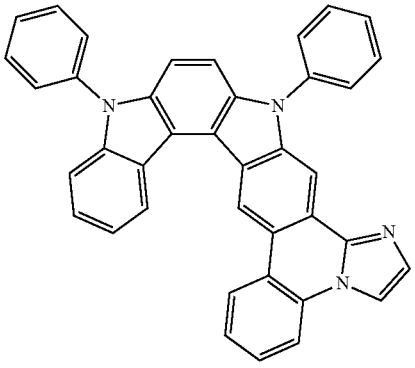

-continued
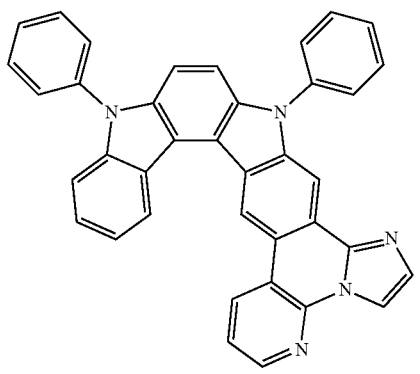
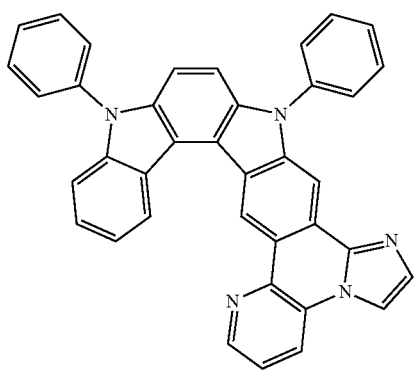
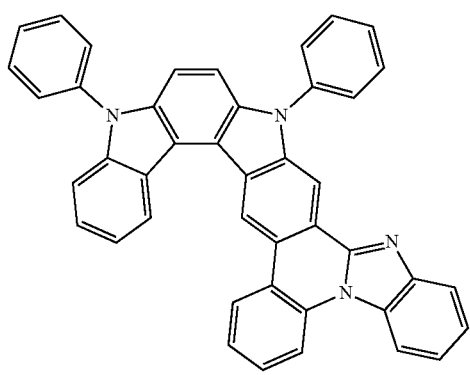
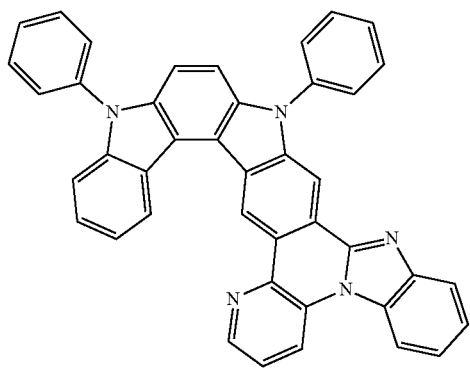
-continued
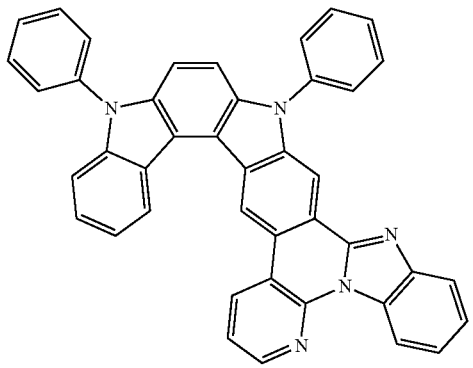
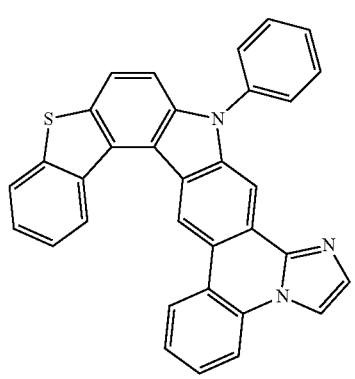
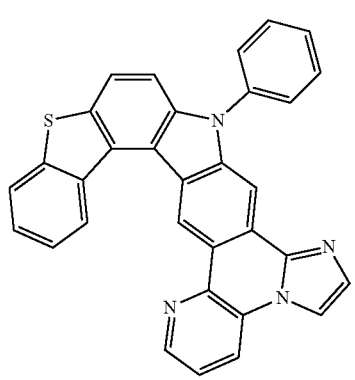
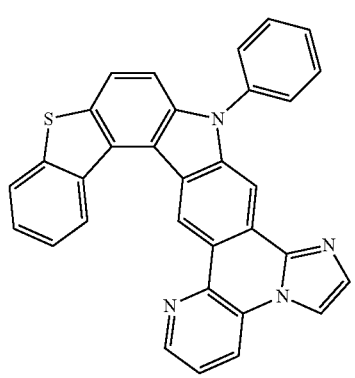

85
-continued
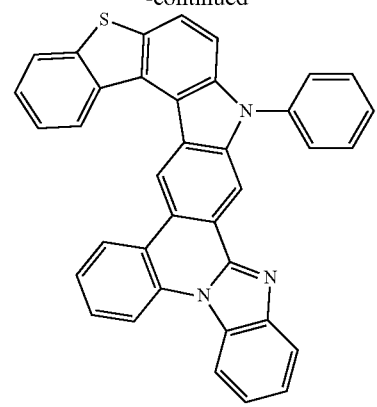
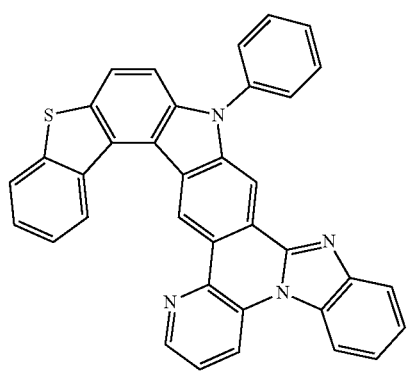
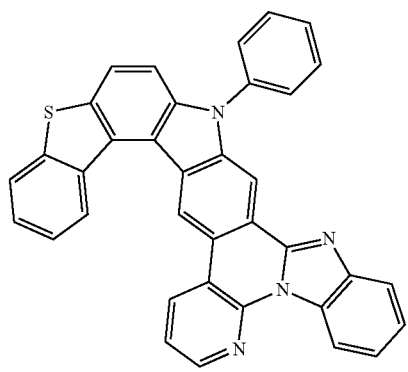
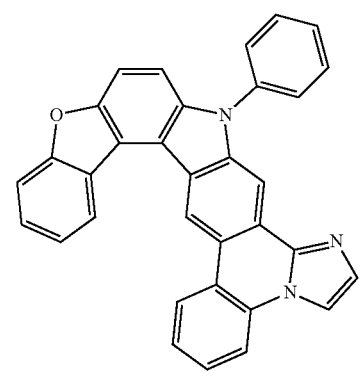
86
-continued
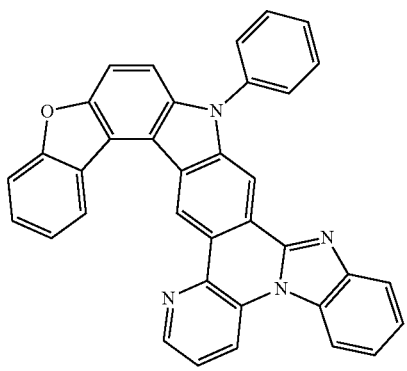
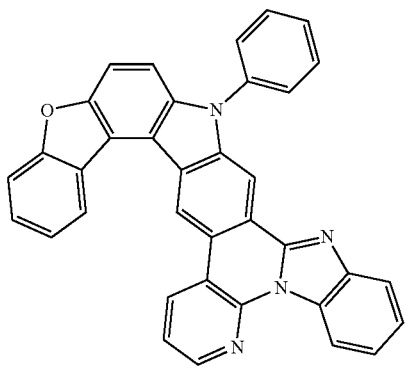
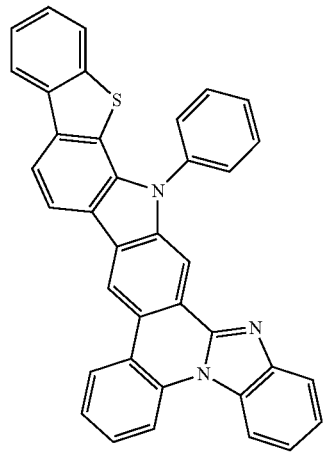
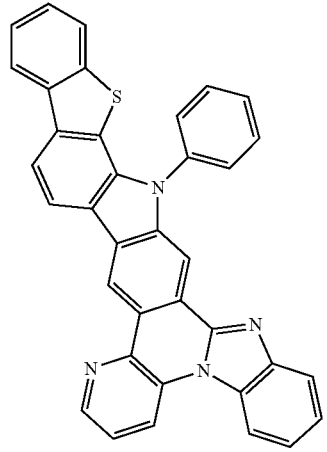

-continued
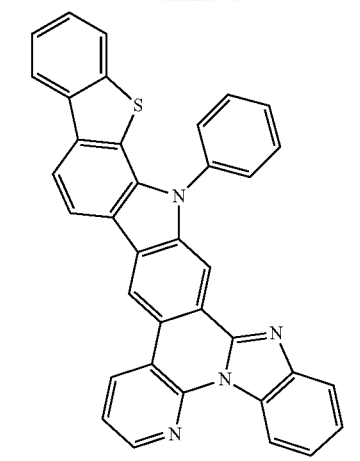
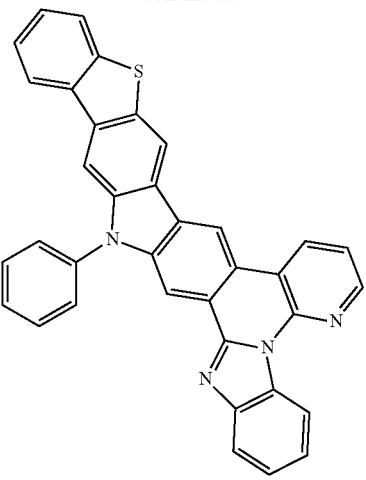
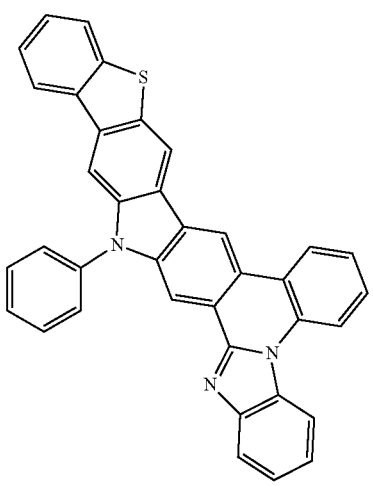
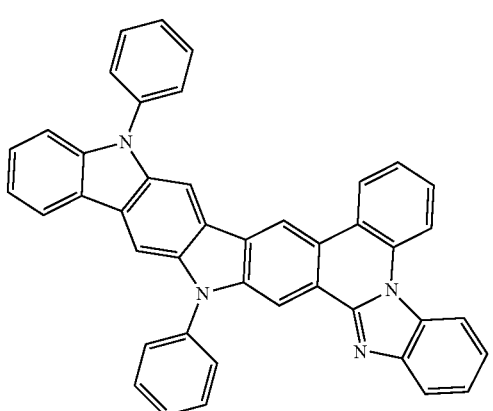
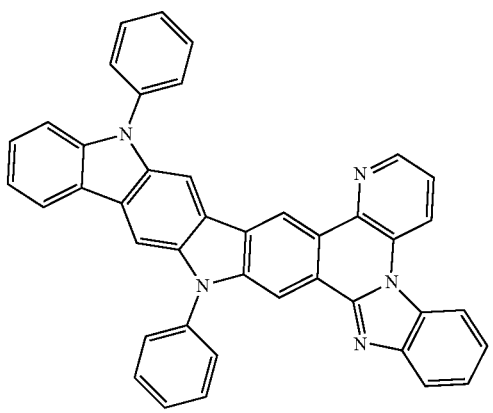
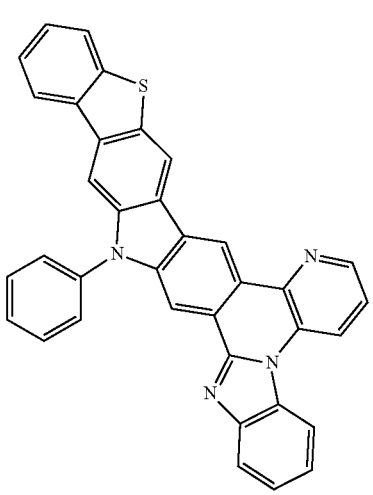
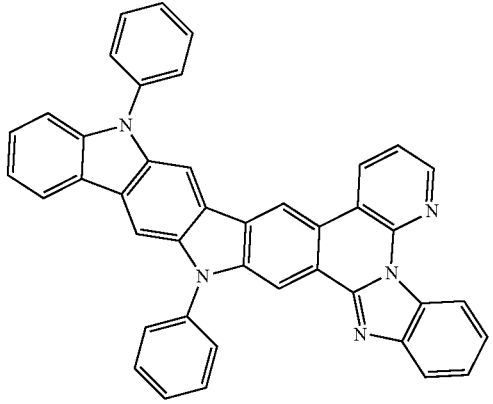

89
-continued
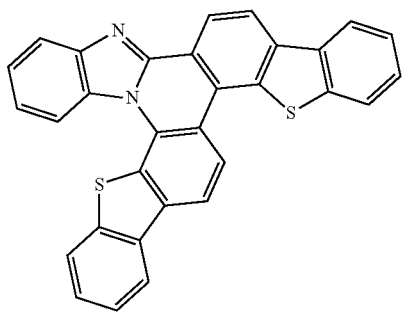
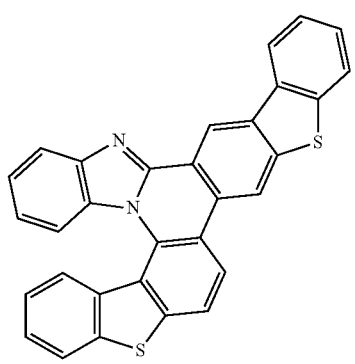
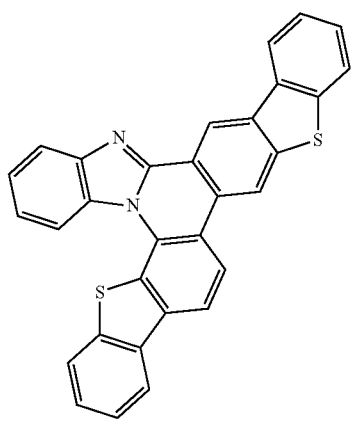
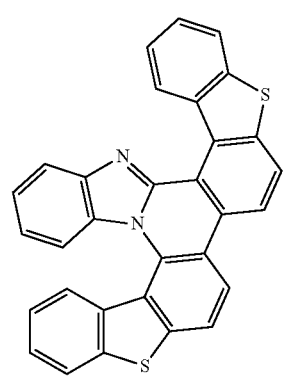
90
-continued
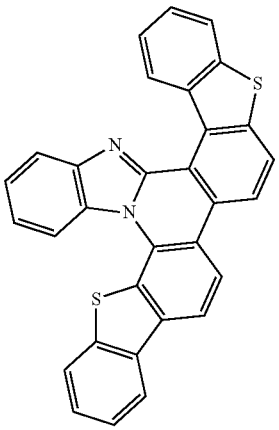
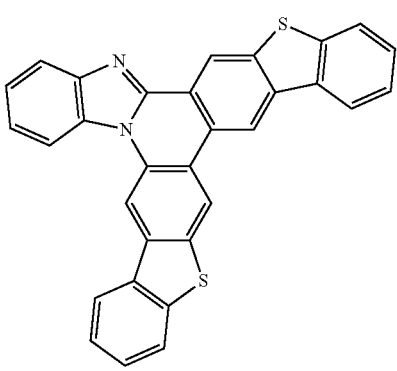
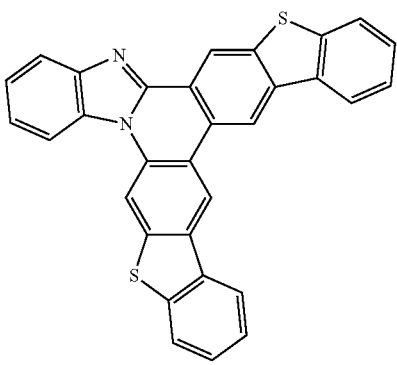
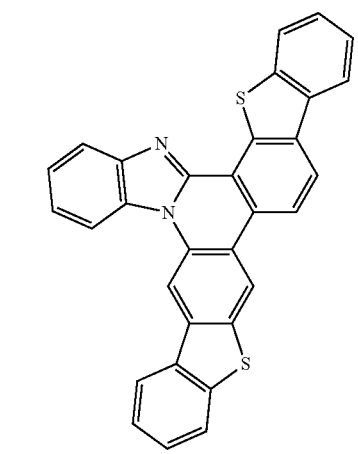

-continued
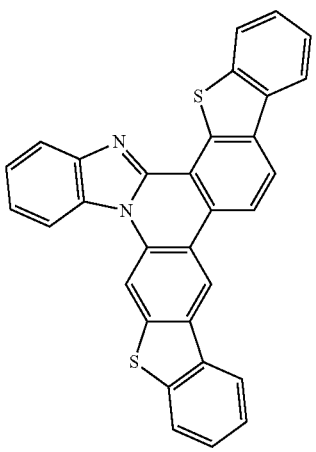
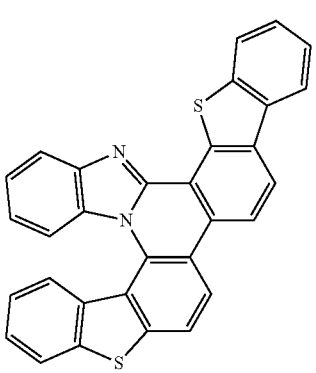
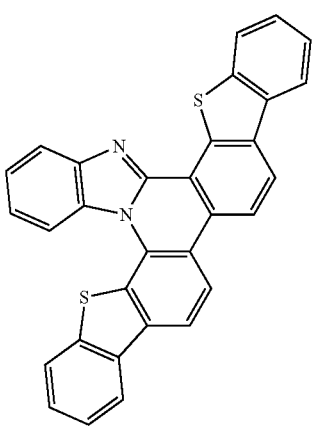
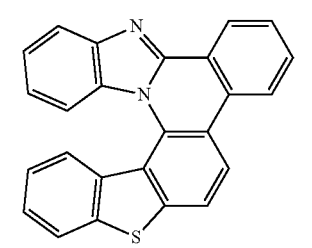
-continued
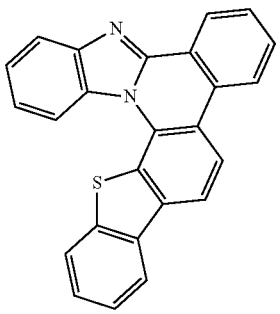
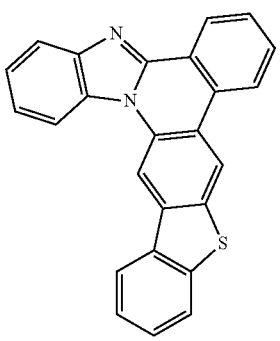
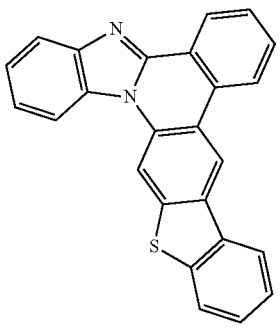
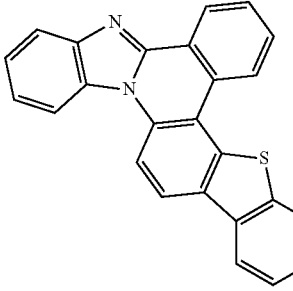
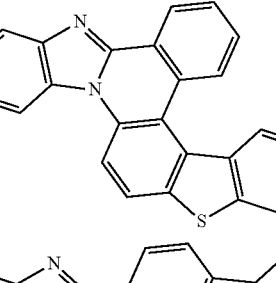
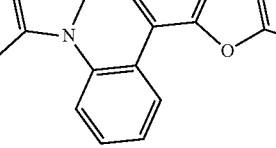

93
-continued
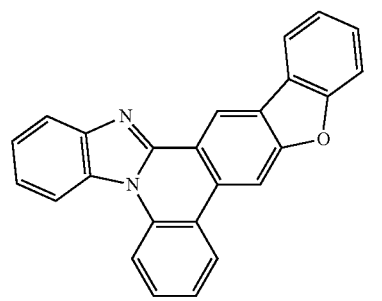
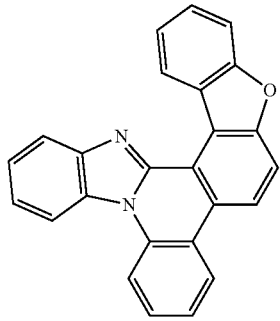
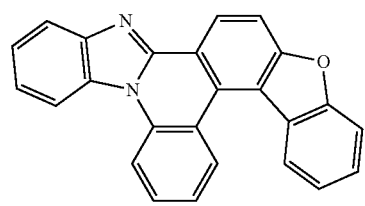
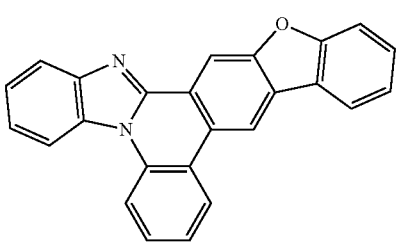
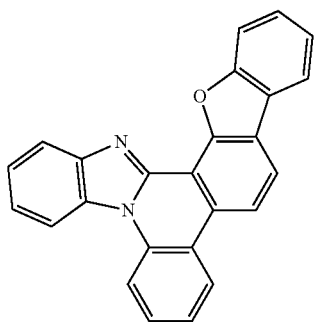
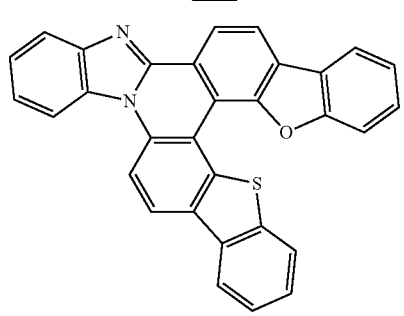
94
-continued
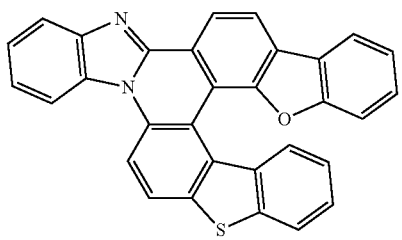
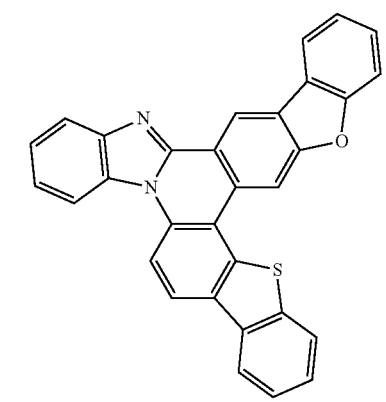
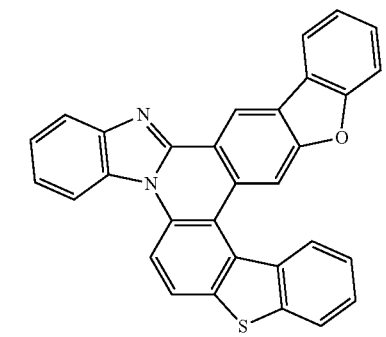
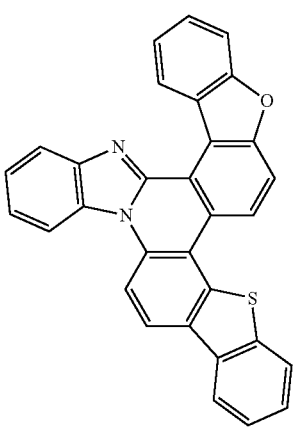

95
-continued
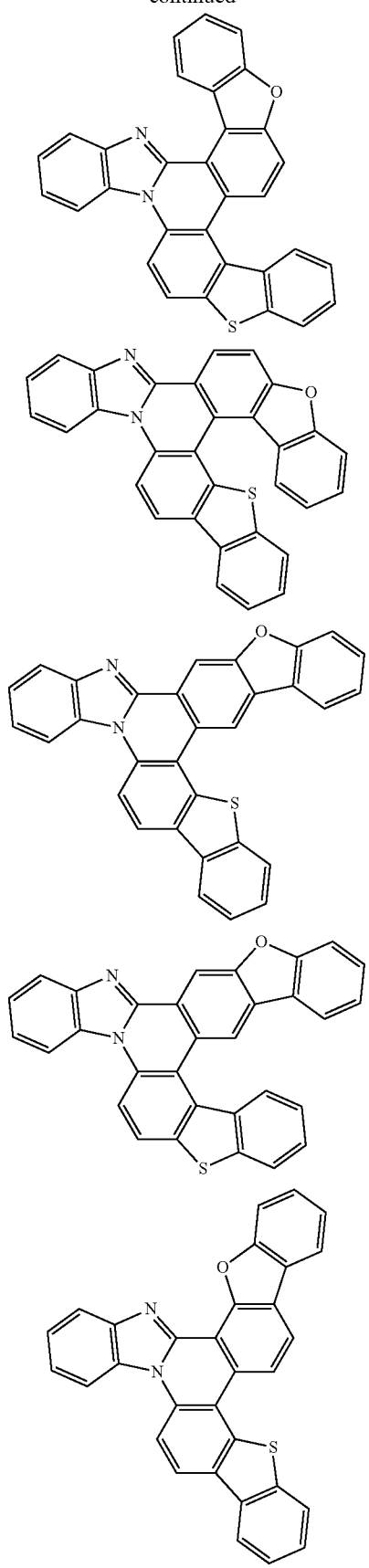
96
-continued
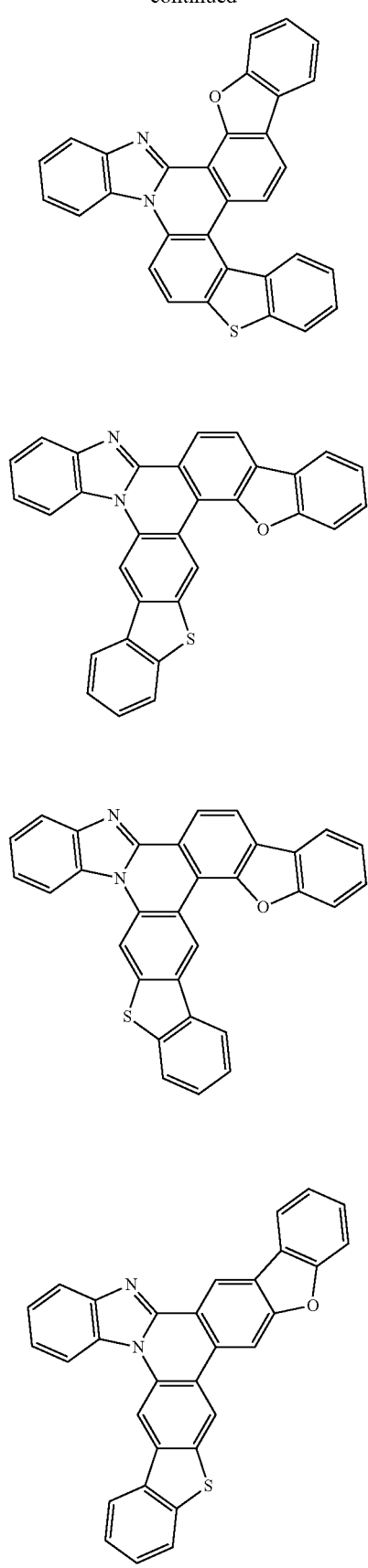

97
-continued
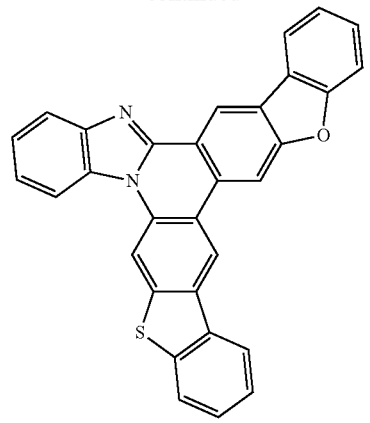
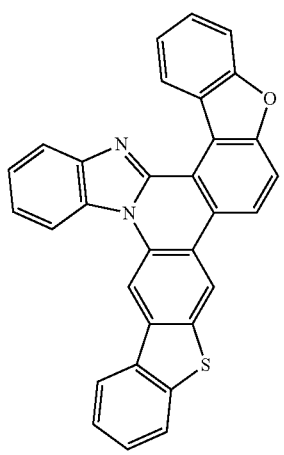
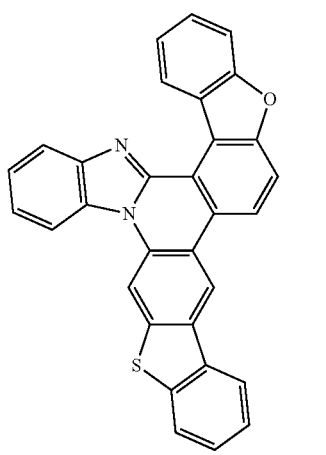
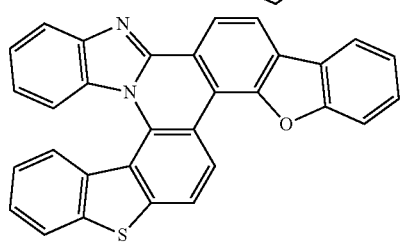
98
-continued
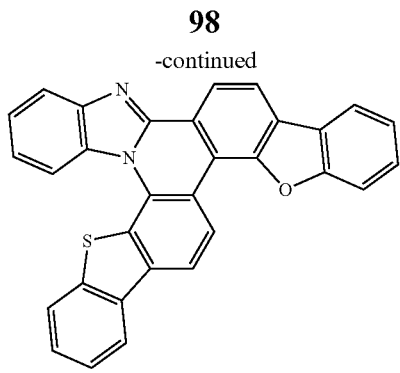
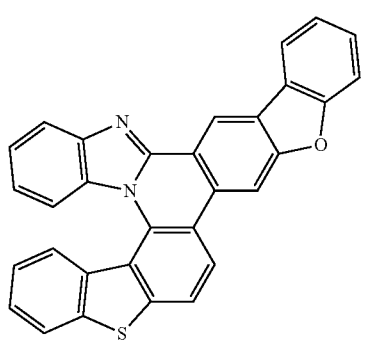
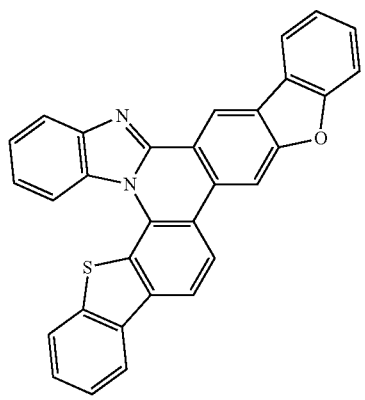
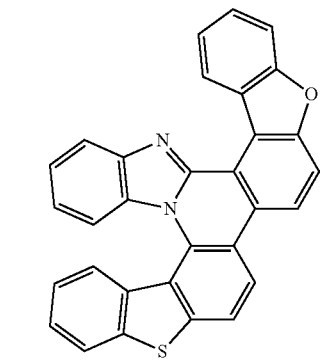

99
-continued
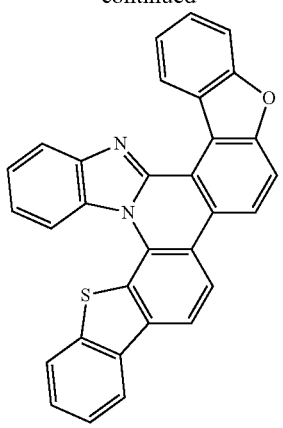
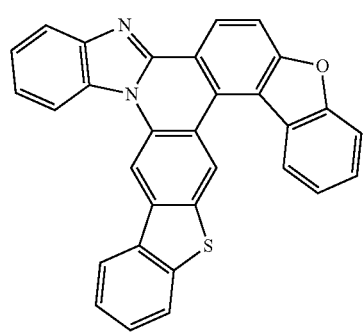
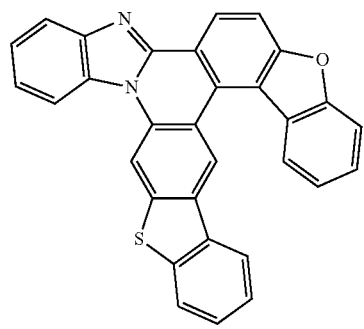
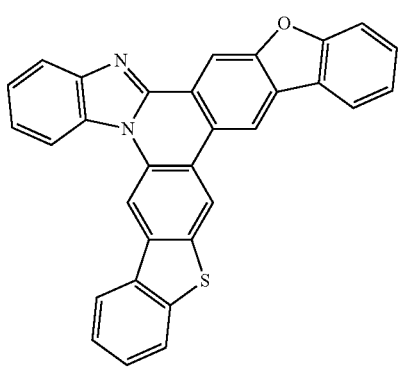
100
-continued
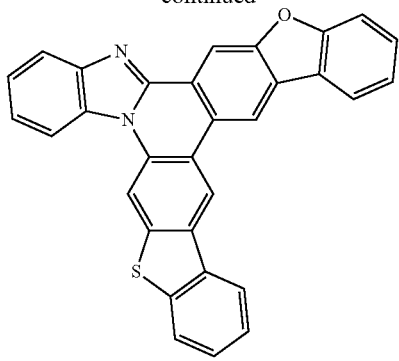
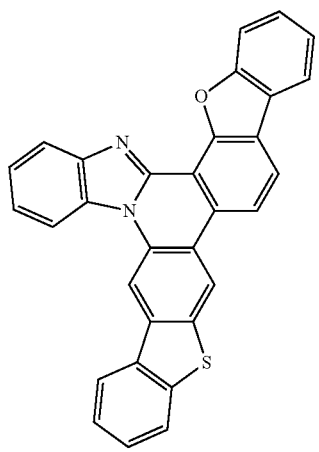
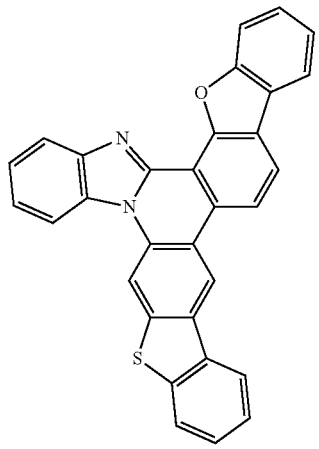
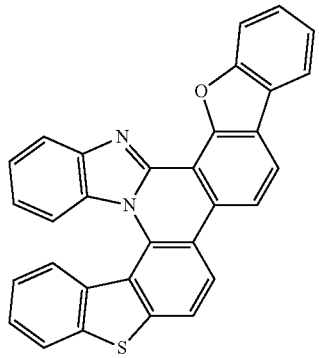

101
-continued
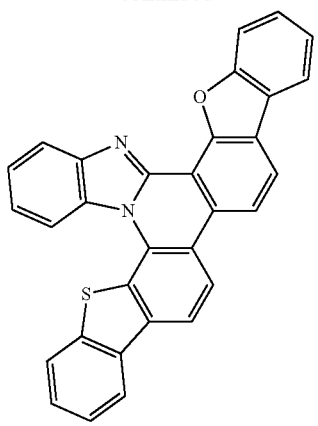
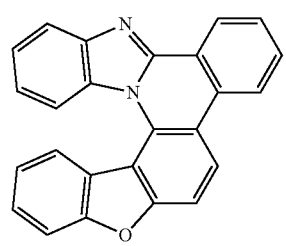
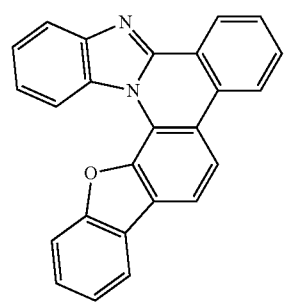
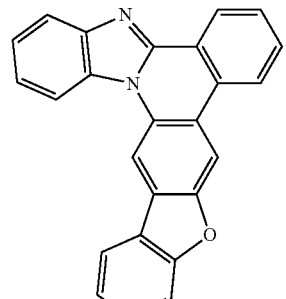
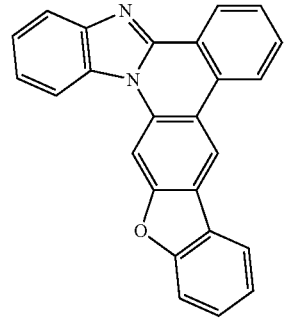
102
-continued
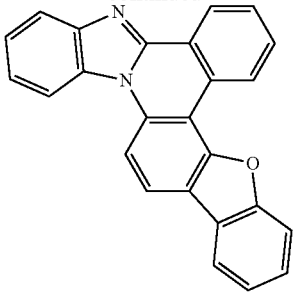
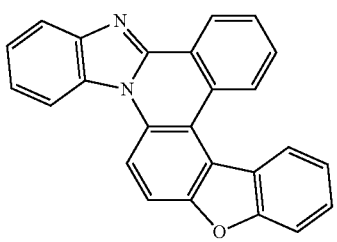
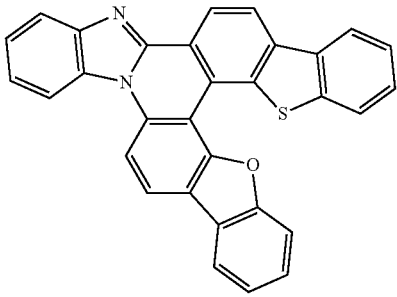
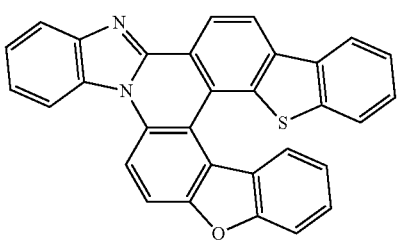
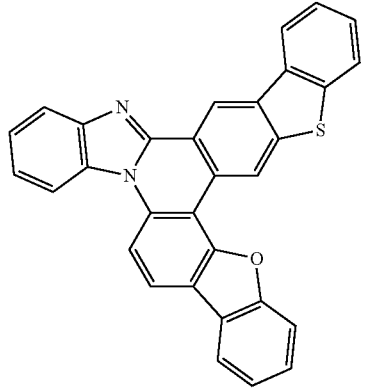

103
-continued
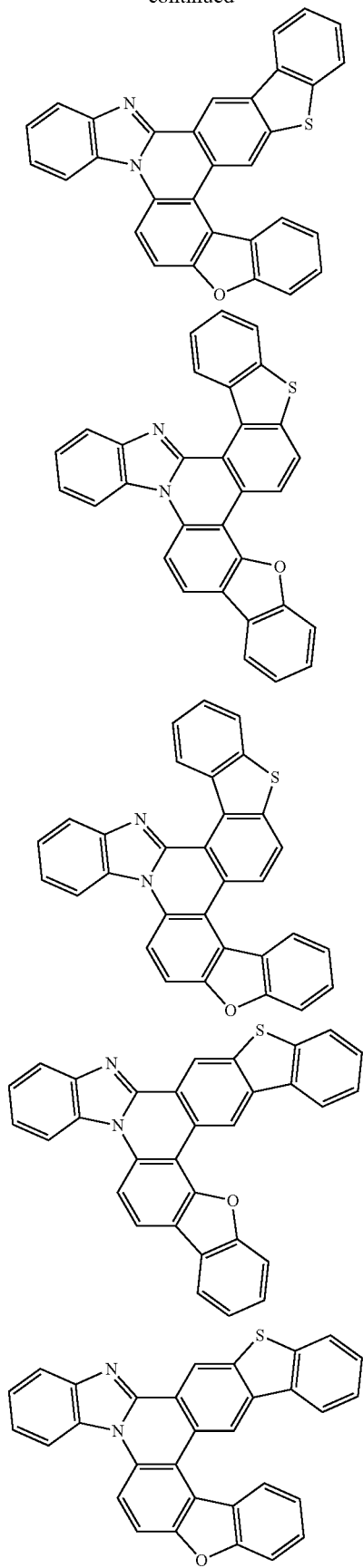
104
-continued
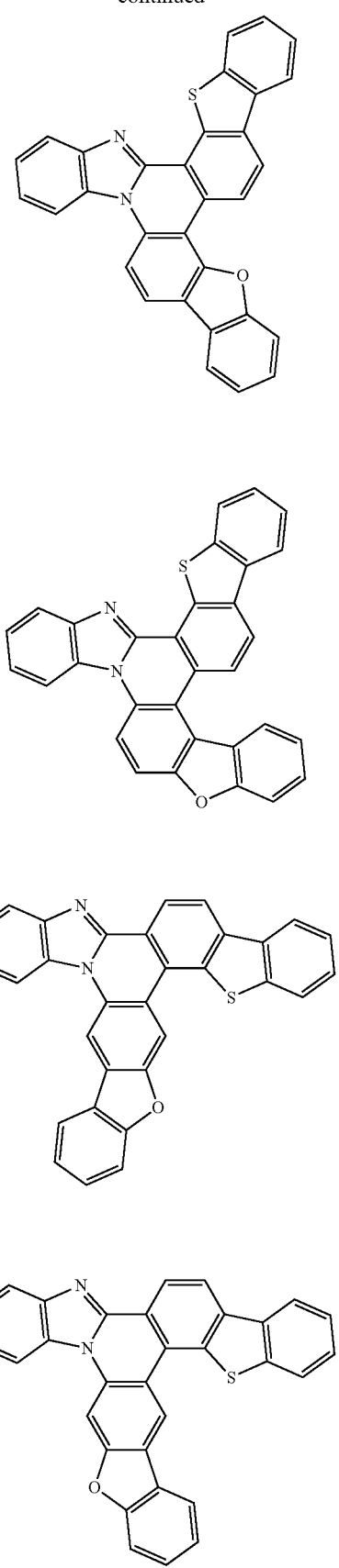

105
-continued
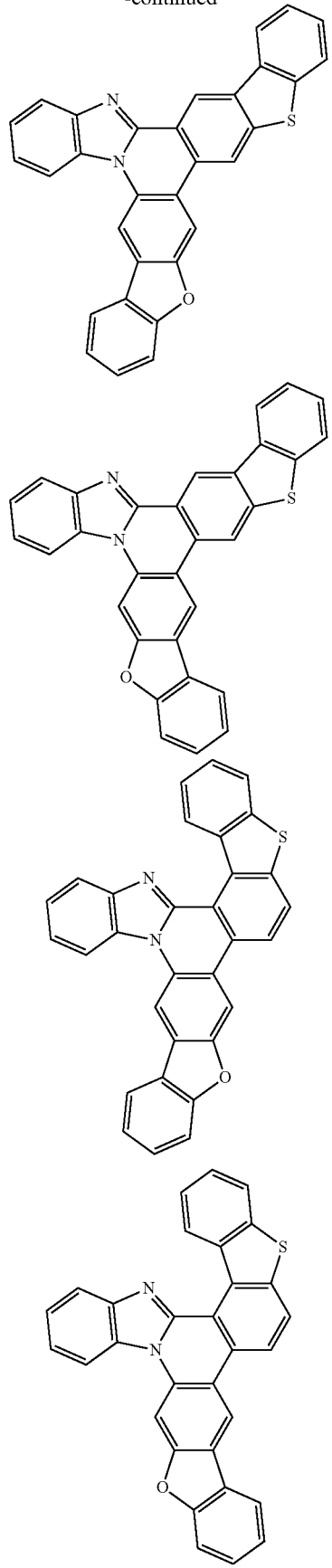
106
-continued
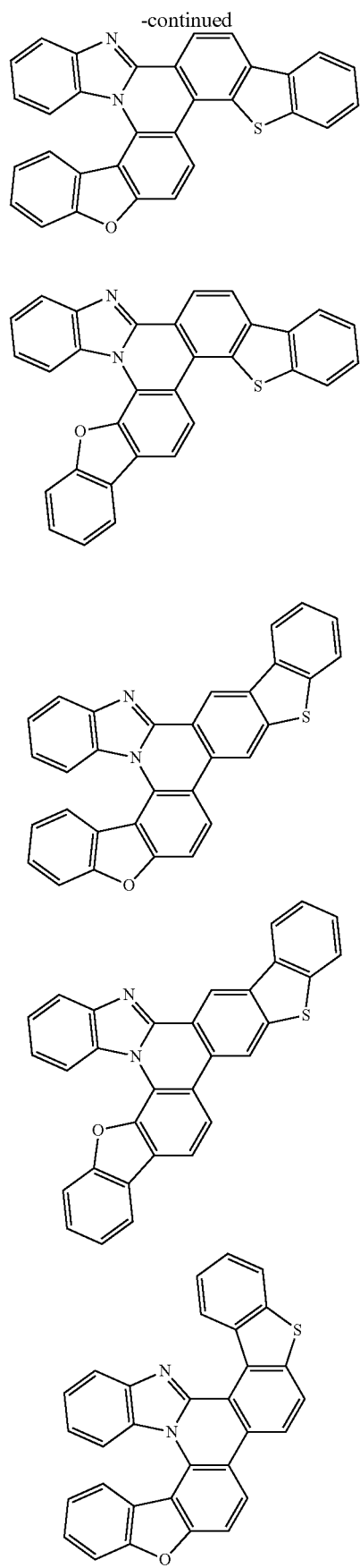

107
-continued
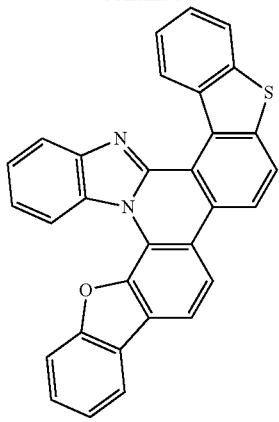
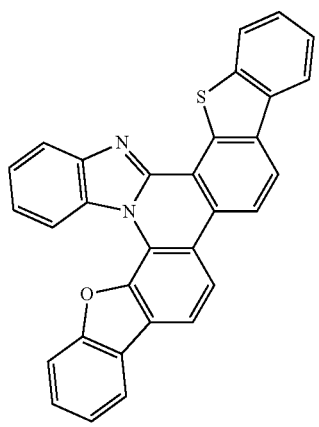
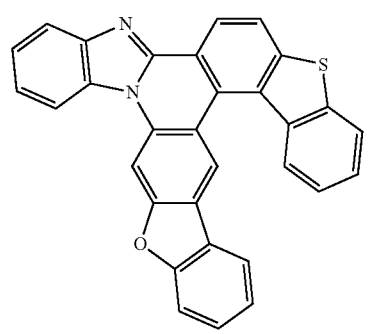
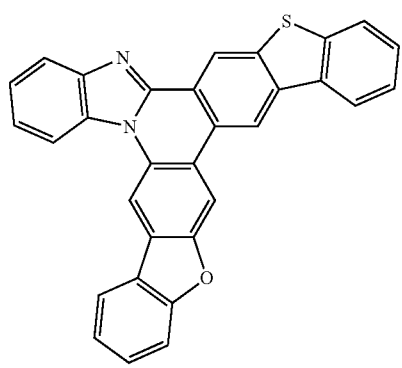
108
-continued
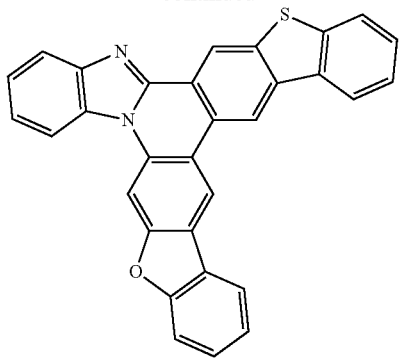
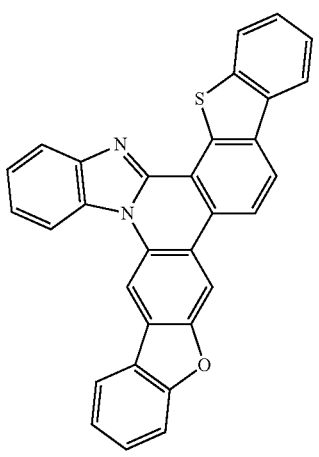
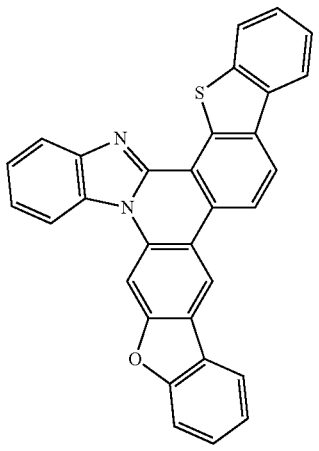
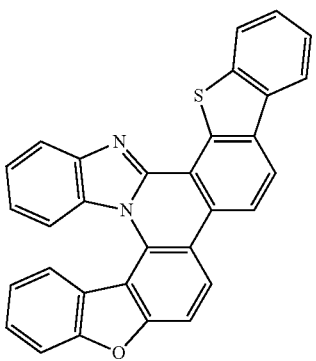

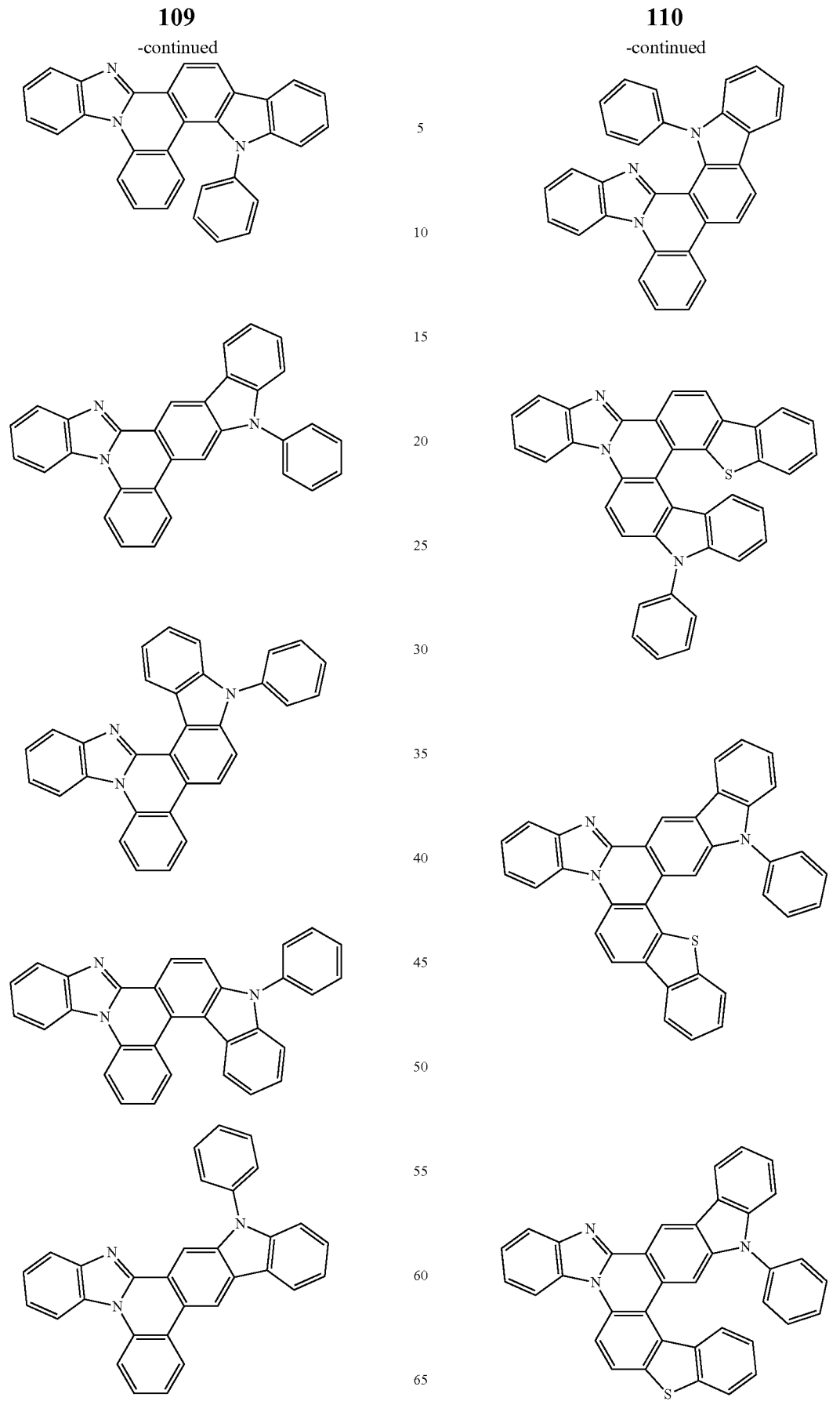

| 109 | 110 |
|---|---|
| -continued | -continued |

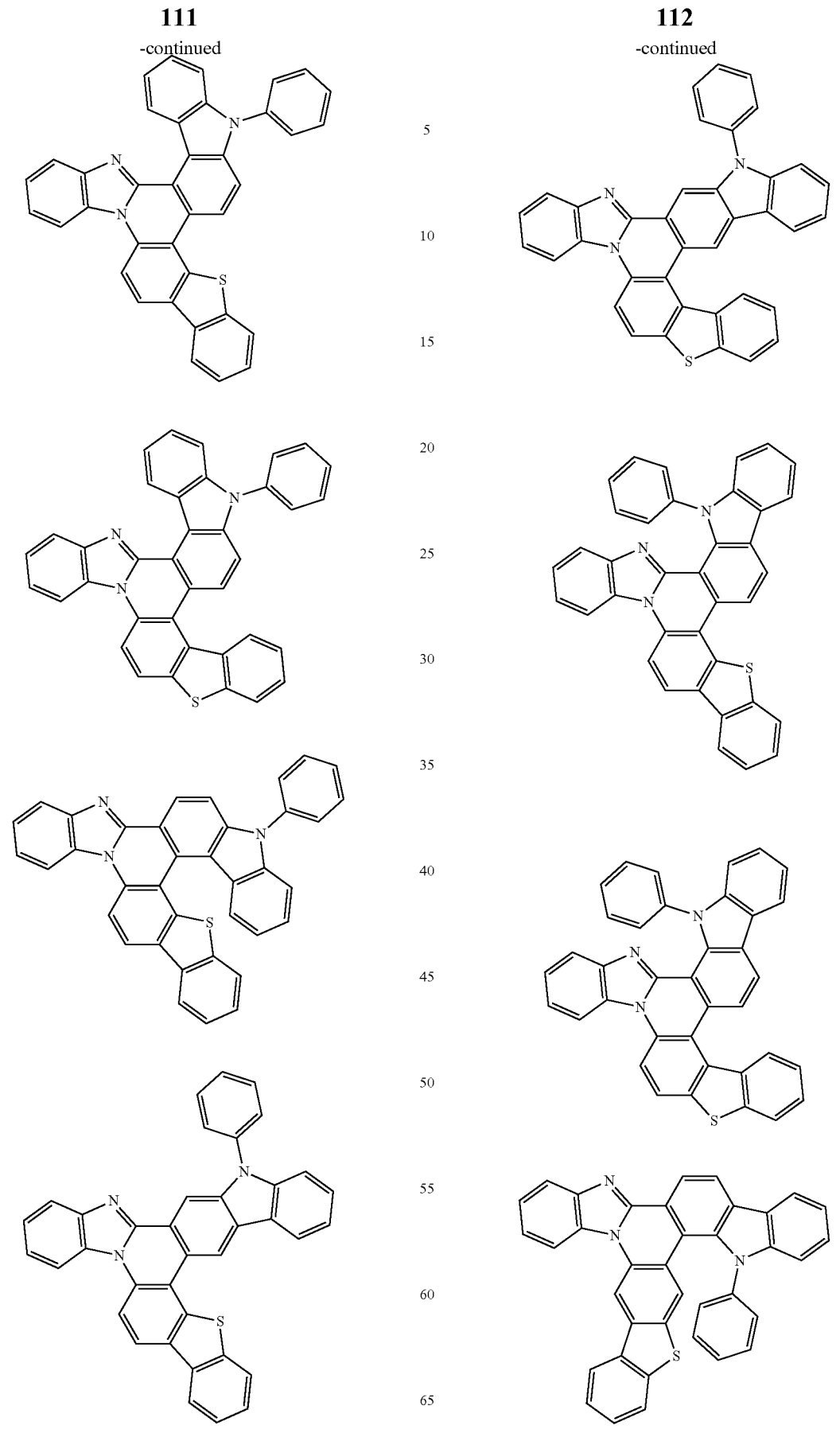

111
-continued

112
-continued

113
-continued
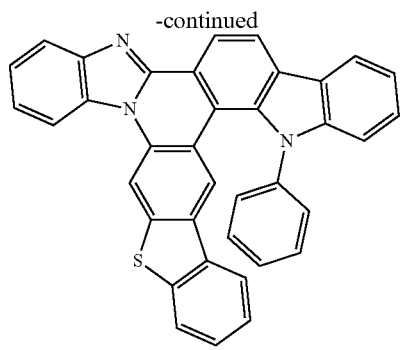
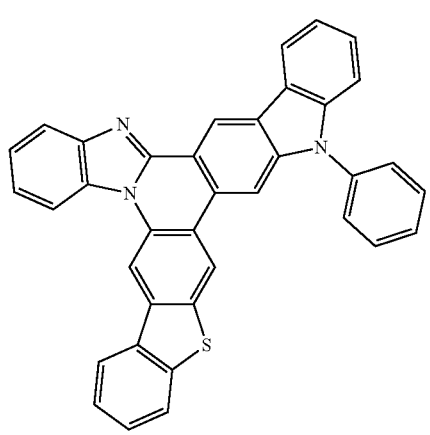
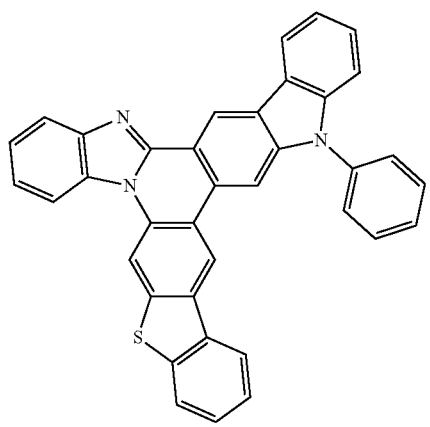
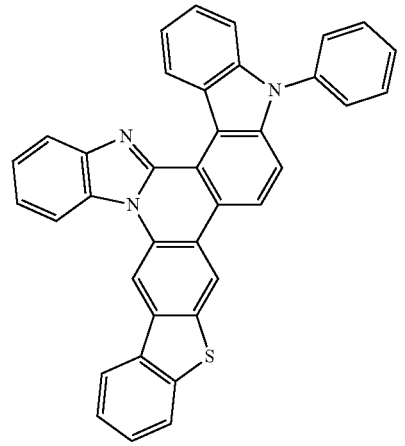
114
-continued
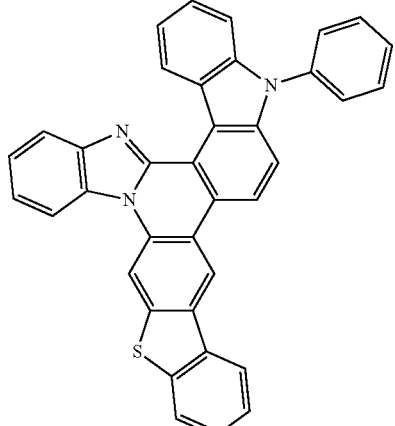
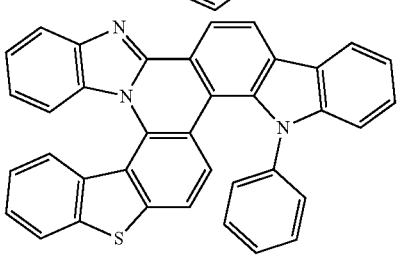
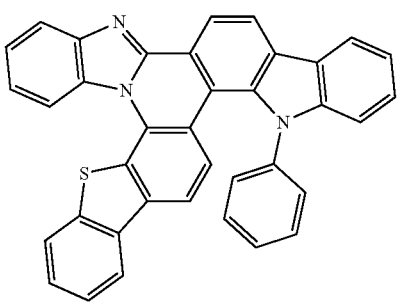
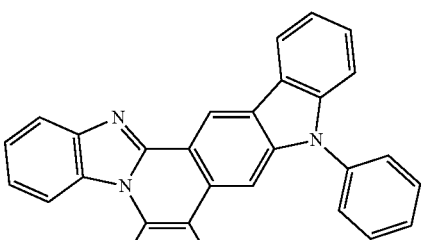
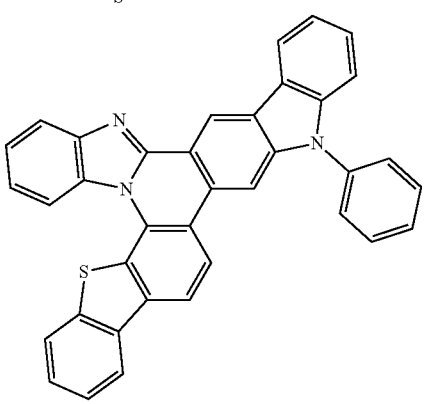

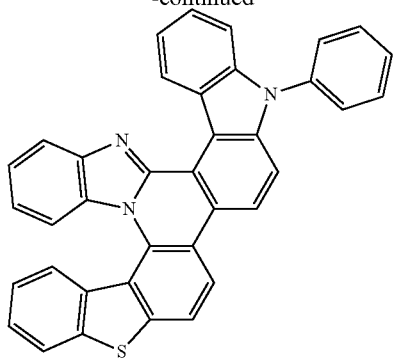
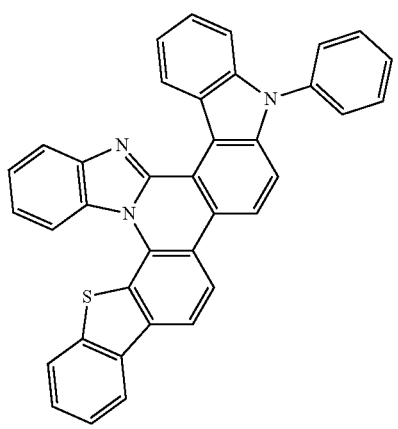
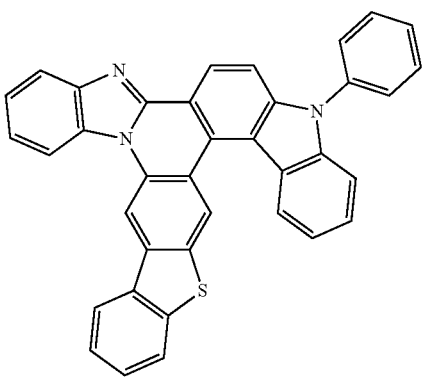
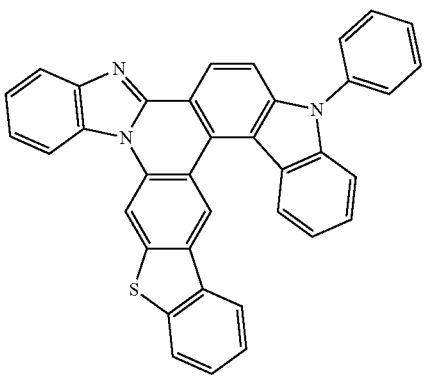
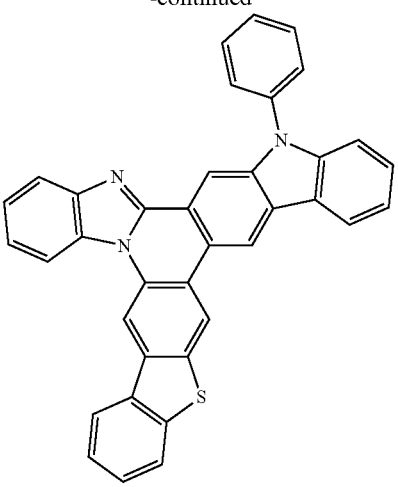
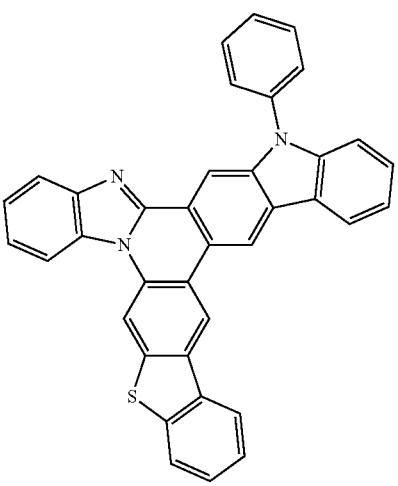
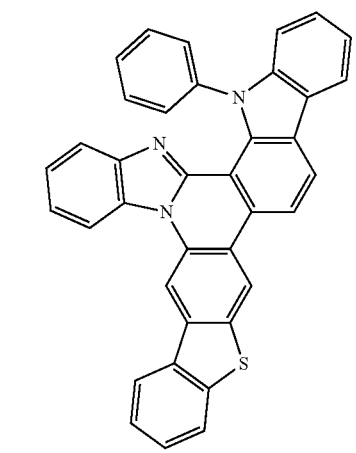

117
-continued
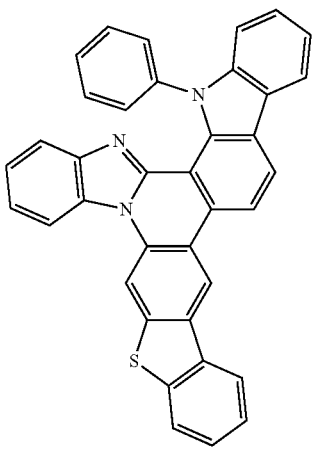
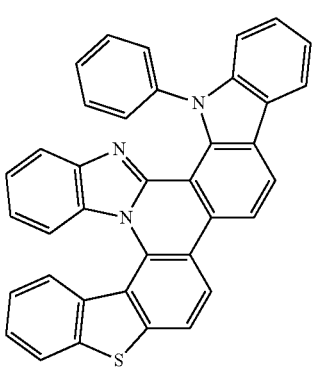
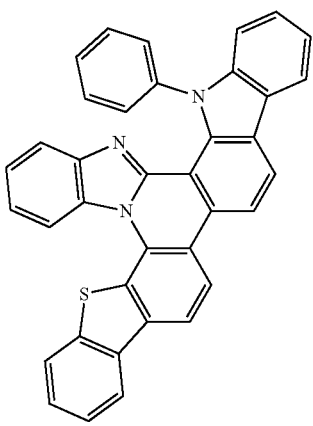
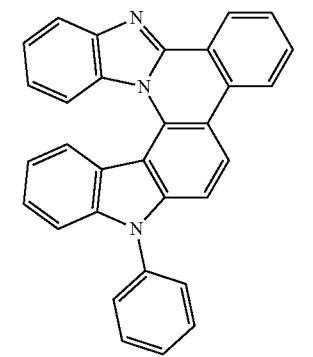
118
-continued
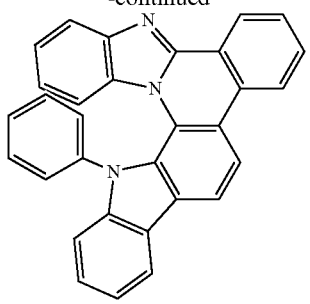
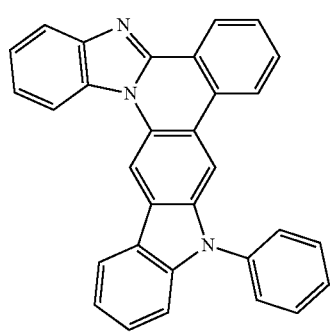
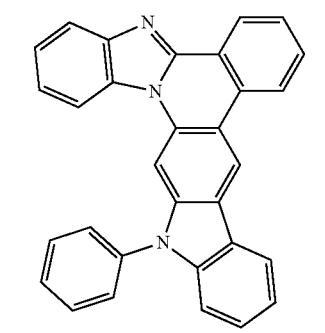
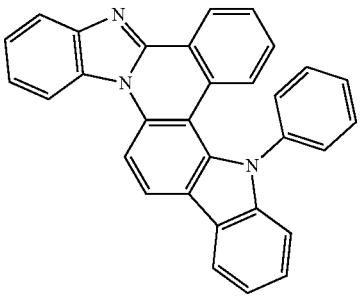
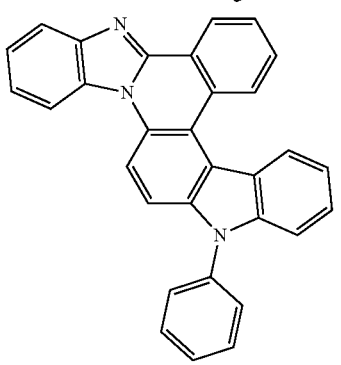

119
-continued
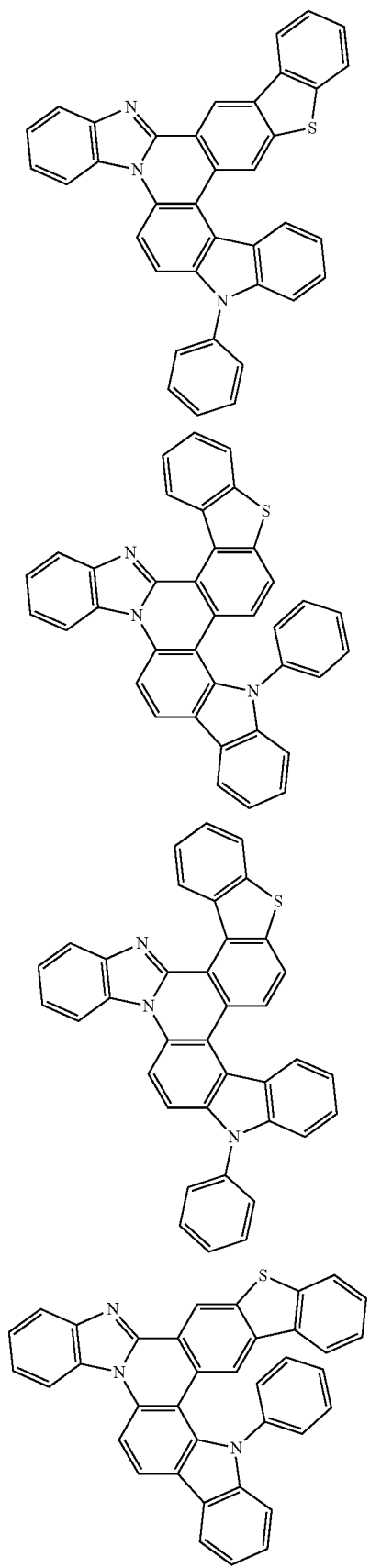
120
-continued
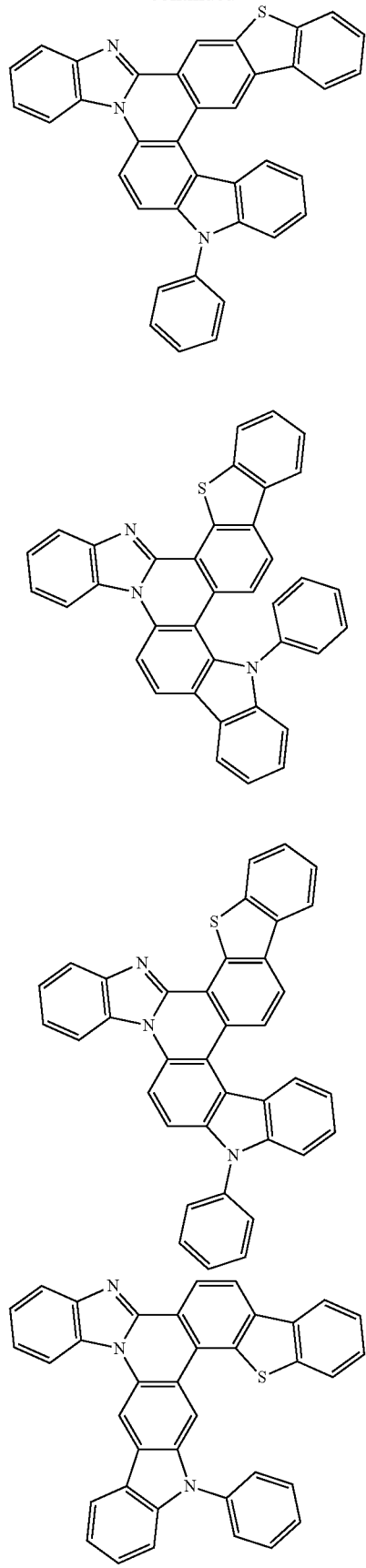

-continued
121
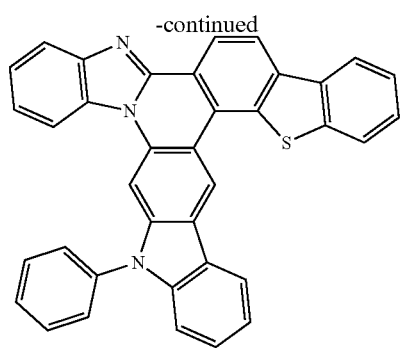
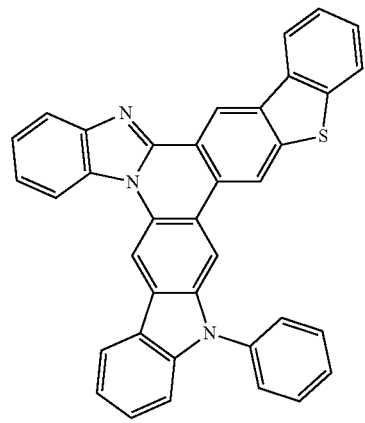
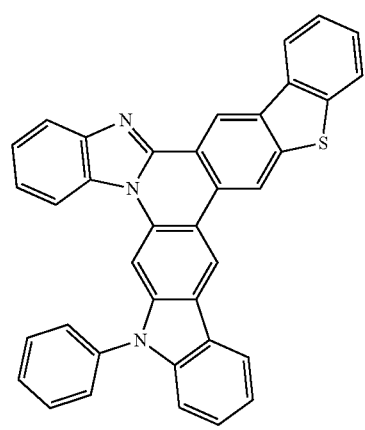
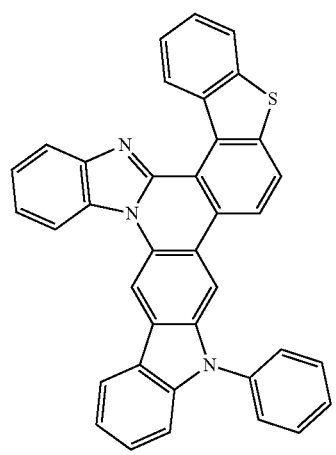
-continued
122
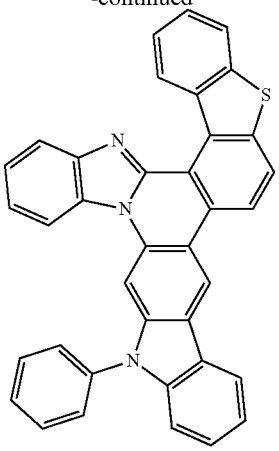
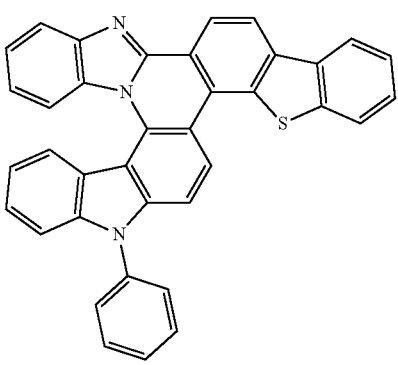
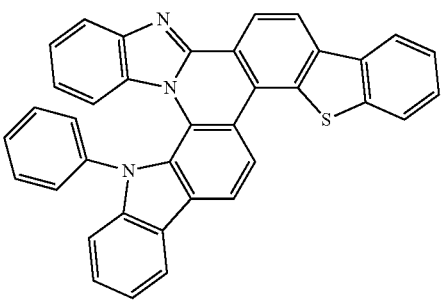
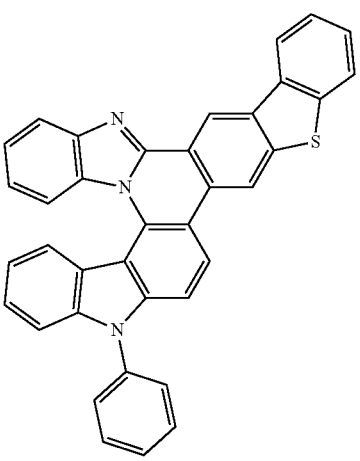

-continued
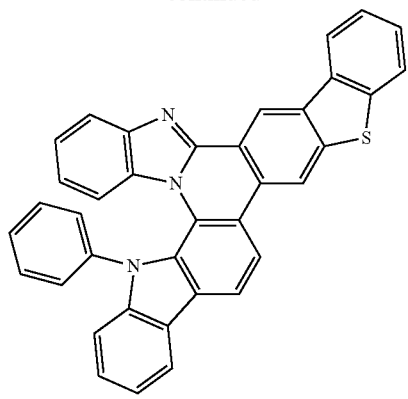
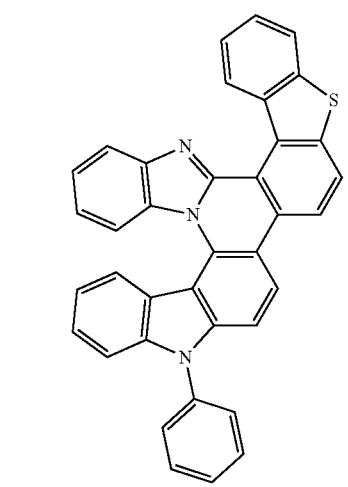
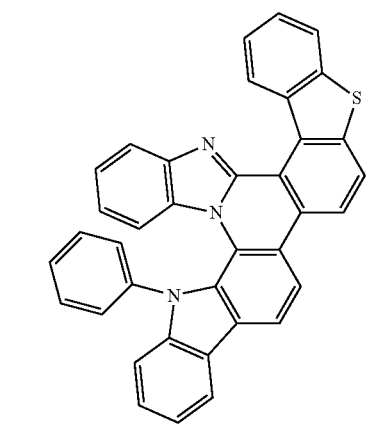
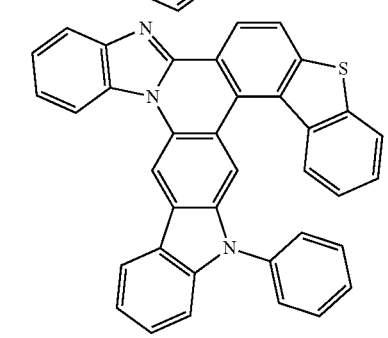
-continued
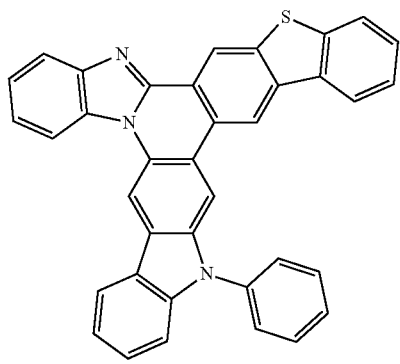
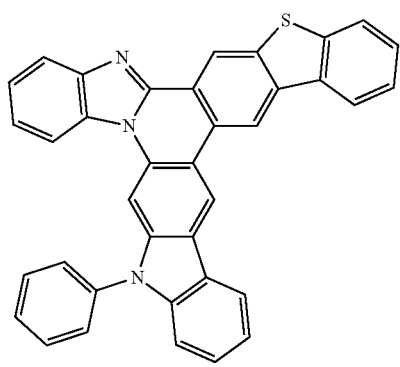
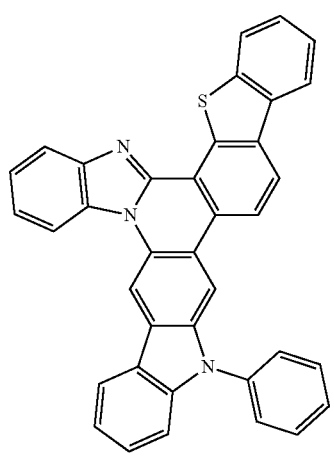

125
-continued
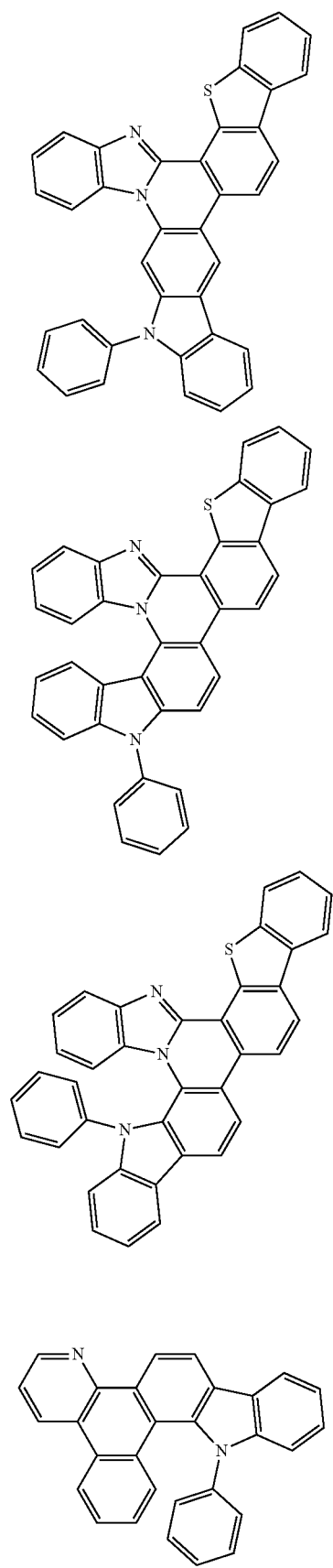
126
-continued
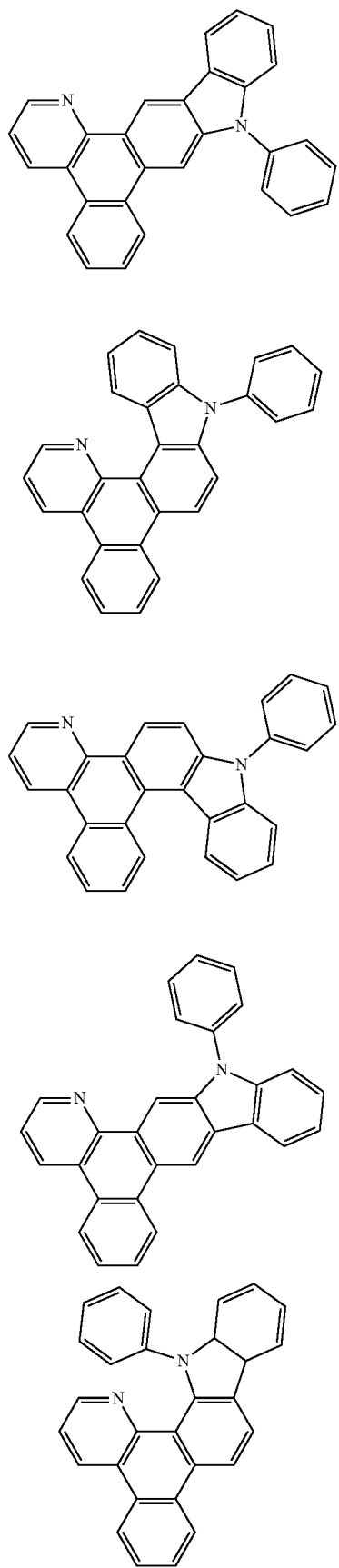

127
-continued
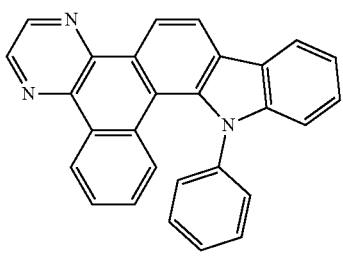
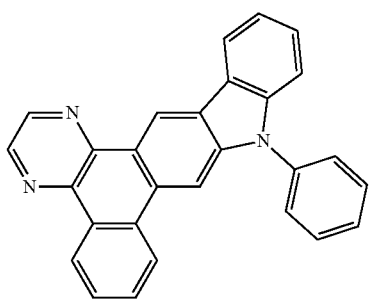
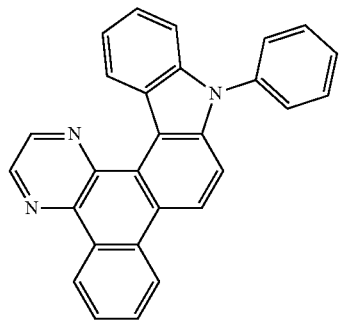
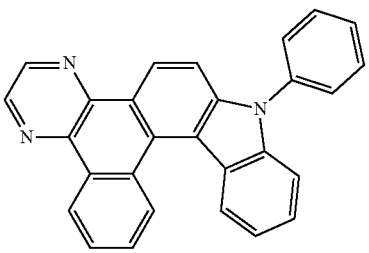
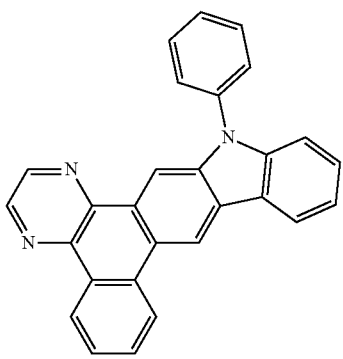
128
-continued
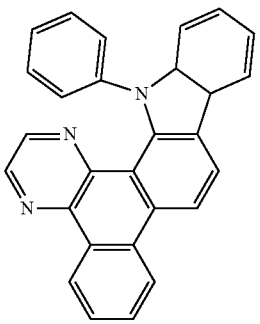
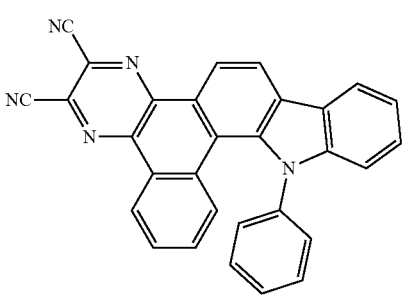
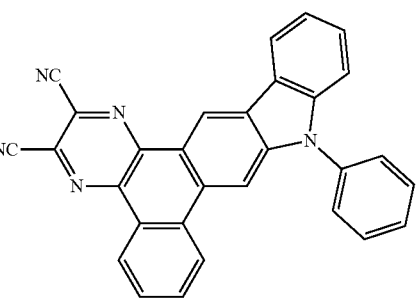
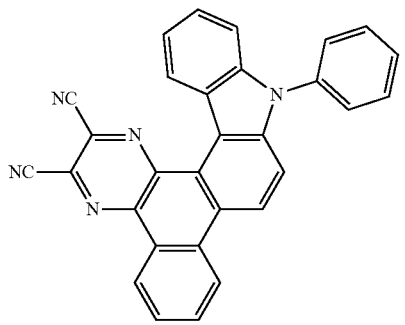
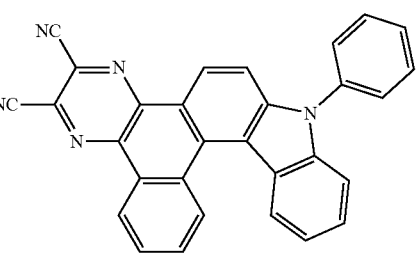

129
-continued
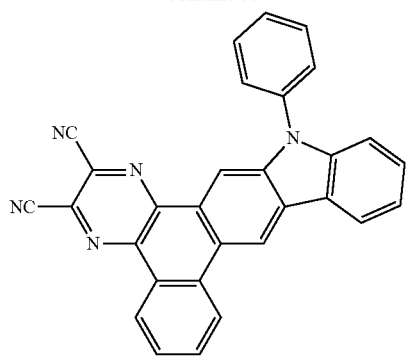
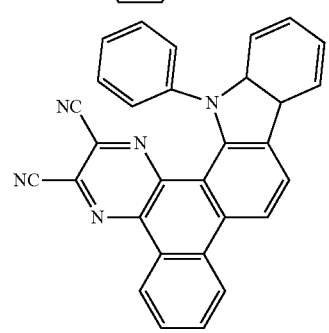
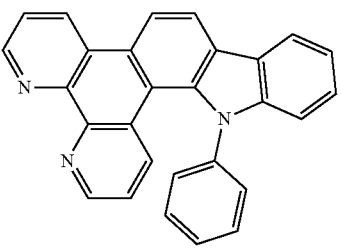
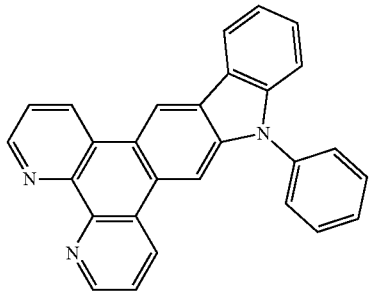
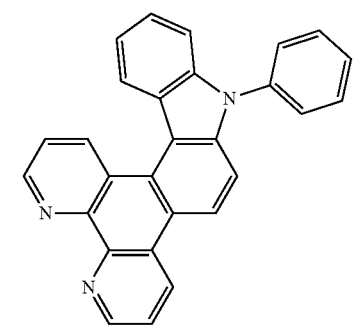
130
-continued
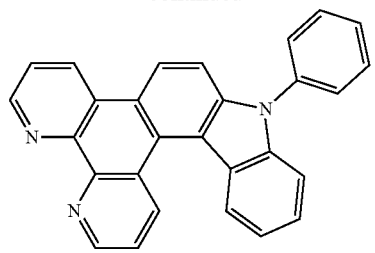
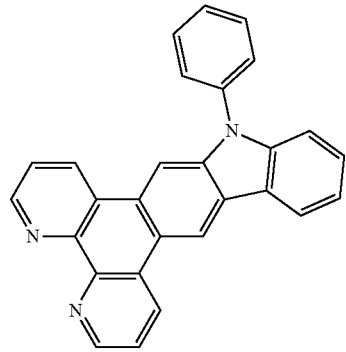
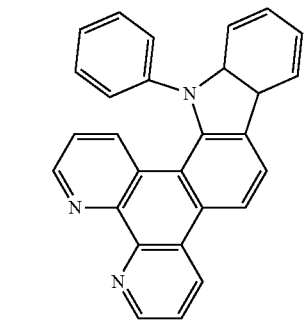
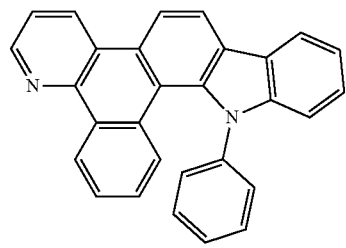
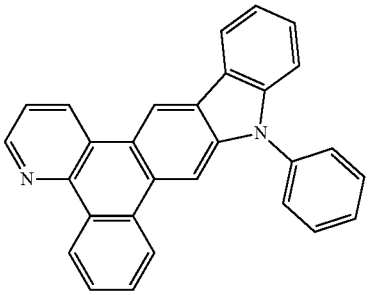

131
-continued
132
-continued
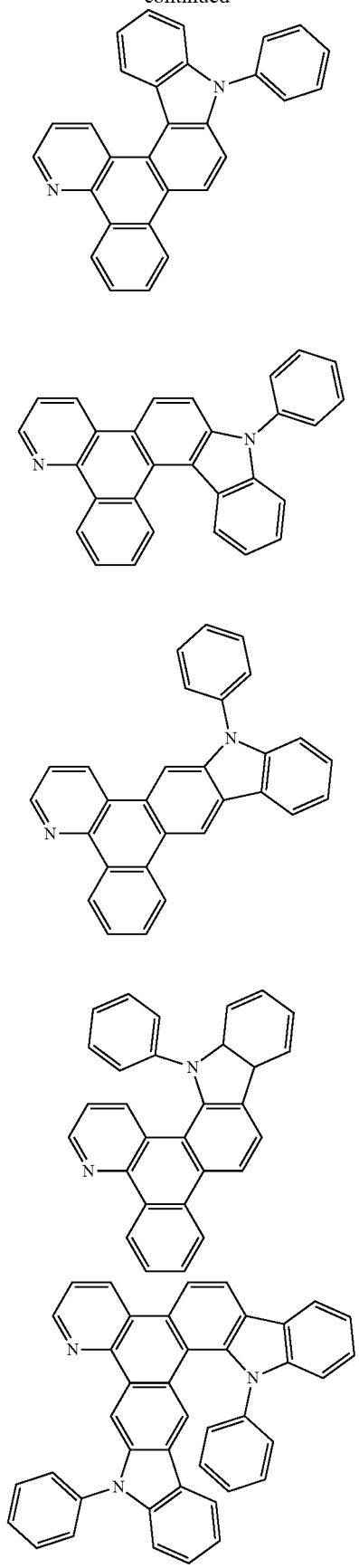
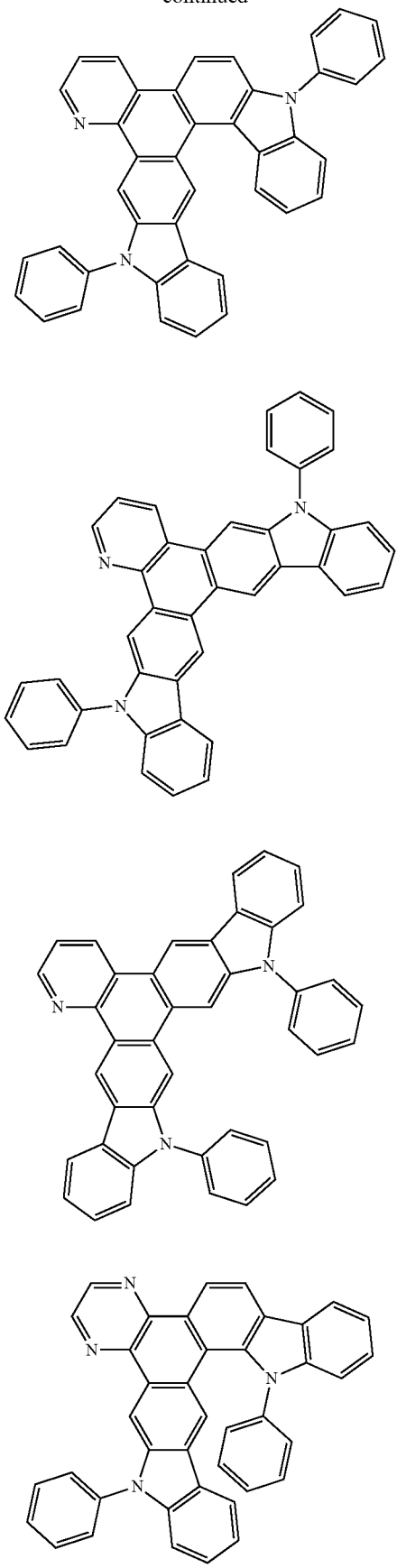

133
-continued
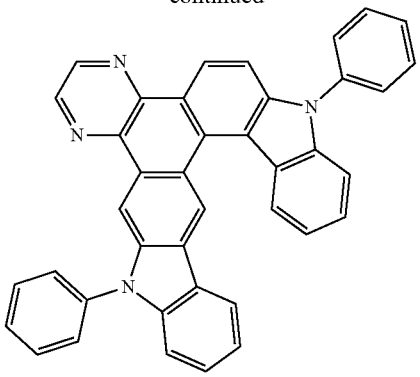
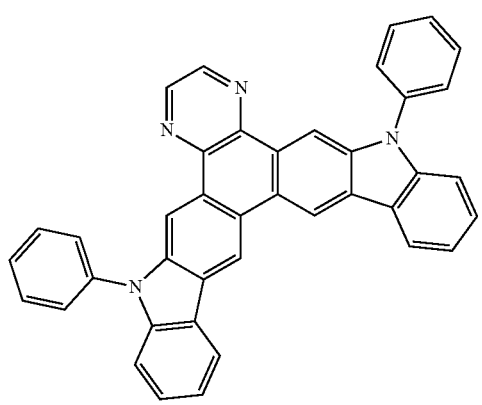
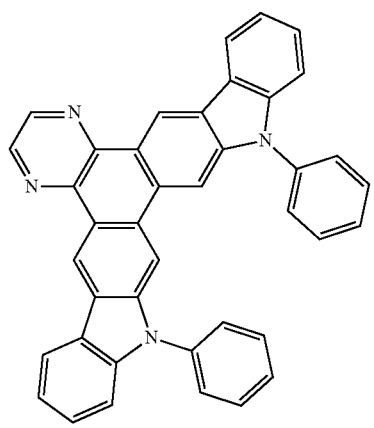
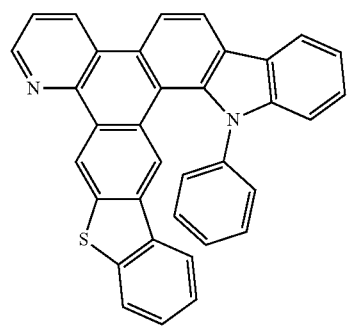
134
-continued
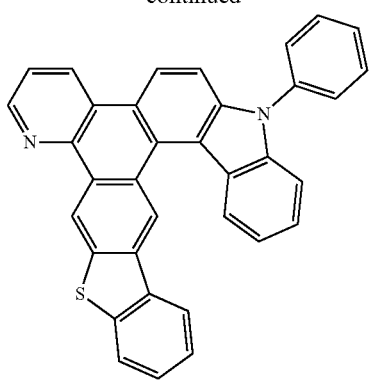
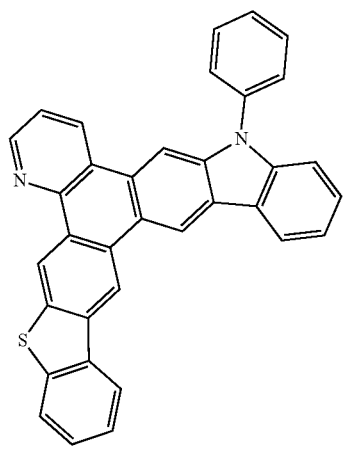
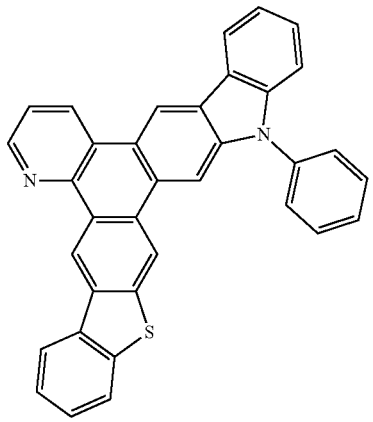
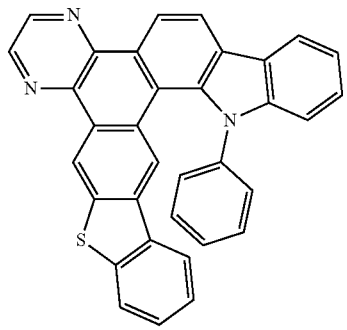

135
-continued
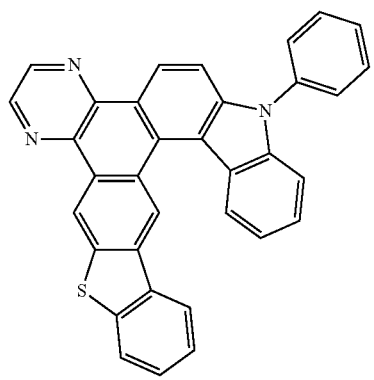
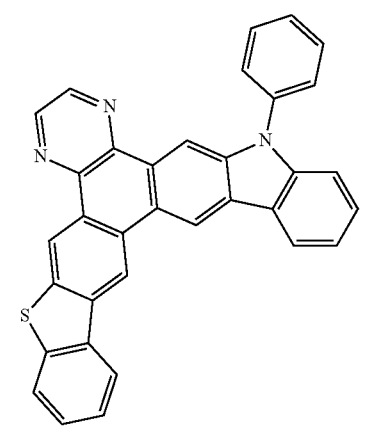
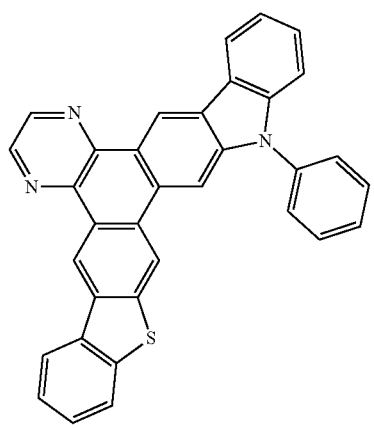
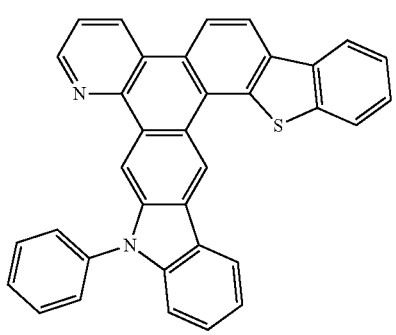
136
-continued
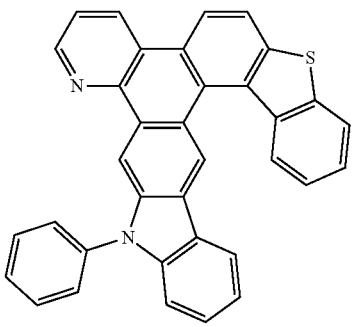
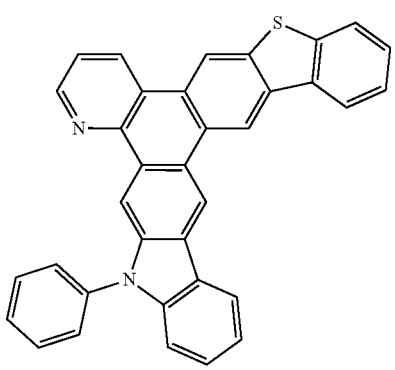
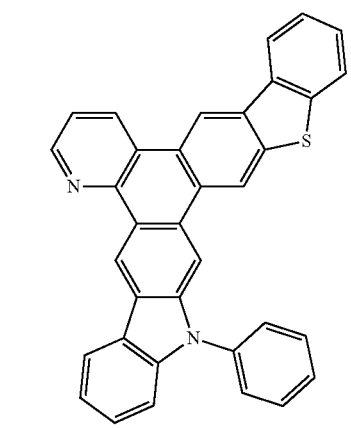
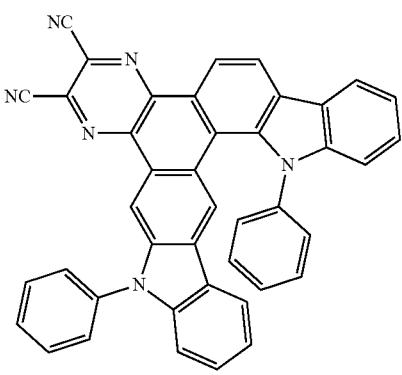

137
-continued
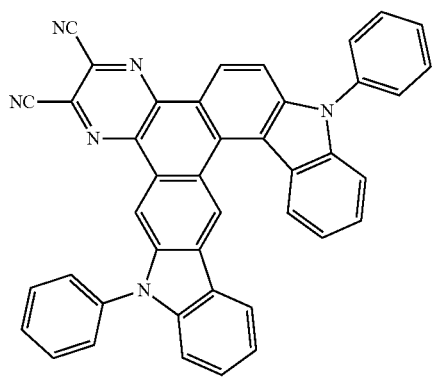
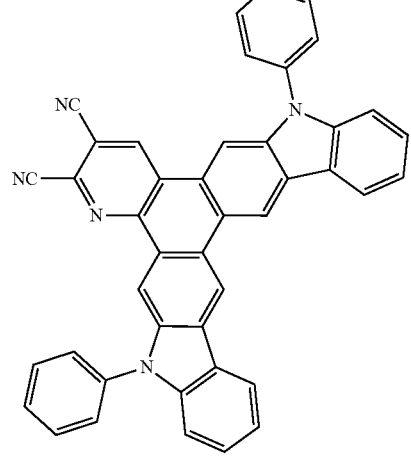
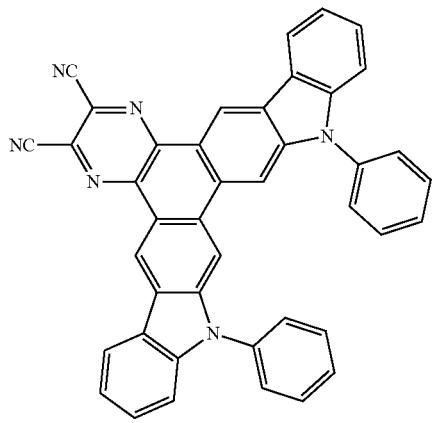
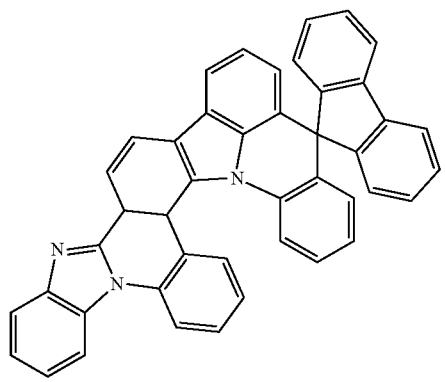
138
-continued
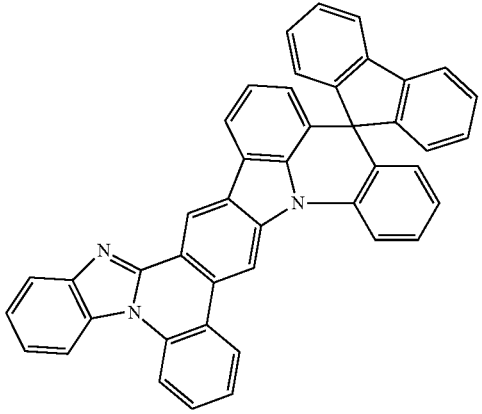
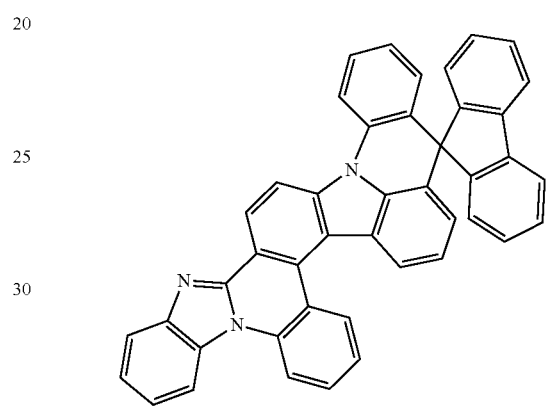
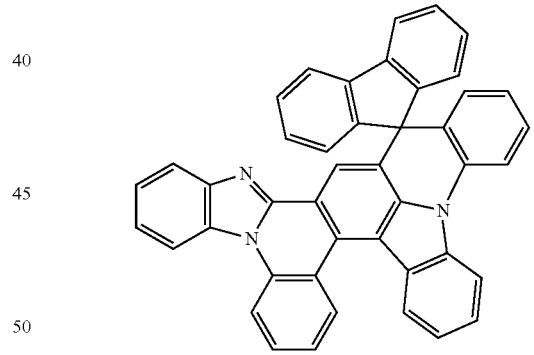
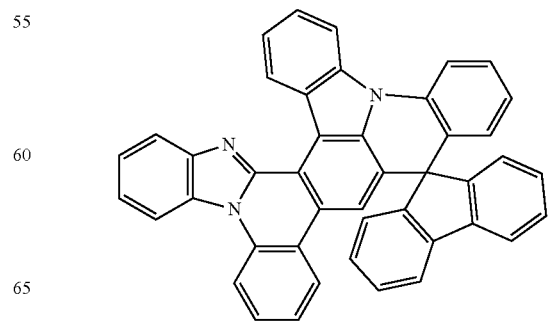

139
-continued
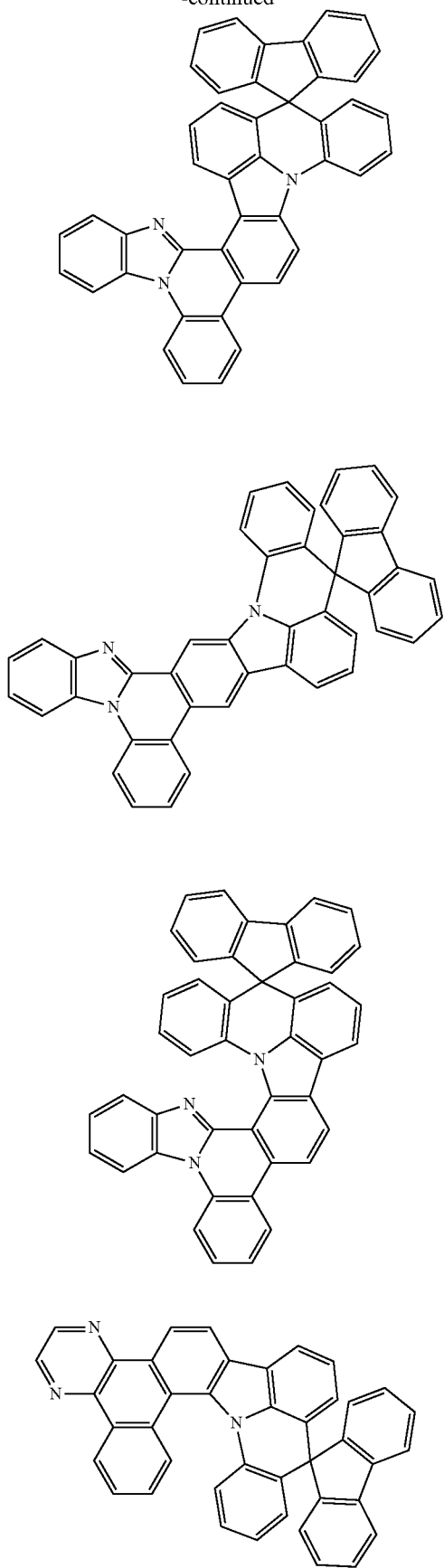
140
-continued
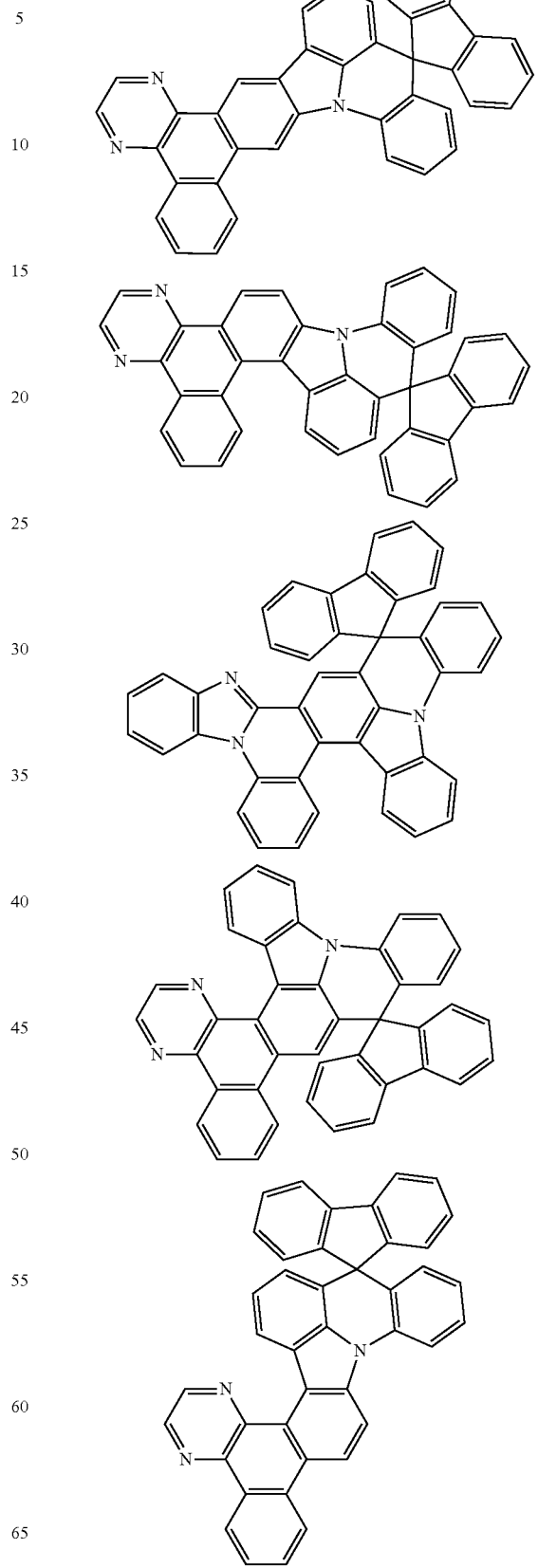

-continued
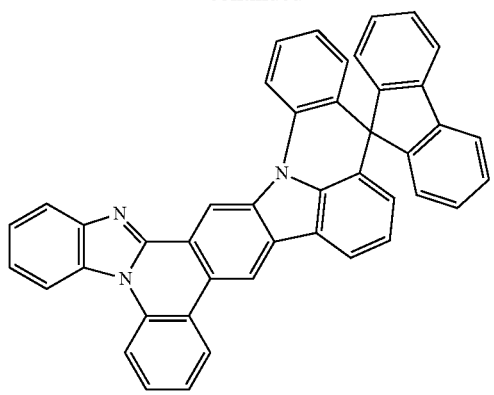
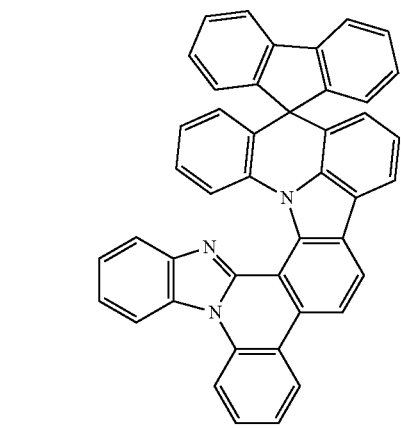
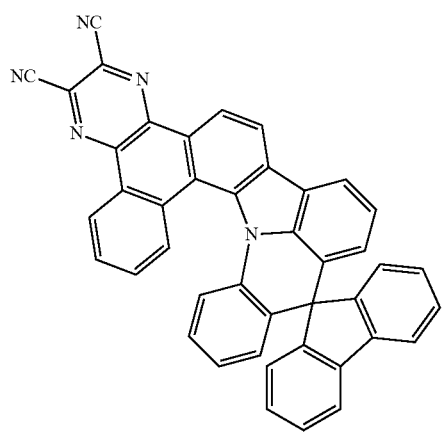
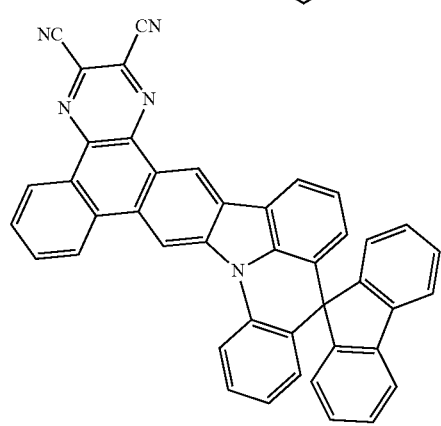
-continued
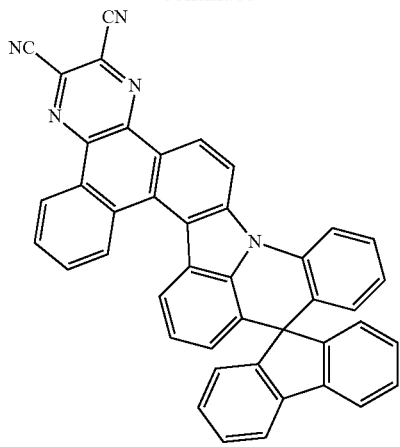
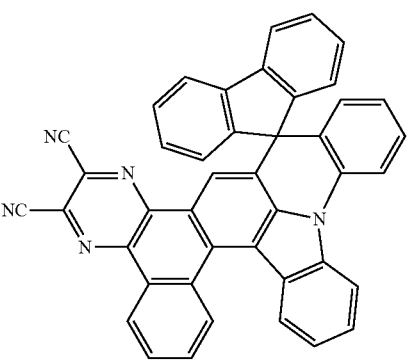
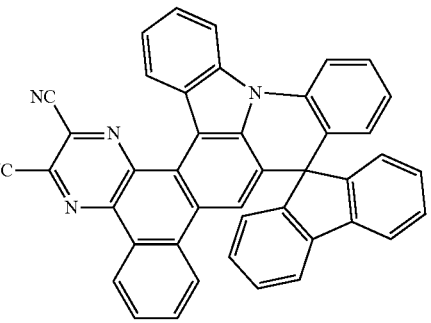
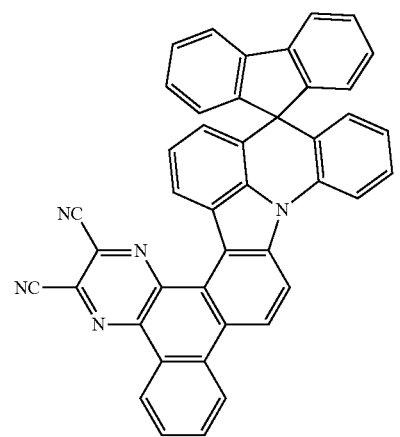

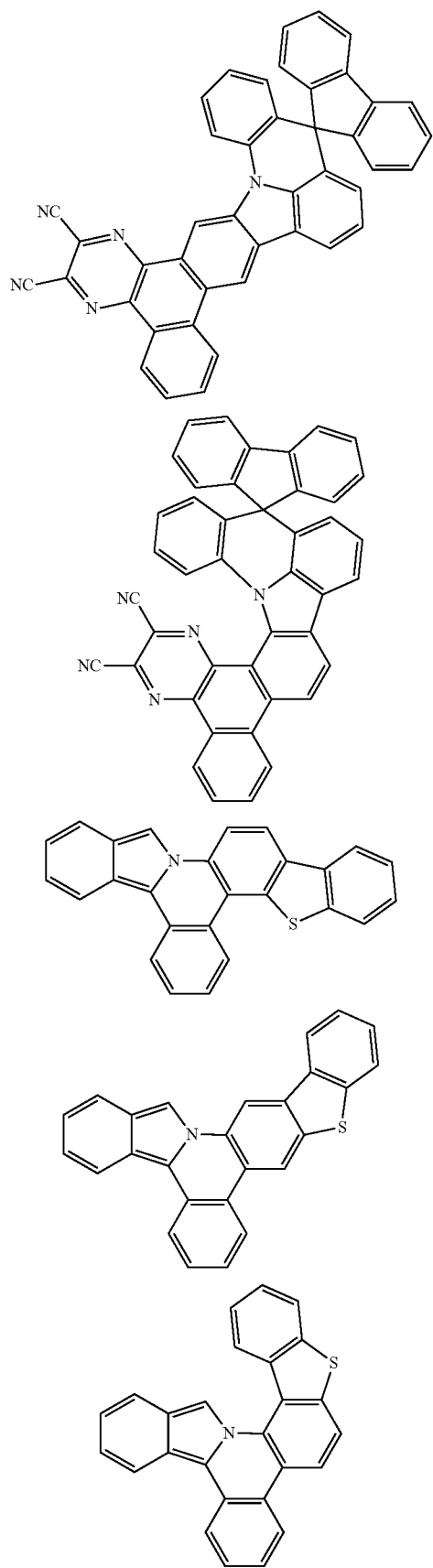
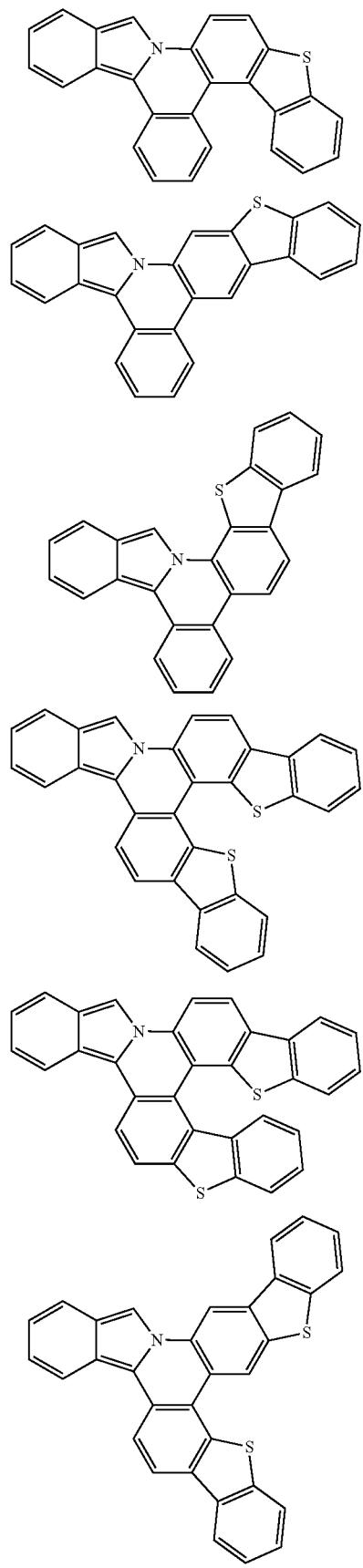

-continued
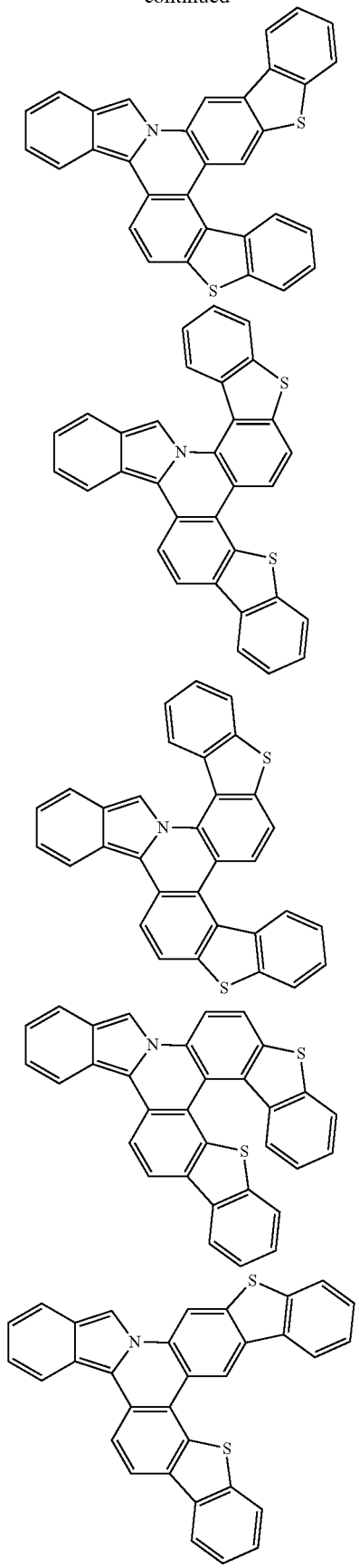
-continued
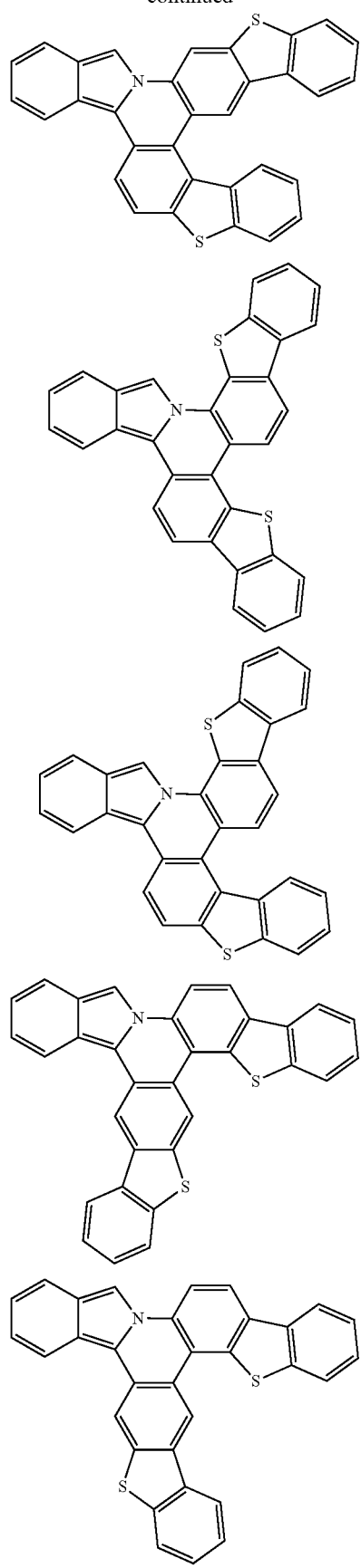

147
-continued
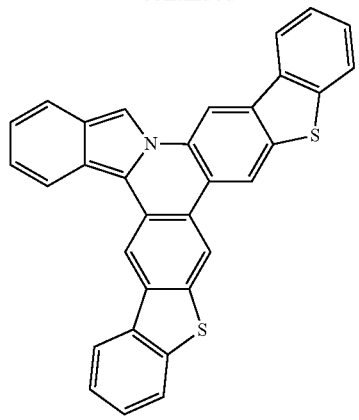
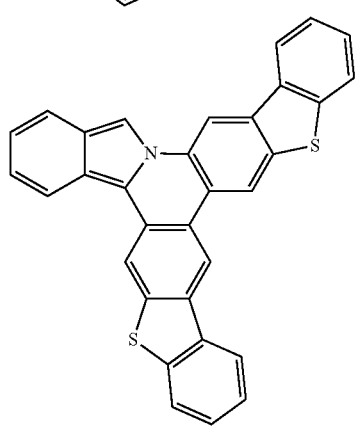
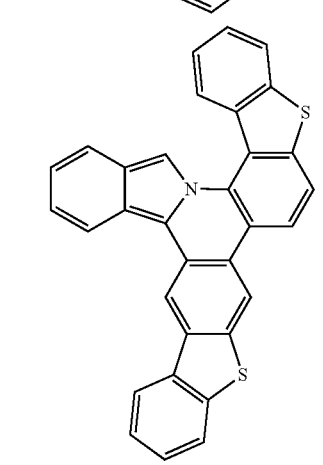
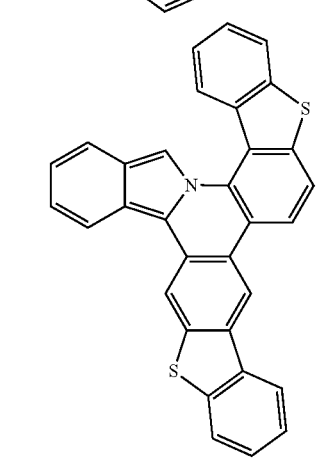
148
-continued
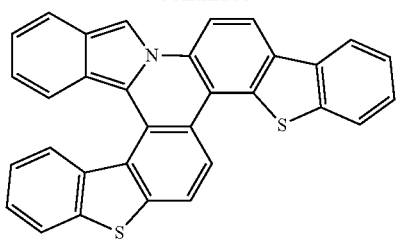
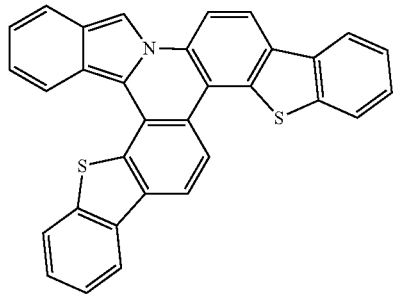
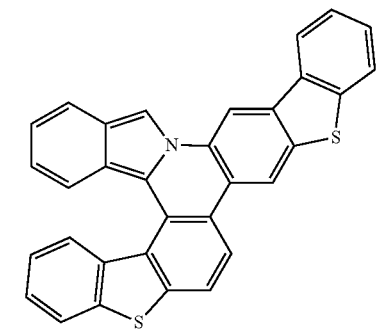
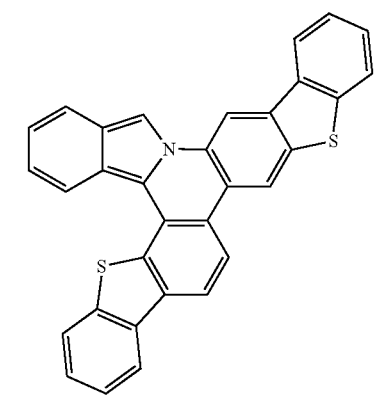
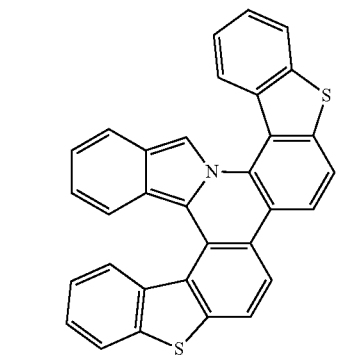

149
-continued
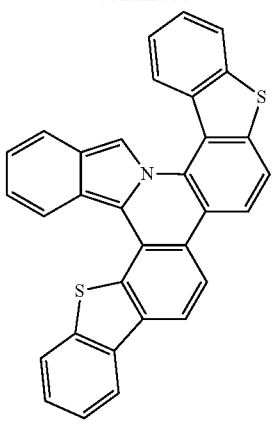
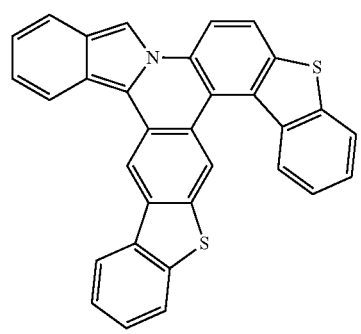
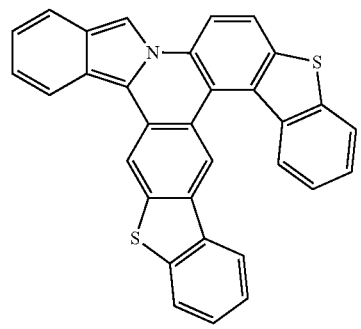
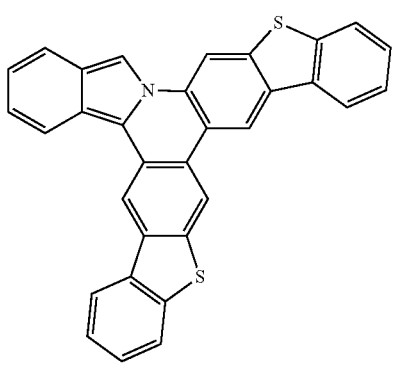
150
-continued
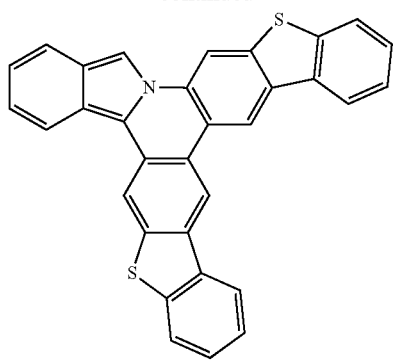
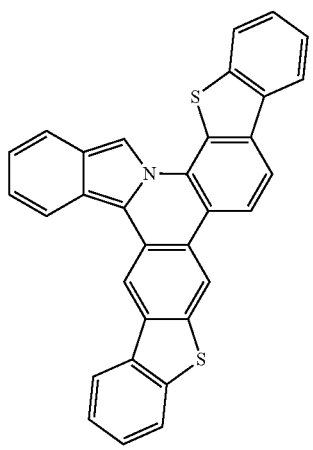
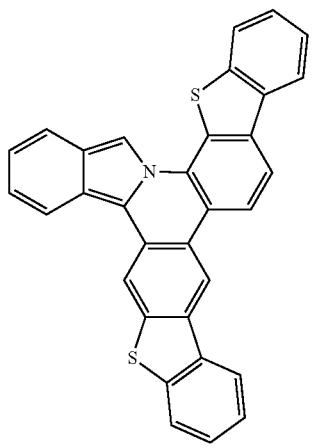
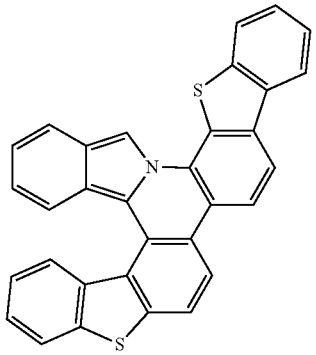

151
-continued
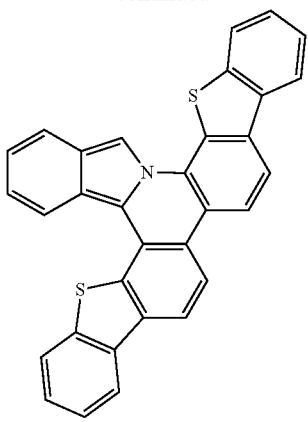
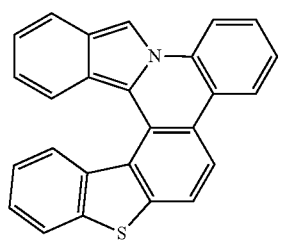
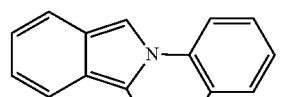
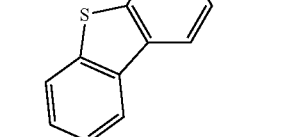
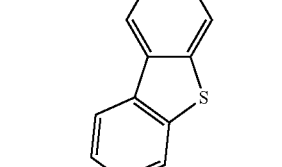
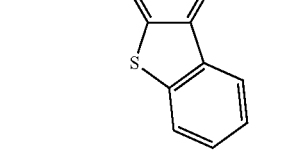
152
-continued
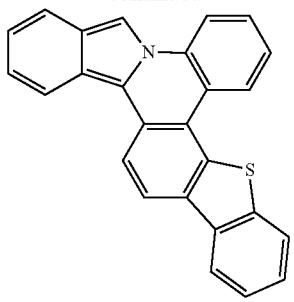
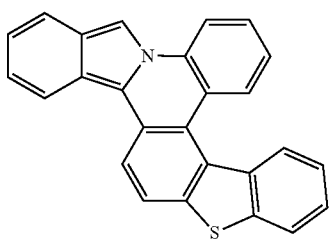
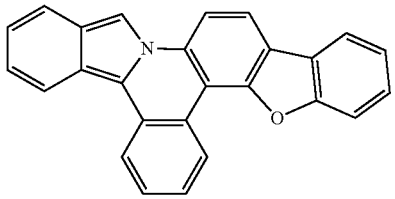
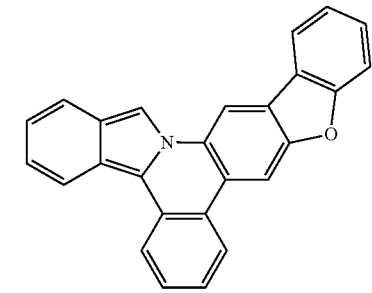
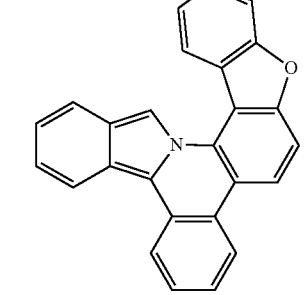
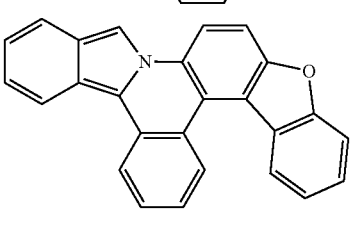

153
-continued
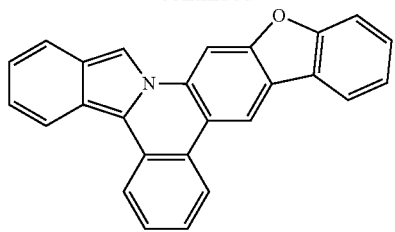
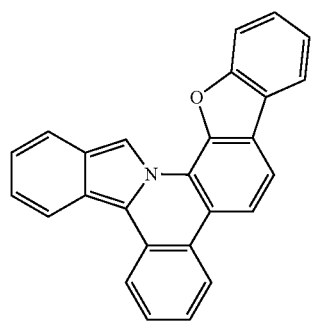
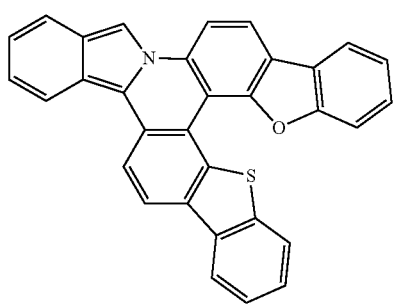
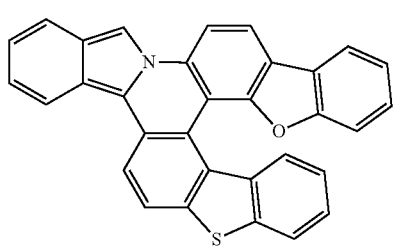
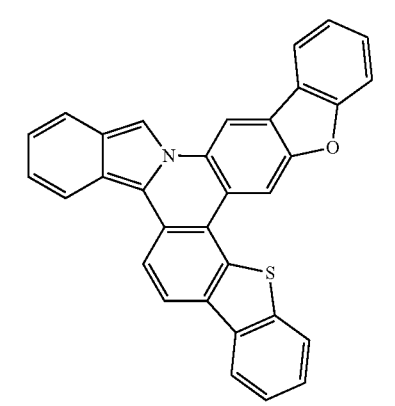
154
-continued
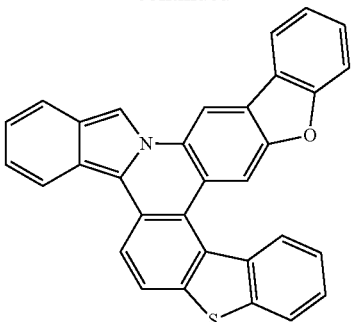
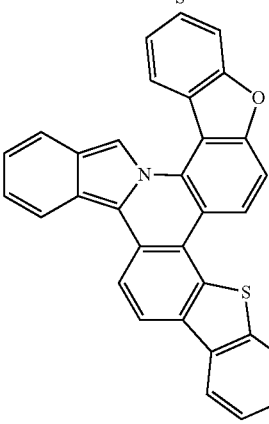
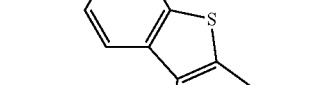

155
-continued
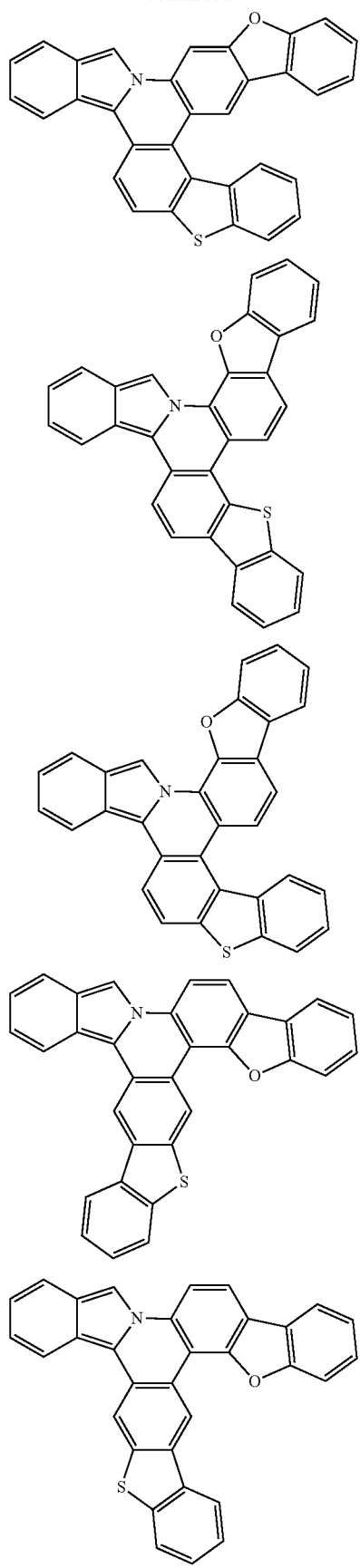
156
-continued
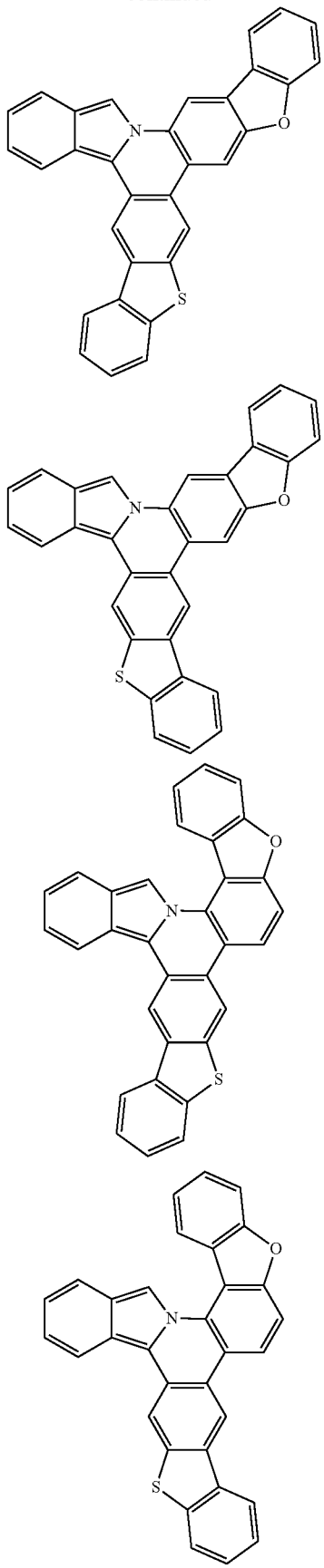

157
-continued
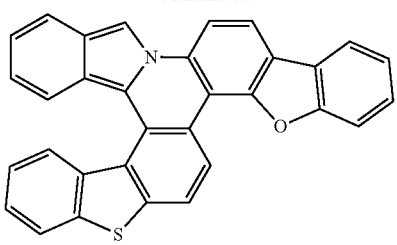
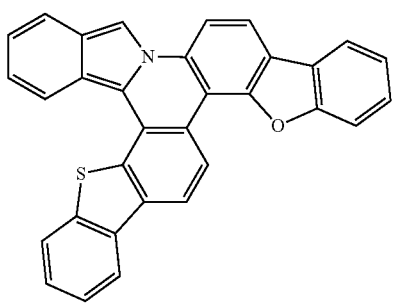
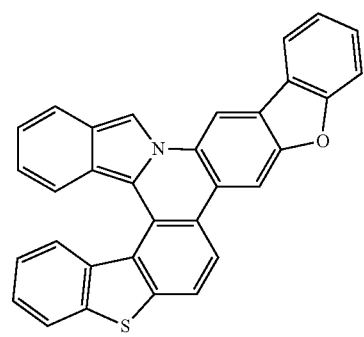
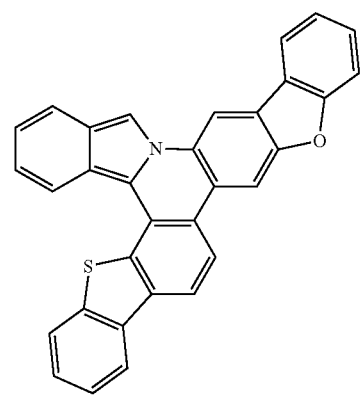
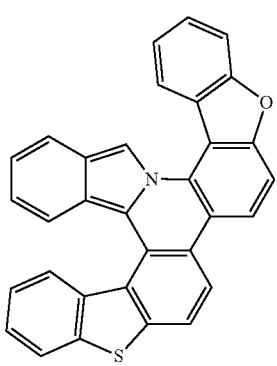
158
-continued
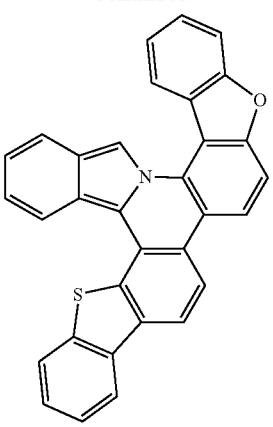
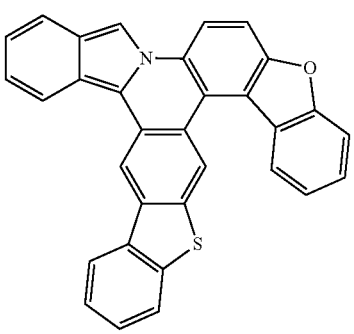
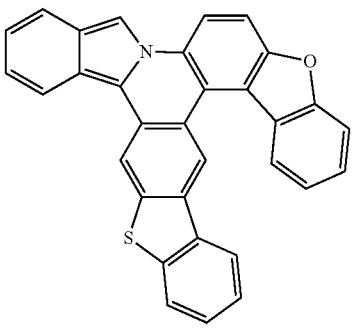
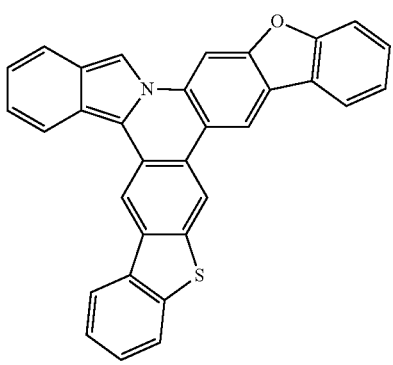

159
-continued
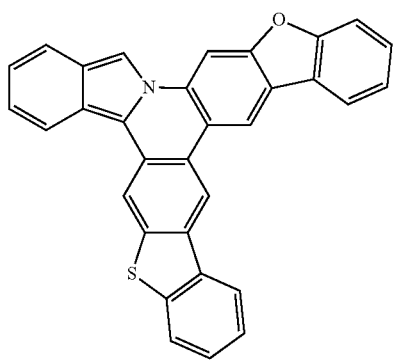
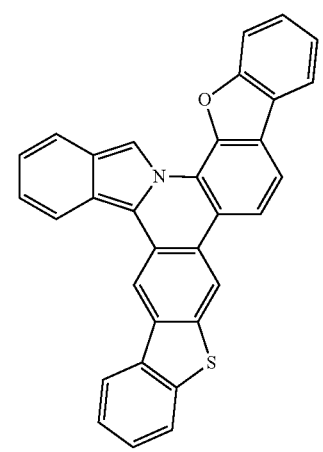
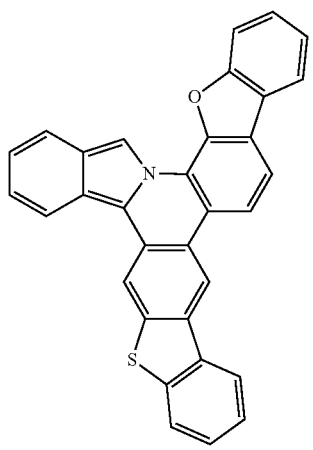
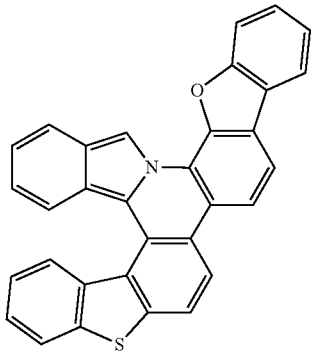
160
-continued
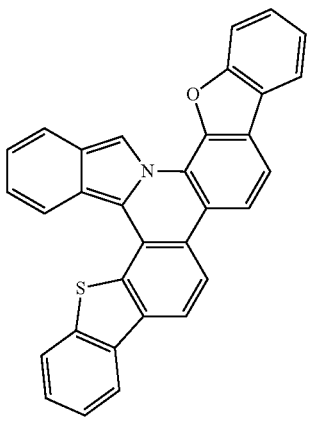
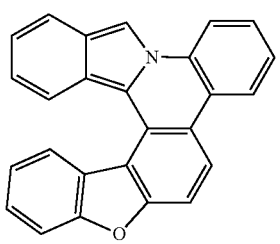
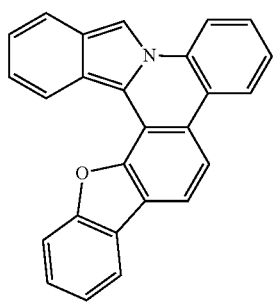
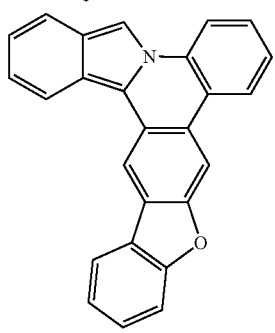
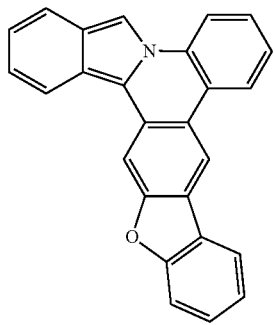

161
-continued
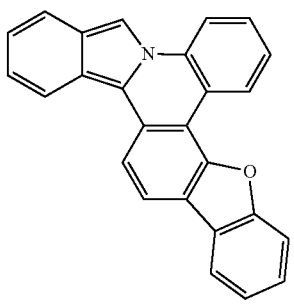
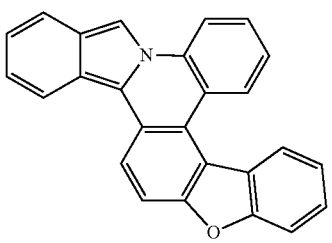
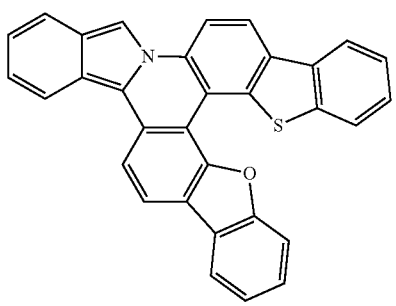
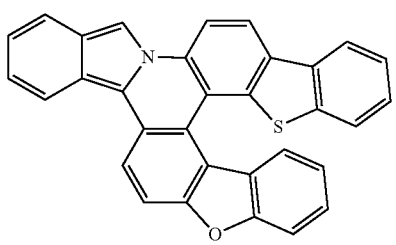
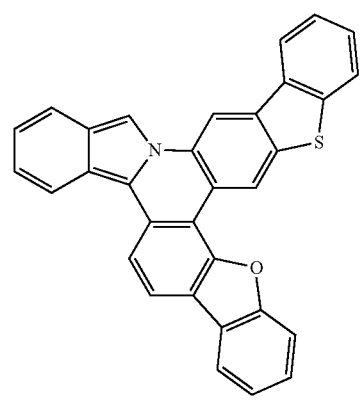
162
-continued
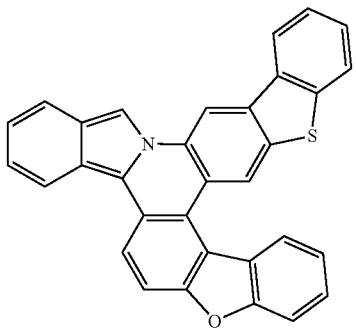
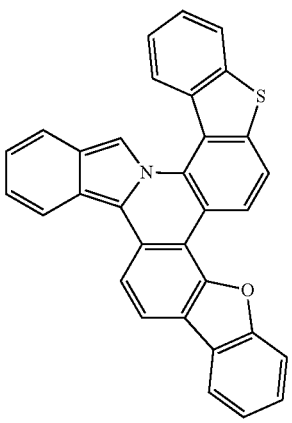
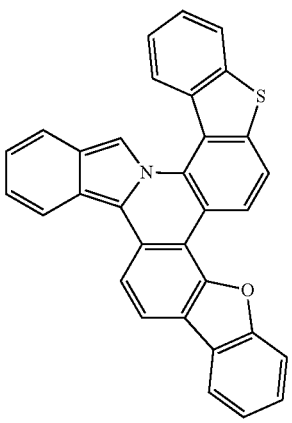
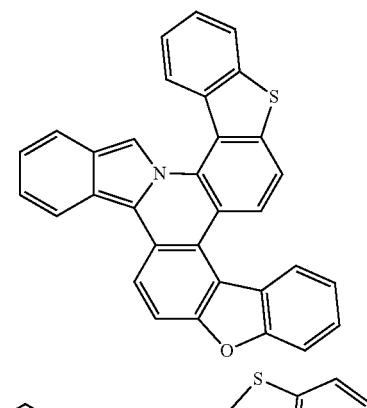
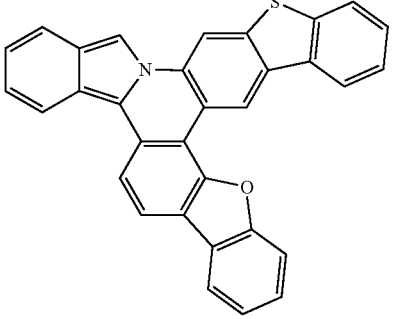
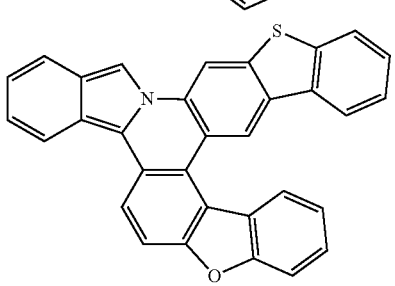

163
-continued
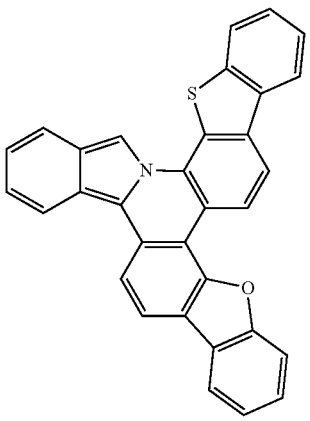
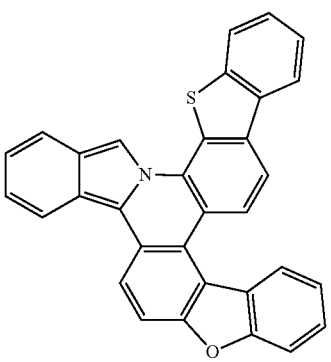
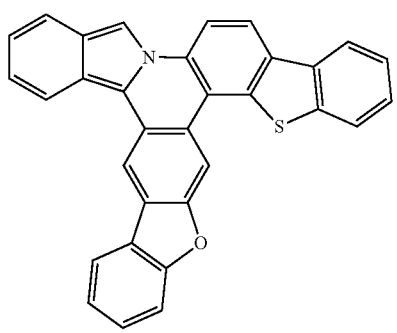
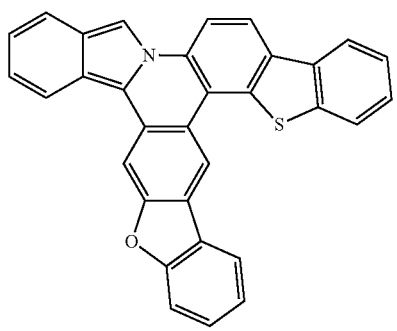
164
-continued
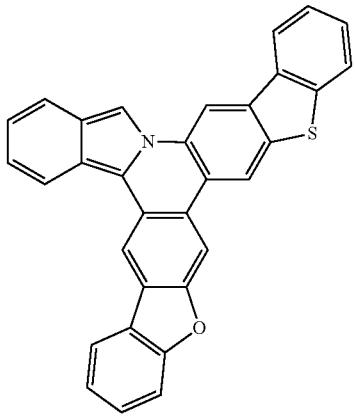
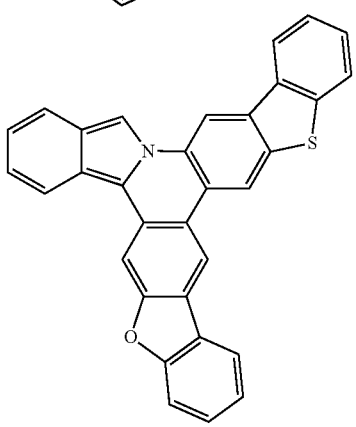
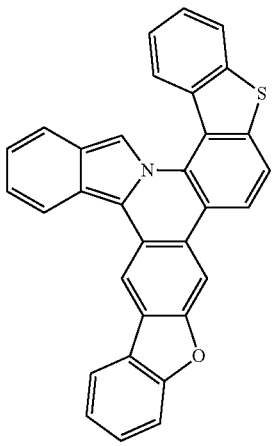
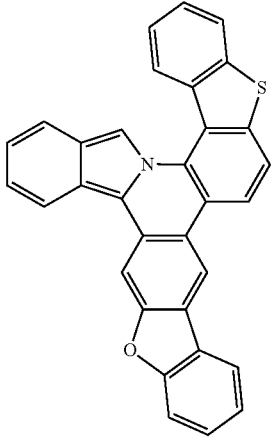

-continued
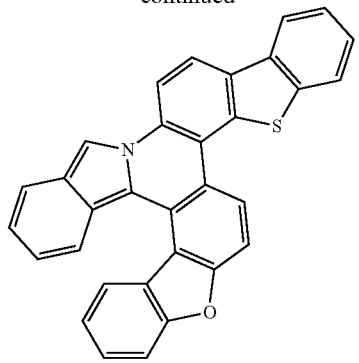
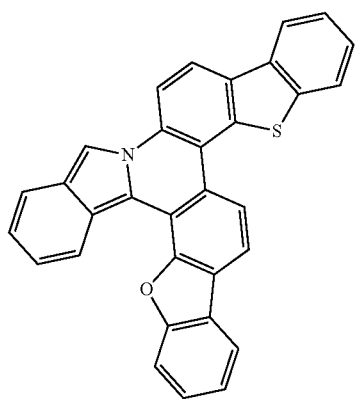
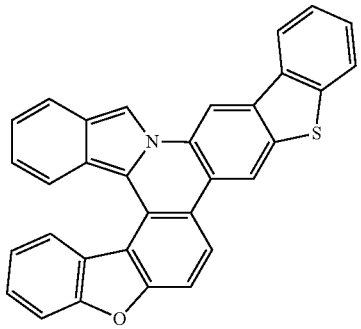
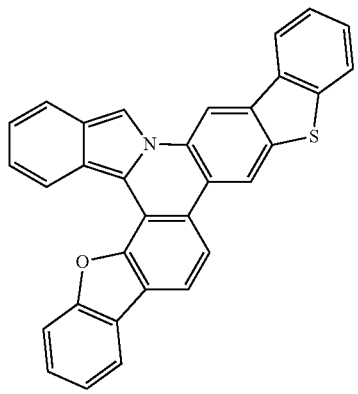
-continued
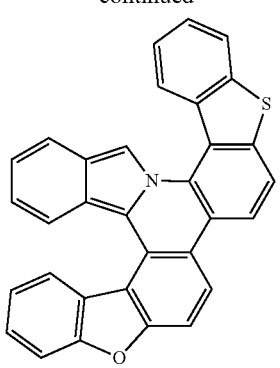
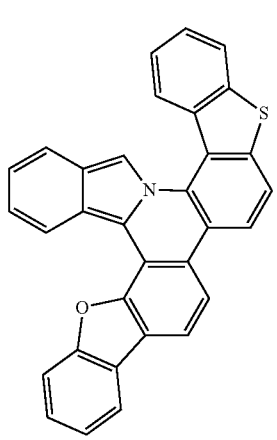
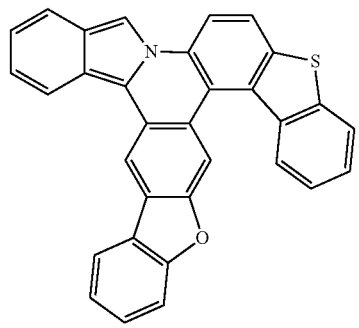
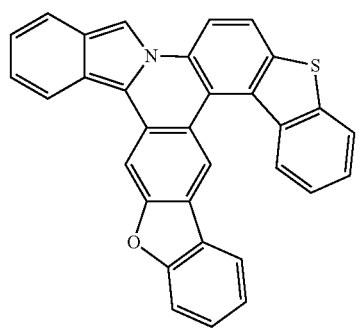

167
-continued
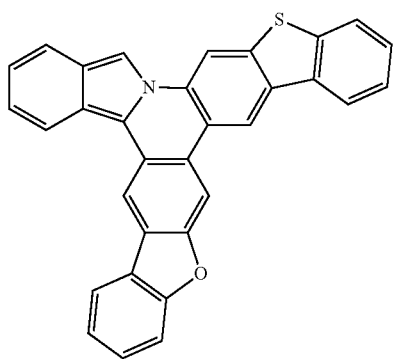
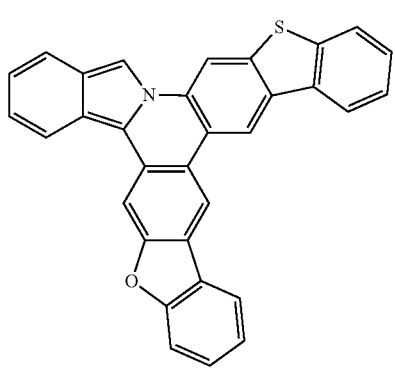
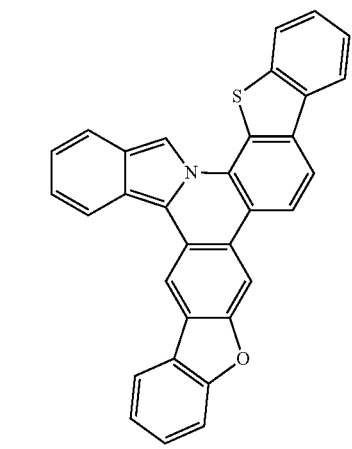
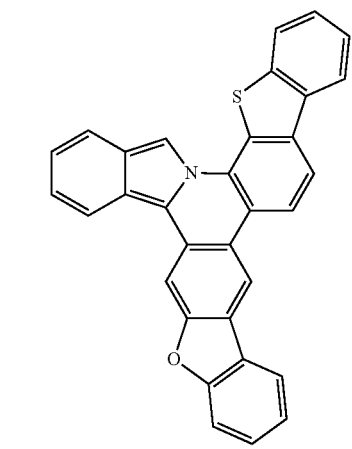
168
-continued
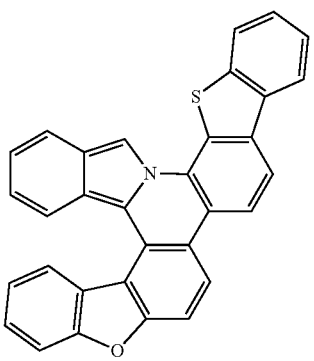
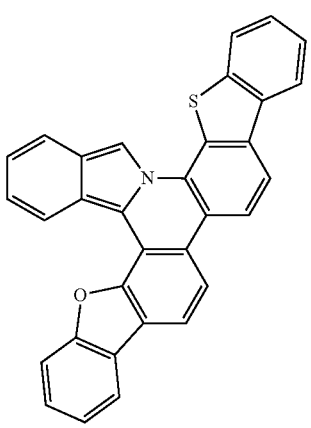
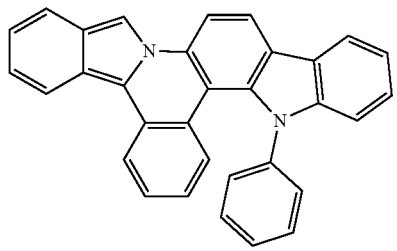
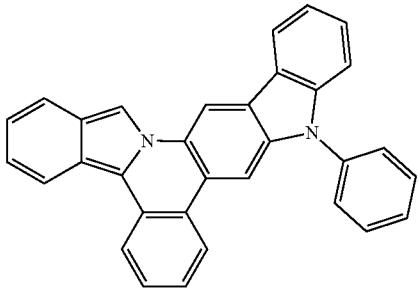
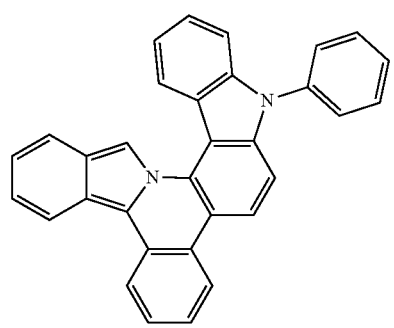

169
-continued
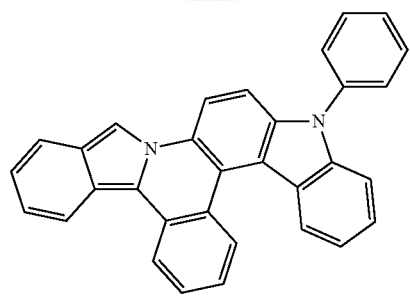
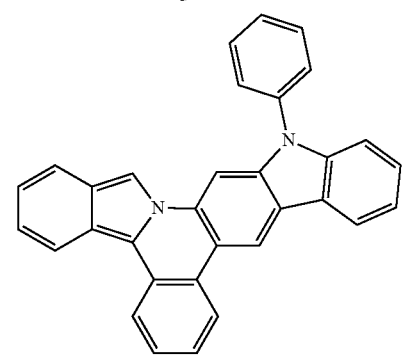
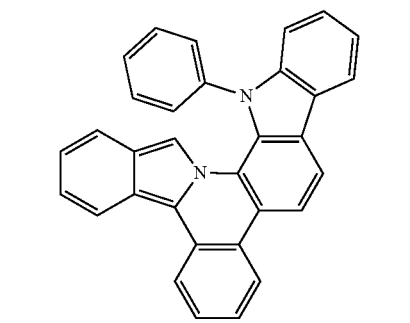
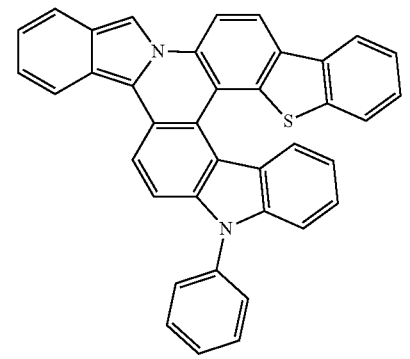
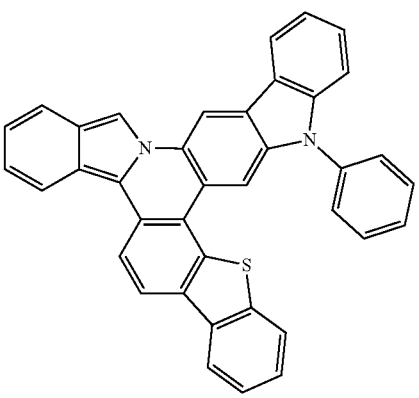
170
-continued
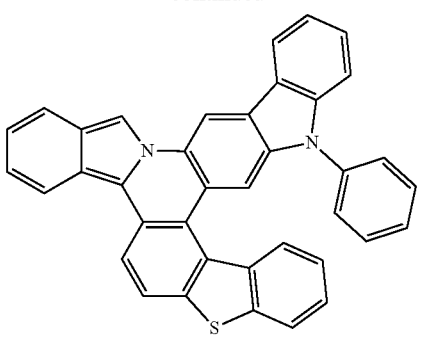
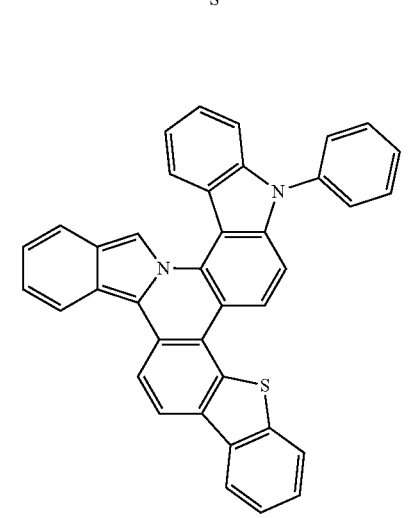
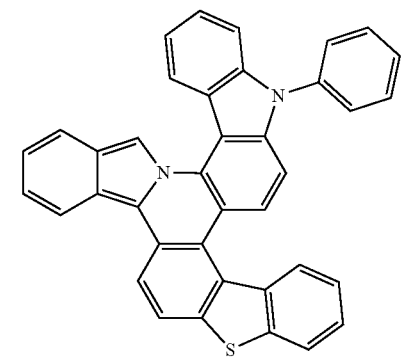
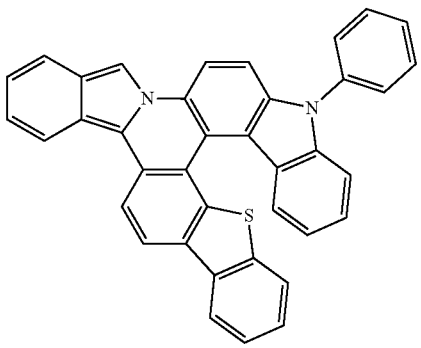

-continued
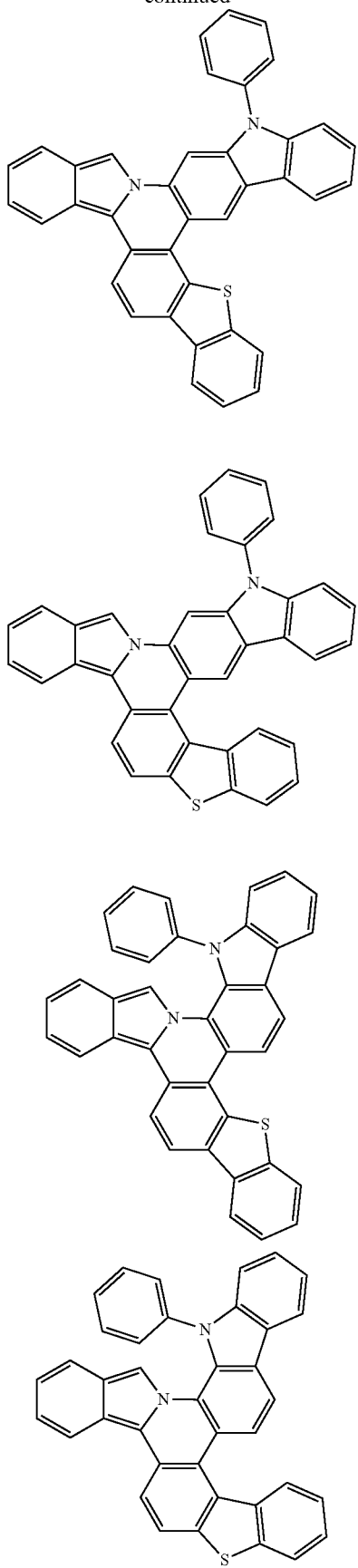
-continued
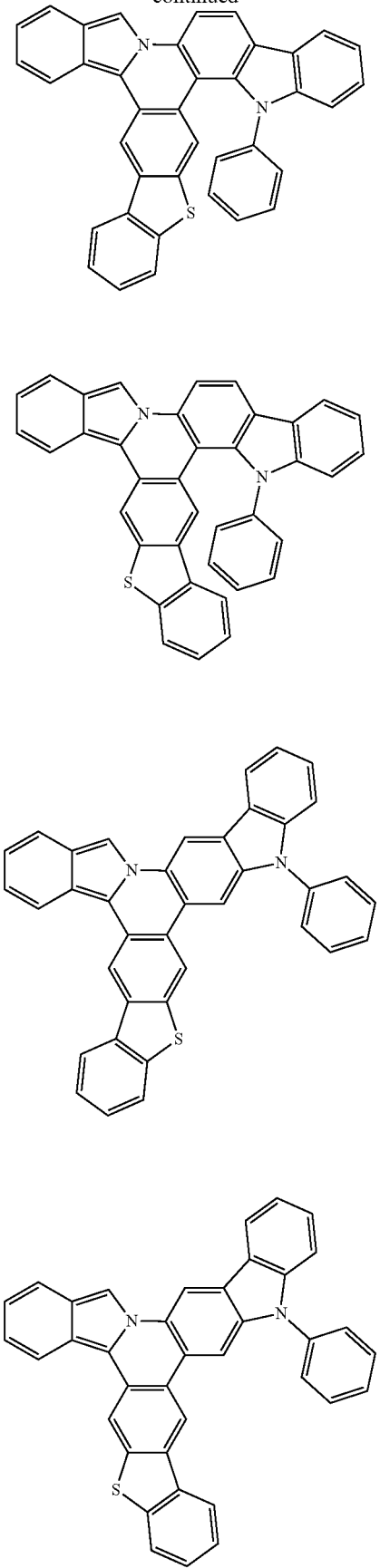

-continued
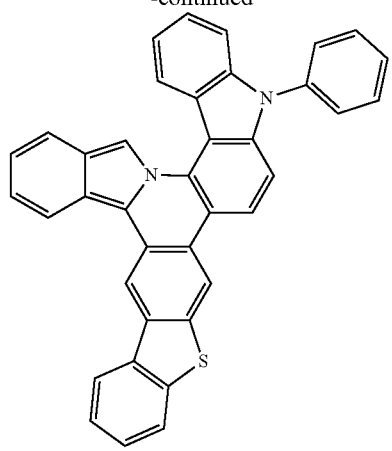
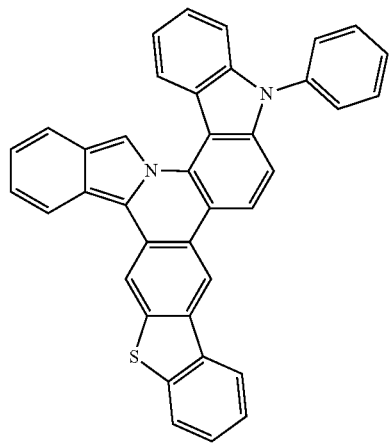
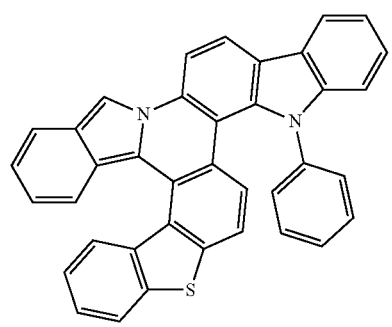
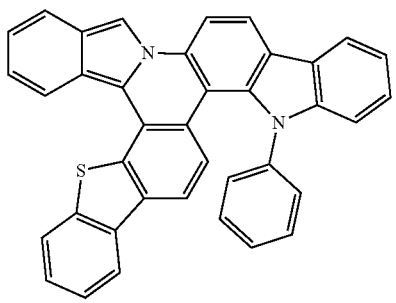
-continued
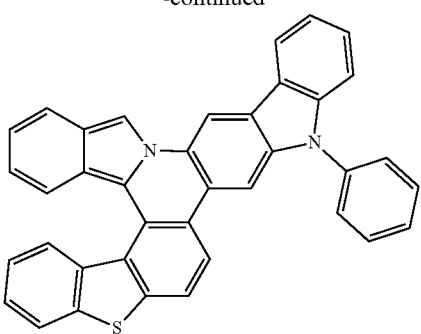
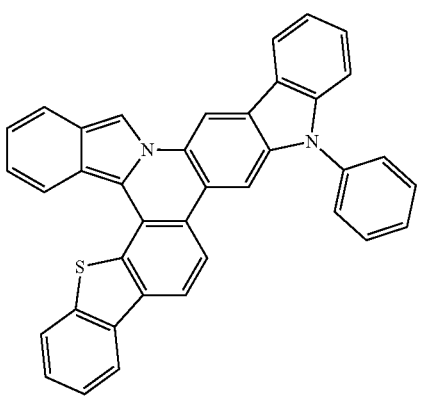
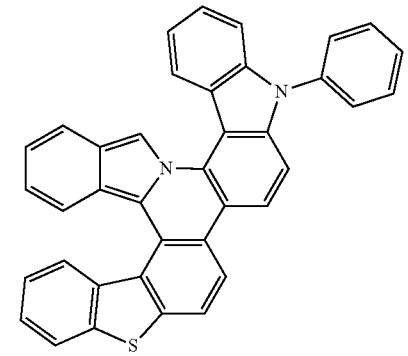
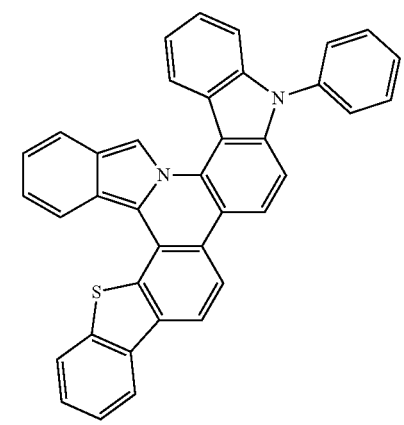

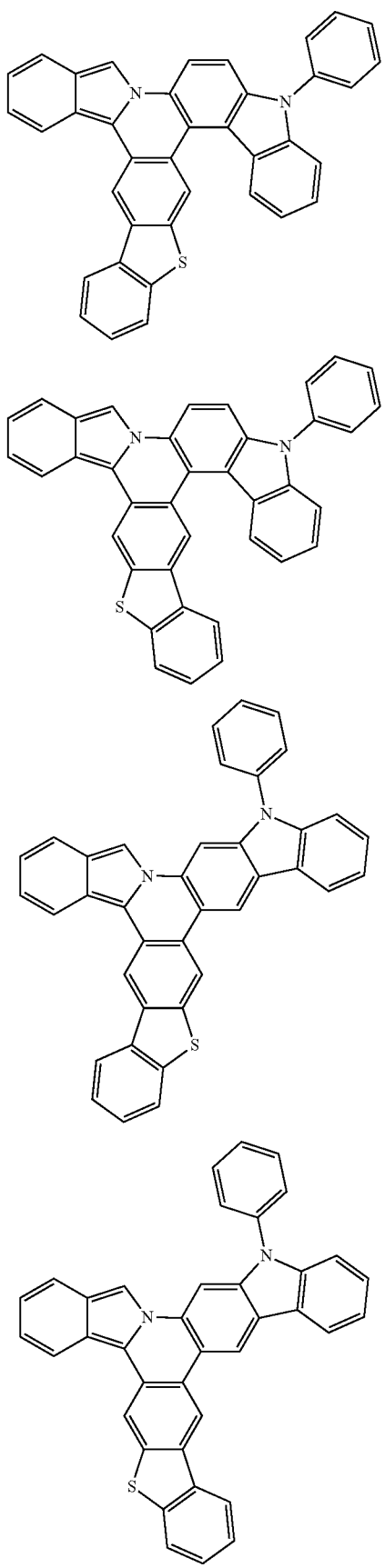
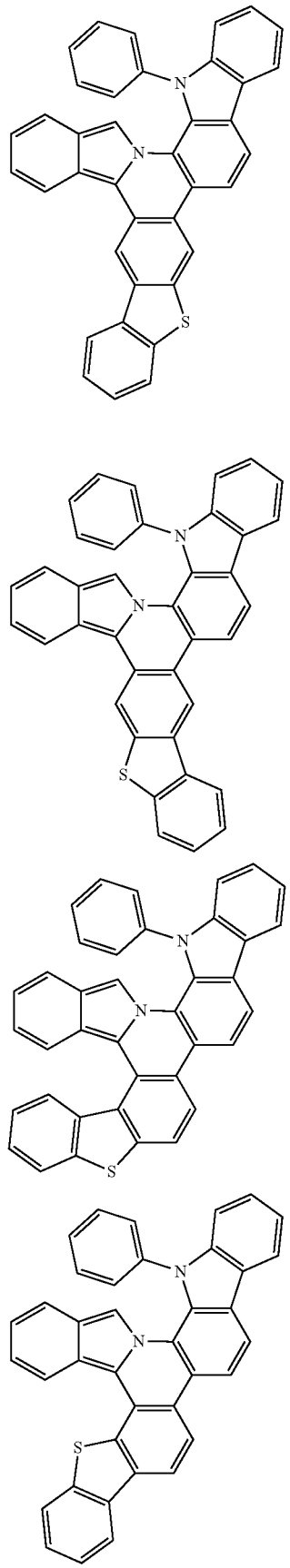

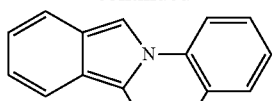
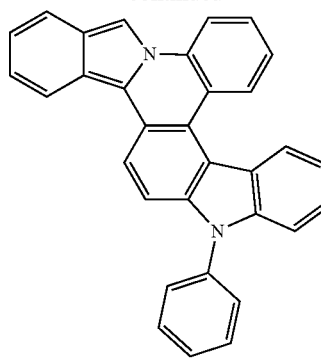
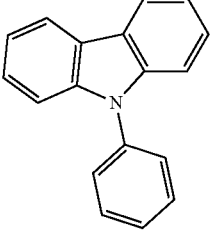
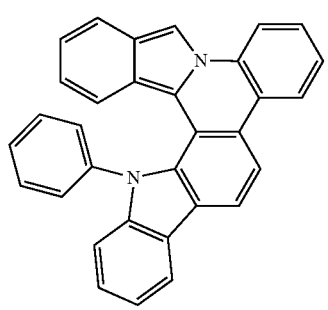
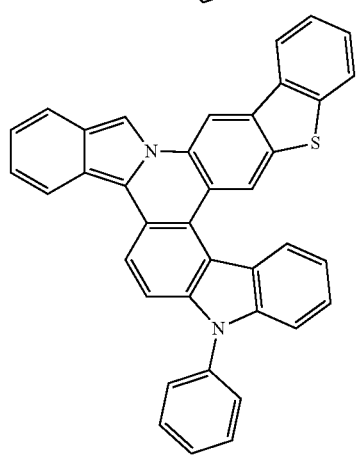
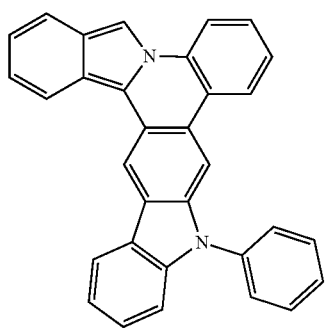
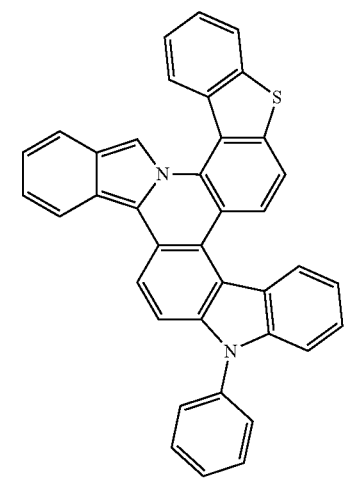
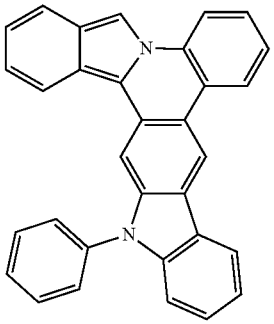
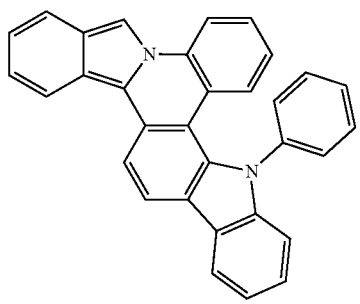
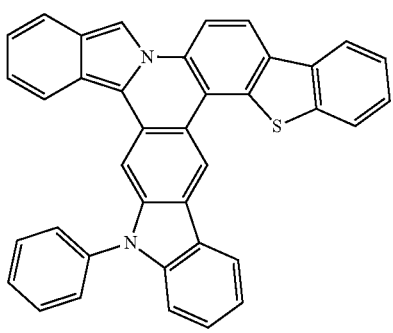

179
-continued
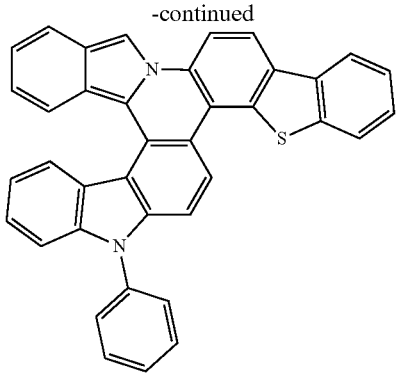
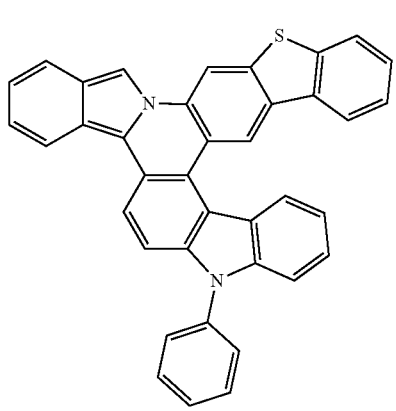
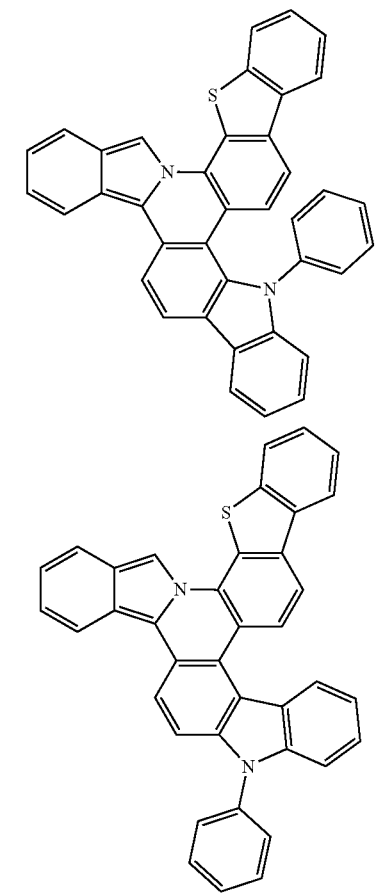
180
-continued
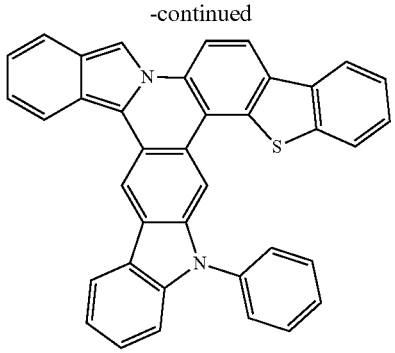
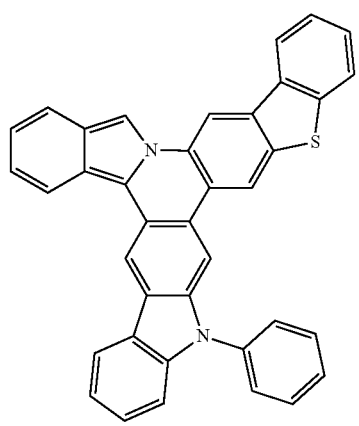
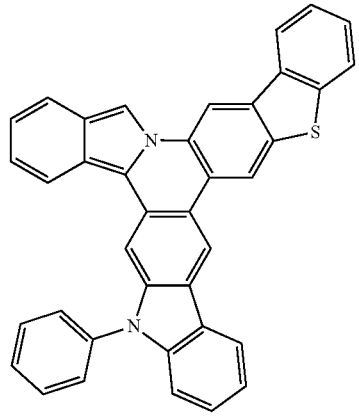
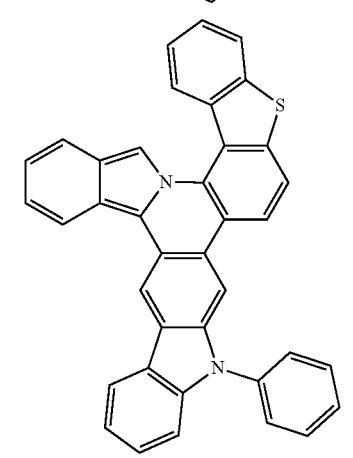

-continued
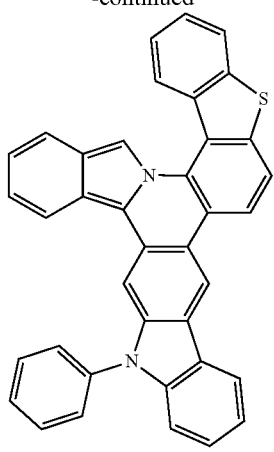
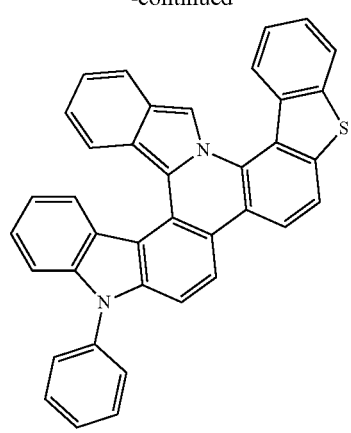
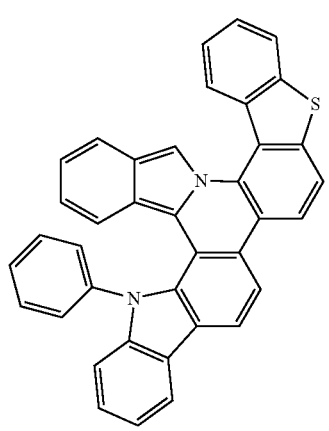
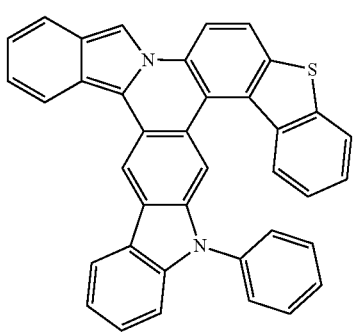
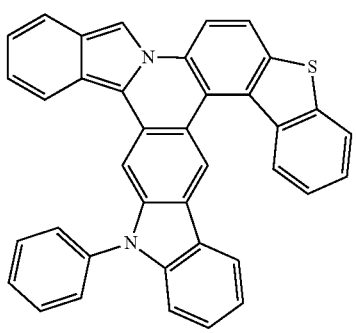

-continued

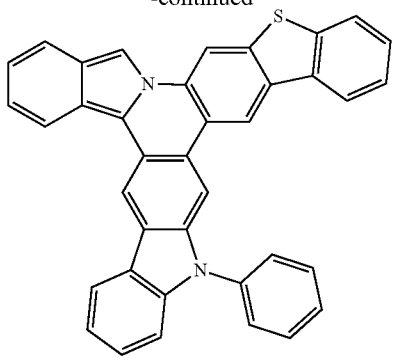

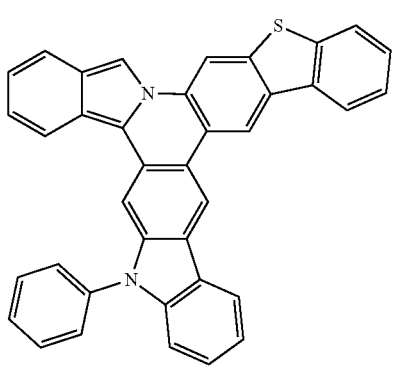

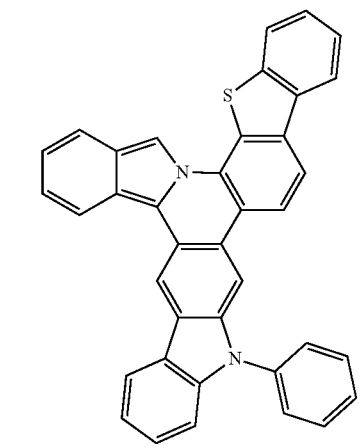

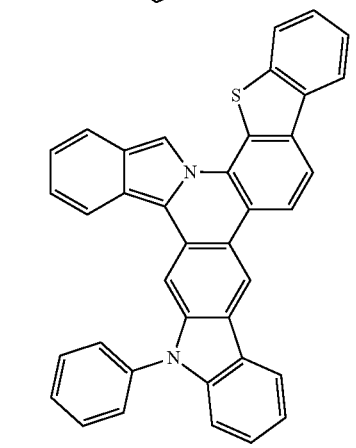

-continued

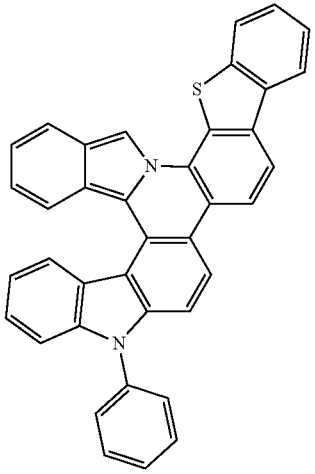

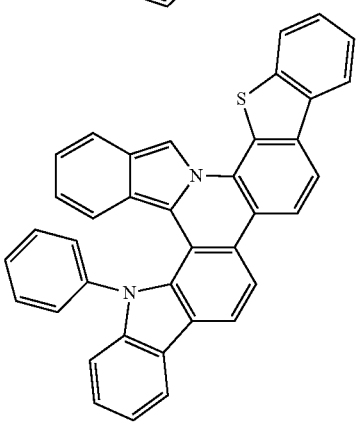

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the F and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbomenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula—$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula— $(A^1O(O)C-A^2-C(O)O)_a$— or —$(A^1O(O)C-A^2-OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula— $(A^1O-A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "cyanide" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein.

Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R," "$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

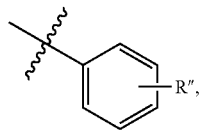

which is understood to be equivalent to a formula:

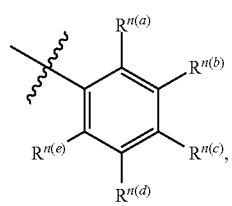

wherein n is typically an integer. That is, $R''$ is understood to represent five independent substituents, $R''^{n(a)}$, $R''^{n(b)}$, $R''^{n(c)}$, $R''^{n(d)}$, $R''^{n(e)}$. By "independent substituents," it is meant that each R substituent can be independently defined. For example, if in one instance $R''^{n(a)}$ is halogen, then $R''^{n(b)}$ is not necessarily halogen in that instance. In a case where there is a single $R''$ (e.g., only $R''^{n(a)}$), $R''$ is referred to as a "single substituent." In a case where there are two or more $R''$ (e.g., at least $R''^{n(a)}$ and $R''^{n(b)}$) $R''$ is referred to as a "multiple substituents."

Several references to R, $R^1$, $R^2$, $R^3$, $R^4$, $R^5$, $R^6$, etc. are made in chemical structures and moieties disclosed and described herein. Any description of R, $R^1$, $R^2$, $R^3$, $R^4$, $R^5$, $R^6$, etc. in the specification is applicable to any structure or moiety reciting R, $R^1$, $R^2$, $R^3$, $R^4$, $R^5$, $R^6$, etc. respectively.

The compounds disclosed herein are suited for use in a wide variety of devices, including, for example, organic light emitting diodes (OLEDs) for full color displays and lighting applications.

Also disclosed herein are compositions including one or more compounds disclosed herein. The present disclosure provides light emitting device that include one or more compositions described herein. The present disclosure also provides a photovoltaic device comprising one or more complexes or compositions described herein. Further, the present disclosure also provides a luminescent display device comprising one or more compounds described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Some of these synthetic examples have been performed. Others are based on an understanding of related synthetic procedures and are predictive in nature Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

Example 1

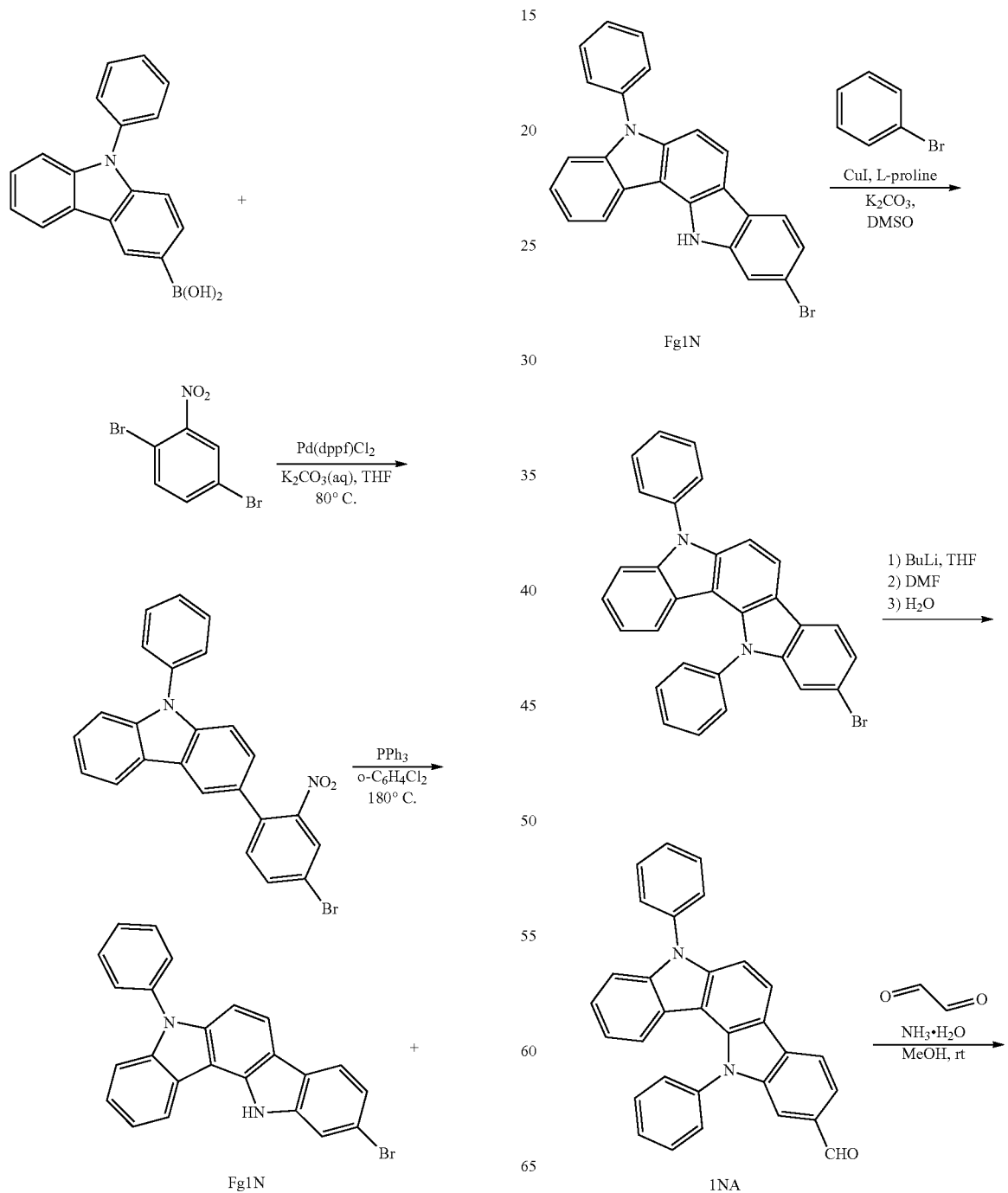
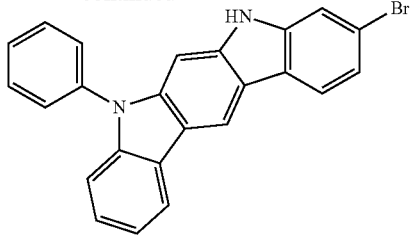

-continued

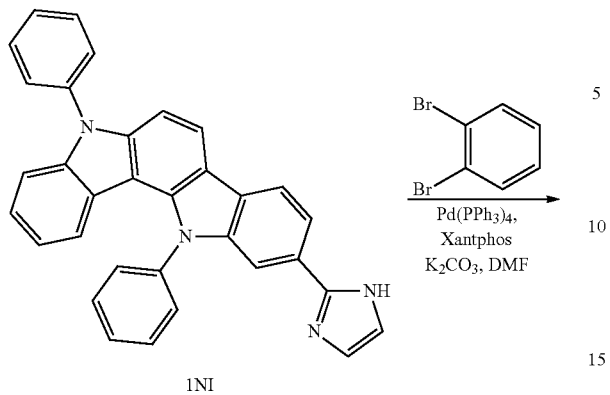

1NI

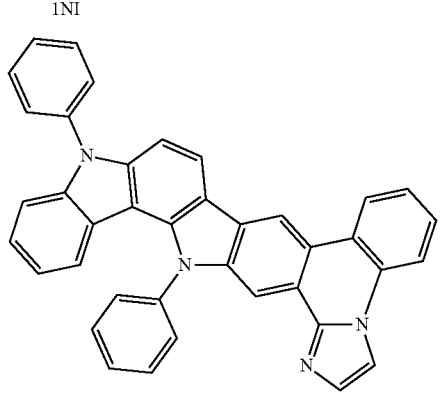

DFE-1N-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-1 in 61% yield.

Example 2

1NI

-continued

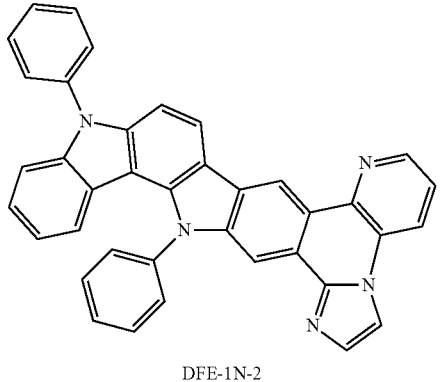

DFE-1N-2

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 1NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1N-2 in 53% yield.

Example 3

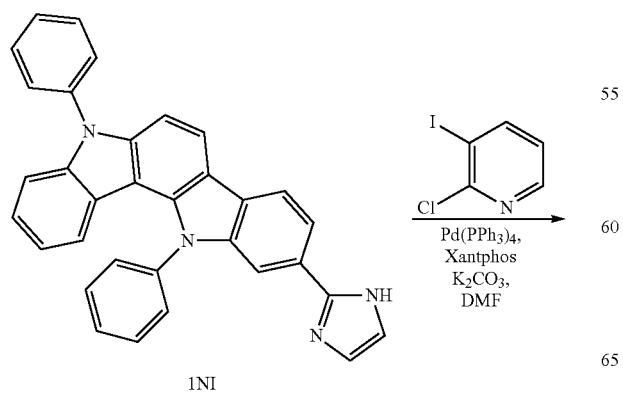

1NI

DFE-1N-3

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 1NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1N-3 in 22% yield.

Example 4

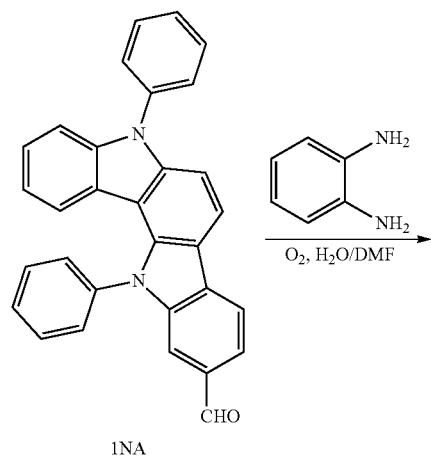

1NA

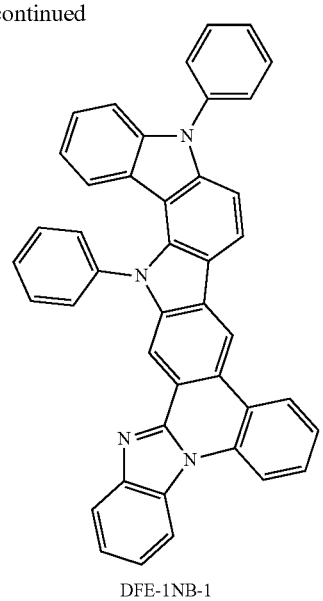

DFE-1NB-1

To a flame-dried flask were added Pd(PPh₃)₄ (10 mol %), Xantphos (10 mol %), Cs₂CO₃ (3eq) and 1,2-dibromobenzene (1.2 eq). Then, 1NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1NB-1 in 55% yield.

Example 5

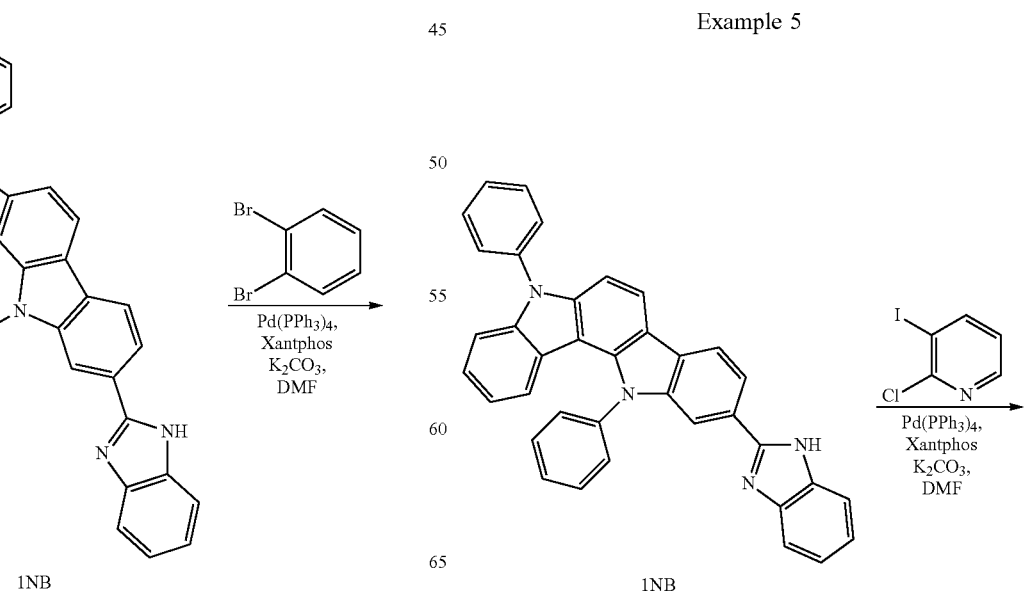

-continued

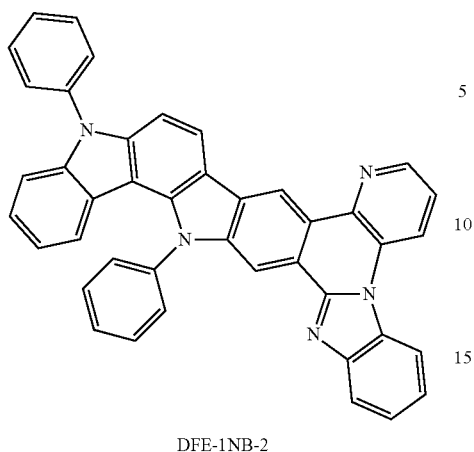

DFE-1NB-2

To a flame-dried flask were added Pd(PPh₃); (10 mol %), Xantphos (10 mol %). Cs₂CO₃ (3eq) and 2-chloro-3-iodopyridine (1.2 eq). Then, 1NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1NB-2 in 42% yield.

Example 6

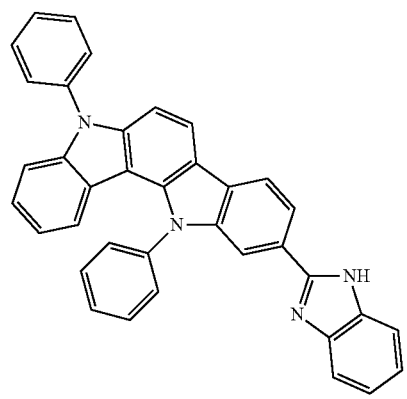

1NB

-continued

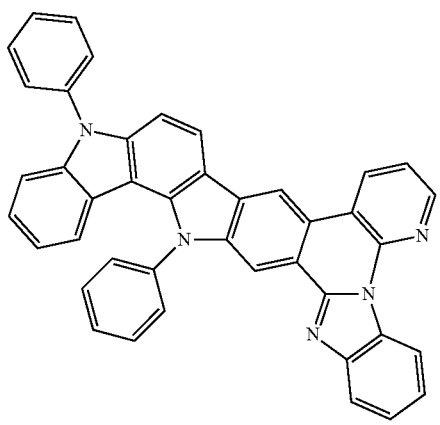

DFE-1NB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 1NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1NB-3 in 35% yield.

Example 7

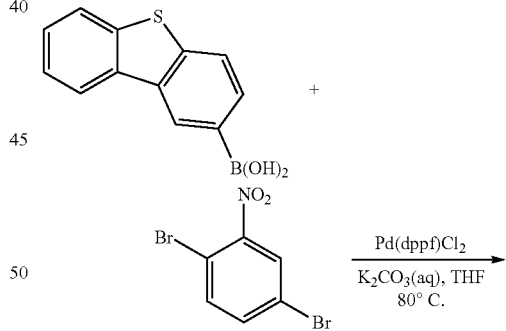

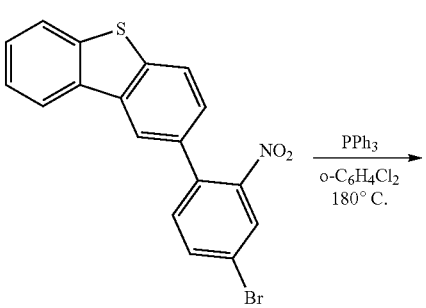

199
-continued

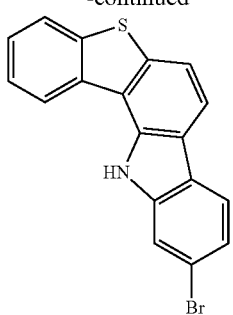
Fg1S

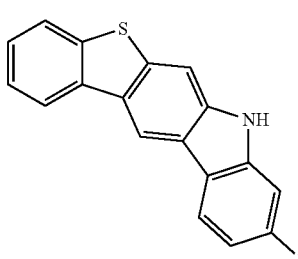
Fg2S

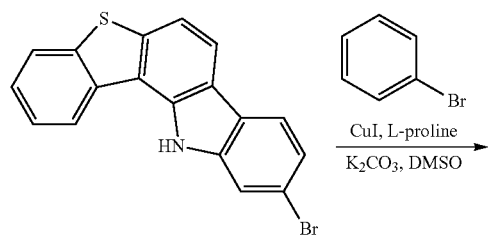
Fg1S

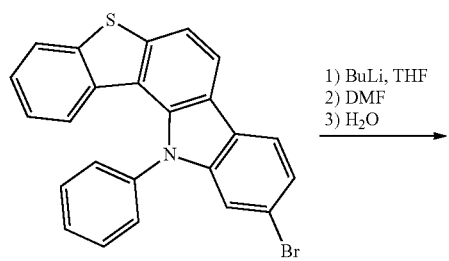

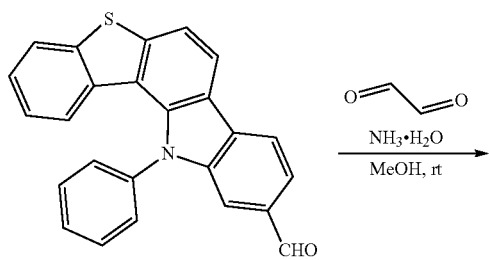
1SA

200
-continued

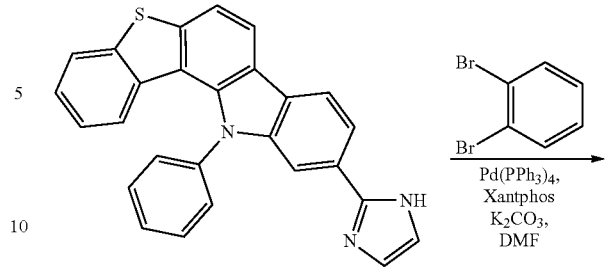
1SI

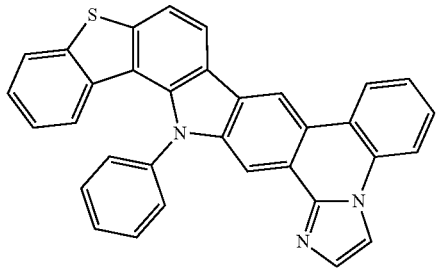
DFE-1S-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-1 in 64% yield.

Example 8

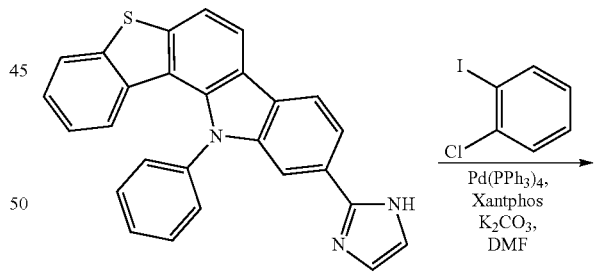
1SI

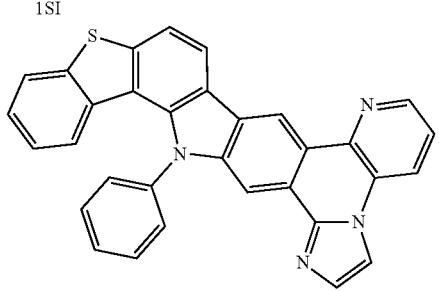
DFE-1S-2

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-2 in 67% yield.

Example 9

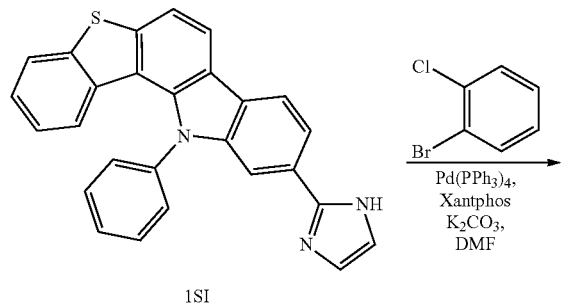

Example 10

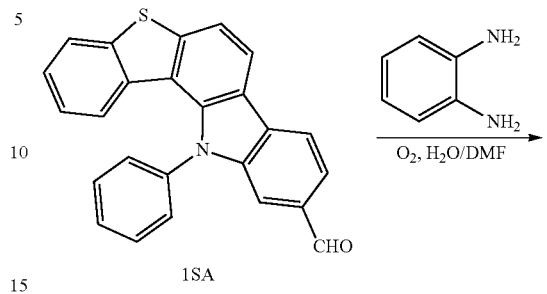

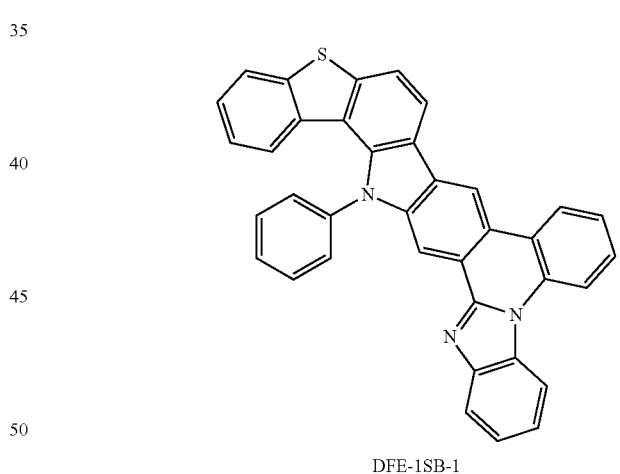

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 1SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1S-3 in 22% yield.

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 1SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-1SB-1 in 66% yield.

Example 11

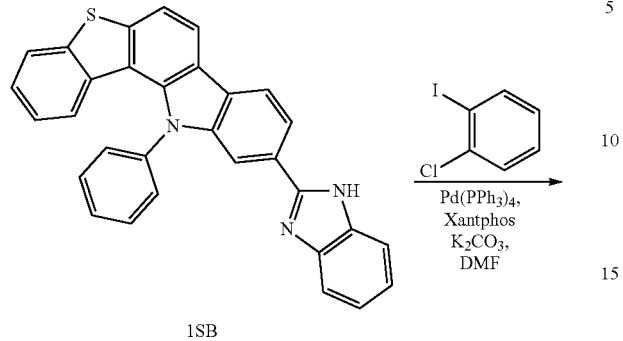

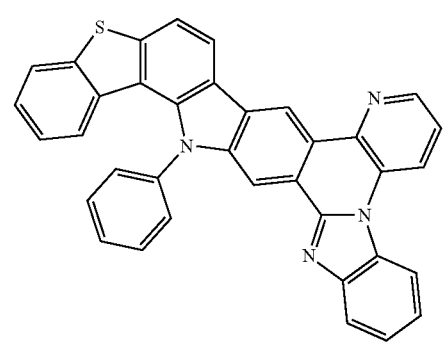

To a flame-dried flask were added Pd(PPh₃)₄ (10 mol %), Xantphos (10 mol %), Cs₂CO₃ (3eq) and 2-chloro-3-iodopyridine (1.2 eq). Then, 1SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1SB-2 in 45% yield.

Example 12

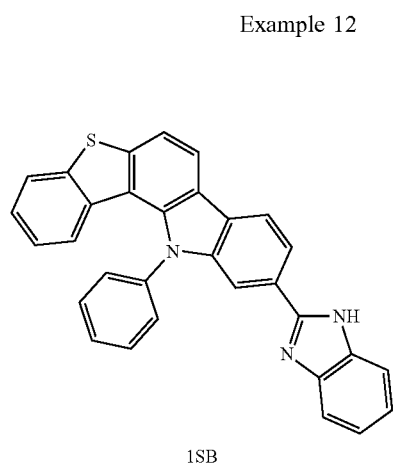

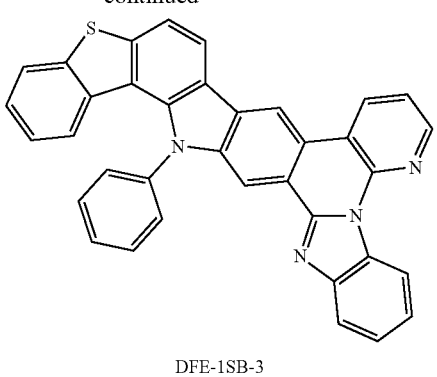

To a flame-dried flask were added Pd(PPh₃)₄ (10 mol %), Xantphos (10 mol %), Cs₂CO₃ (3eq) and 2-bromo-3-chloropyridine (1.2 eq). Then, 1SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1SB-3 in 39% yield.

Example 13

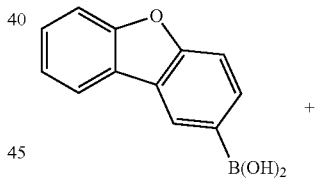

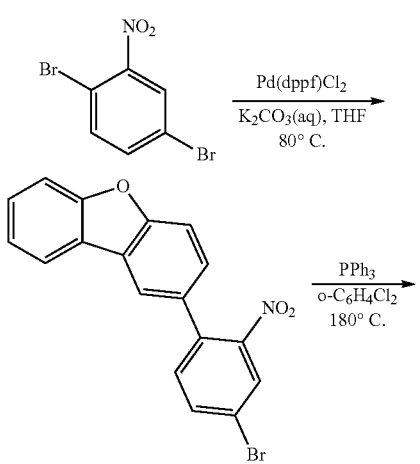

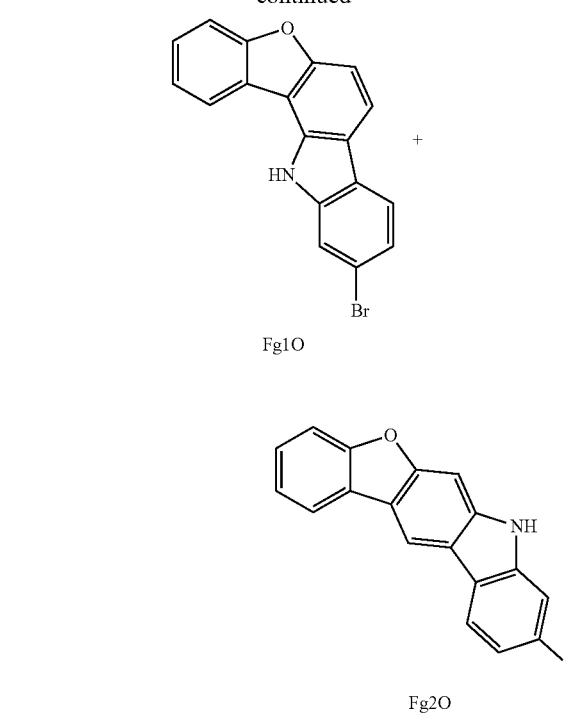

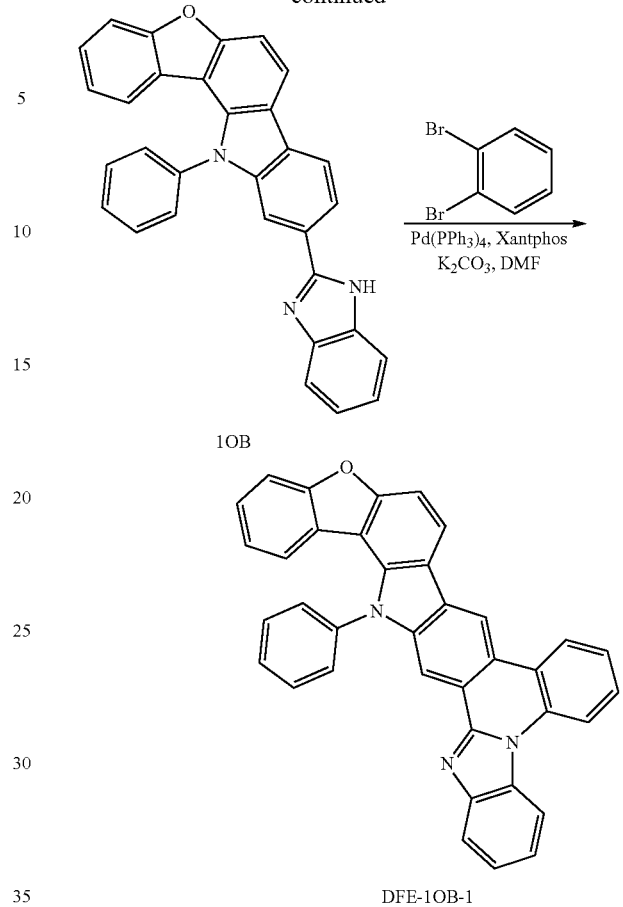

To a flame-dried flask were added Pd(PPh₃)₄ (10 mol %), Xantphos (10 mol %), Cs₂CO₃ (3eq) and 1,2-dibromobenzene (1.2 eq). Then, 1OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1OB-1 in 61% yield.

Example 14

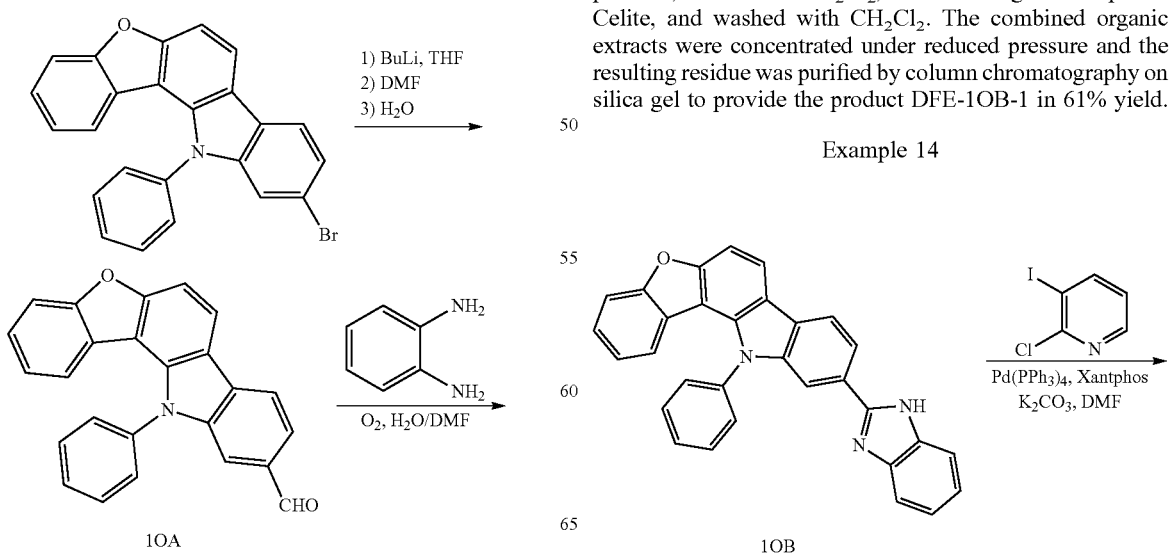

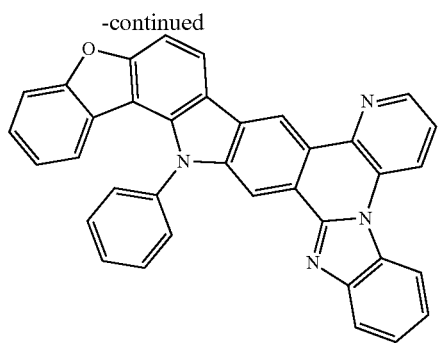

DFE-1OB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 1OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1OB-2 in 41% yield.

Example 15

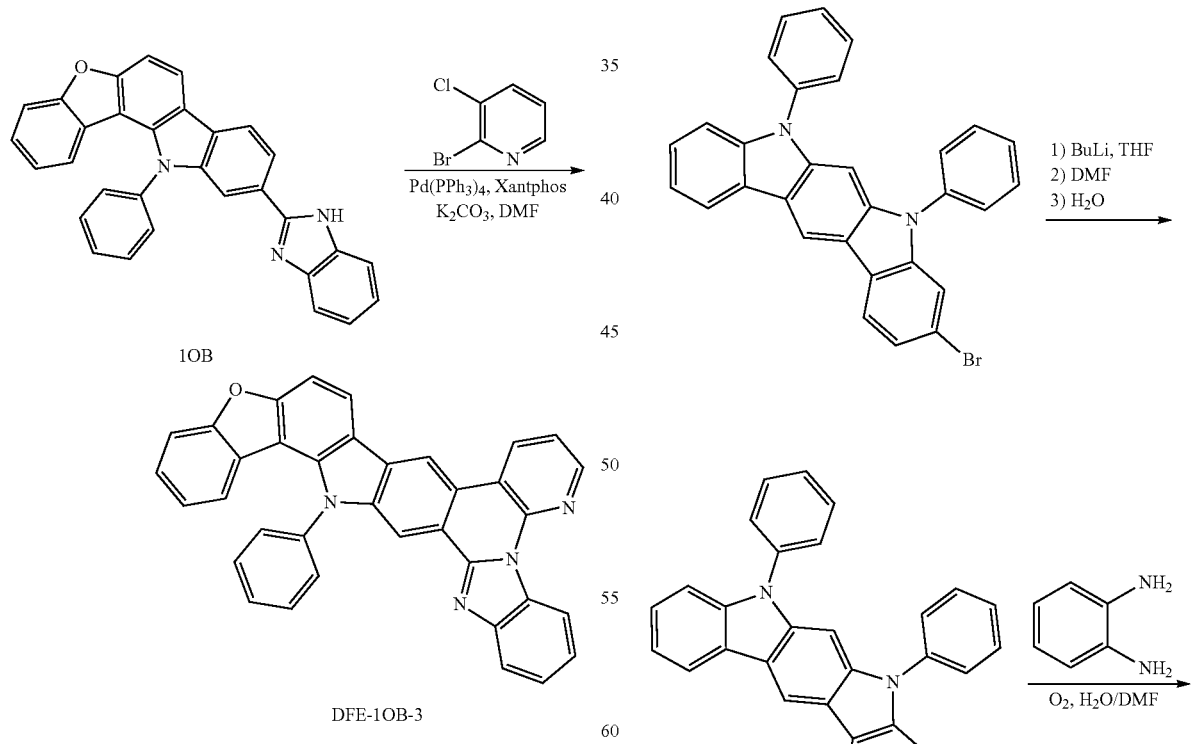

1OB

DFE-1OB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 1OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-1OB-3 in 36% yield.

Example 16

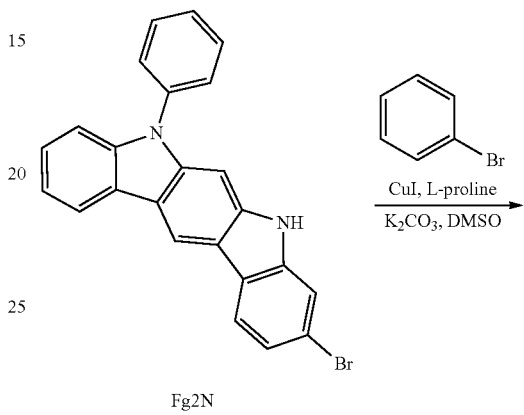

Fg2N

2NA

Example 17

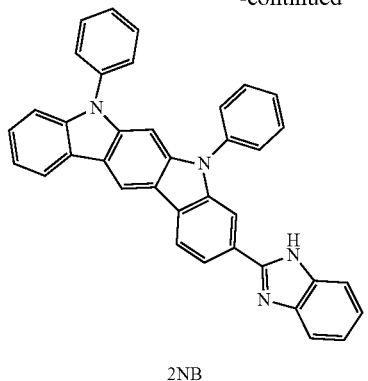

2NB

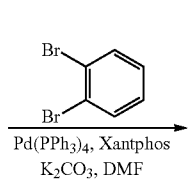

Pd(PPh₃)₄, Xantphos
K₂CO₃, DMF

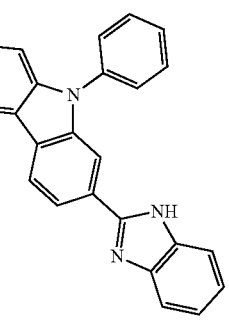

2NB

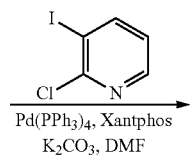

Pd(PPh₃)₄, Xantphos
K₂CO₃, DMF

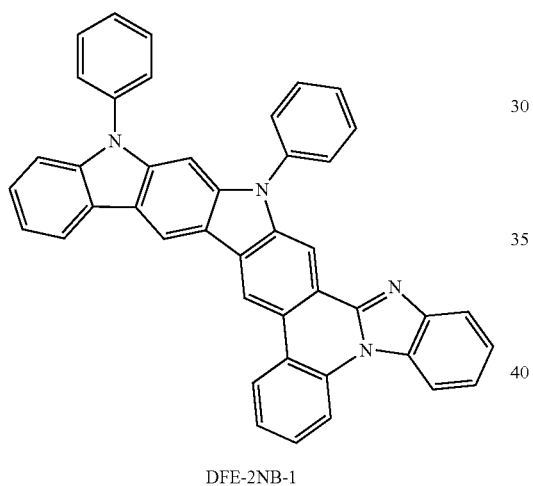

DFE-2NB-1

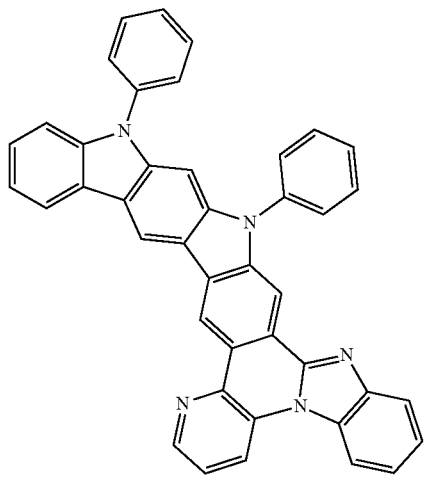

DFE-2NB-2

To a flame-dried flask were added Pd(PPh₃)₄ (10 mol %), Xantphos (10 mol %), Cs₂CO₃ (3eq) and 1,2-dibromobenzene (1.2 eq). Then, 2NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2NB-1 in 55% yield.

To a flame-dried flask were added Pd(PPh₃)₄ (10 mol %), Xantphos (10 mol %), Cs₂CO₃ (3eq) and 2-chloro-3-iodopyridine (1.2 eq). Then, 2NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2NB-2 in 37% yield.

Example 18

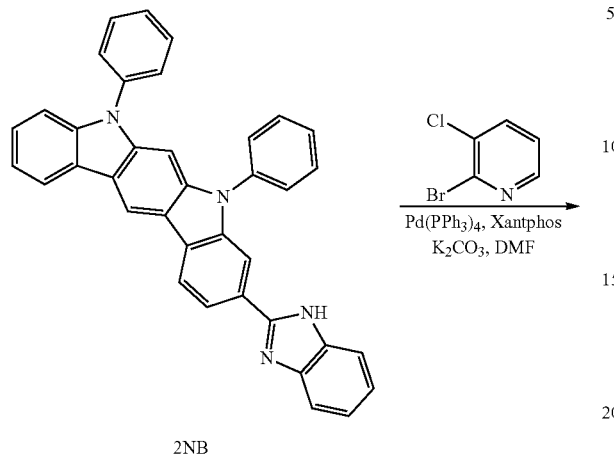

2NB

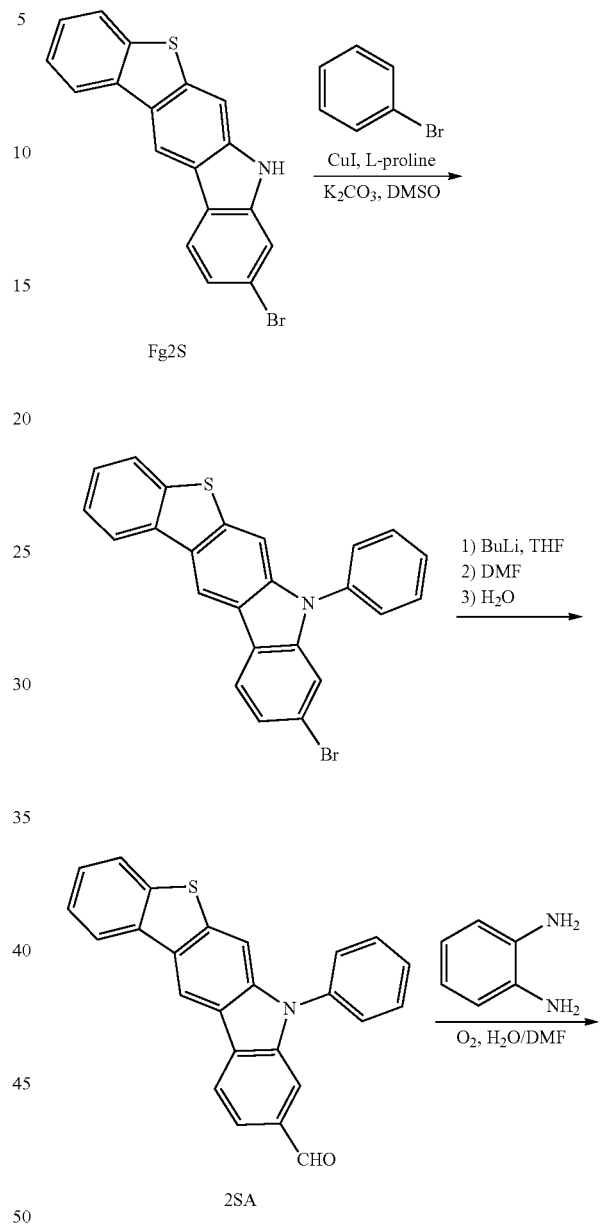

Example 19

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 2NB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2NB-3 in 33% yield.

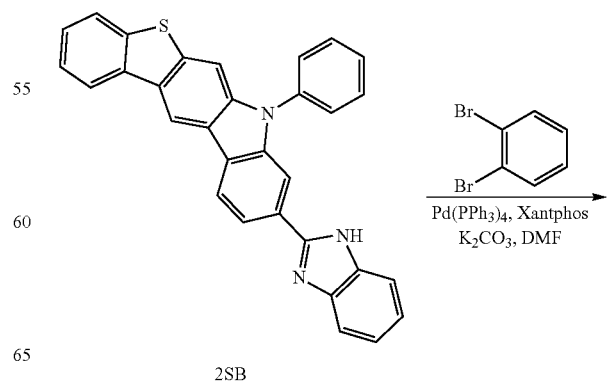

2SB

-continued

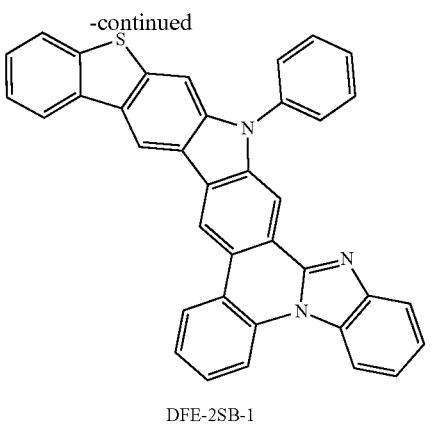

DFE-2SB-1

To a flame-dried flask were added Pd(PPh₃)₄ (10 mol %), Xantphos (1 mol %), Cs₂CO₃ (3eq) and 1,2-dibromobenzene (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-1 in 73% yield.

Example 20

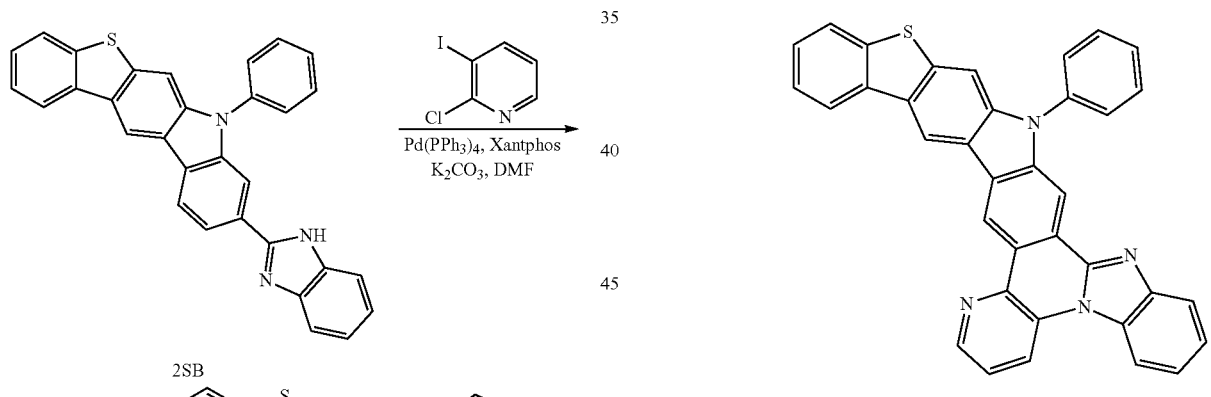

DFE-2SB-2

To a flame-dried flask were added Pd(PPh₃); (10 mol %), Xantphos (10 mol %), Cs₂CO₃ (3eq) and 2-chloro-3-iodopyridine (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-2 in 42% yield.

Example 21

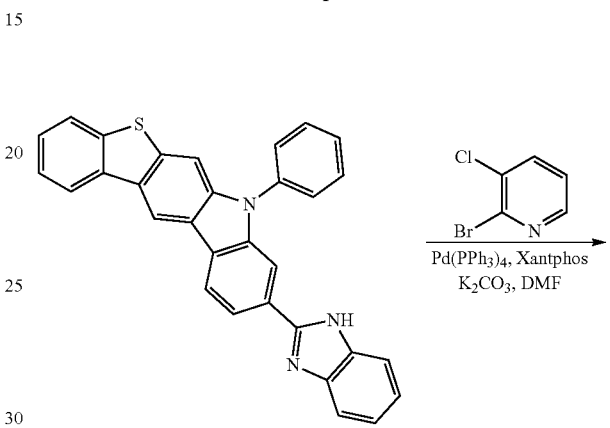

2SB

DFE-2SB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 2SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2SB-3 in 38% yield.

Example 22

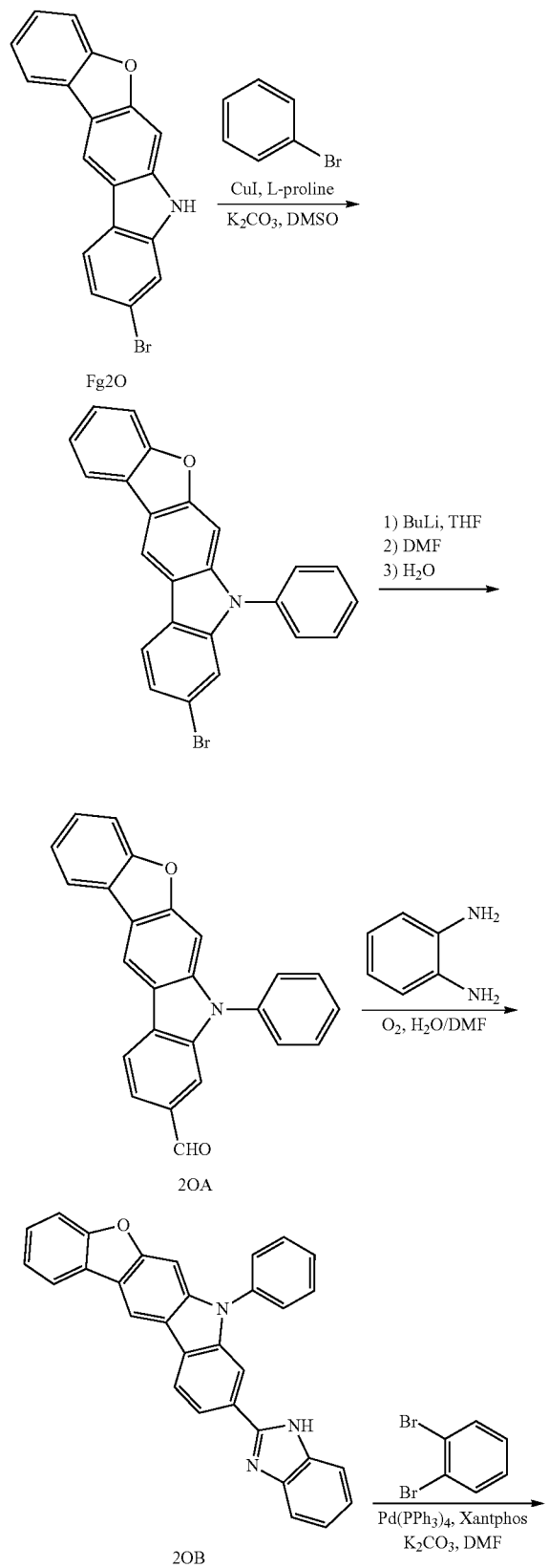

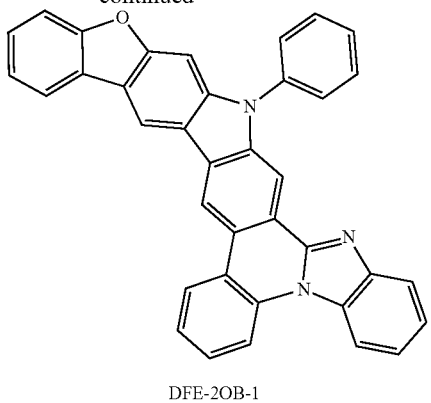

DFE-2OB-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 2OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-2OB-1 in 68% yield.

Example 23

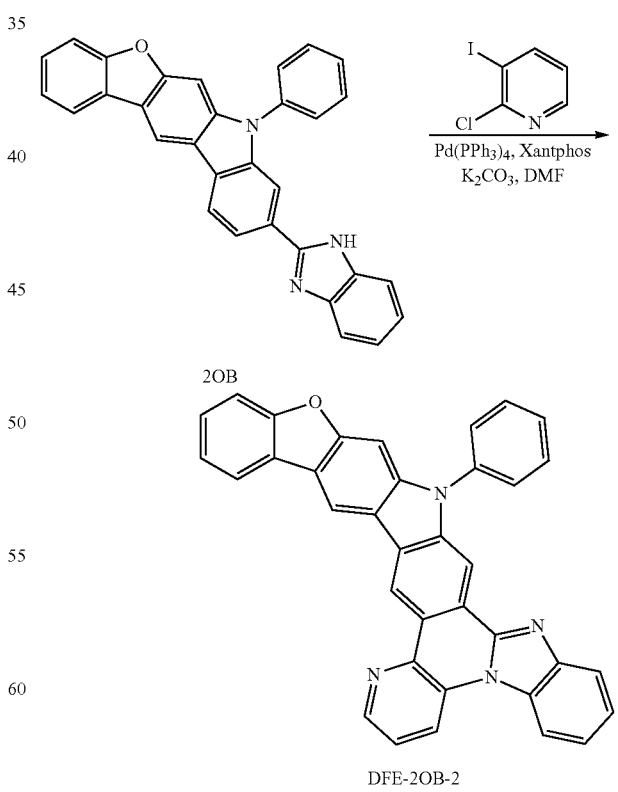

DFE-2OB-2

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 2OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2OB-2 in 34% yield.

Example 24

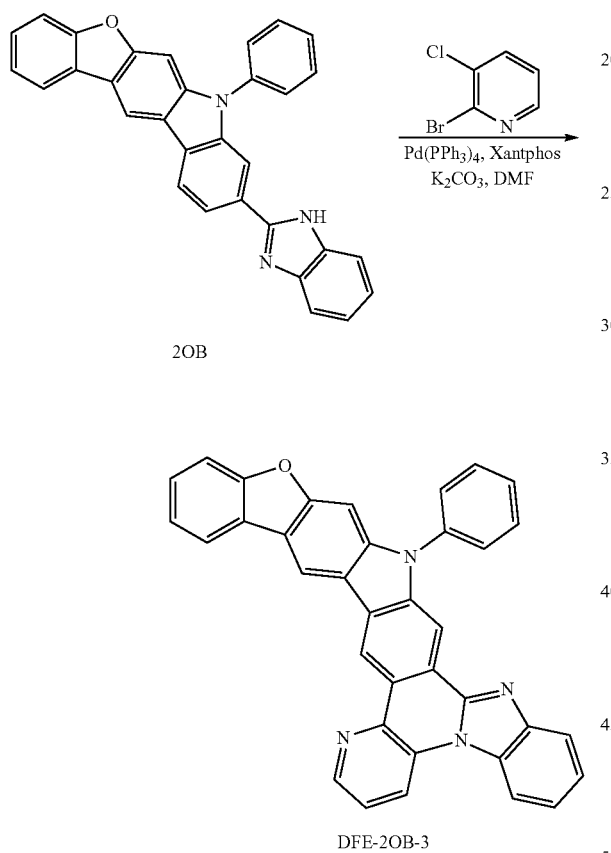

Example 25

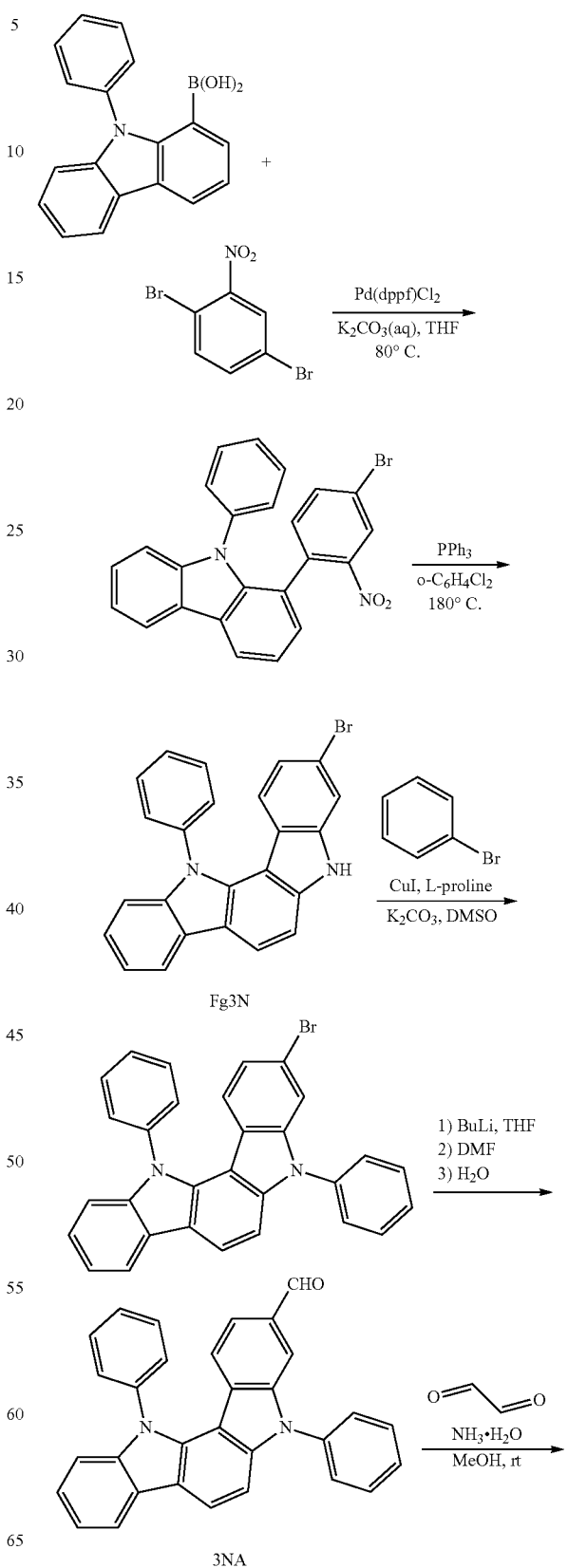

To a flame-dried flask were added Pd(PPh₃)₄ (10 mol %), Xantphos (10 mol %), Cs₂CO₃ (3eq) and 2-bromo-3-chloropyridine (1.2 eq). Then, 2OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-2OB-3 in 32% yield.

-continued

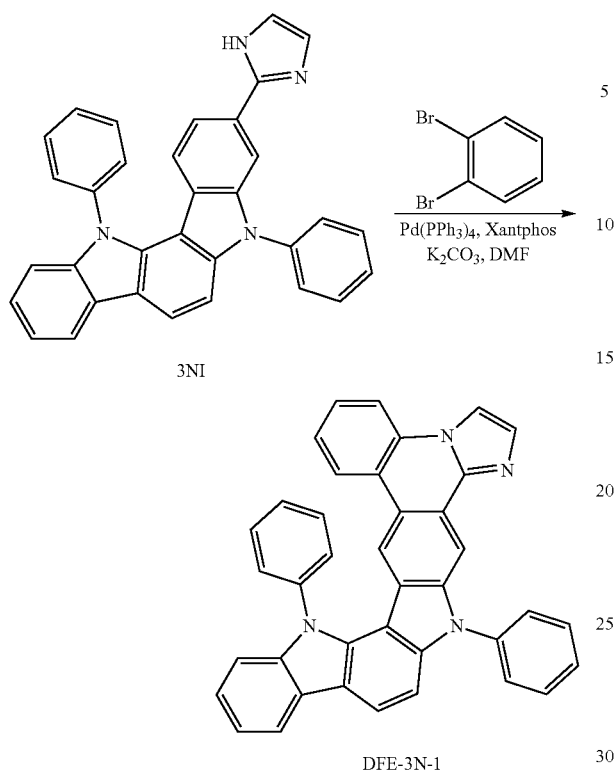

3NI

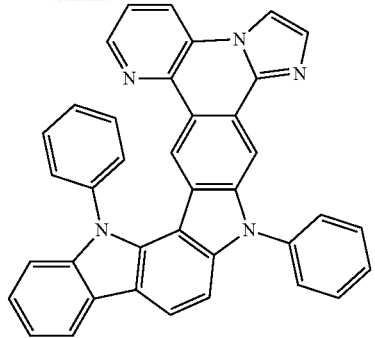

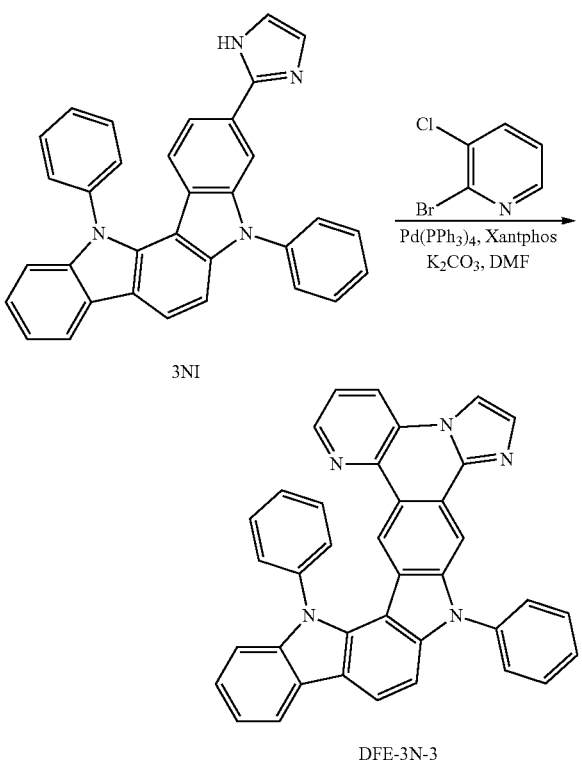 [SMILES: c1ccc(-n2c3cc(-c4ncc[nH]4)ccc3c3c2ccc2c4ccccc4n(-c4ccccc4)c23)cc1 ; Clc1cccnc1Br ; c1ccc(-n2c3cc4c(cc3c3c2ccc2c5ccccc5n(-c5ccccc5)c23)c2ncccc2n2ccnc42)cc1]

DFE-3N-2

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-2 in 30% yield.

Example 27

DFE-3N-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 3NI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3N-1 in 71% yield.

Example 26

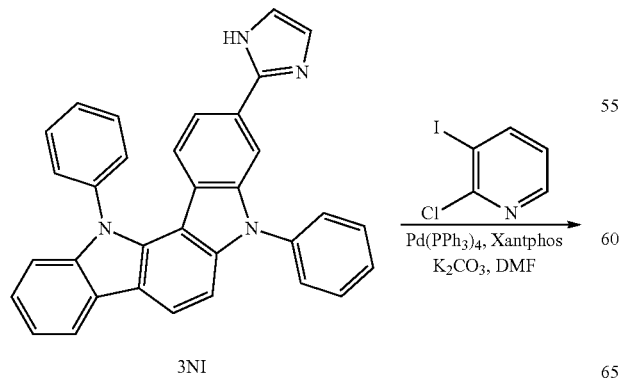

3NI

DFE-3N-3

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 3NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3N-3 in 24% yield.

Example 28 and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3NB-1 in 66% yield.

Example 29

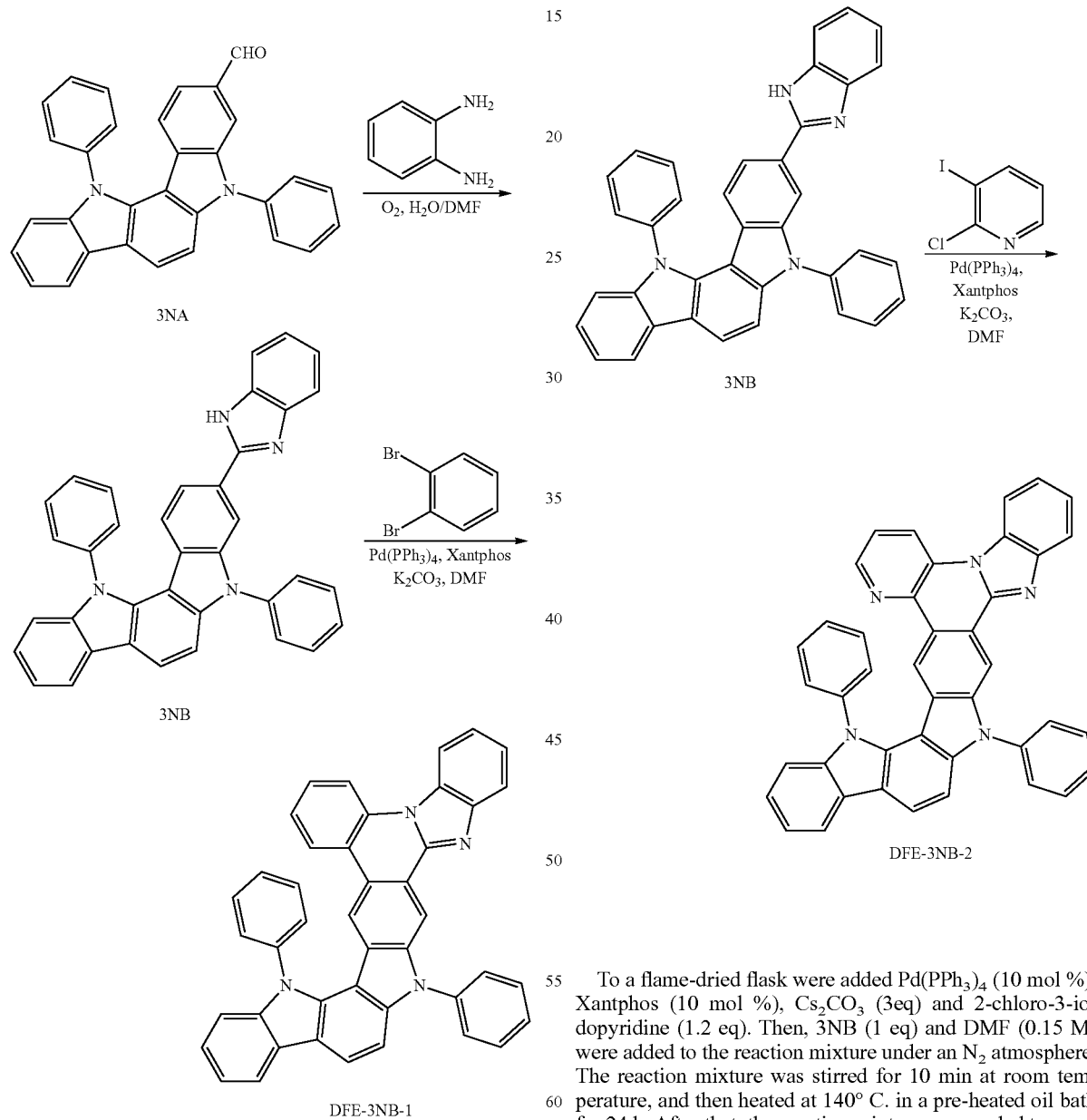

To a flame-dried flask were added Pd(PPh₃)₄ (10 mol %), Xantphos (10 mol %), Cs₂CO₃ (3eq) and 1,2-dibromobenzene (1.2 eq). Then, 3NB (1 eq) and DMF (0.15 M) were added to the reaction mixture under an N₂ atmosphere. The reaction mixture was stirred for 10 min at room temperature, To a flame-dried flask were added Pd(PPh₃)₄ (10 mol %), Xantphos (10 mol %), Cs₂CO₃ (3eq) and 2-chloro-3-iodopyridine (1.2 eq). Then, 3NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3N-2 in 44% yield.

Example 30

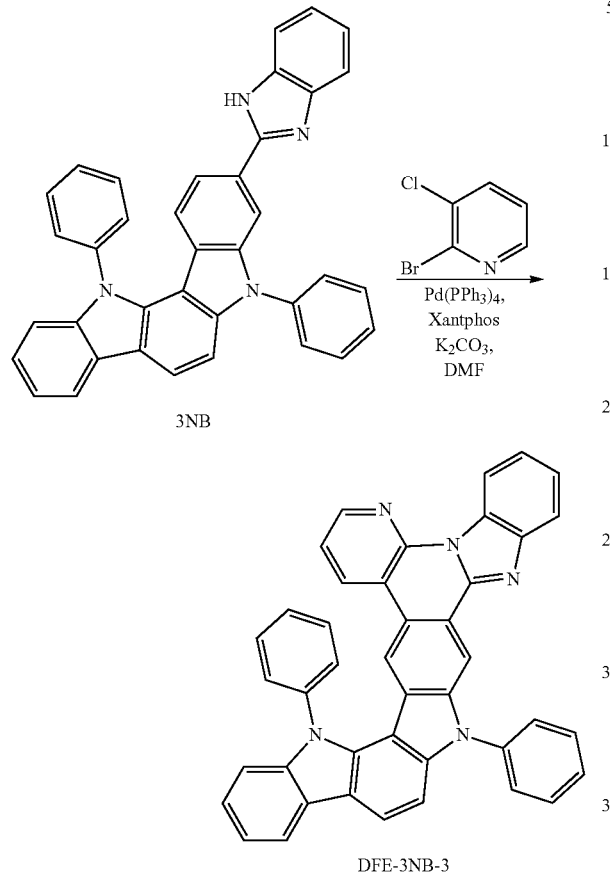

To a flame-dried flask were added Pd(PPh₃)₄ (10 mol %), Xantphos (10 mol %), Cs₂CO₃ (3eq) and 2-bromo-3-chloropyridine (1.2 eq). Then, 3NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3NB-3 in 21% yield.

Example 31

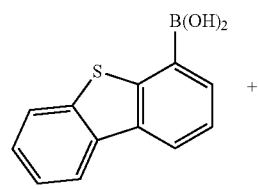

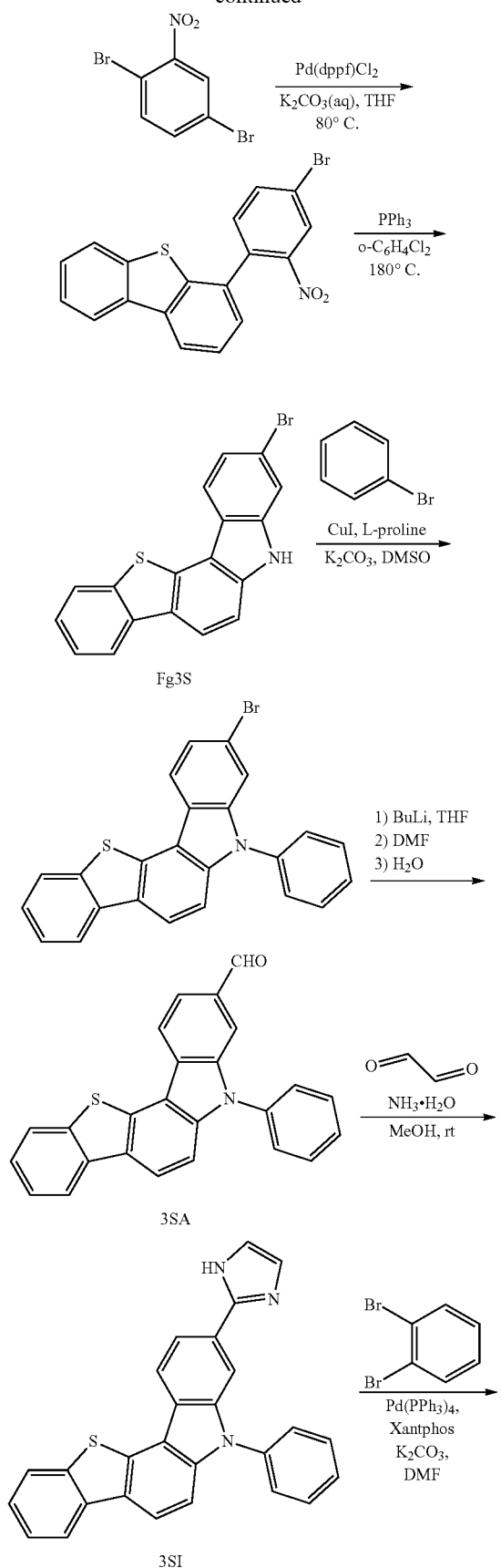

-continued

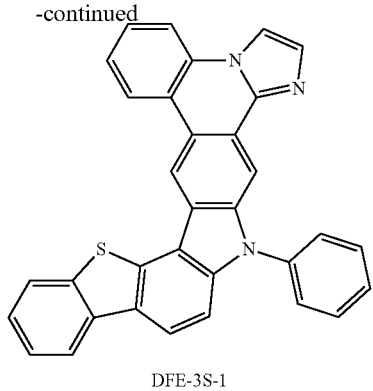

DFE-3S-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 3SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$CO$_2$. The combined organic extracts were concentrated under reduced pressure and the resulting residue was purified by column chromatography on silica gel to provide the product DFE-3S-1 in 75% yield.

Example 32

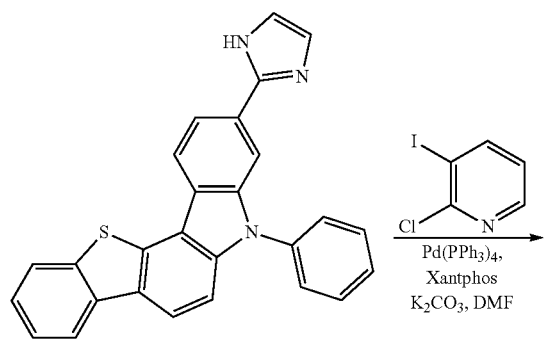

DFE-3S-2

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 3SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3S-2 in 64% yield.

Example 33

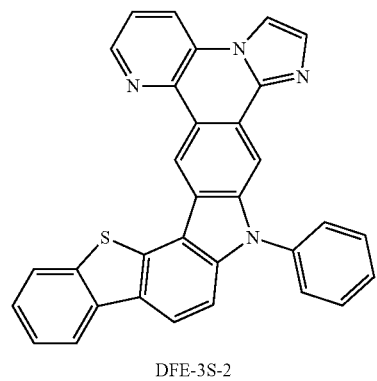

DFE-3S-2

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 3SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3S-3 in 29% yield.

Example 34

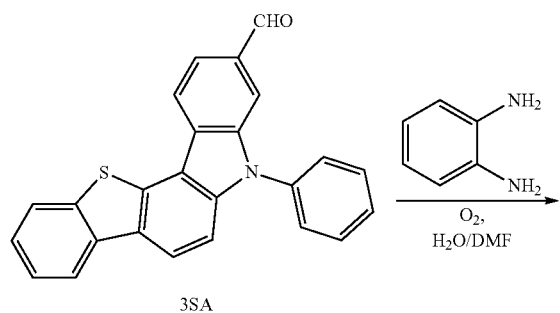

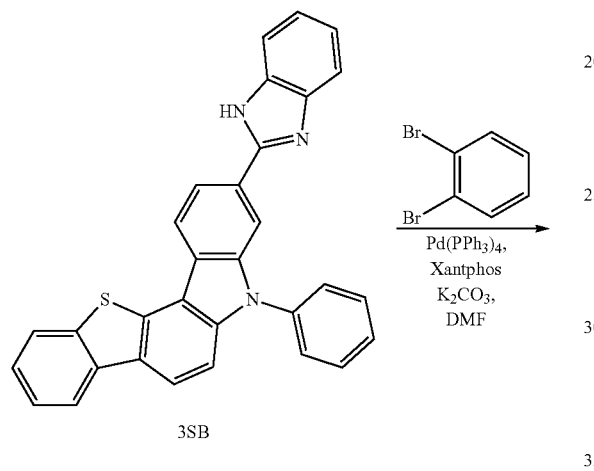

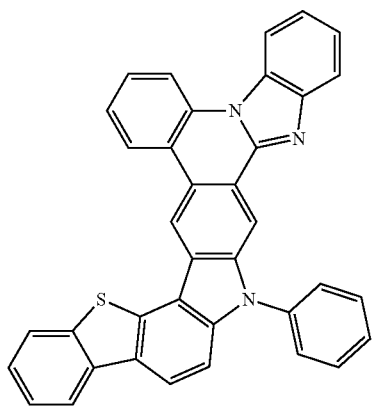

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 3SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3SB-1 in 72% yield.

Example 35

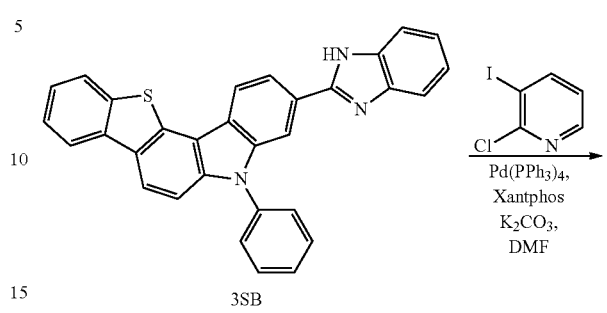

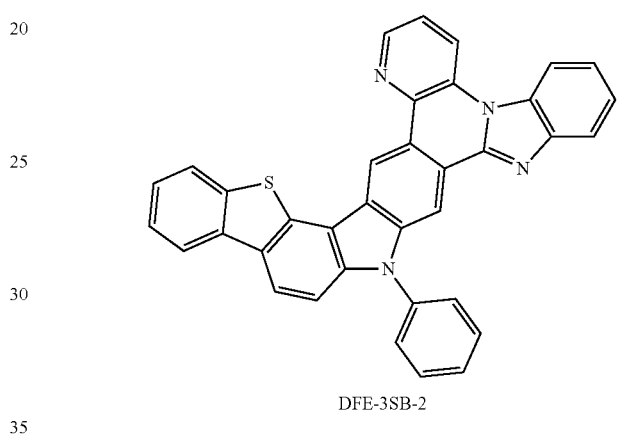

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 3SB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3SB-2 in 59% yield.

Example 36

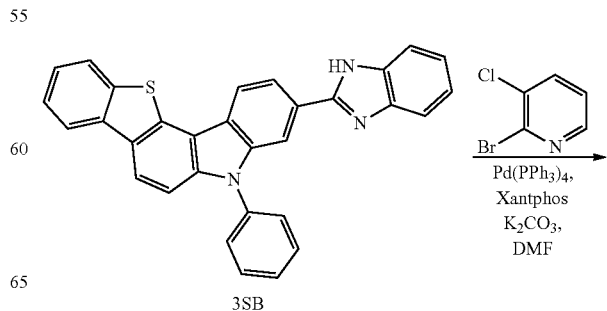

229
-continued

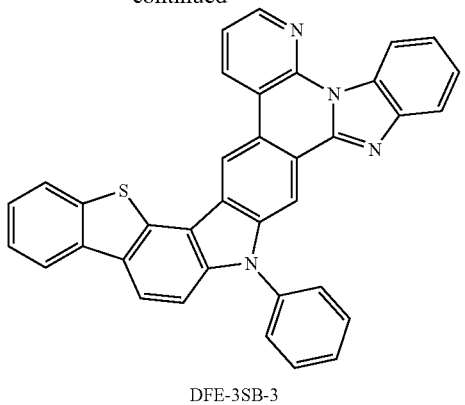

DFE-3SB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 3SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3SB-3 in 24% yield.

Example 37

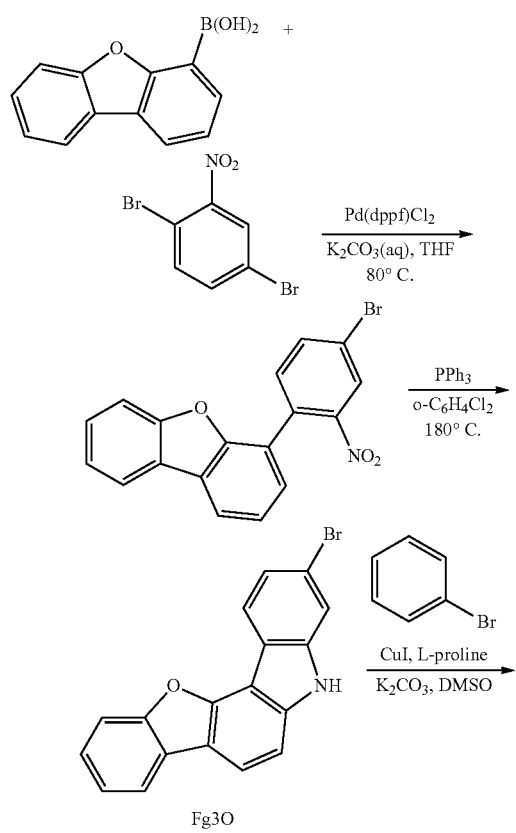

230
-continued

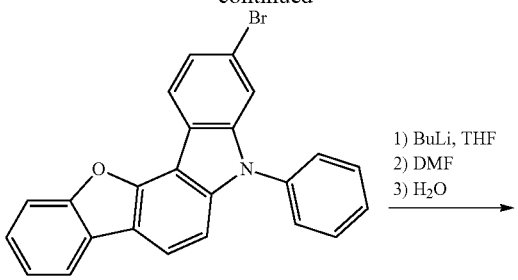

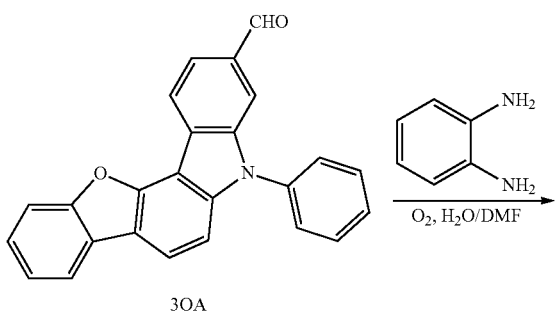

3OA

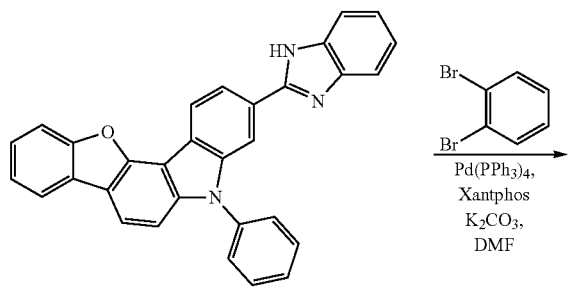

3OB

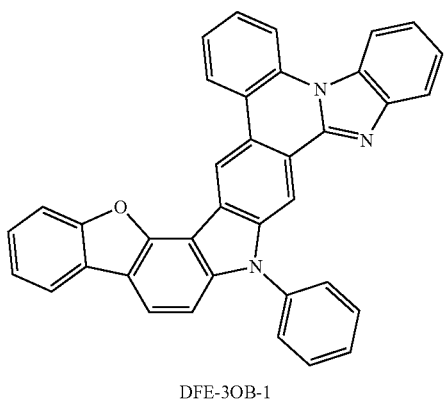

DFE-3OB-1

To a flame-dried flask were added Pd(PPh₃)₄ (10 mol %), Xantphos (10 mol %), Cs₂CO₃ (3eq) and 1,2-dibromobenzene (1.2 eq). Then, 3OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-3OB3-1 in 68% yield.

Example 38

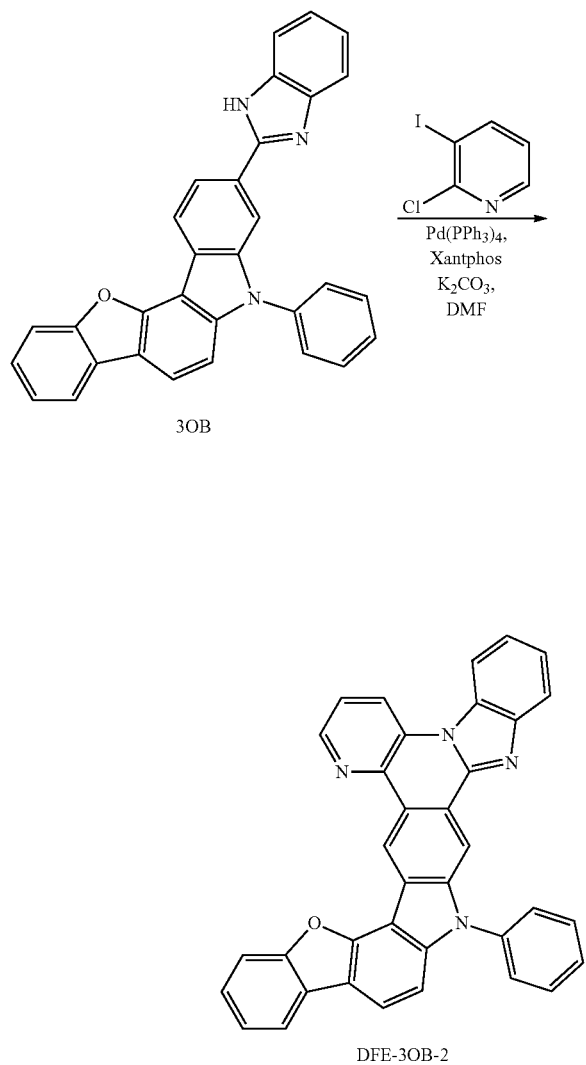

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-2 in 62% yield.

Example 39

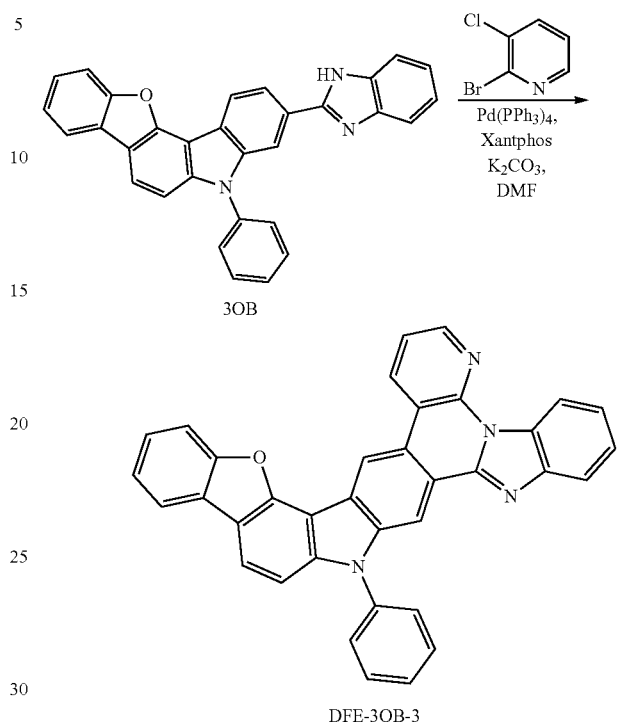

To a flame-dried flask were added Pd(PPh$_3$)$_4$ (10 mol %), Xantphos (10 mol %), Cs$_2$CO$_3$ (3eq) and 2-bromo-3-chloropyridine (1.2 eq). Then, 3OB (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-3OB-3 in 32% yield.

Example 40

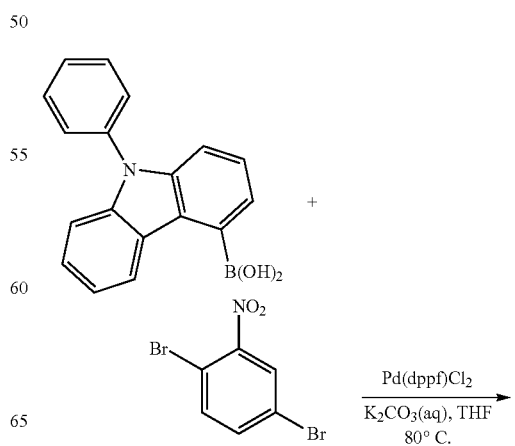

233

-continued

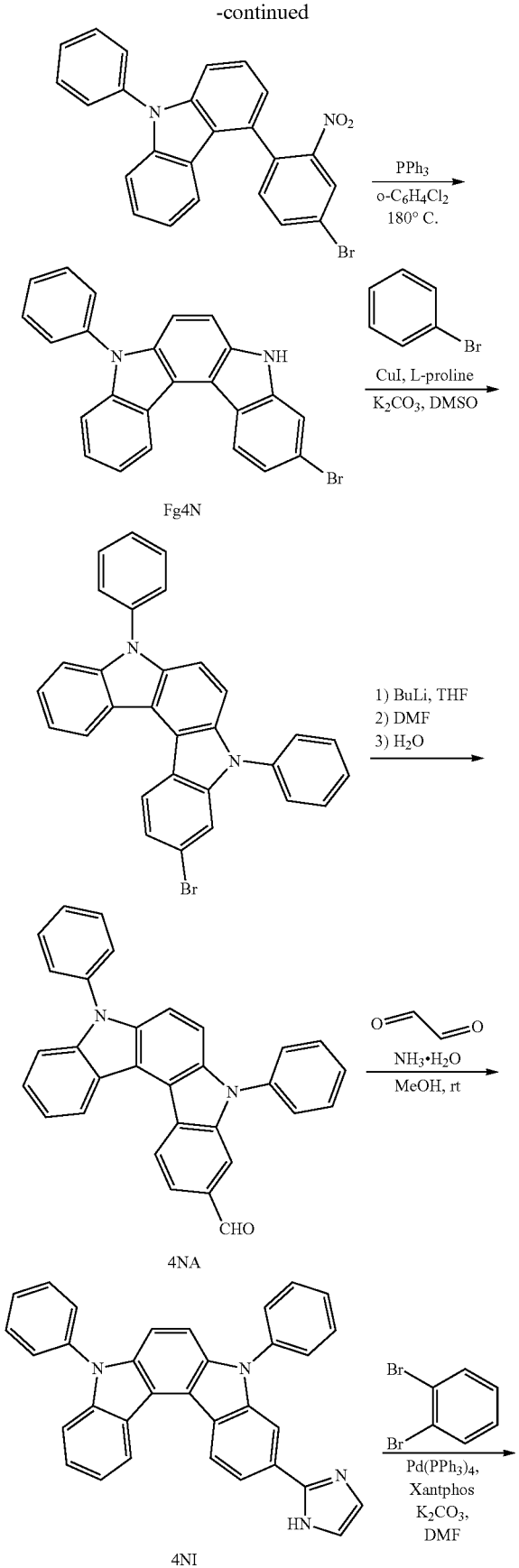

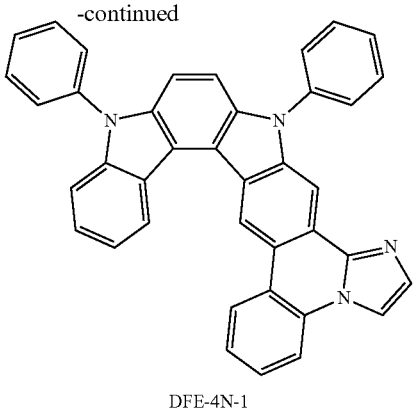

DFE-4N-1

To a flame-dried flask were added Pd(PPh₁)₄ (10 mol %), Xantphos (10 mol %), Cs₂CO₃ (3eq) and 1,2-dibromobenzene (1.2 eq). Then, 4NI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂CO₂. The combined organic extracts were concentrated under reduced pressure and the resulting residue was purified by column chromatography on silica gel to provide the product DFE-4N-1 in 61% yield.

Example 41

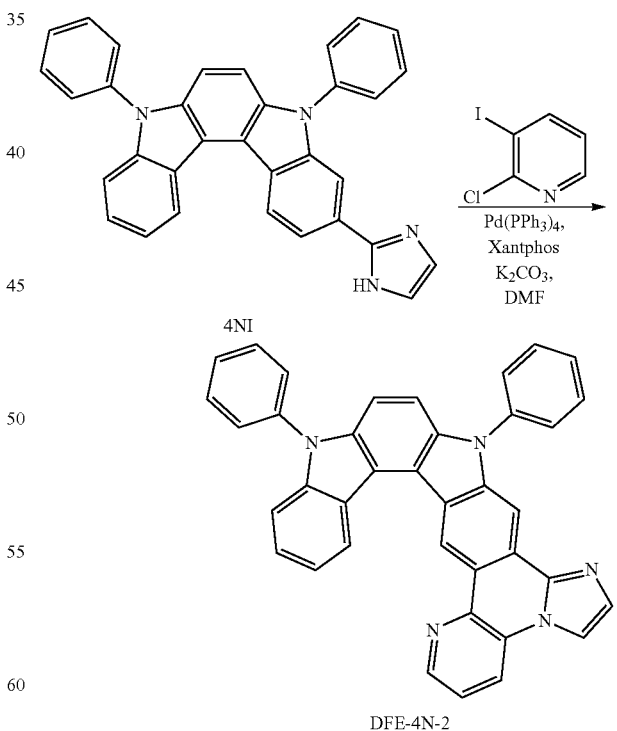

DFE-4N-2

To a flame-dried flask were added Pd(PPh₃)₄ (10 mol %), Xantphos (10 mol %), Cs₂CO₃ (3eq) and 2-chloro-3-iodopyridine (1.2 eq). Then, 4NI (1 eq) and DMF (0.15 M) were added to the reaction mixture under an N₂ atmosphere.

235

The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4N-2 in 51% yield.

Example 42

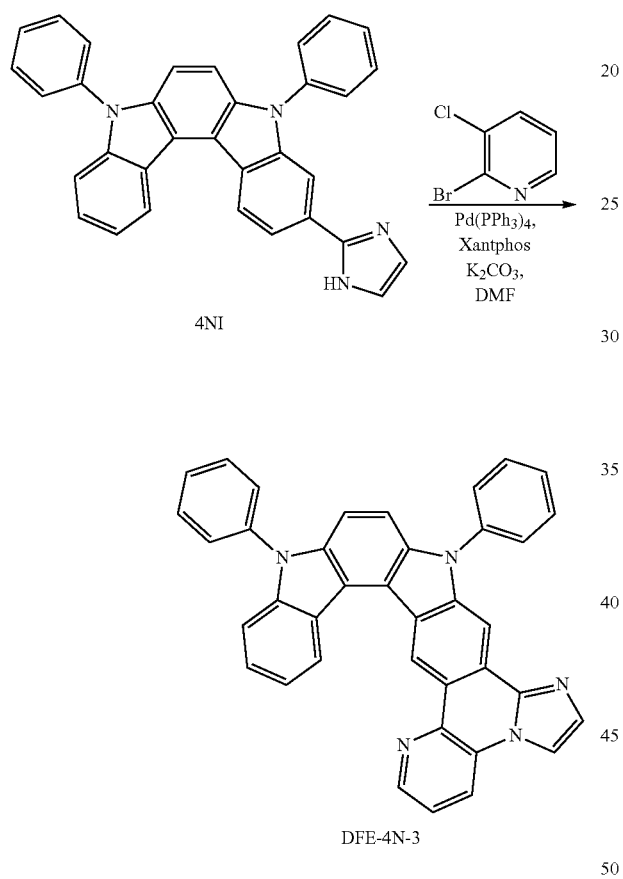

To a flame-dried flask were added $Pd(PPh_3)_4$ (10 mol %), Xantphos (10 mol %), $Cs_2CO_3$ (3eq) and 2-bromo-3-chloropyridine (1.2 eq). Then, 4NI (1 eq) and DMF (0.15 M) were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4N-3 in 27% yield.

236

Example 43

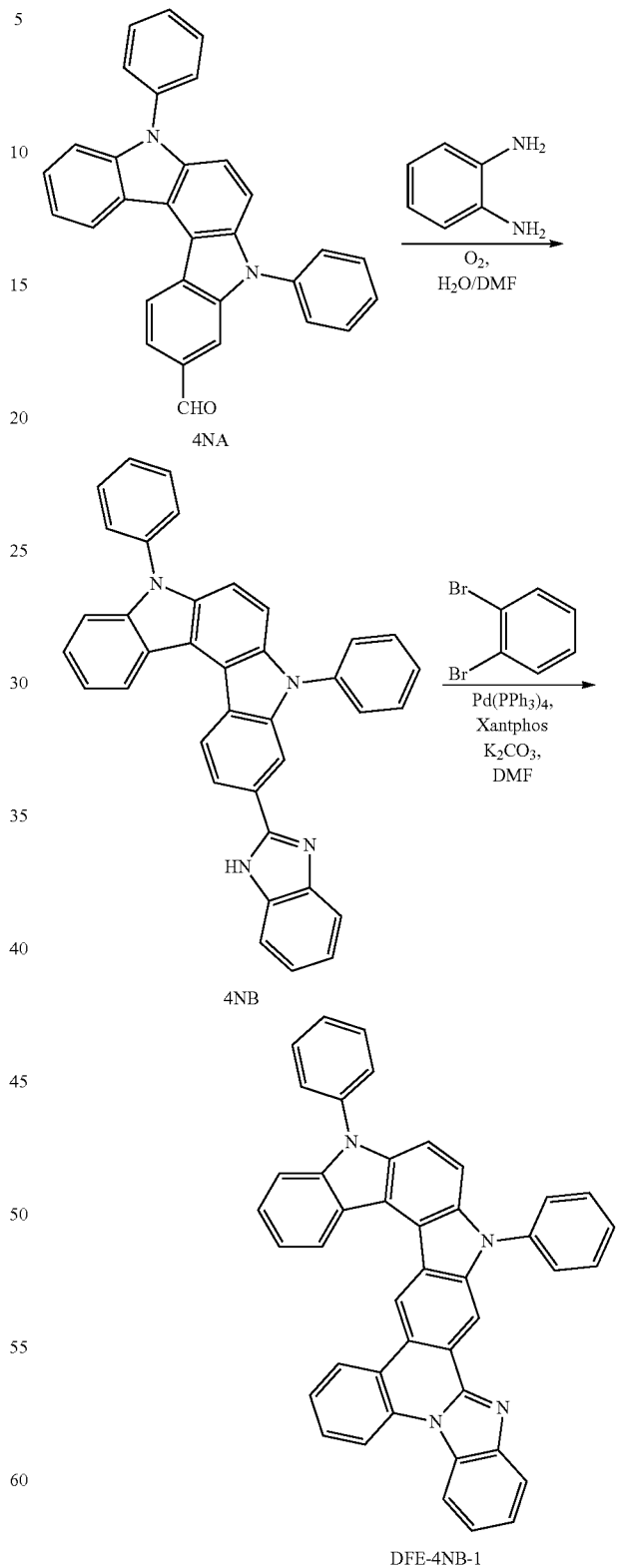

To a flame-dried flask were added $Pd(PPh_3)_4$ (10 mol %), Xantphos (10 mol %), $Cs_2CO_3$ (3eq) and 1,2-dibromobenzene (1.2 eq). Then, 4NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4NB-1 in 57% yield.

Example 44

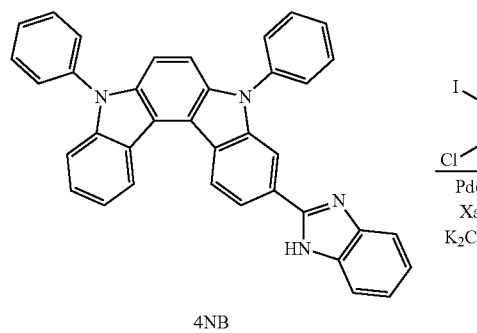

4NB

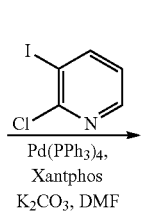

$$\xrightarrow[\text{K}_2\text{CO}_3, \text{DMF}]{\text{Pd(PPh}_3)_4, \text{Xantphos}}$$

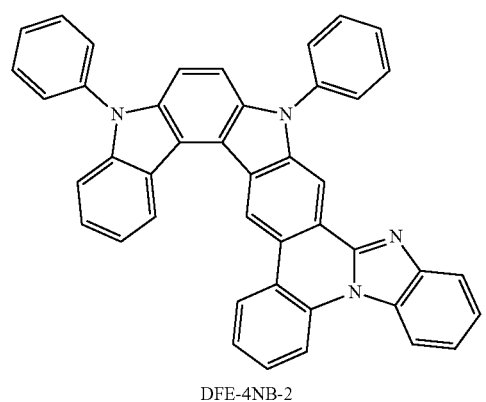

DFE-4NB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 4NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4NB-2 in 43% yield.

Example 45

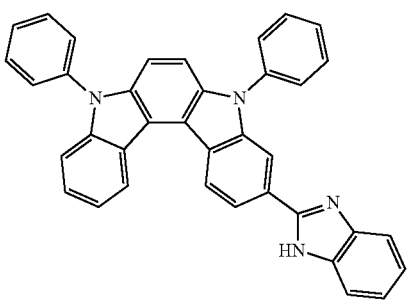

4NB

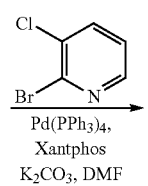

$$\xrightarrow[\text{K}_2\text{CO}_3, \text{DMF}]{\text{Pd(PPh}_3)_4, \text{Xantphos}}$$

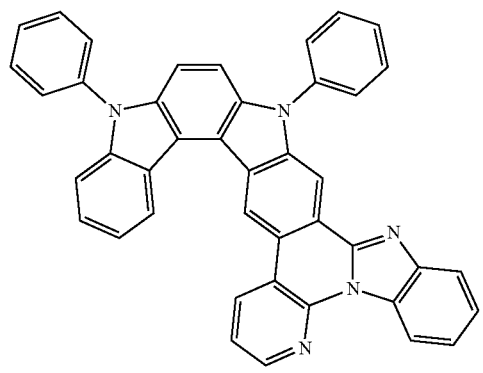

DFE-4NB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 4NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4NB-3 in 22% yield.

Example 46

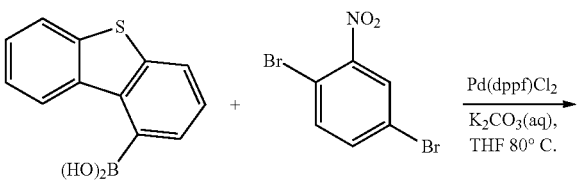

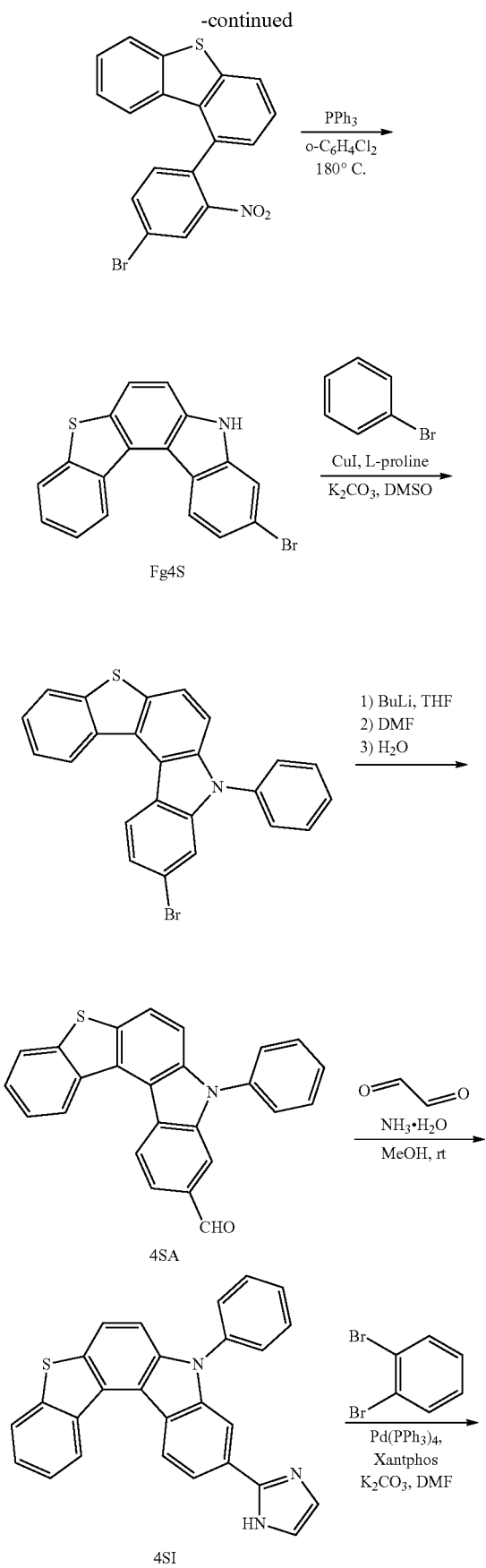

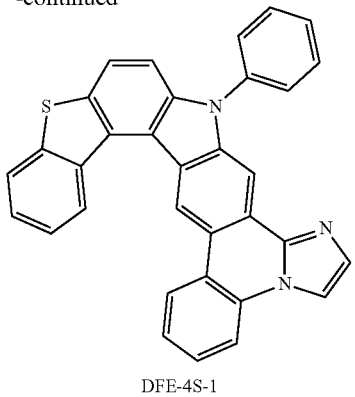

DFE-4S-1

To a flame-dried flask were added Pd(PPh$_3$)$_4$ (10 mol %), Xantphos (10 mol %), Cs$_2$CO$_3$ (3eq) and 1,2-dibromobenzene (1.2 eq). Then, 4SI (1 eq) and DMF (0.15 M) were added to the reaction mixture under an N$_2$ atmosphere. The reaction mixture was stirred for 10 min at room temperature, and then heated at 140° C. in a pre-heated oil bath for 24 h. After that, the reaction mixture was cooled to room temperature, diluted with CH$_2$Cl$_2$, filtered through a short pad of Celite, and washed with CH$_2$Cl$_2$. The combined organic extracts were concentrated under reduced pressure and the resulting residue was purified by column chromatography on silica gel to provide the product DFE-4S-1 in 57% yield.

Example 47

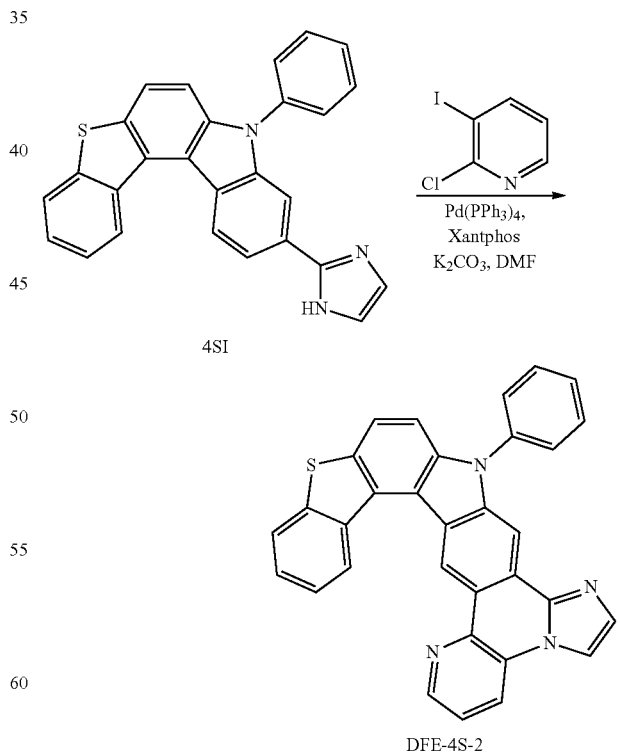

To a flame-dried flask were added Pd(PPh$_3$)$_4$ (10 mol %), Xantphos (10 mol %), Cs$_2$CO$_3$ (3eq) and 2-chloro-3-iodopyridine (1.2 eq). Then, 4SI (1 eq) and DMF (0.15 M)

were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4S-2 in 44% yield.

Example 48

Example 49

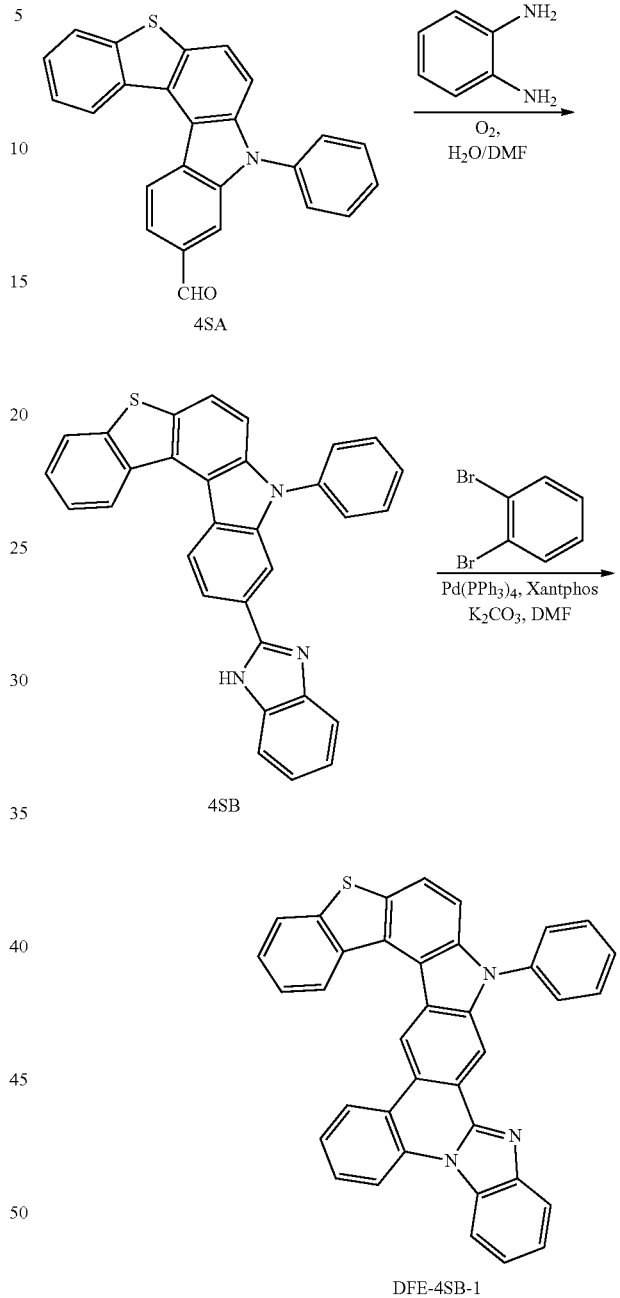

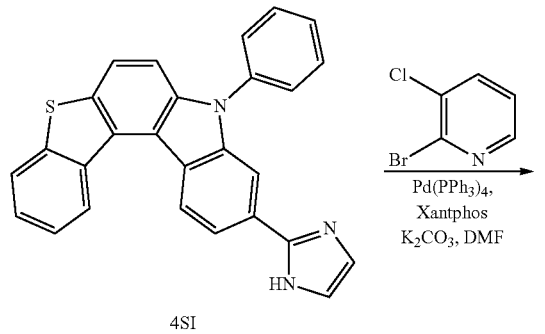

To a flame-dried flask were added $Pd(PPh_3)_4$ (10 mol %), Xantphos (10 mol %), $Cs_2CO_3$ (3eq) and 2-bromo-3-chloropyridine (1.2 eq). Then, 4SI (1 eq) and DMF (0.15 M) were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4S-3 in 23% yield.

To a flame-dried flask were added $Pd(PPh_3)_4$ (10 mol %), Xantphos (10 mol %), $Cs_2CO_3$ (3eq) and 1,2-dibromobenzene (1.2 eq). Then, 4SB (1 eq) and DMF (0.15 M) were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-4SB-1 in 51% yield.

Example 50

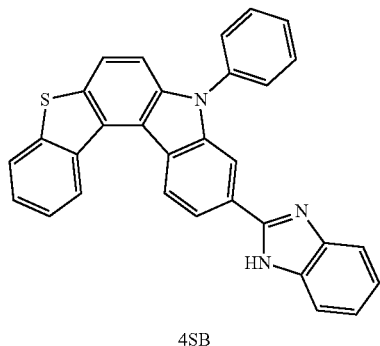
4SB

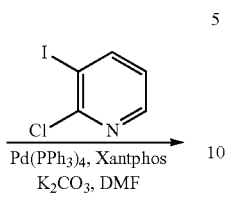

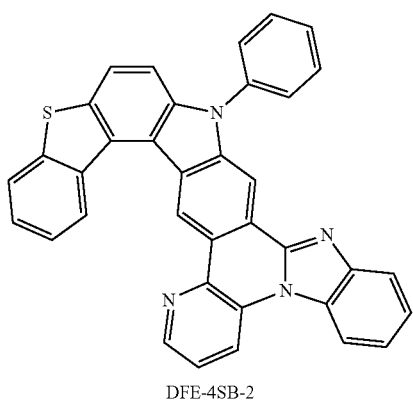
DFE-4SB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 4SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4SB-2 in 39% yield.

Example 51

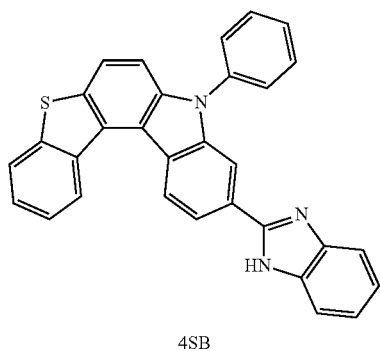
4SB

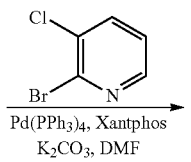

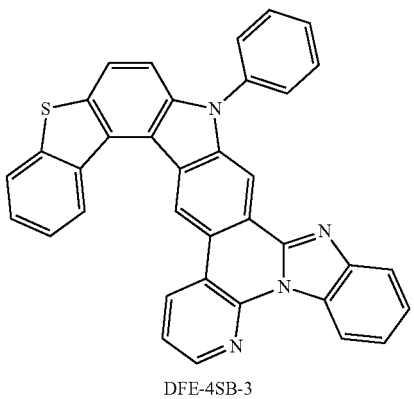
DFE-4SB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 4SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4SB-3 in 31% yield.

Example 52

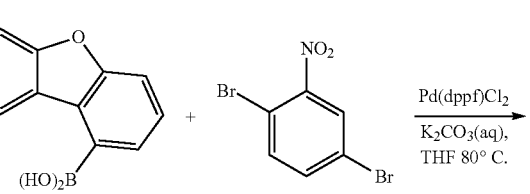

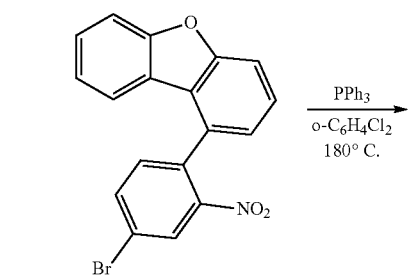

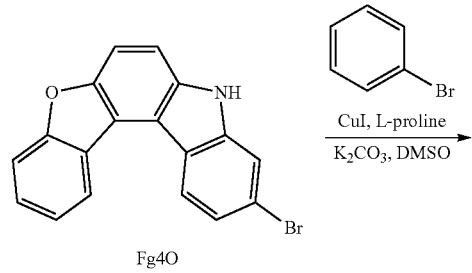
Fg4O

-continued

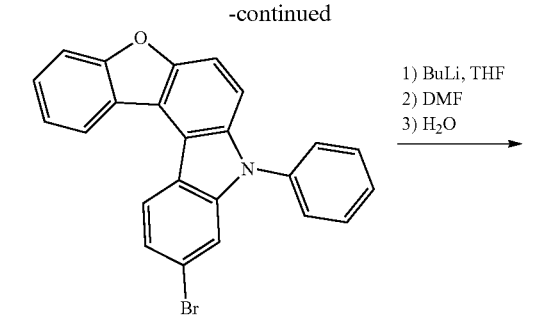

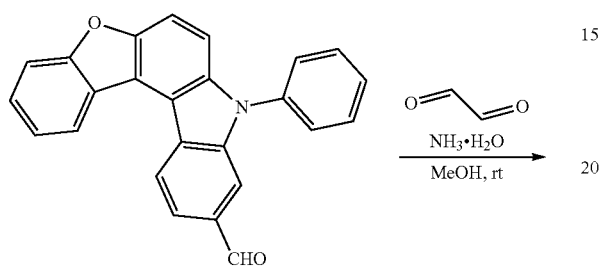
4OA

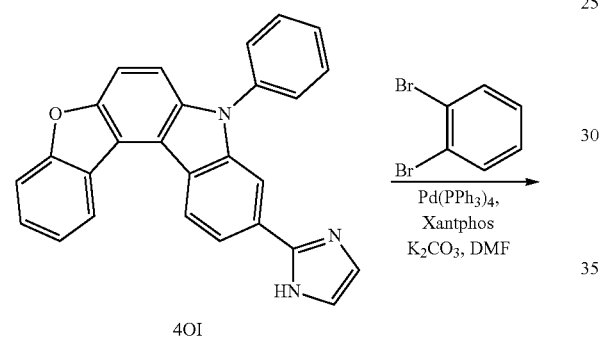
4OI

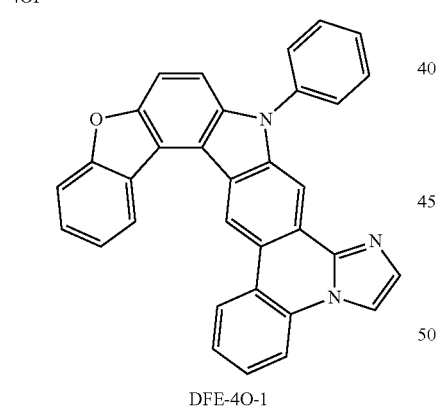
DFE-4O-1

To a flame-dried flask were added Pd(PPh₃)₄ (10 mol %), Xantphos (10 mol %), Cs₂CO₃ (3eq) and 1,2-dibromobenzene (1.2 eq). Then, 4OI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4O-1 in 64% yield.

Example 53

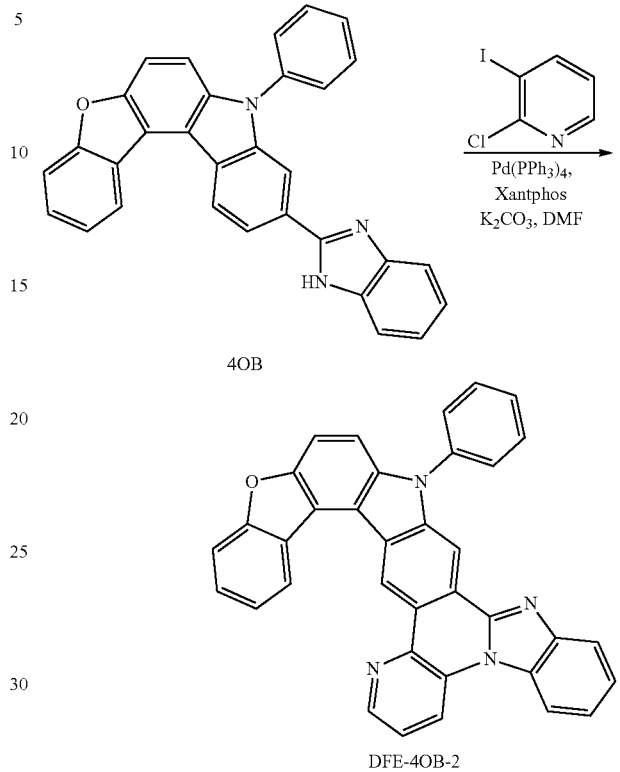
4OB

DFE-4OB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 4OI (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4O-2 in 37% yield.

Example 54

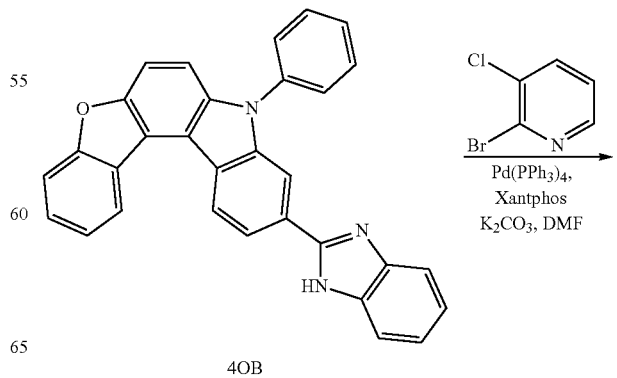
4OB

247

-continued

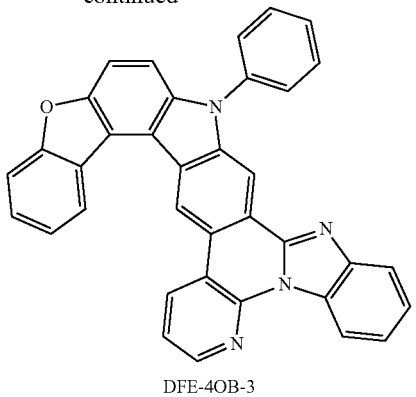

DFE-4OB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 4OB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-4OB-3 in 26% yield.

Example 55

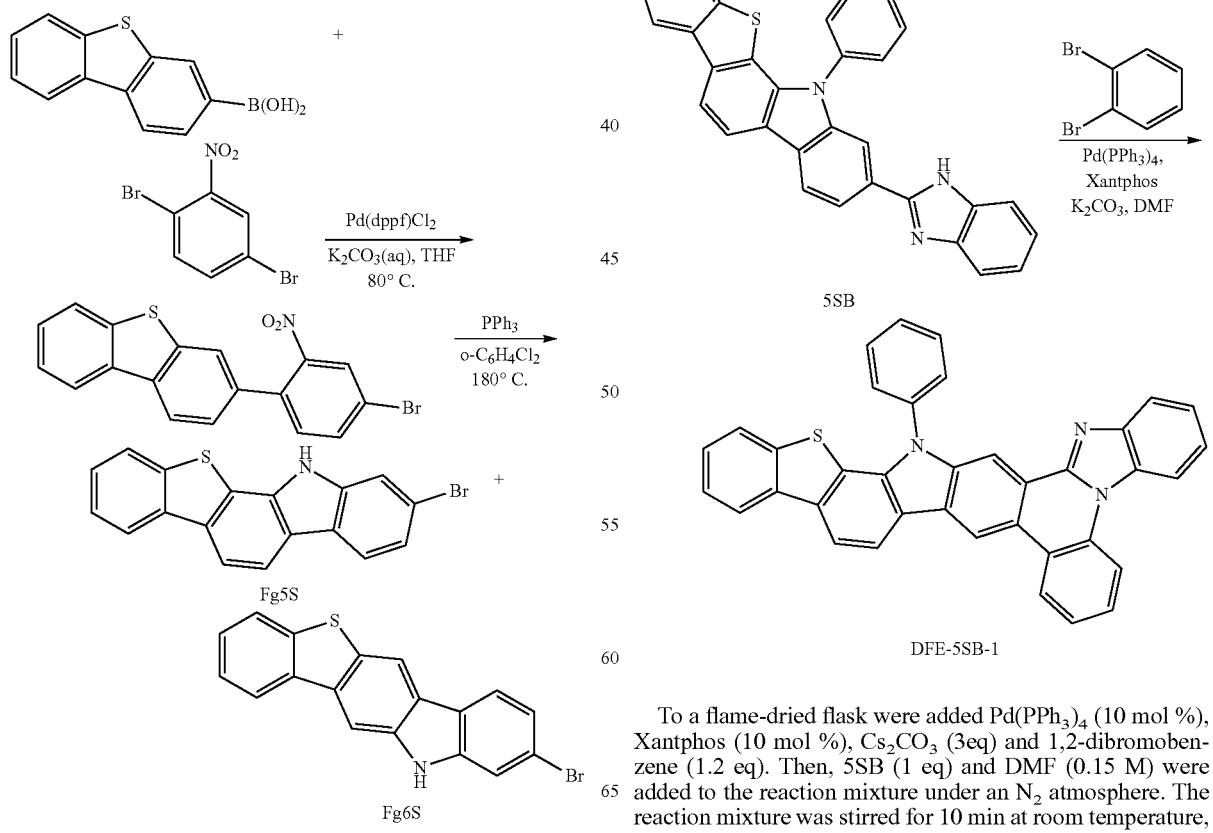

248

-continued

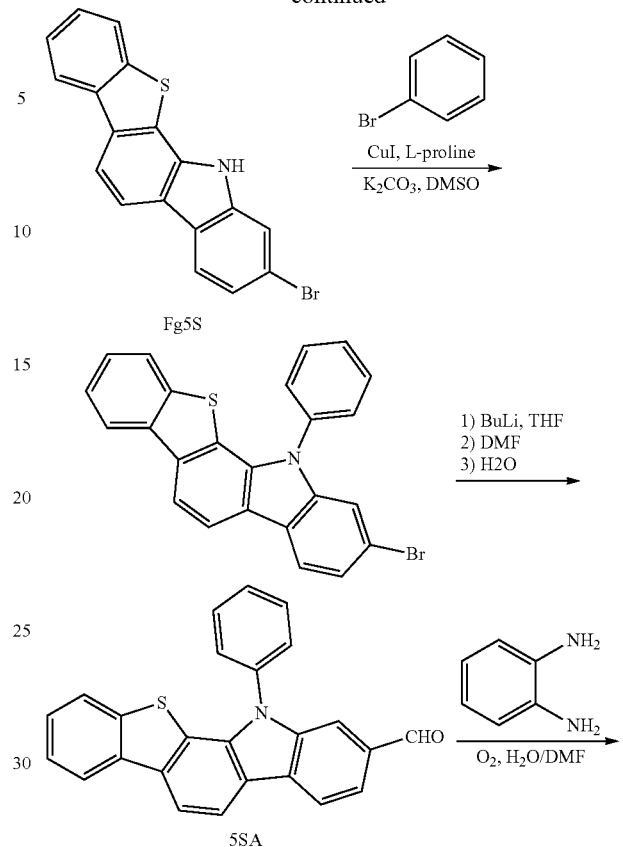

To a flame-dried flask were added Pd(PPh₃)₄ (10 mol %), Xantphos (10 mol %), Cs₂CO₃ (3eq) and 1,2-dibromobenzene (1.2 eq). Then, 5SB (1 eq) and DMF (0.15 M) were added to the reaction mixture under an N₂ atmosphere. The reaction mixture was stirred for 10 min at room temperature, and then heated at 140° C. in a pre-heated oil bath for 24 h.

After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5SB-1 in 56% yield.

Example 56

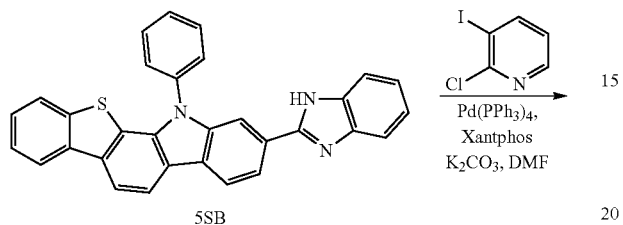

5SB

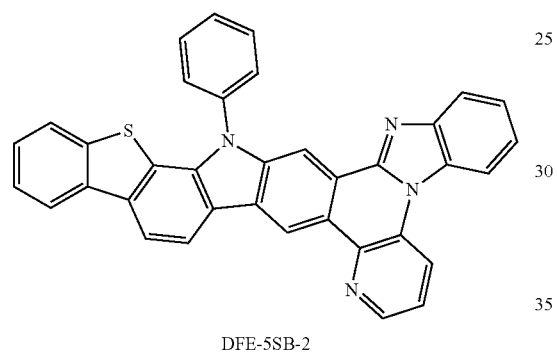

DFE-5SB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 5SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5SB-2 in 33% yield.

Example 57

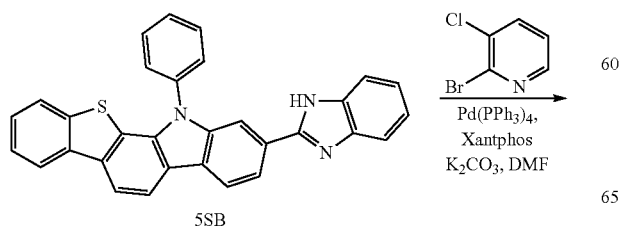

5SB

-continued

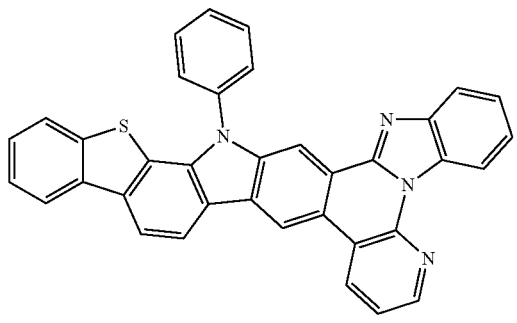

DFE-5SB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 5SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5SB-3 in 35% yield.

Example 58

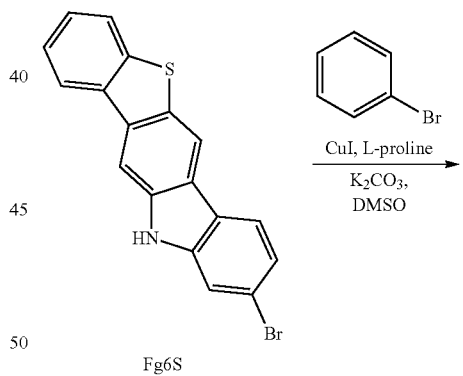

-continued

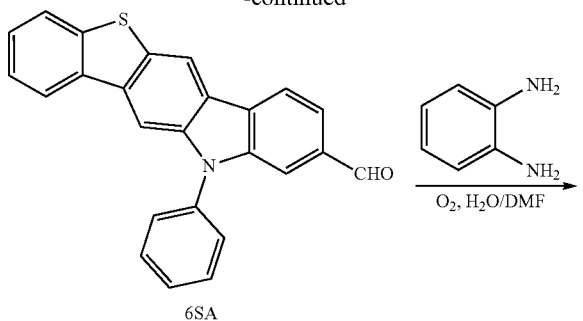

6SA

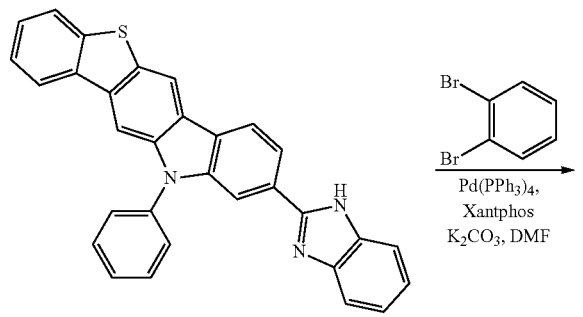

6SB

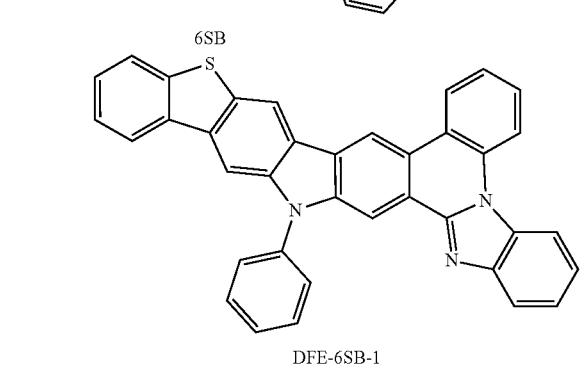

DFE-6SB-1

To a flame-dried flask were added Pd(PPh₃)₄ (10 mol %), Xantphos (10 mol %), Cs₂CO₃ (3eq) and 1,2-dibromobenzene (1.2 eq). Then, 6SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-6SB-1 in 59% yield.

Example 59

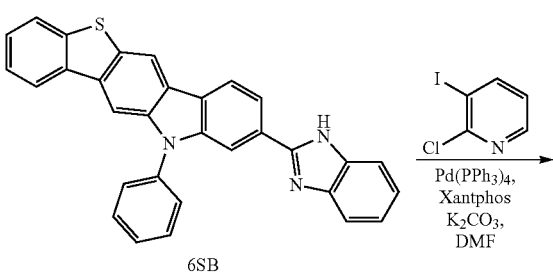

6SB

-continued

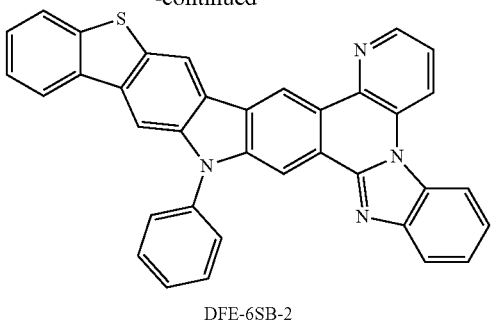

DFE-6SB-2

To a flame-dried flask were added Pd(PPh₃)₄ (10 mol %), Xantphos (10 mol %), Cs₂CO₃ (3eq) and 2-chloro-3-iodopyridine (1.2 eq). Then, 6SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-6SB-2 in 39% yield.

Example 60

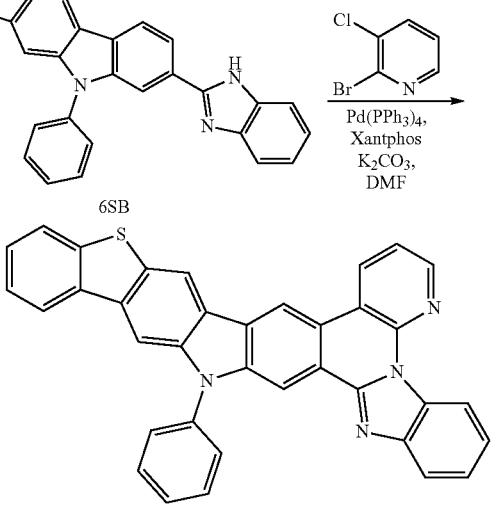

6SB

DFE-6SB-3

To a flame-dried flask were added Pd(PPh₃)₄ (10 mol %), Xantphos (10 mol %), Cs₂CO₃ (3eq) and 2-bromo-3-chloropyridine (1.2 eq). Then, 6SB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-6SB-3 in 28% yield.

Example 61

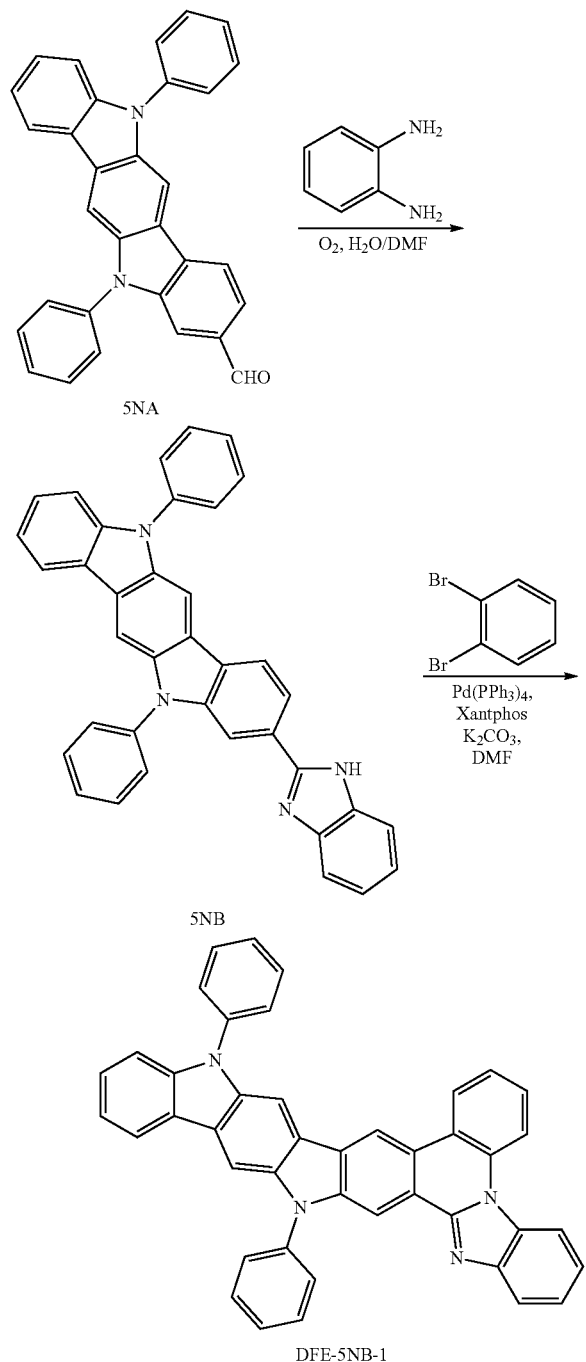 [SMILES: O=Cc1ccc2c3cc4c(cc3n(-c3ccccc3)c2c1)c1ccccc1n4-c1ccccc1 ; Nc1ccccc1N ; c1ccc(-n2c3ccccc3c3cc4c(cc32)c2ccc(-c3nc5ccccc5[nH]3)cc2n4-c2ccccc2)cc1 ; Brc1ccccc1Br ; c1ccc(-n2c3ccccc3c3cc4c(cc32)c2cc3c5ccccc5n5c6ccccc6nc5c3cc2n4-c2ccccc2)cc1]

Example 62

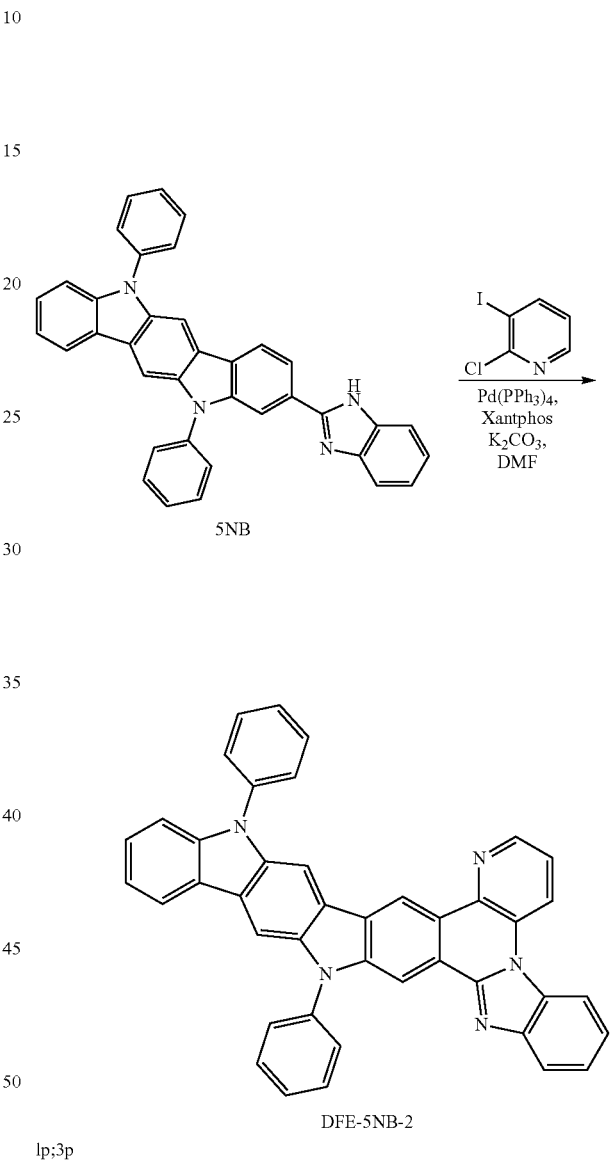

After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-5NB-1 in 54% yield.

To a flame-dried flask were added $Pd(PPh_3)_4$ (10 mol %), Xantphos (10 mol %), $Cs_2CO_3$ (3eq) and 1,2-dibromobenzene (1.2 eq). Then, 5NB (1 eq) and DMF (0.15 M) were added to the reaction mixture under an $N_2$ atmosphere. The reaction mixture was stirred for 10 min at room temperature, and then heated at 140° C. in a pre-heated oil bath for 24 h.

To a flame-dried flask were added $Pd(PPh_3)_4$ (10 mol %), Xantphos (10 mol %), $Cs_2CO_3$ (3eq) and 2-chloro-3-iodopyridine (1.2 eq). Then, 5NB (1 eq) and DMF (0.15 M) were added to the reaction mixture under an $N_2$ atmosphere. The reaction mixture was stirred for 10 min at room temperature, and then heated at 140° C. in a pre-heated oil bath for 24 h. After that, the reaction mixture was cooled to room temperature, diluted with $CH_2Cl_2$, filtered through a short pad of Celite, and washed with $CH_2Cl_2$. The combined organic extracts were concentrated under reduced pressure and the resulting residue was purified by column chromatography on silica gel to provide the product DFE-5NB-2 in 43% yield.

Example 63

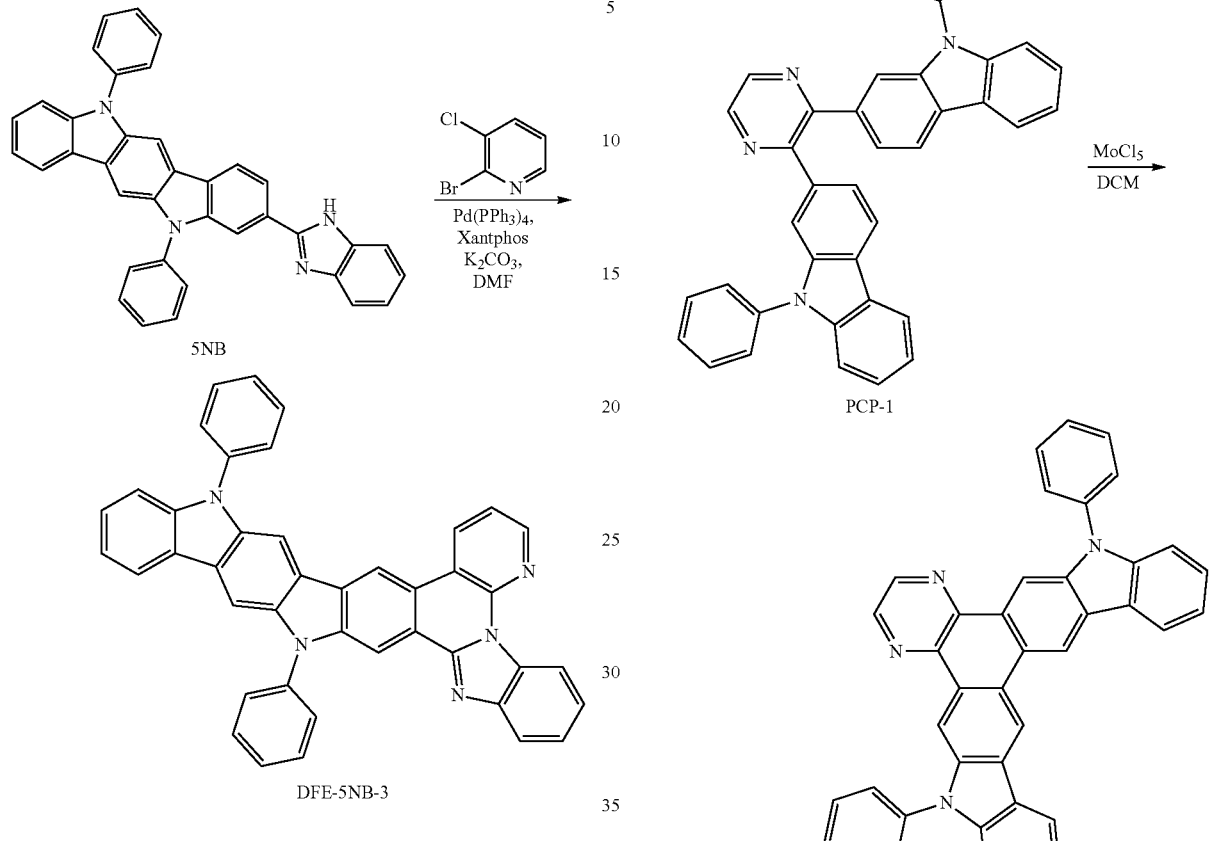

To a flame-dried flask were added Pd(PPh₃)₄ (10 mol %), Xantphos (10 mol %), Cs₂CO₃ (3eq) and 2-bromo-3-chloropyridine (1.2 eq). Then, 5NB (1 eq) and DMF (0.15 M) were added to the reaction mixture under an N₂ atmosphere. The reaction mixture was stirred for 10 min at room temperature, and then heated at 140° C. in a pre-heated oil bath for 24 h. After that, the reaction mixture was cooled to room temperature, diluted with CH₂Cl₂, filtered through a short pad of Celite, and washed with CH₂Cl₂. The combined organic extracts were concentrated under reduced pressure and the resulting residue was purified by column chromatography on silica gel to provide the product DFE-5NB-3 in 25% yield.

MoCl₅ (1.0 equiv) was added quickly to a solution of PCP-1 (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-1 in 45% yield.

Example 64

Example 65

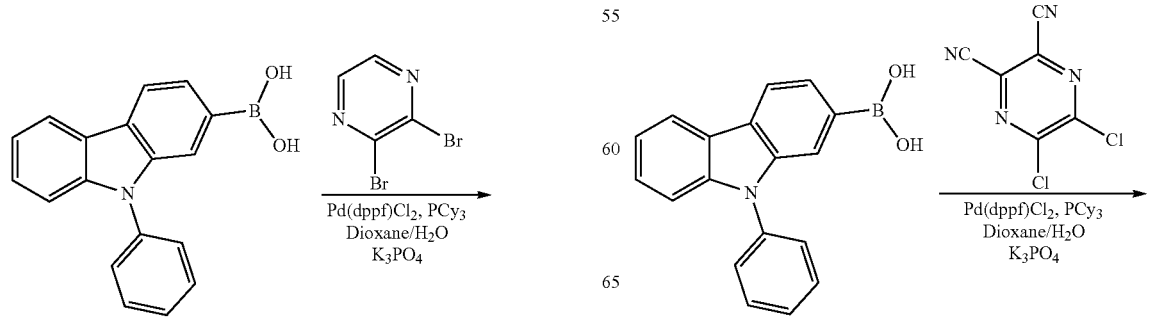

-continued

PCP-2

DFE-2

MoCl$_5$ (1.0 equiv) was added quickly to a solution of PCP-2 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-2 in 41% yield.

Example 66

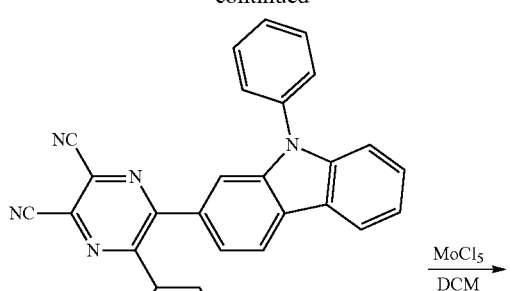

+

-continued

PCB

DFE-3

MoCl$_5$ (1.0 equiv) was added quickly to a solution of PCB (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-3 in 38% yield.

Example 67

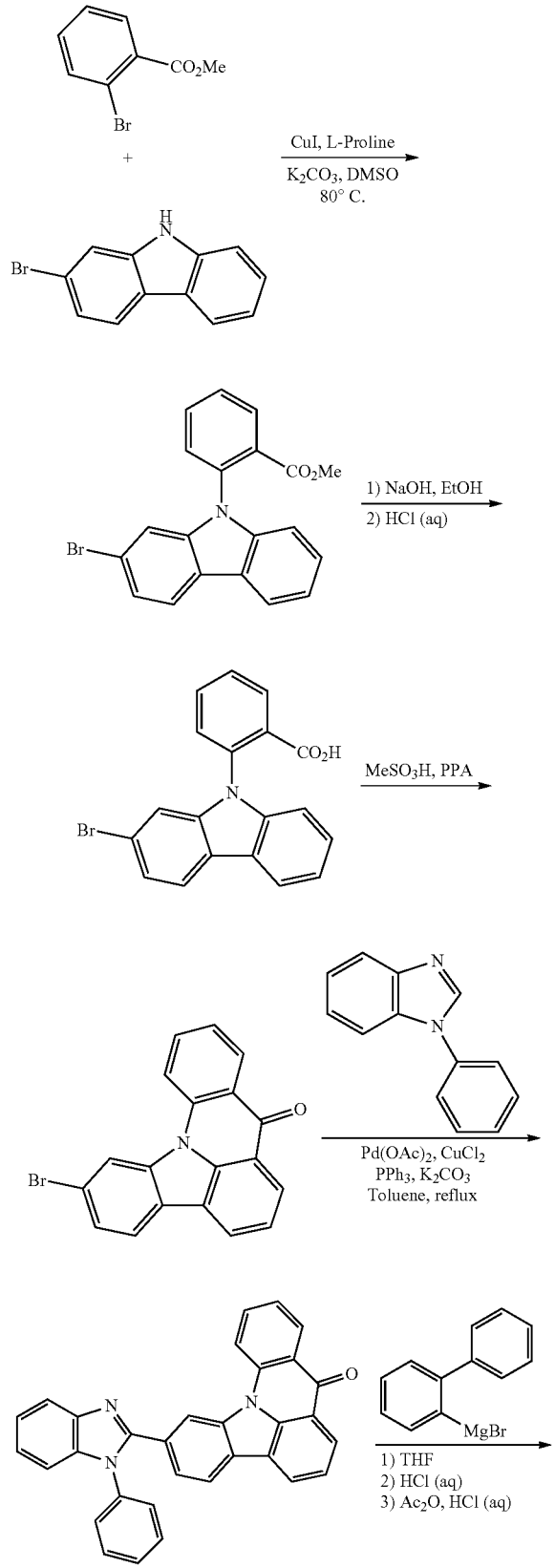

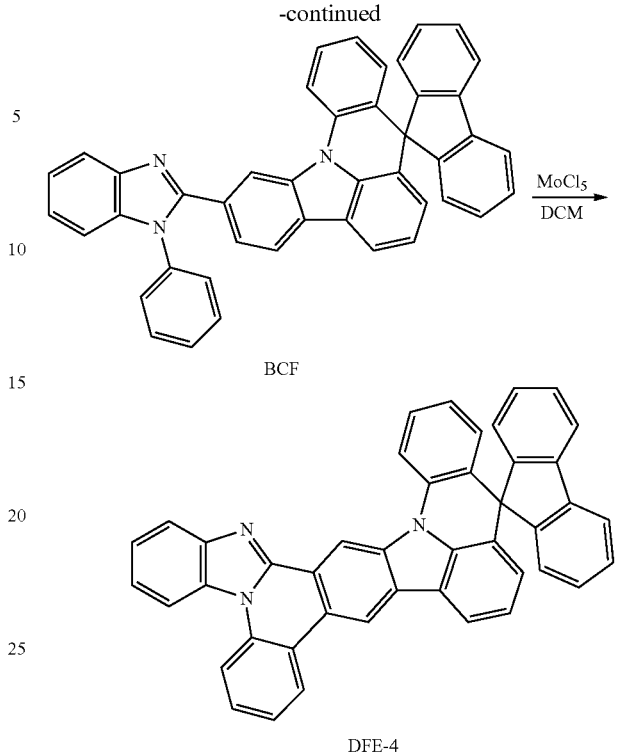

MoCl$_5$ (1.0 equiv) was added quickly to a solution of BCF (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-4 in 42% yield.

Example 68

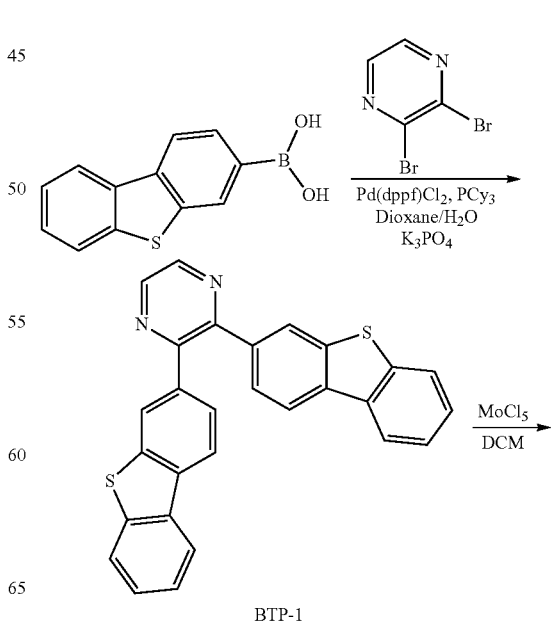

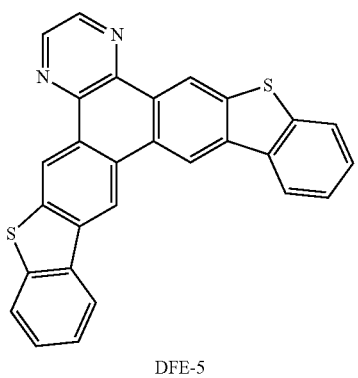

DFE-5

MoCl$_5$ (1.0 equiv) was added quickly to a solution of BTP-1 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-5 in 49% yield.

Example 69

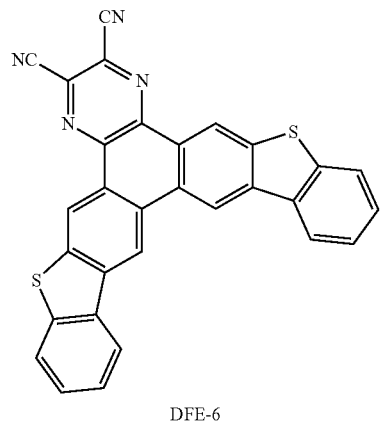

DFE-6

MoCl$_5$ (1.0 equiv) was added quickly to a solution of BTP-2 (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-6 in 38% yield.

Example 70

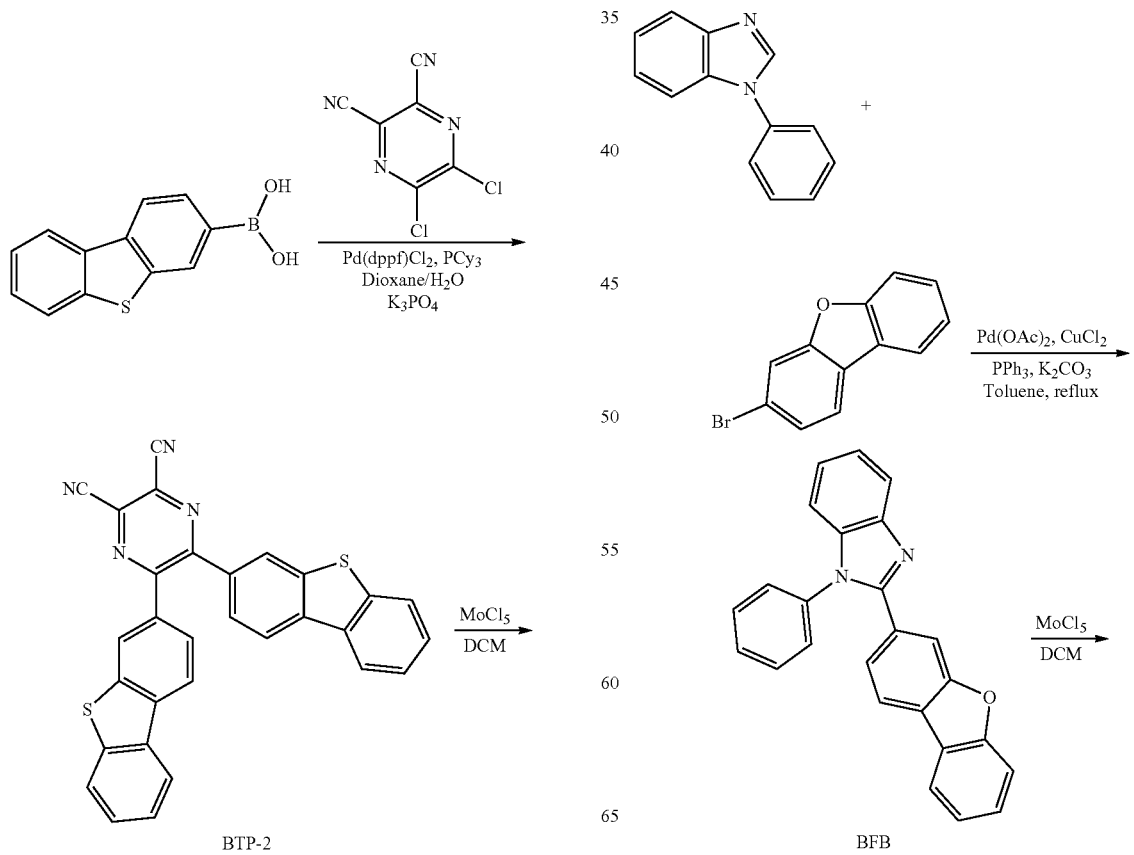

263

-continued

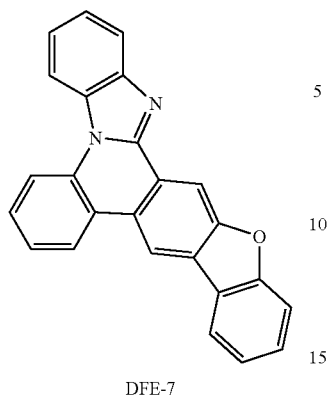

DFE-7

MoCl$_5$ (1.0 equiv) was added quickly to a solution of BFB (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-7 in 34% yield.

Example 71

264

-continued

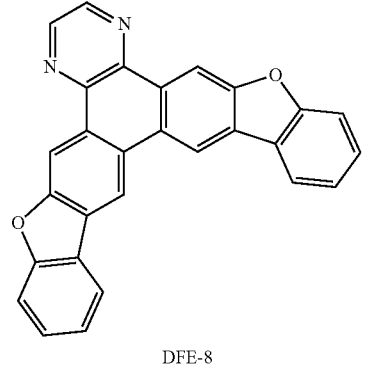

DFE-8

MoCl$_5$ (1.0 equiv) was added quickly to a solution of BFP (1.00 equiv) in CH$_2$Cl$_2$ (0.05 M) under nitrogen. The mixture was stirred at room temperature for 24 h; then the other one equiv of MoCl$_5$ was added quickly to the mixture again. After being stirred for 24 h, the mixture was quenched by methanol and stirred for another 1 h, filtered, and washed with CH$_2$Cl$_2$. The filtrate was concentrated, and the residue was purified through column chromatography on silica gel to afford the product DFE-8 in 52% yield.

Example 72

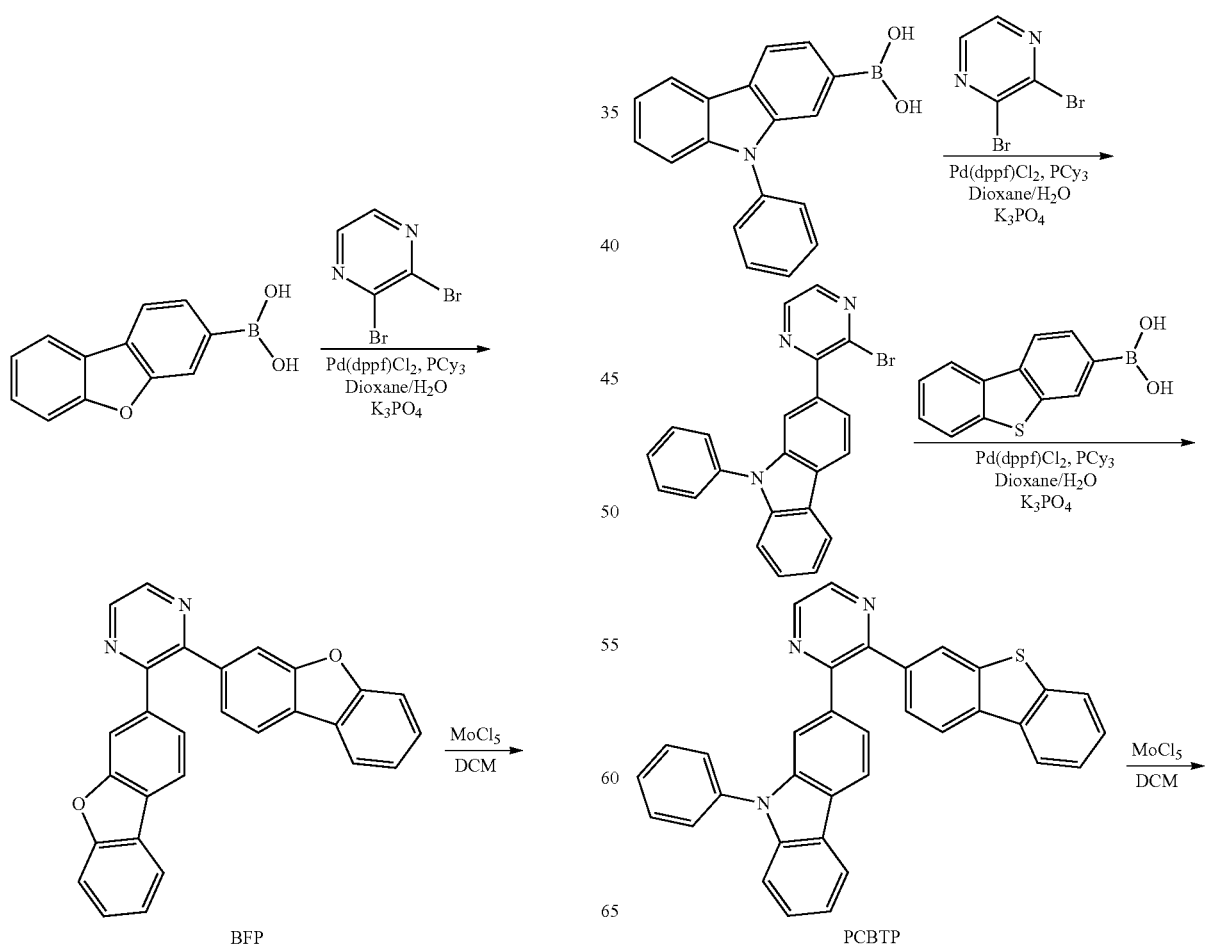

265
-continued

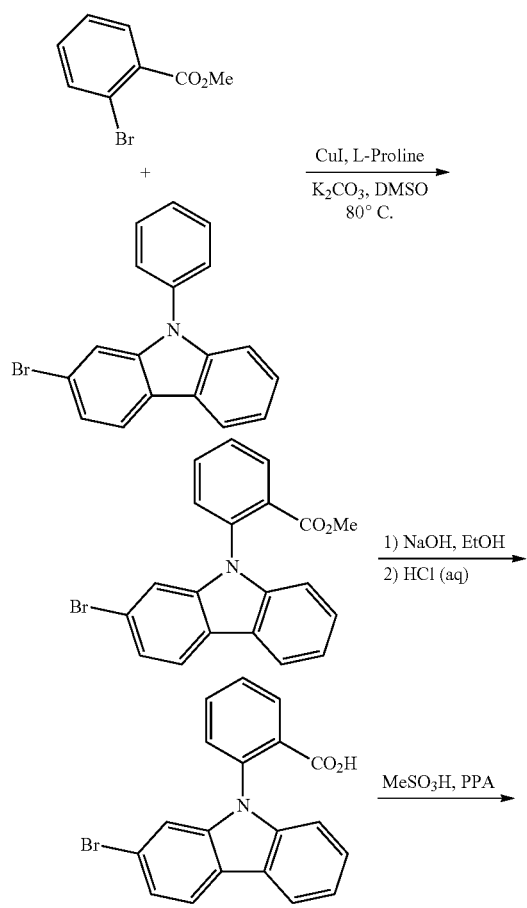

DFE-9

MoCl₅ (1.0 equiv) was added quickly to a solution of PCBTP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-8 in 49% yield.

Example 73

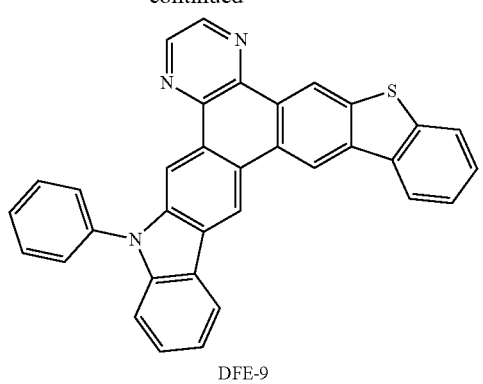

266
-continued

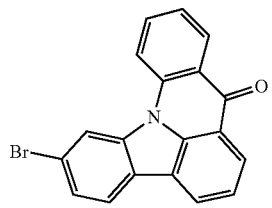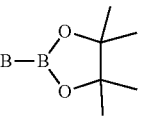
Pd(dppf)Cl₂
KOAc, Dioxane

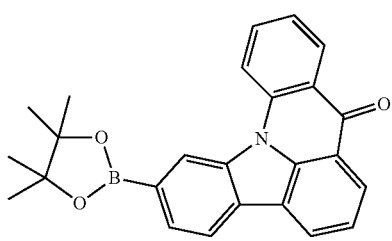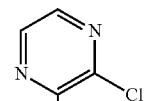
Pd(dppf)Cl₂, PCy₃
Dioxane/H₂O
K₃PO₄

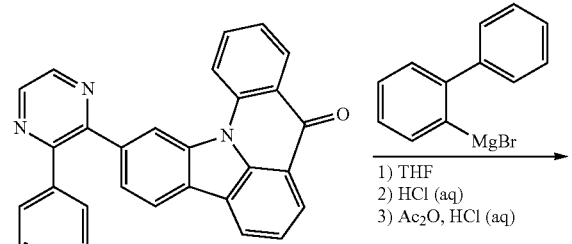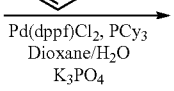
1) THF
2) HCl (aq)
3) Ac₂O, HCl (aq)

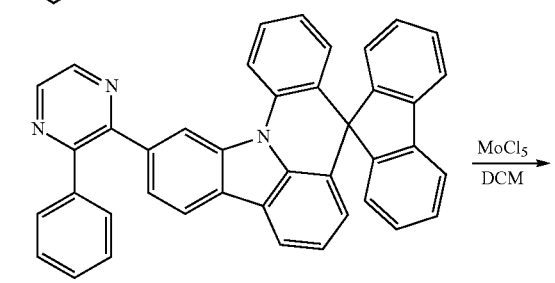
MoCl₅
DCM

PCFP

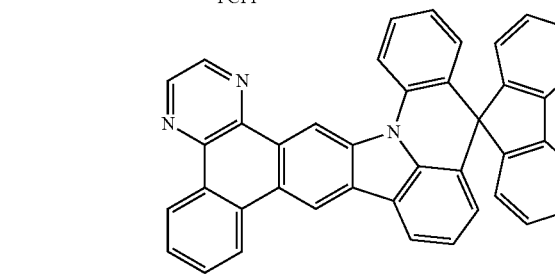

DFE-10

MoCl₅ (1.0 equiv) was added quickly to a solution of PCFP (1.00 equiv) in CH₂Cl₂ (0.05 M) under nitrogen. The mixture was stirred at room temperature for 24 h; then the other one equiv of MoCl₅ was added quickly to the mixture again. After being stirred for 24 h, the mixture was quenched by methanol and stirred for another 1 h, filtered, and washed with CH₂Cl₂. The filtrate was concentrated, and the residue was purified through column chromatography on silica gel to afford the product DFE-10 in 33% yield.

Only a few implementations are described and illustrated. Variations, enhancements and improvements of the described implementations and other implementations can be made based on what is described and illustrated in this document.

What is claimed is:

1. A compound represented by General Formula I:

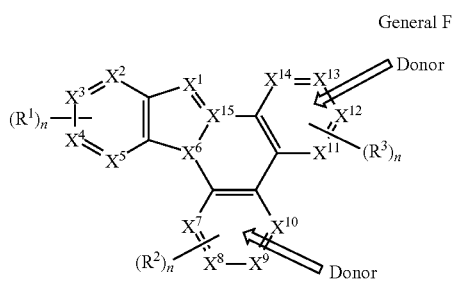

General Formula I wherein:
each occurrence of Donor represents no substitution or represents a group of Formula A, provided that at least one Donor represents a group of Formula A:

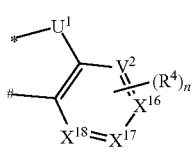

Formula A wherein, in Formula A, * and # represent bonds to adjacent positions on General Formula I:
represents hydrogen, cyanide, halogen, hydroxy, amino, nitro, thiol, or substituted or unsubstituted: $C_1$-$C_4$ alkyl, alkoxy, or aryl; or two adjacent groups $R^4$ together form a group of Formula B

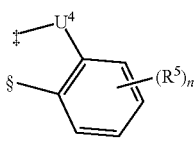

Formula B wherein, in Formula B, ‡ and § represent bonds to adjacent positions on Formula A;
each $U^1$ and $U^4$ independently represents O, S, CRR', SiRR', or NAr*, where R and R' each independently represents hydrogen, cyanide, halogen, hydroxy, amino, nitro, thiol, or optionally substituted $C_1$-$C_4$ alkyl, alkoxy, or aryl, and Ar* represents a substituted or unsubstituted: phenyl, pyridyl, naphthyl, pyrimidyl, pyridazinyl, pyrazinyl, pyrazolyl, imidazolyl, oxazolyl, or thiazolyl ring, and Ar* is optionally covalently bonded to $V^2$ to form one or more 5-membered or 6-membered rings,
$R^1$, $R^2$, $R^3$, and $R^5$ each independently represents hydrogen, cyanide, halogen, hydroxy, amino, nitro, thiol, or substituted or unsubstituted; $C_1$-$C_4$ alkyl, alkoxy, or aryl, and
$V^2$ represents N or substituted or unsubstituted C, each $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, and $X^{18}$ independently represents substituted or unsubstituted; C, N, Si, O, or S, valency permitting,
each n is independently an integer as permitted by valence, and
wherein at least one of the following conditions (i) and (ii) is true:
(i) at least two occurrences of Donor represent a group of Formula A; or
(ii) at least two adjacent groups $R^4$ together form a group of Formula B.

2. The compound of claim 1, wherein the compound is represented by one of the following structures:

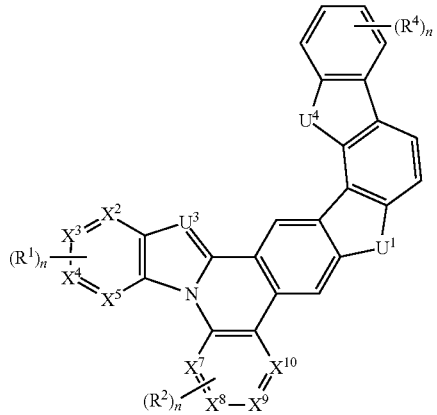

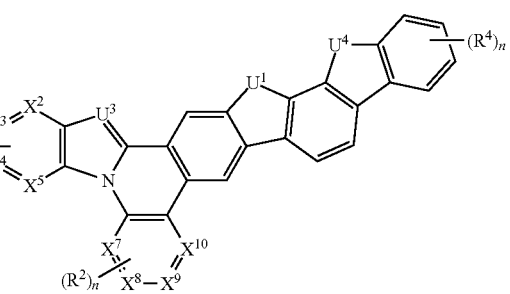

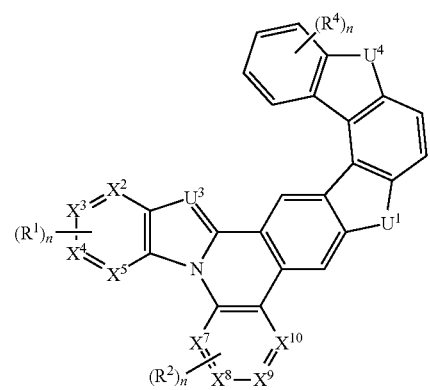

-continued
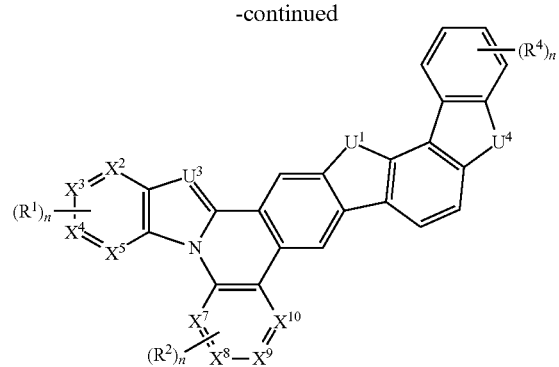
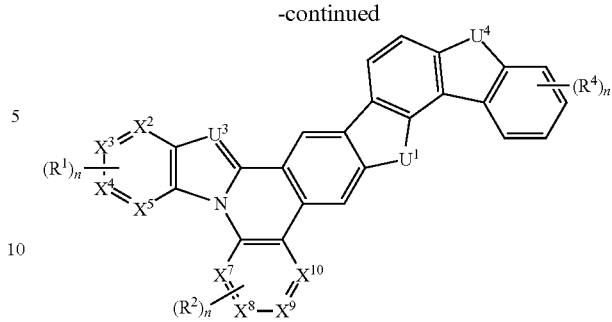
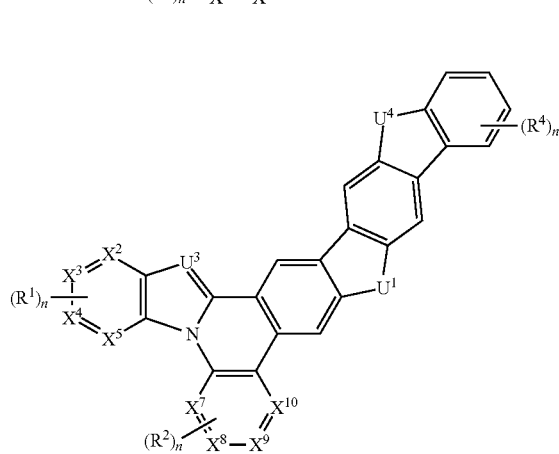
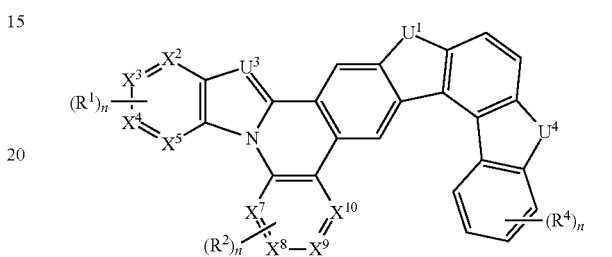
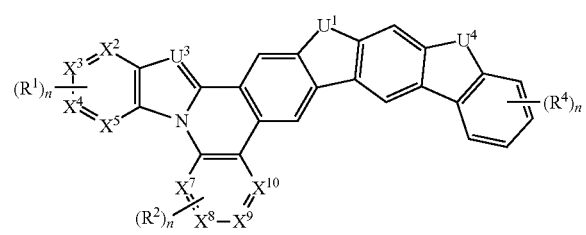
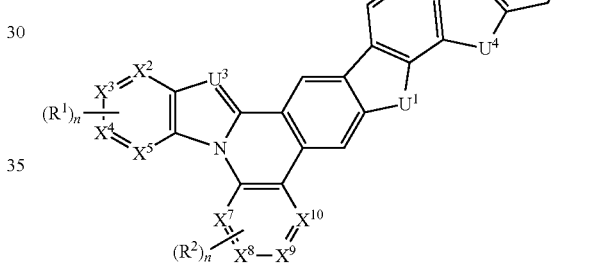
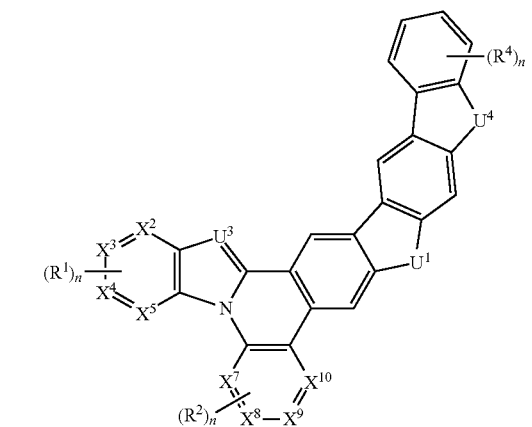
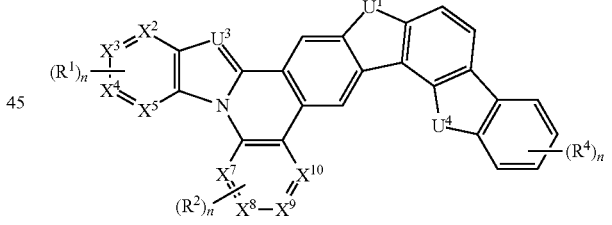
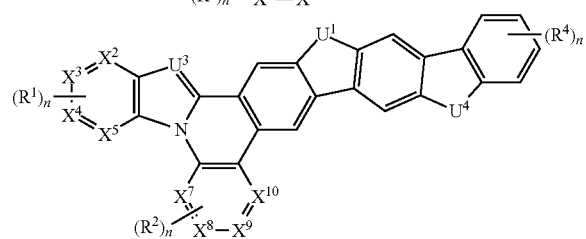
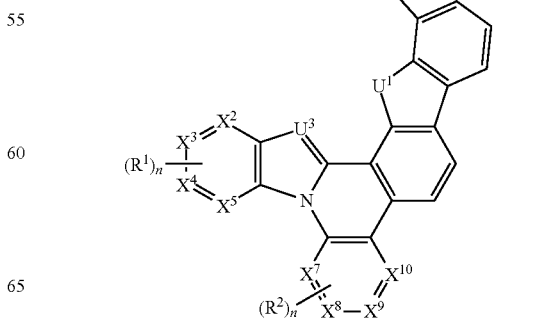

-continued
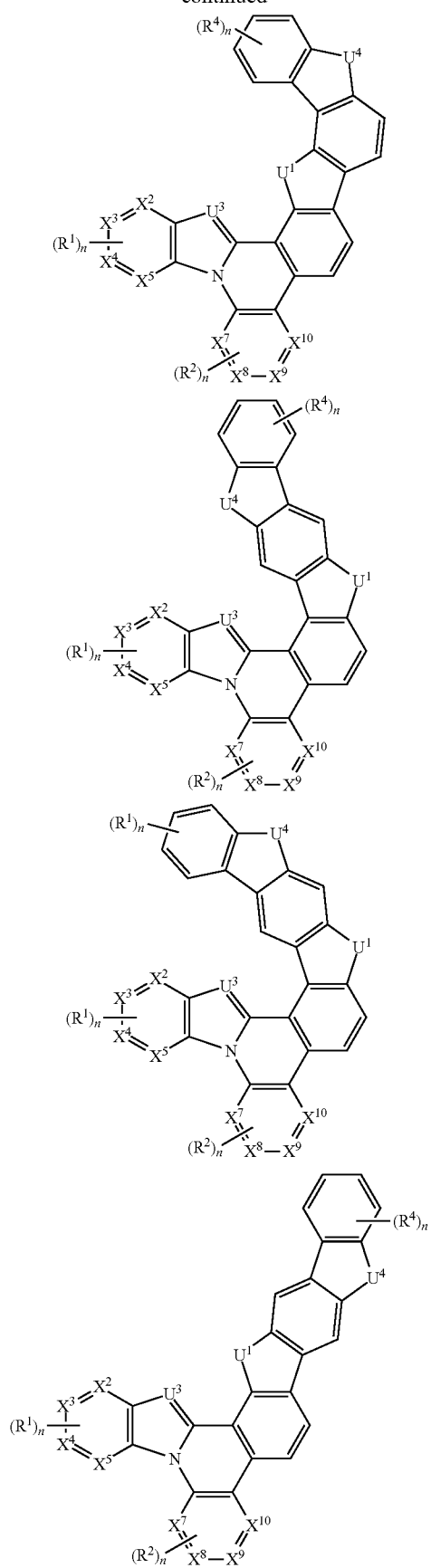
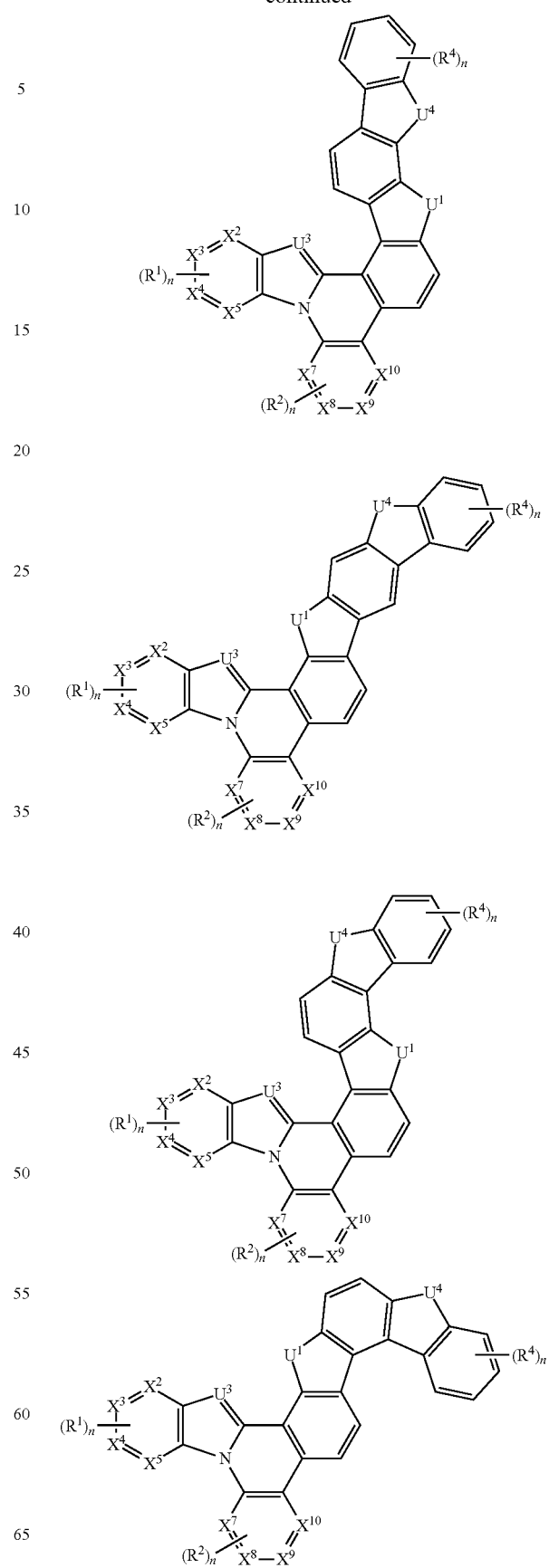

-continued
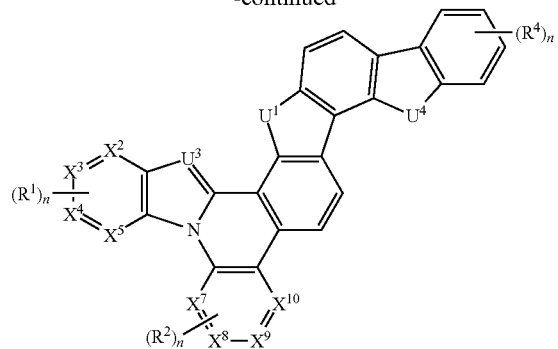
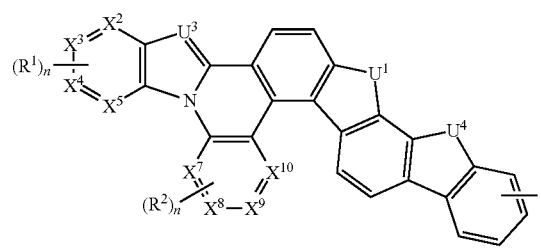
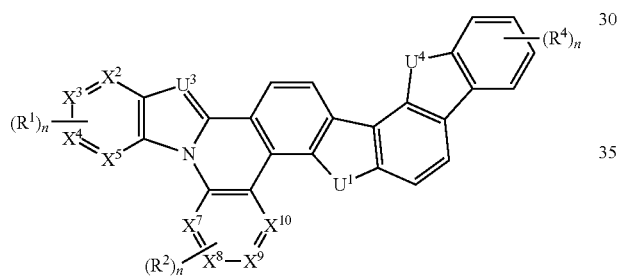
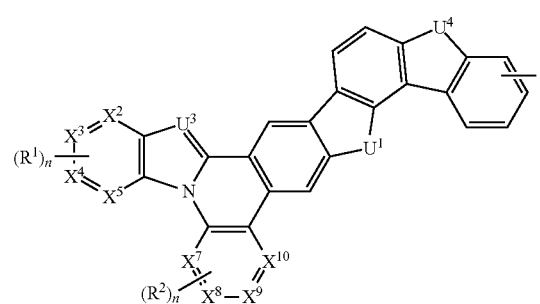
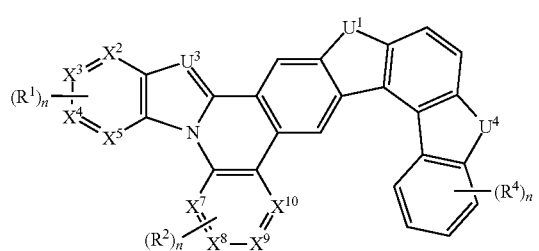
-continued
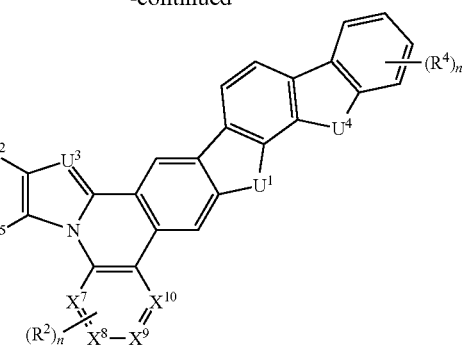
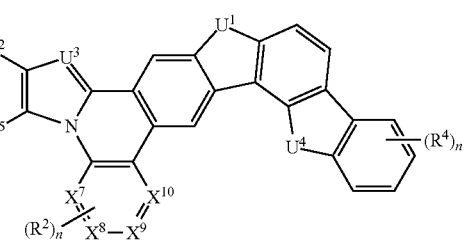
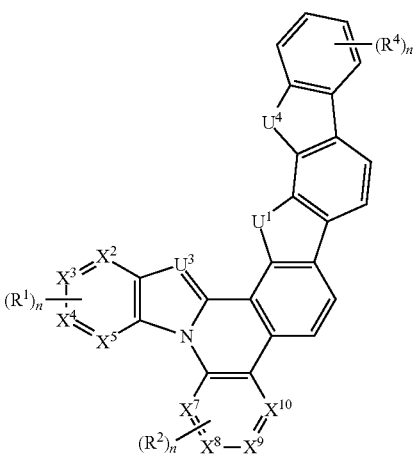
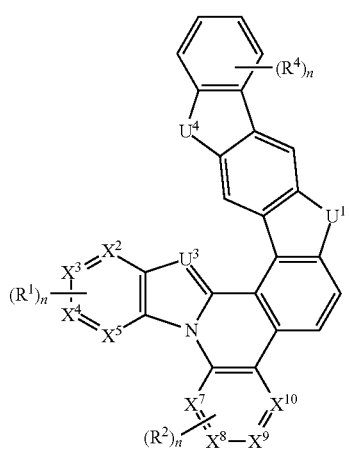

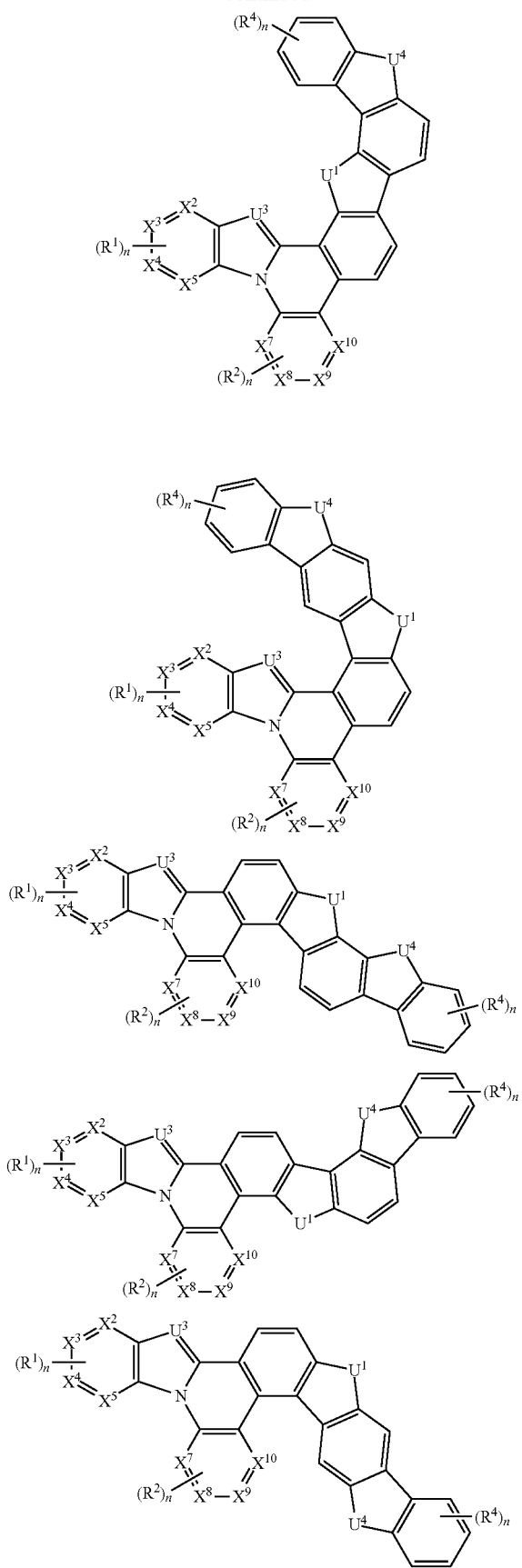
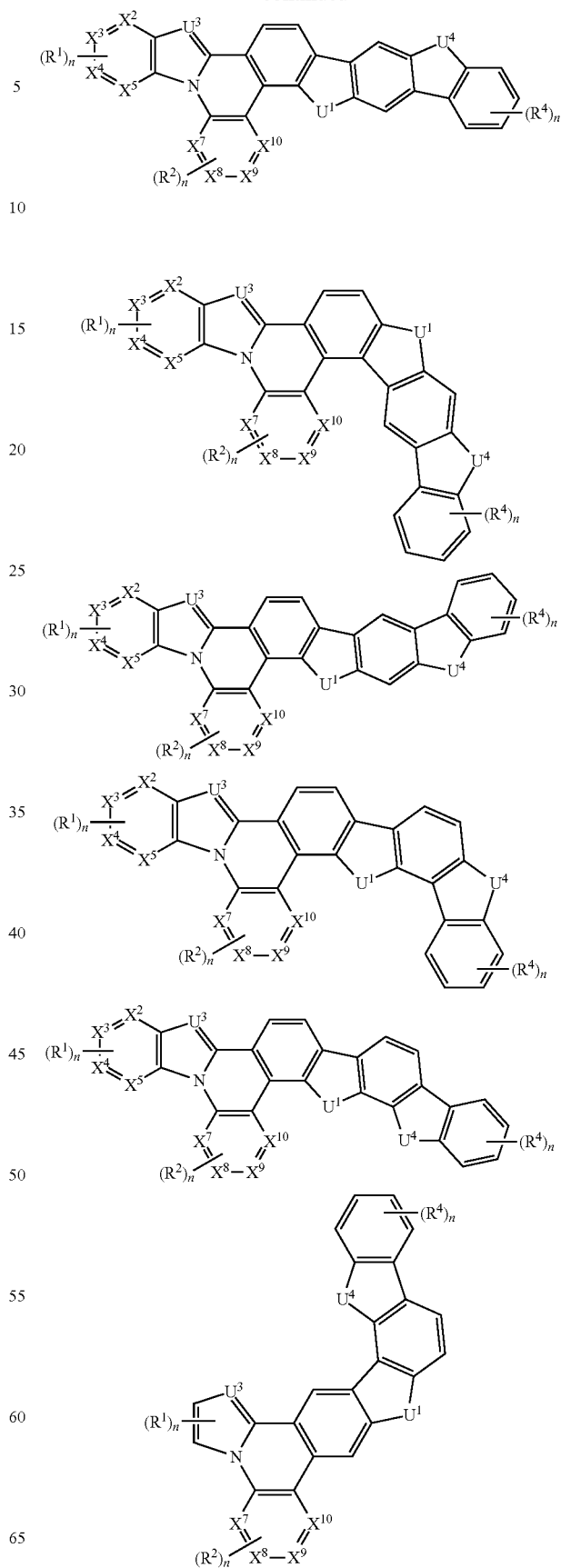

-continued
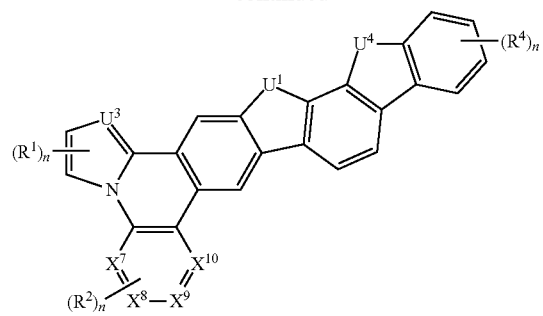
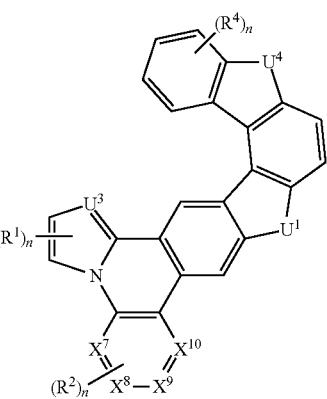
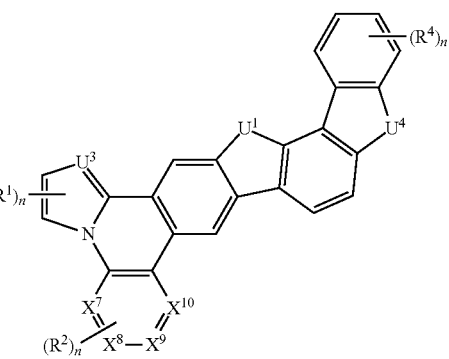
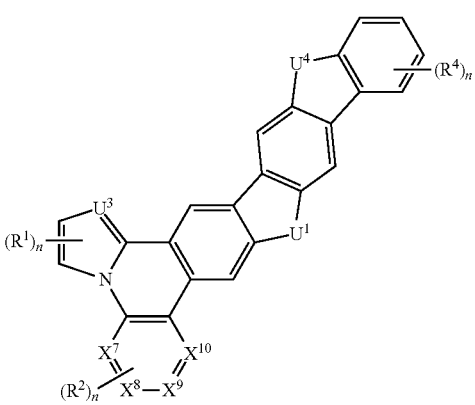
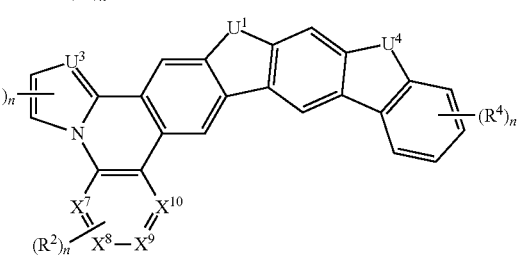
-continued
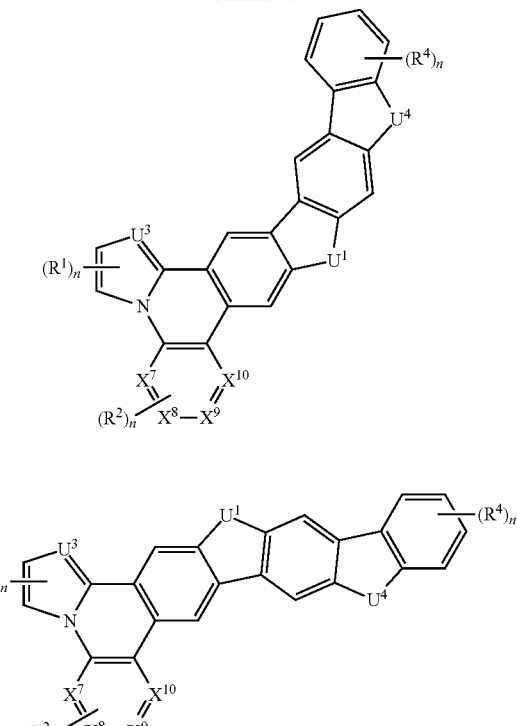
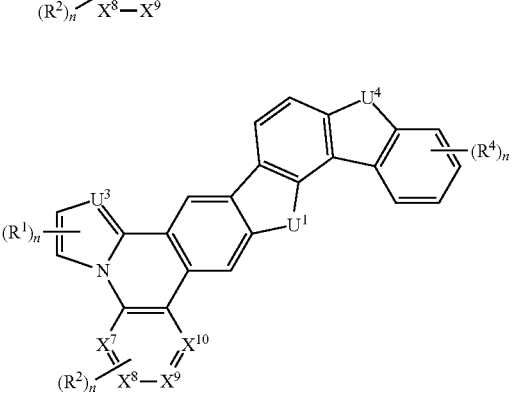
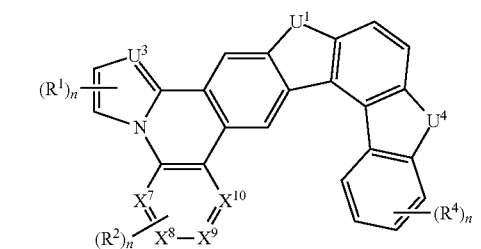
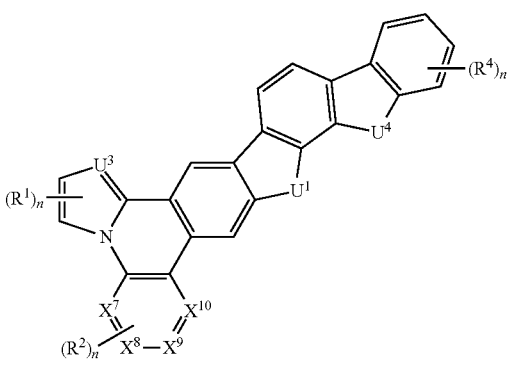

-continued
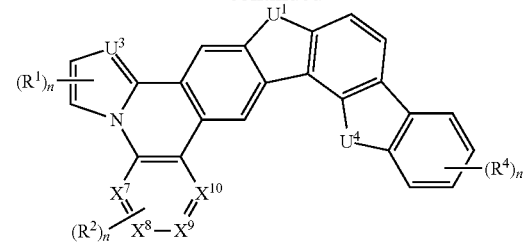
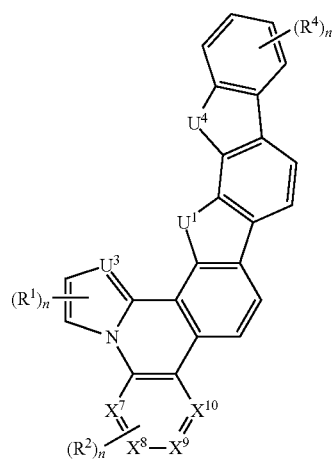
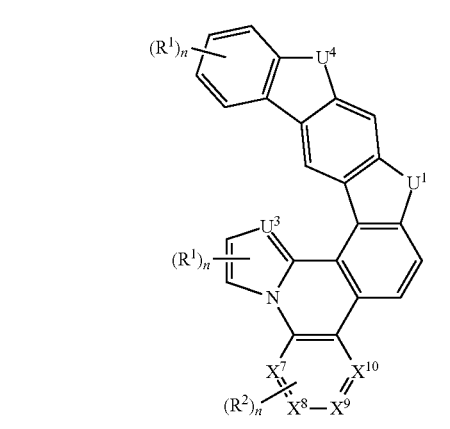 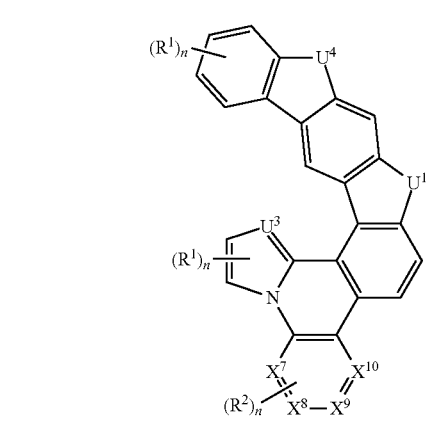
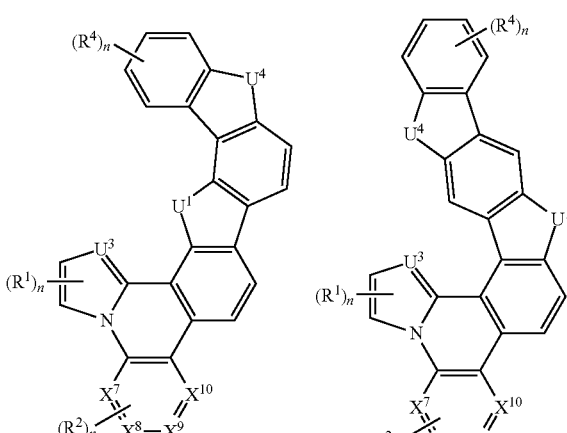
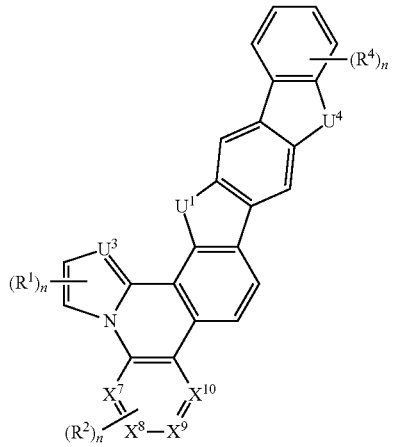
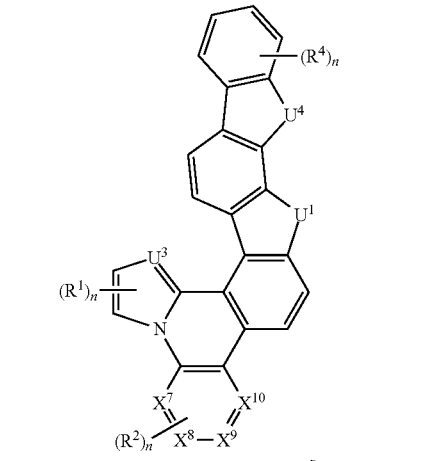
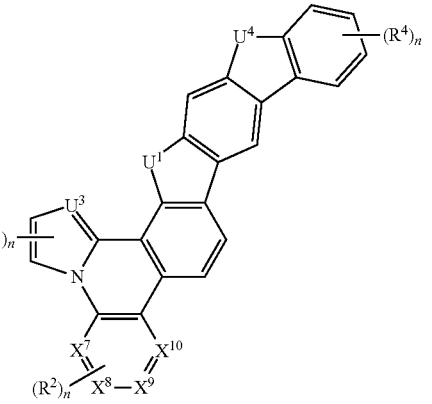
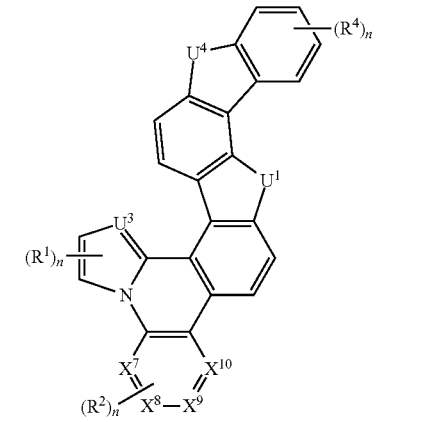

-continued
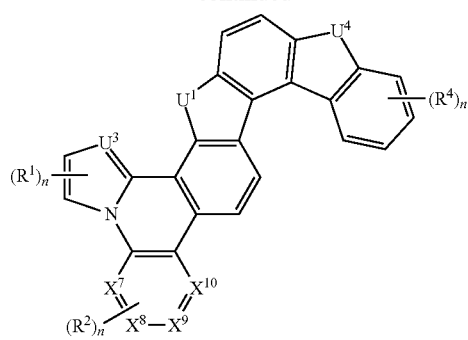
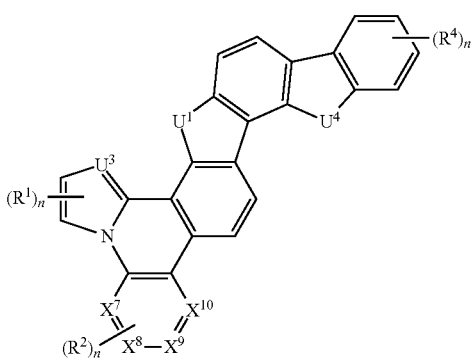
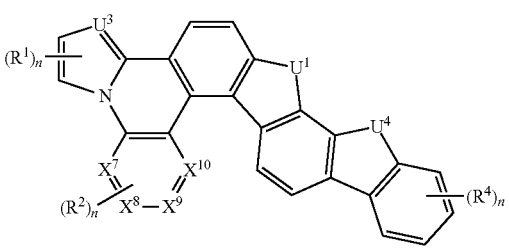
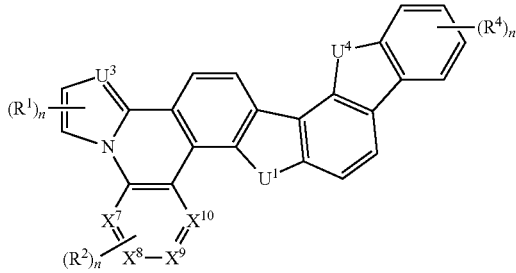
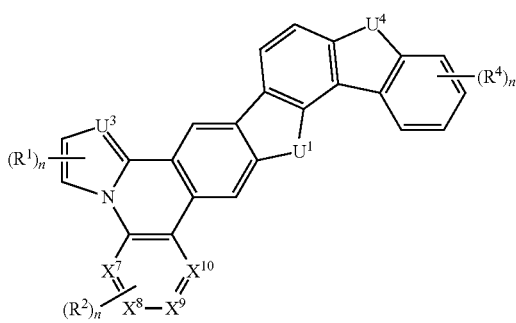
-continued
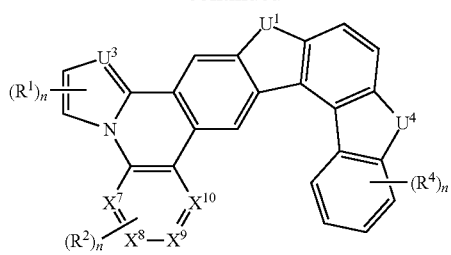
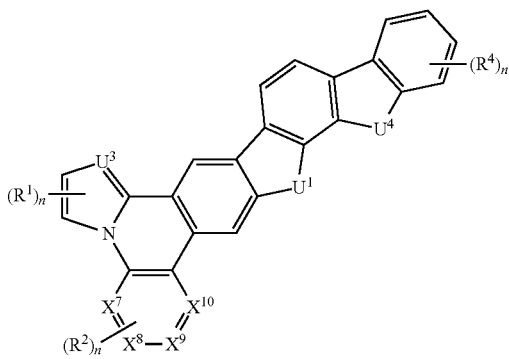
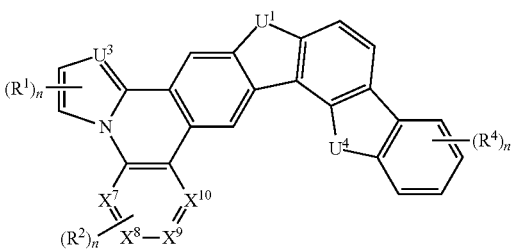
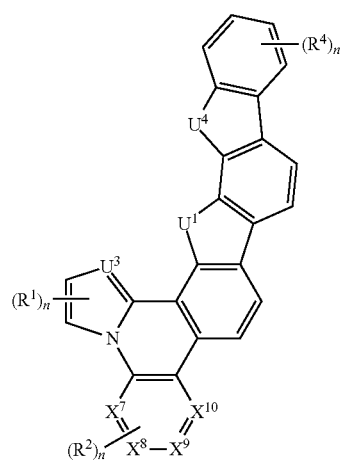

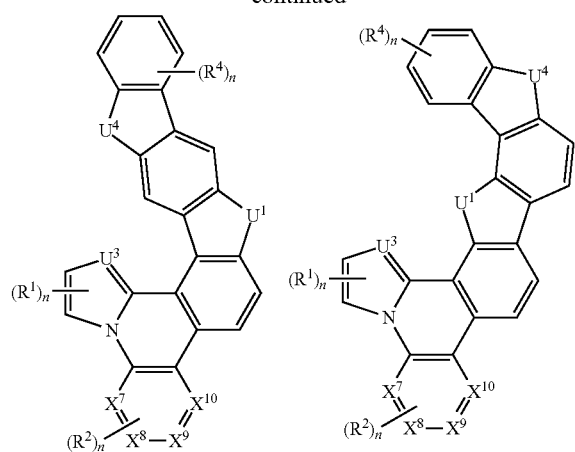
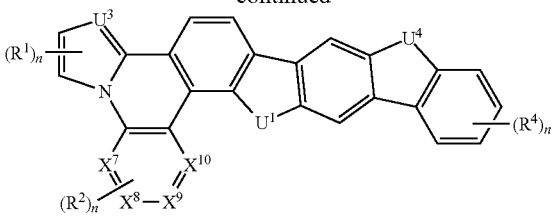
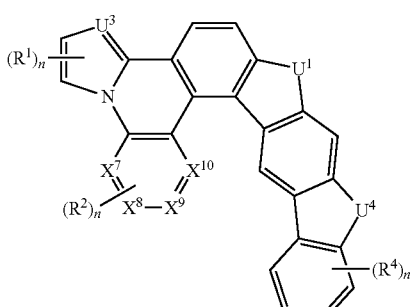
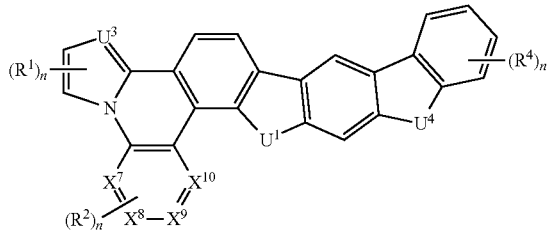
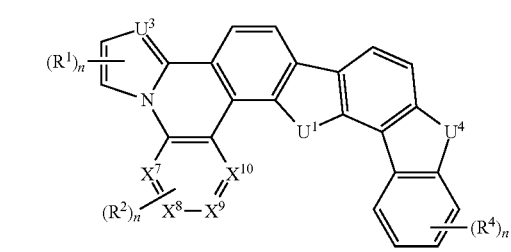
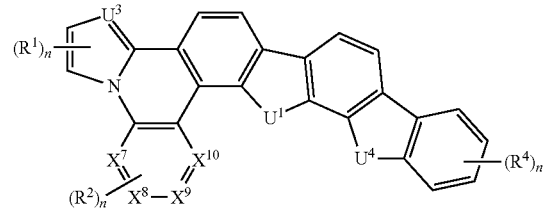
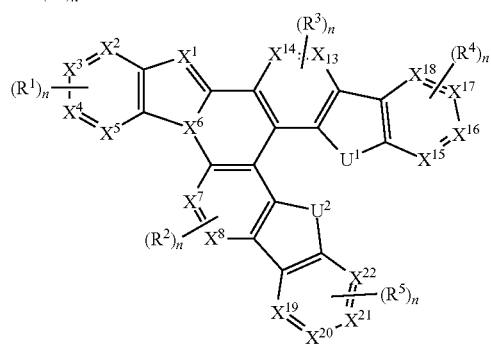

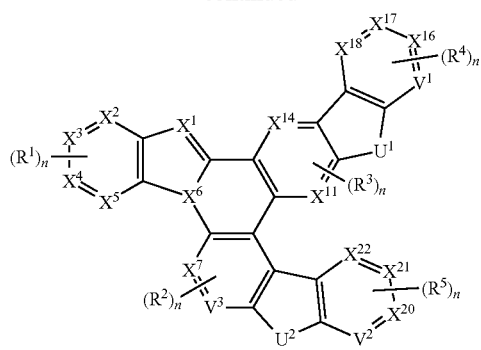
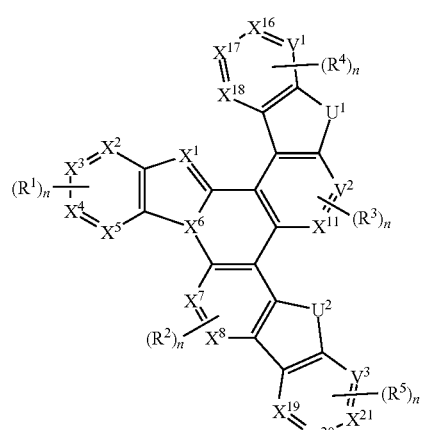
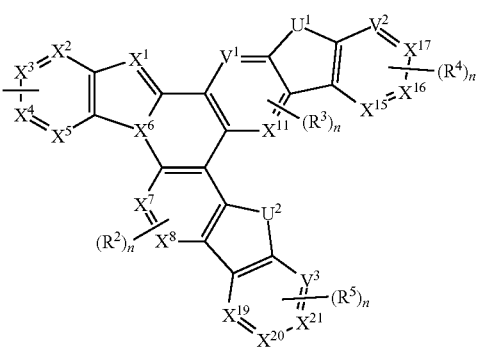
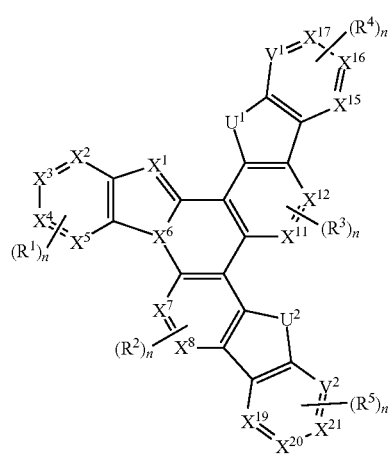
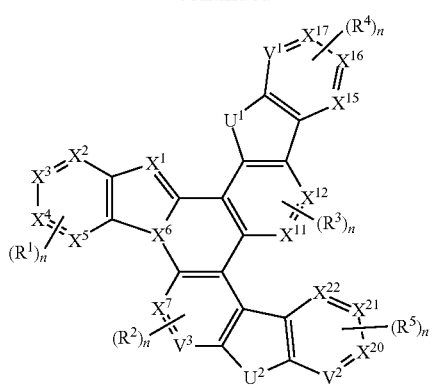
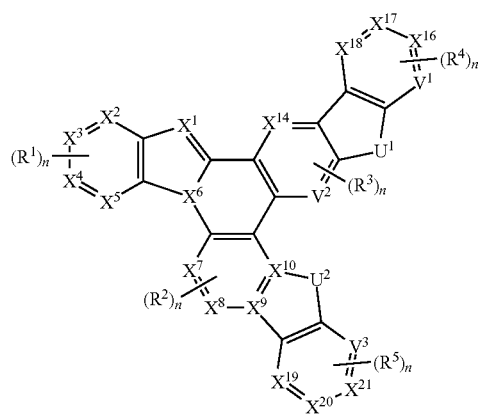
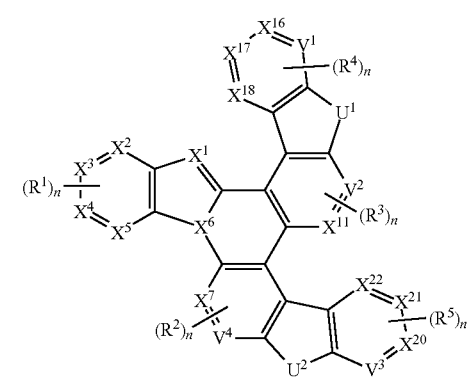
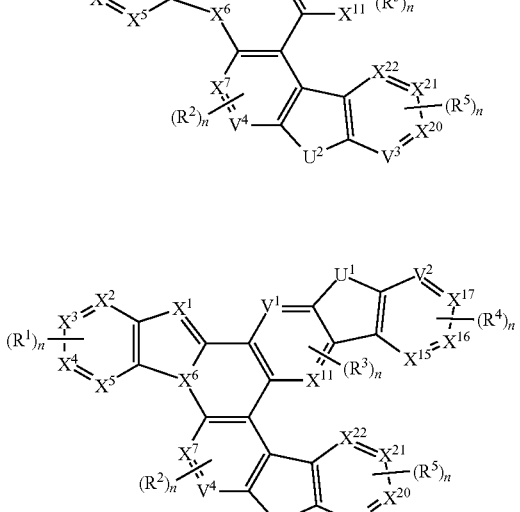

287
-continued
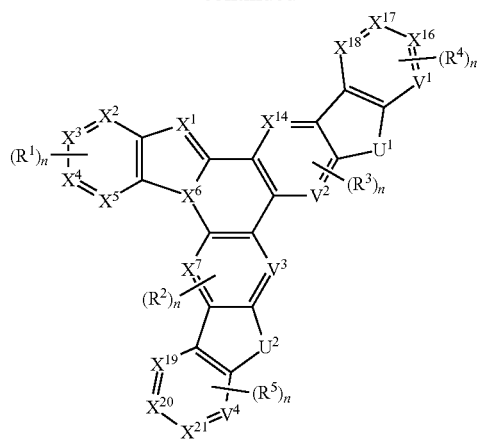
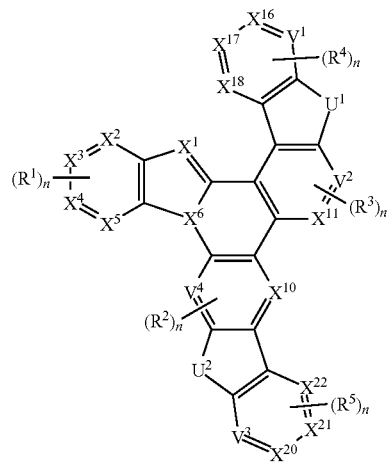
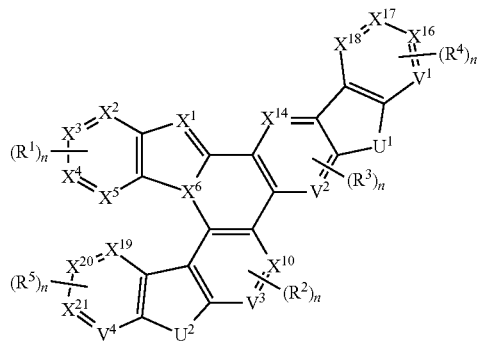
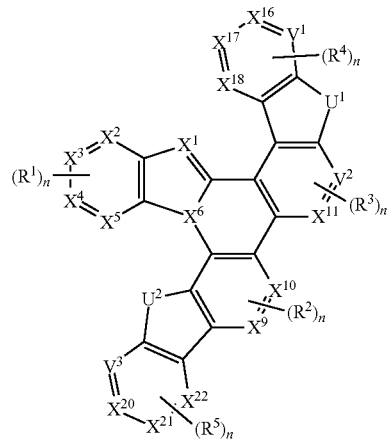
288
-continued
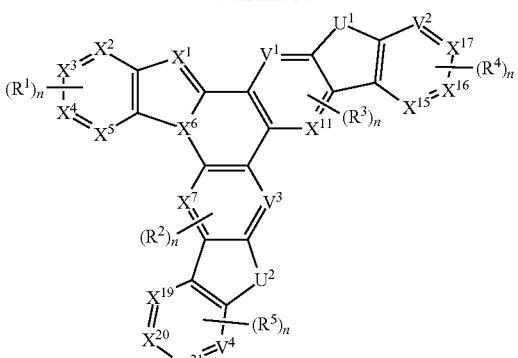
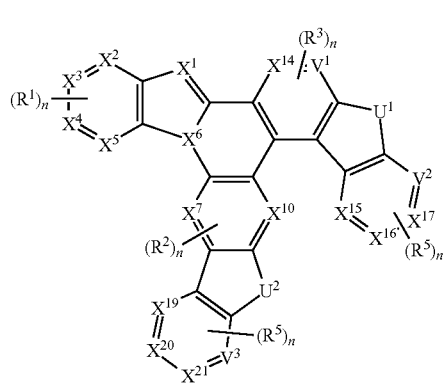
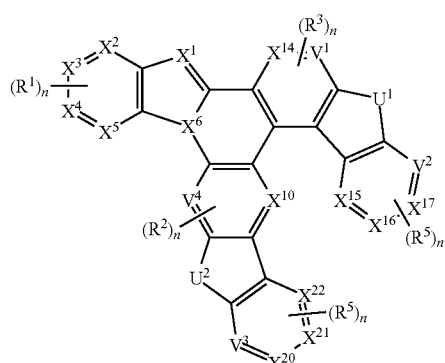
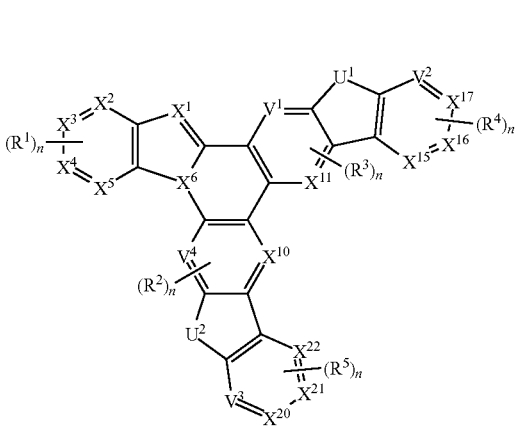

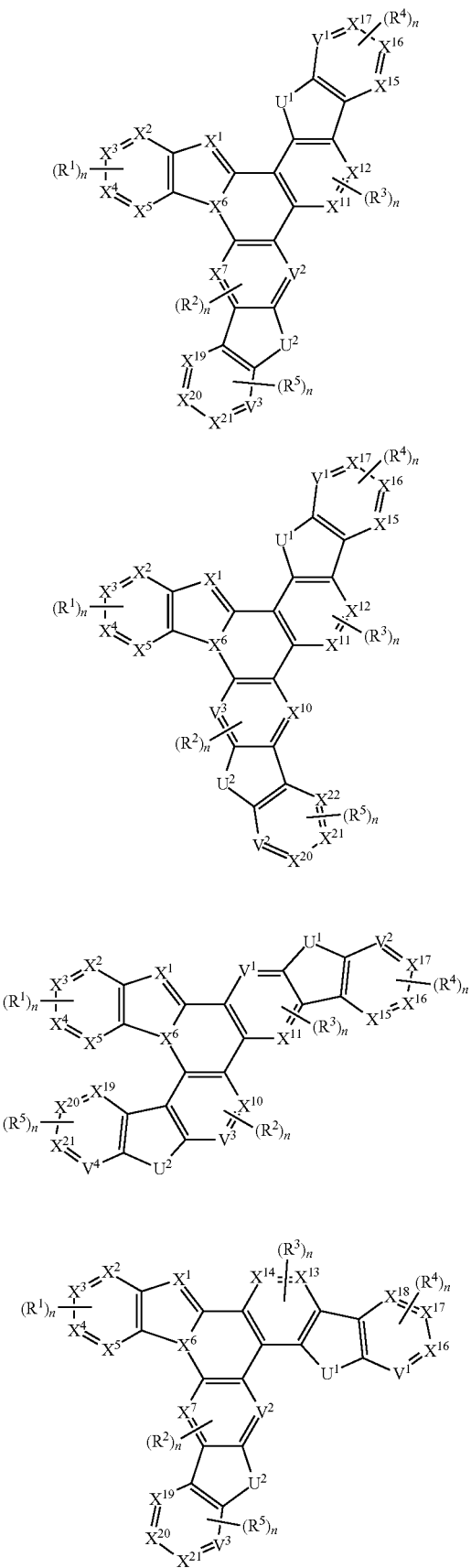
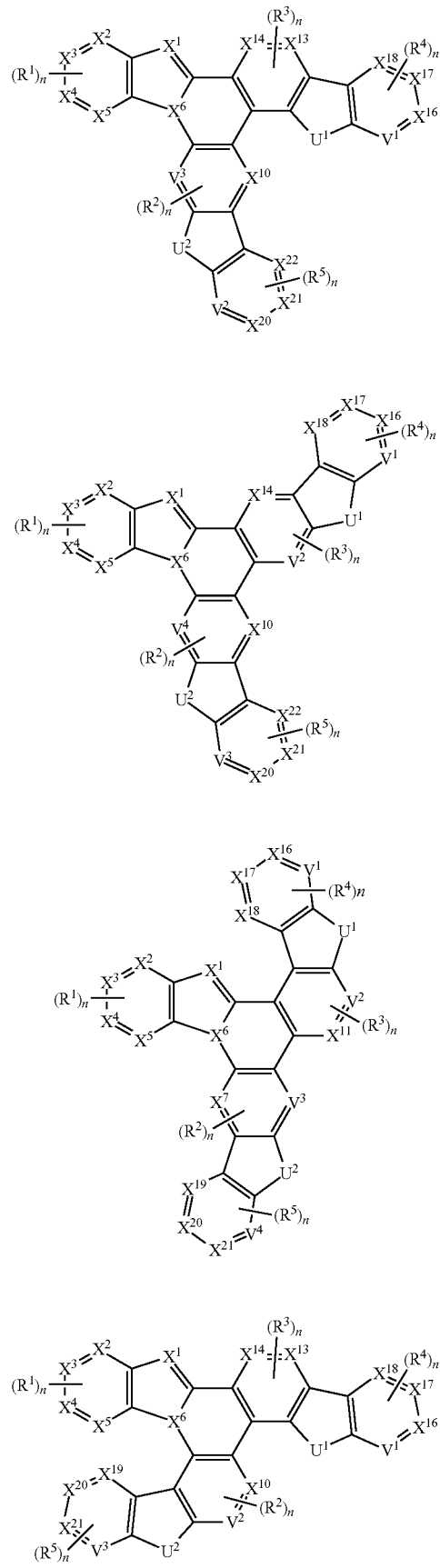

291
-continued
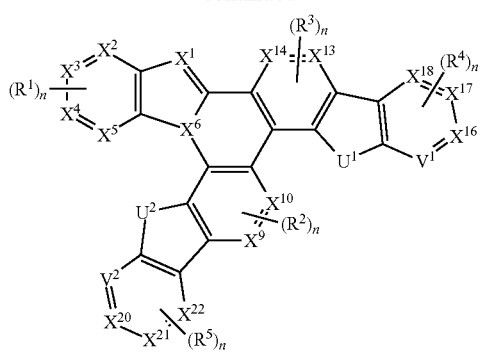
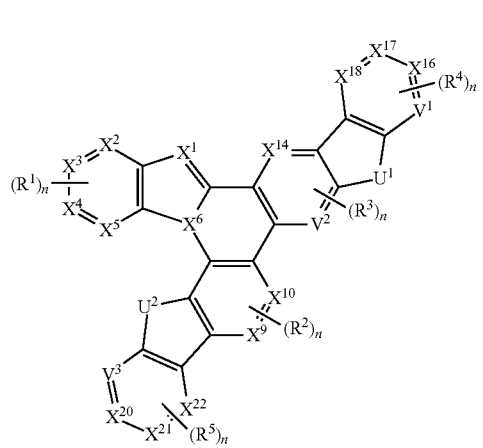
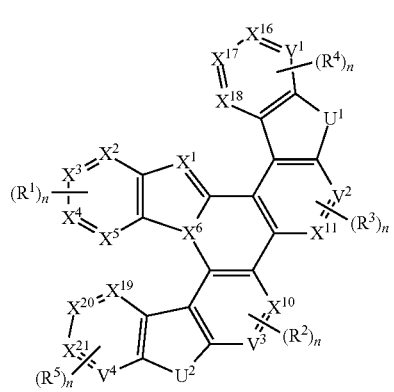
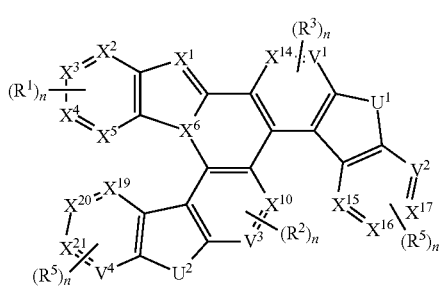
292
-continued
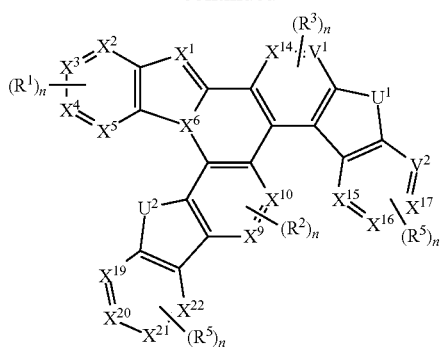
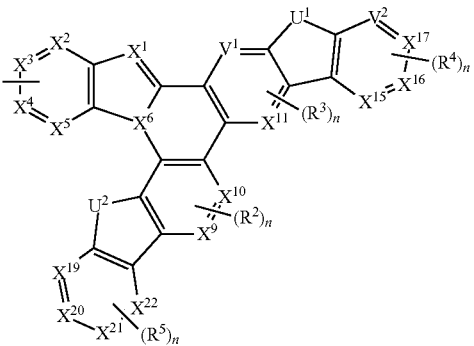
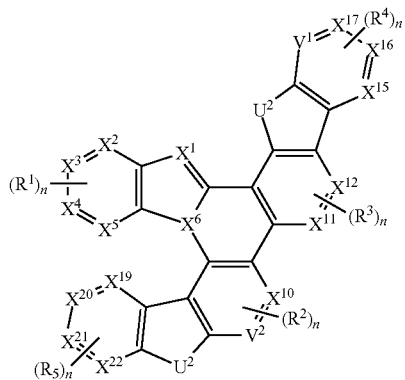
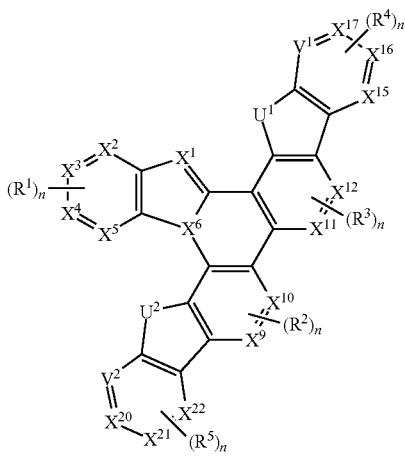

-continued
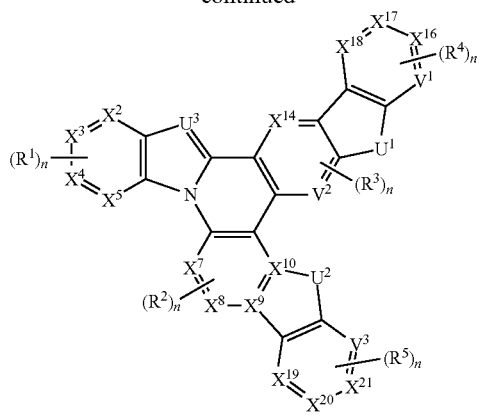
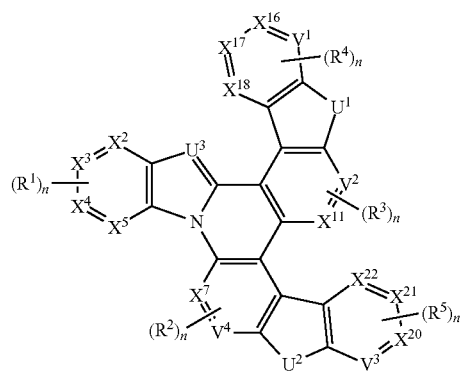
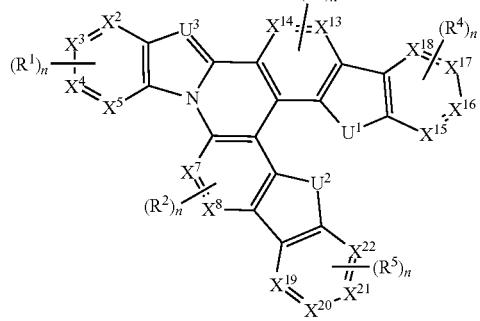
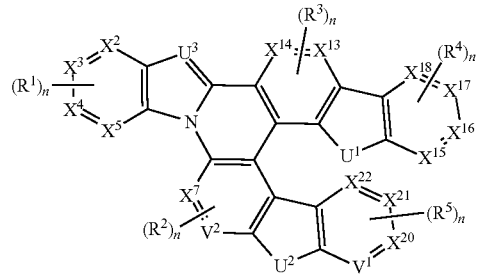
-continued
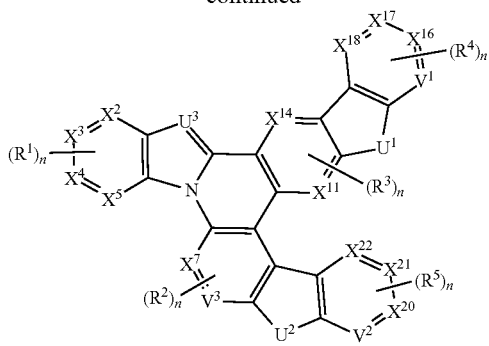
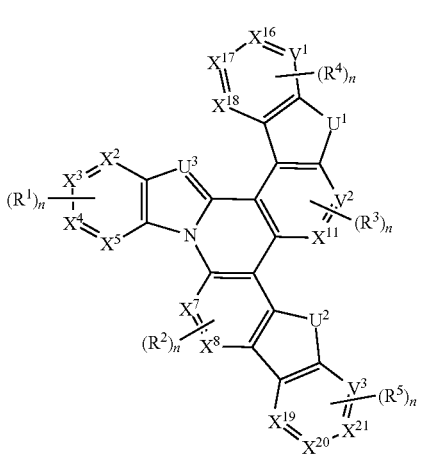
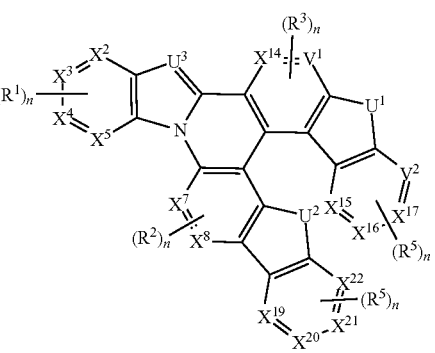
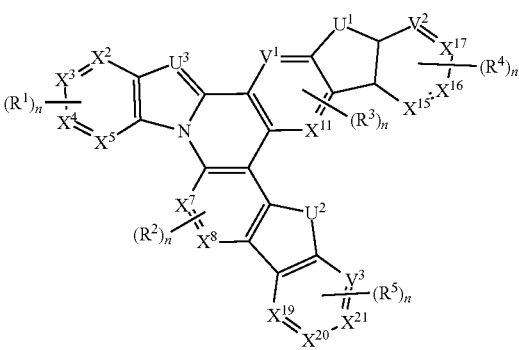

-continued
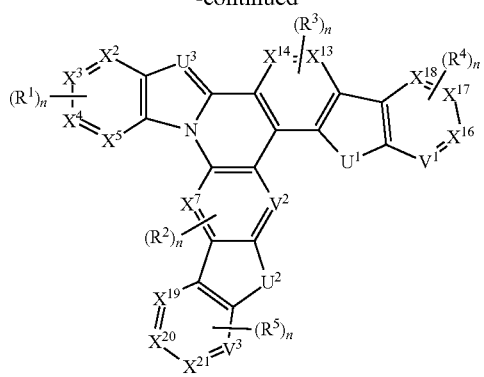
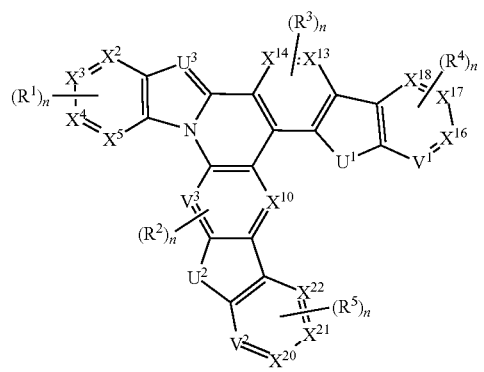
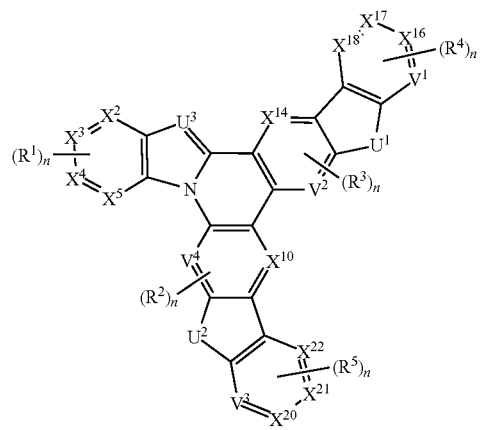
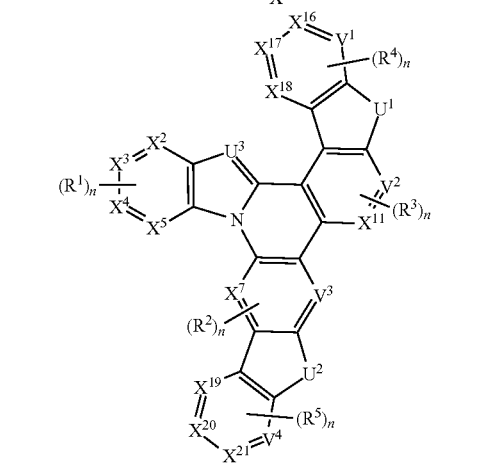
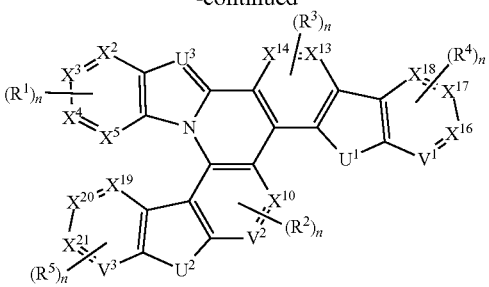
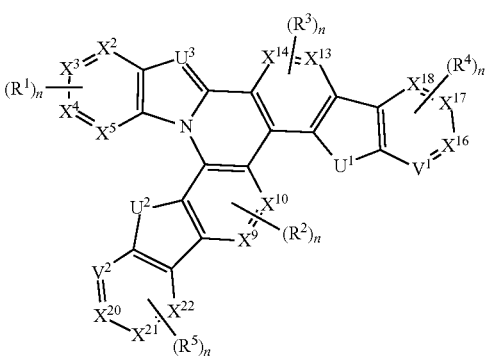
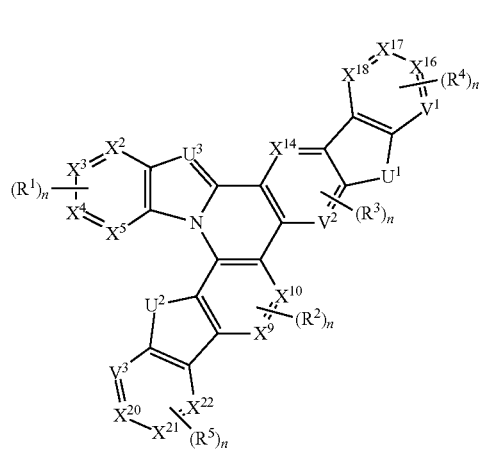
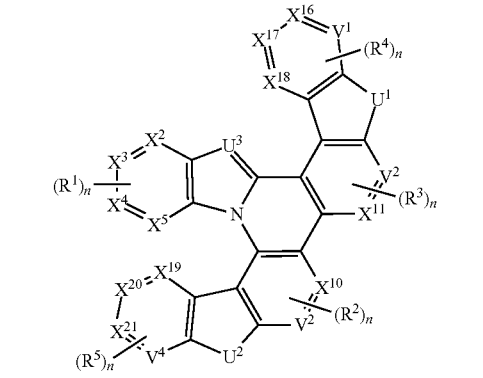

297
-continued
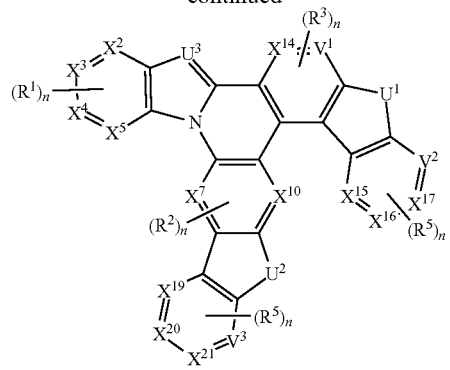
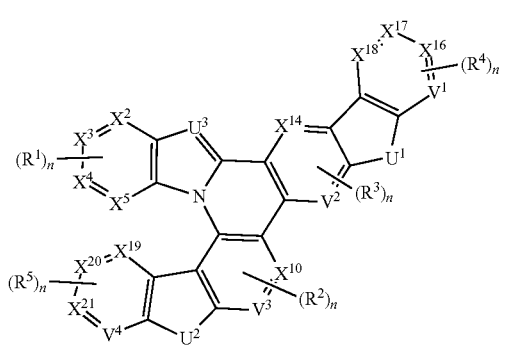
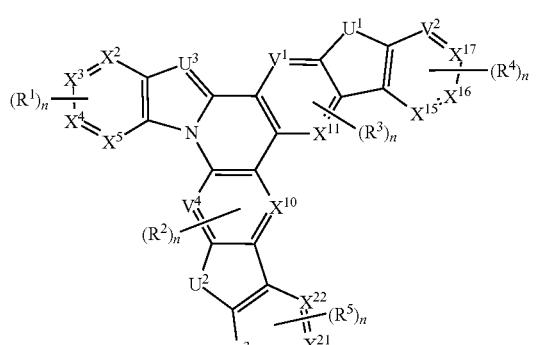
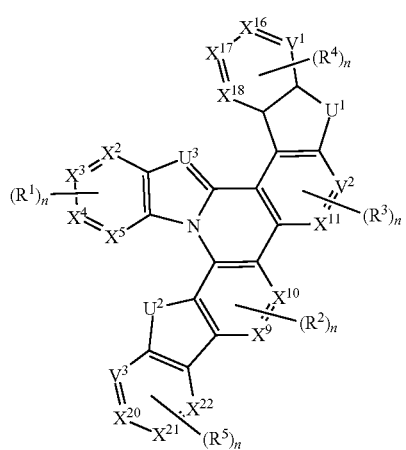
298
-continued
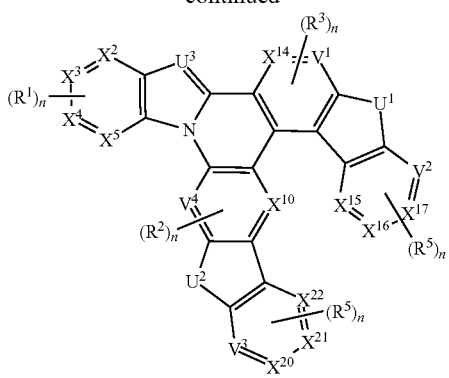
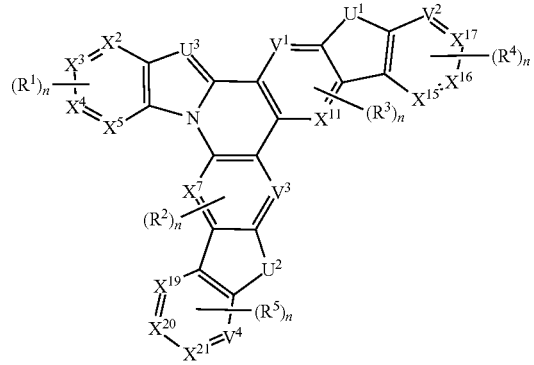
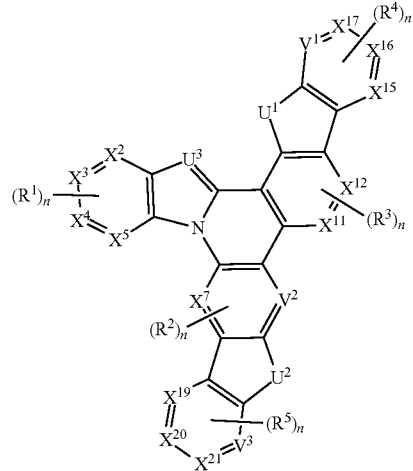
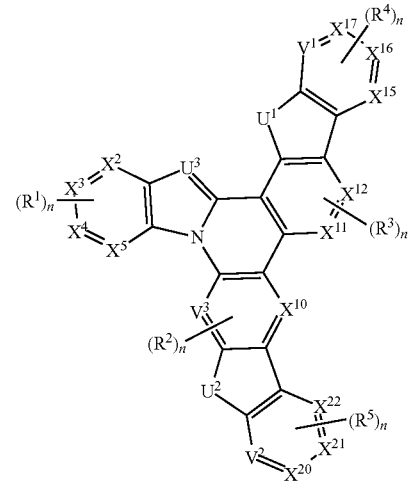

299
-continued
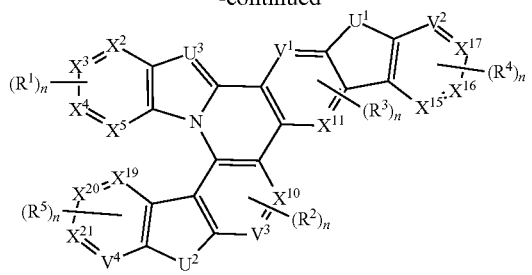
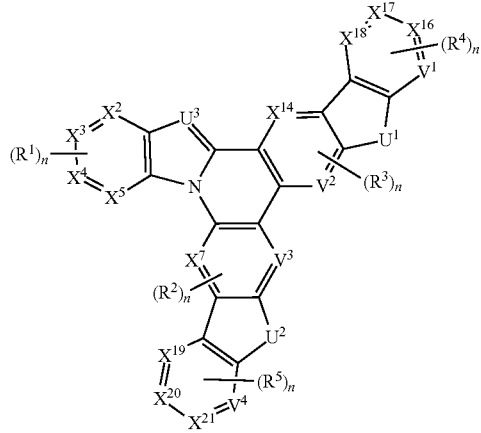
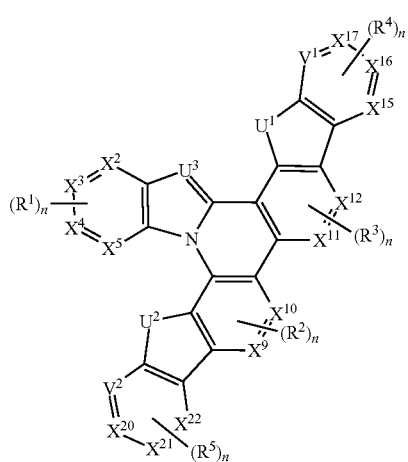
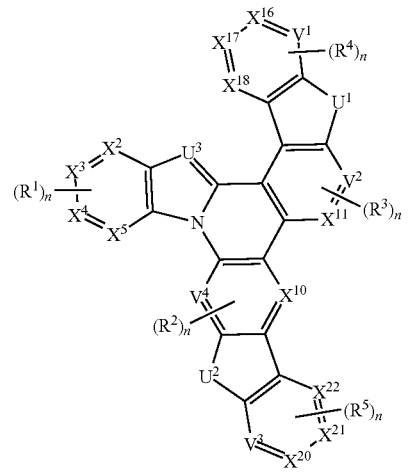
300
-continued
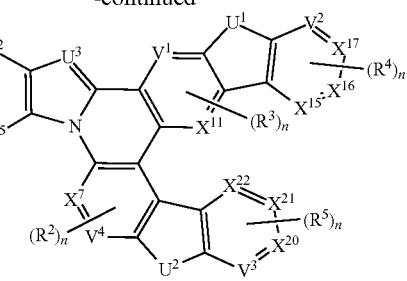
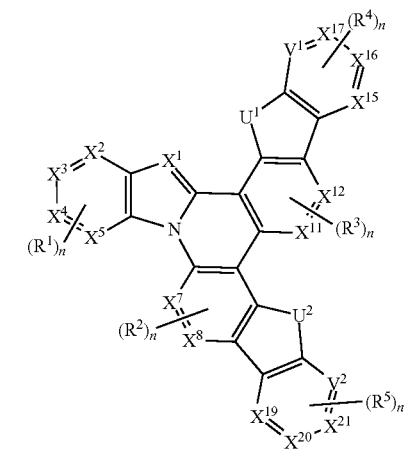
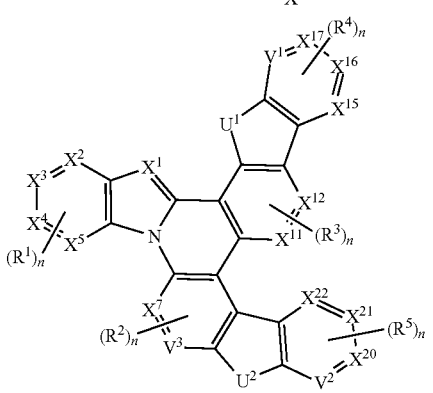
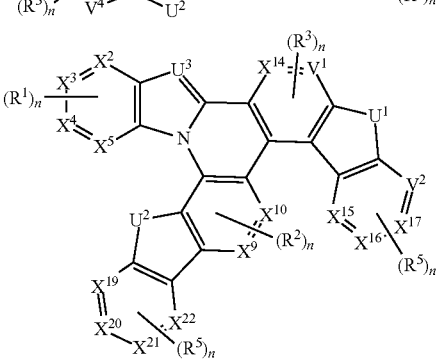

301
-continued
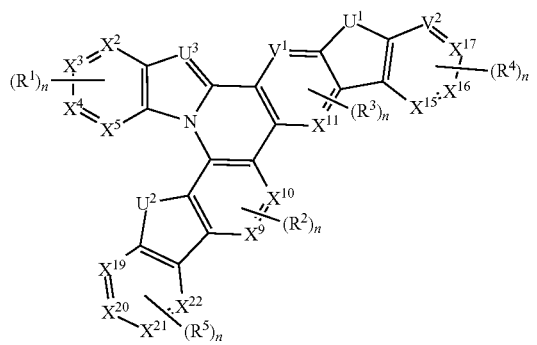
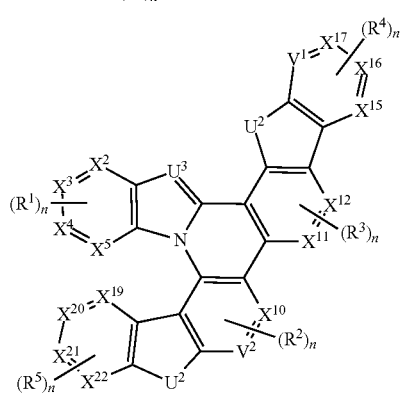
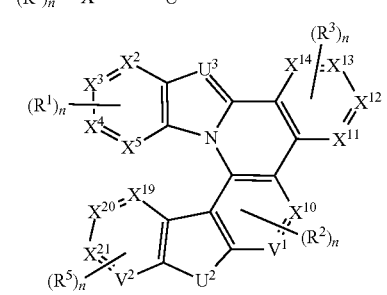
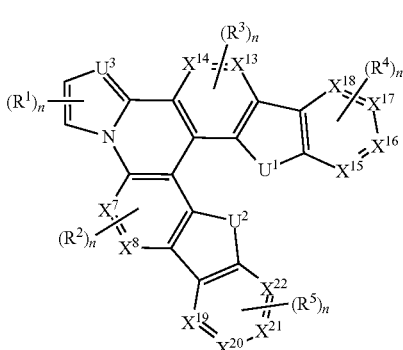
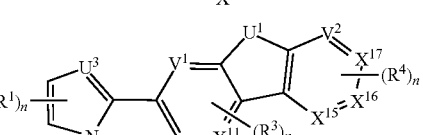
302
-continued
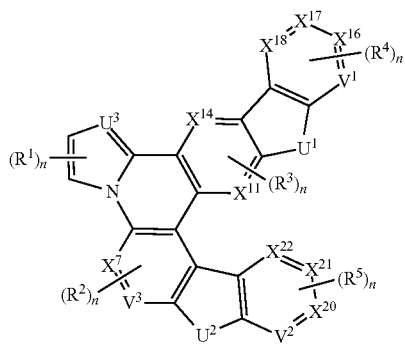
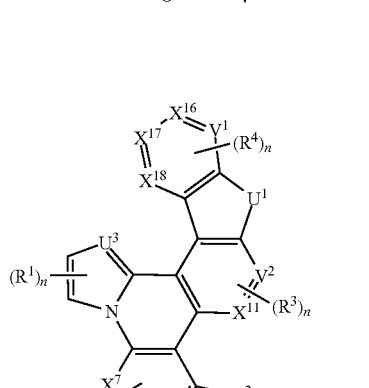
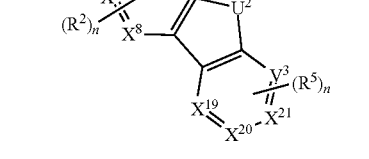
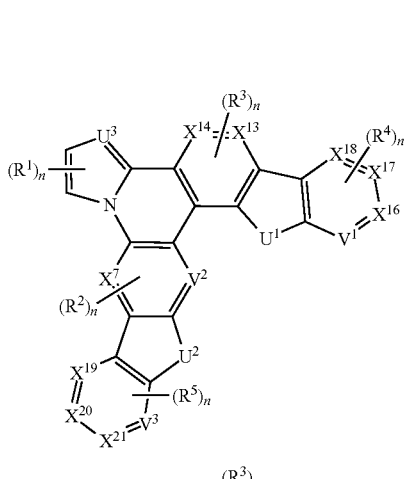
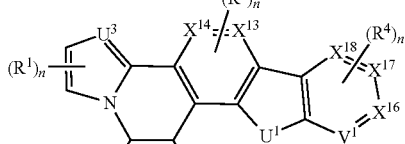
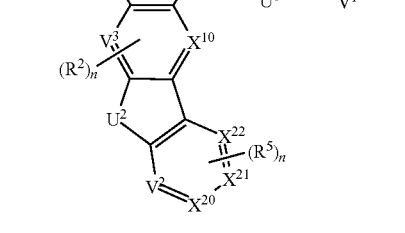

-continued
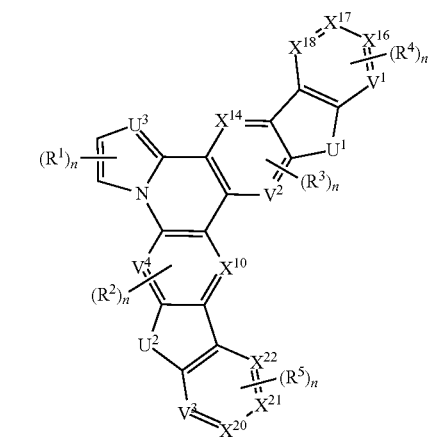
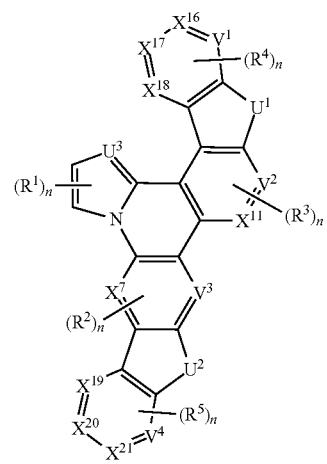
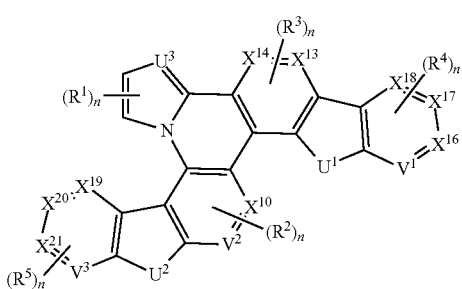
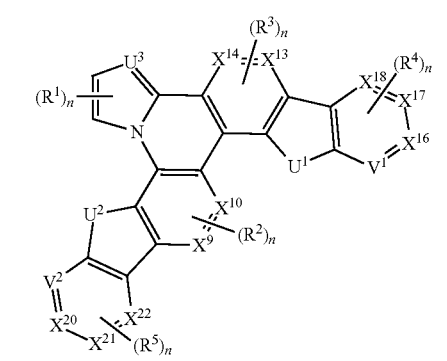
-continued
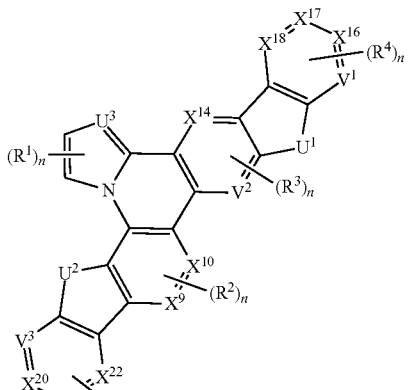
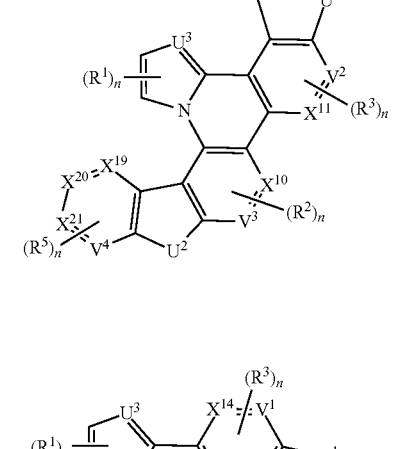
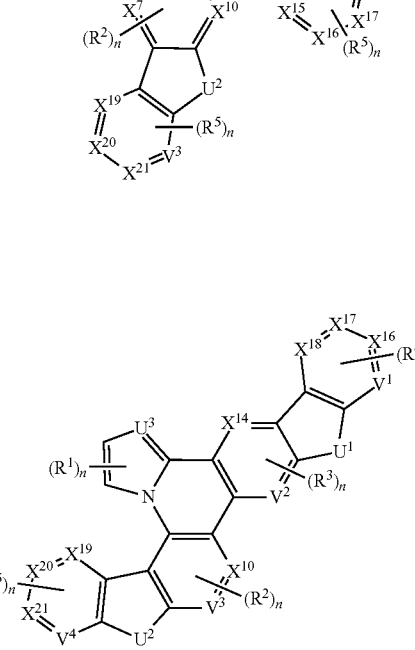
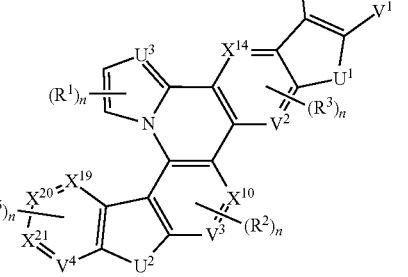

305
-continued

306
-continued

-continued
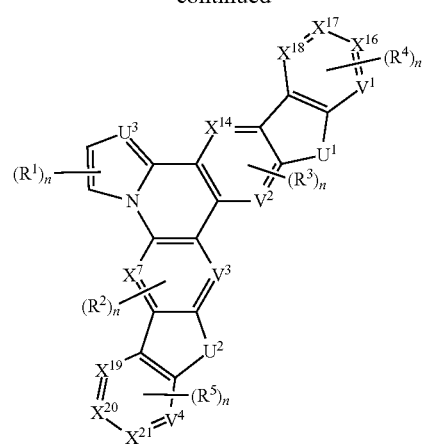
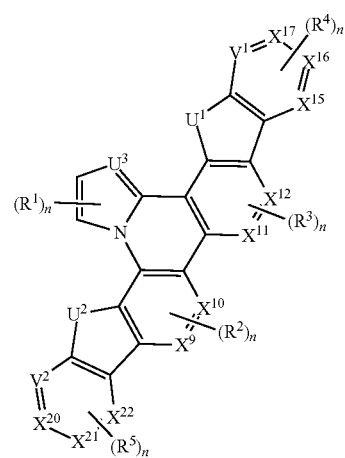
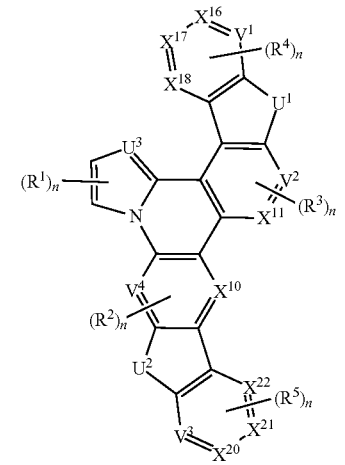
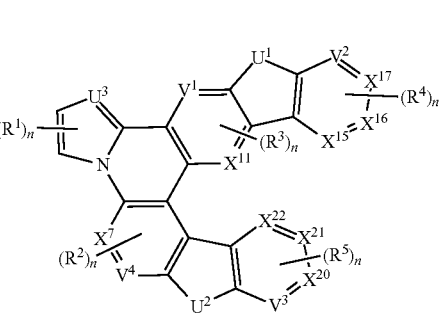
-continued
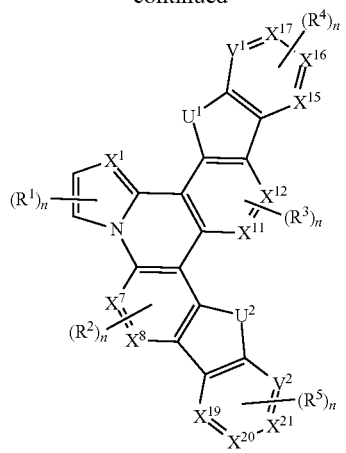
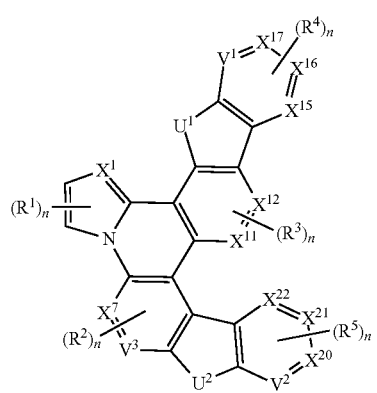
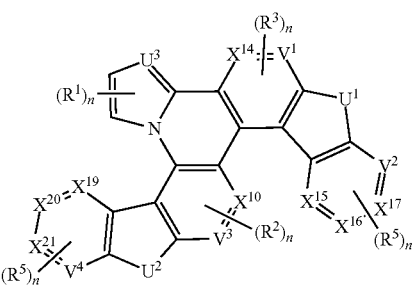
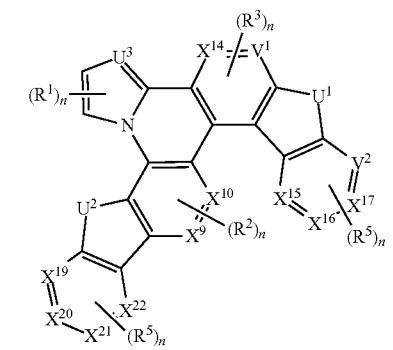

-continued
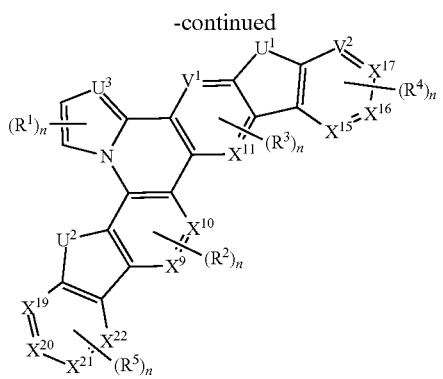
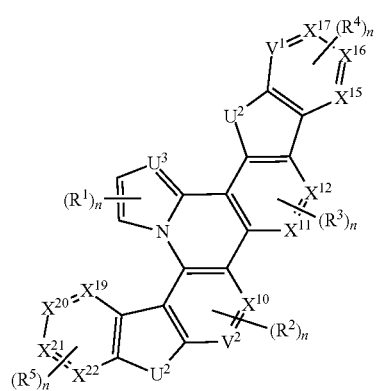
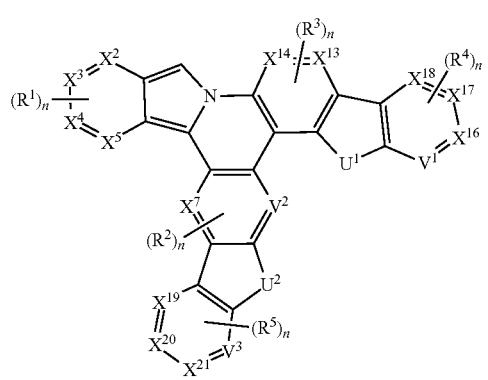
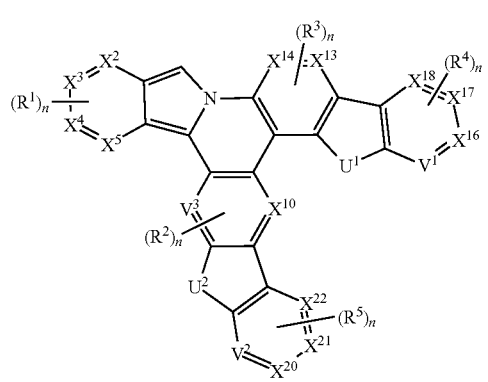
-continued
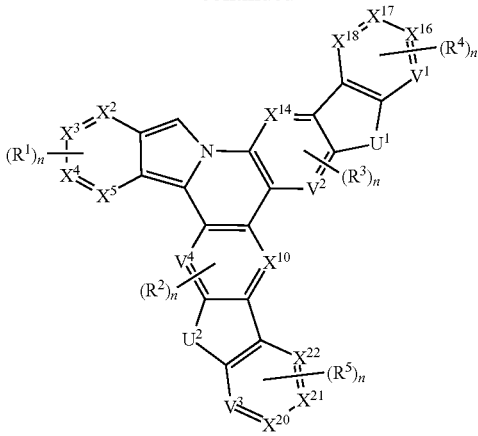
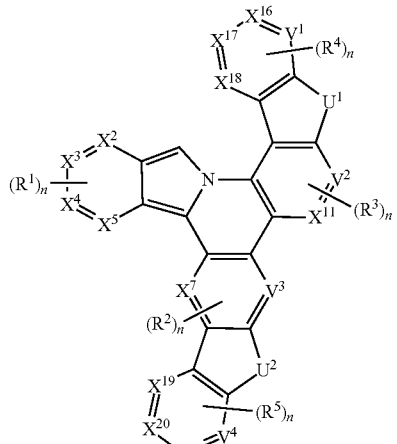
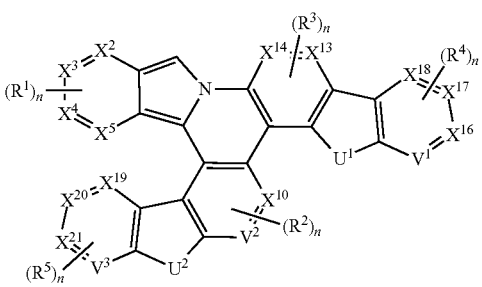
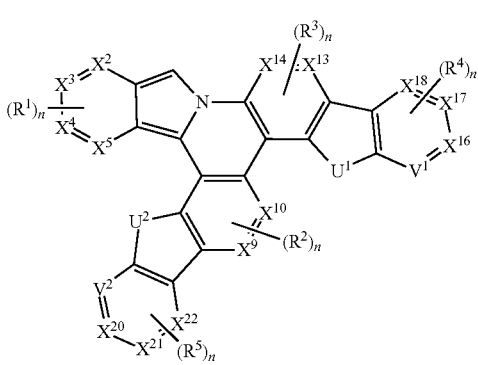

311
-continued
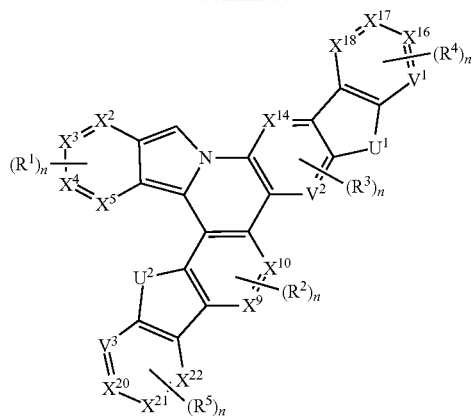
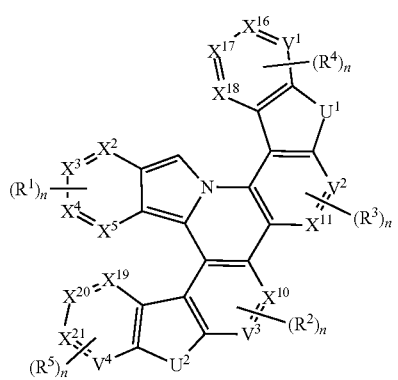
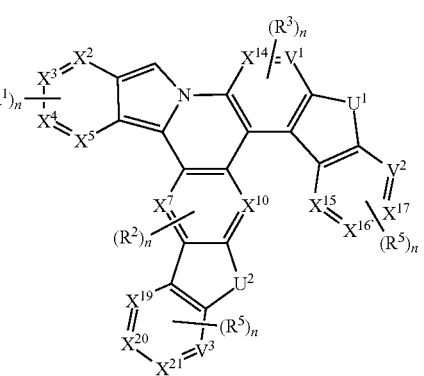
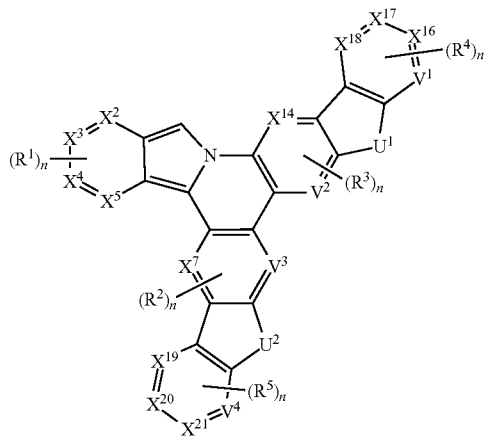
312
-continued
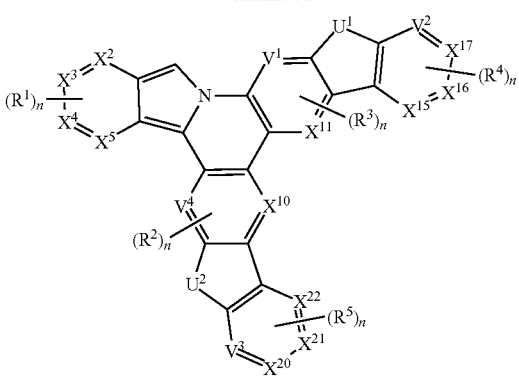
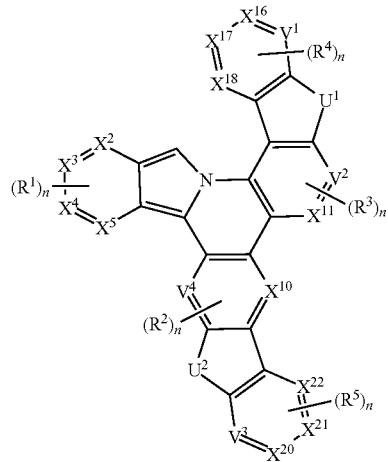
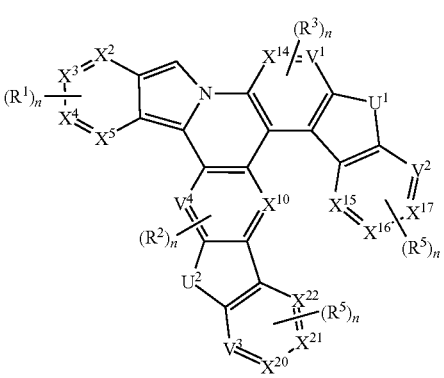
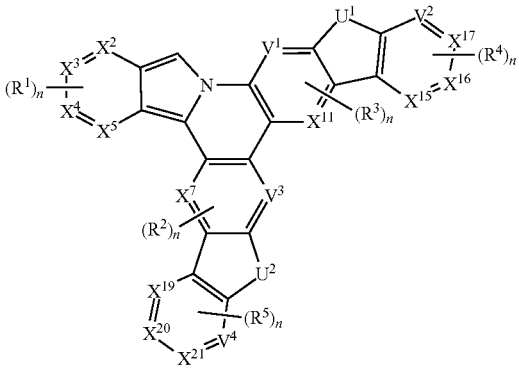

313
-continued
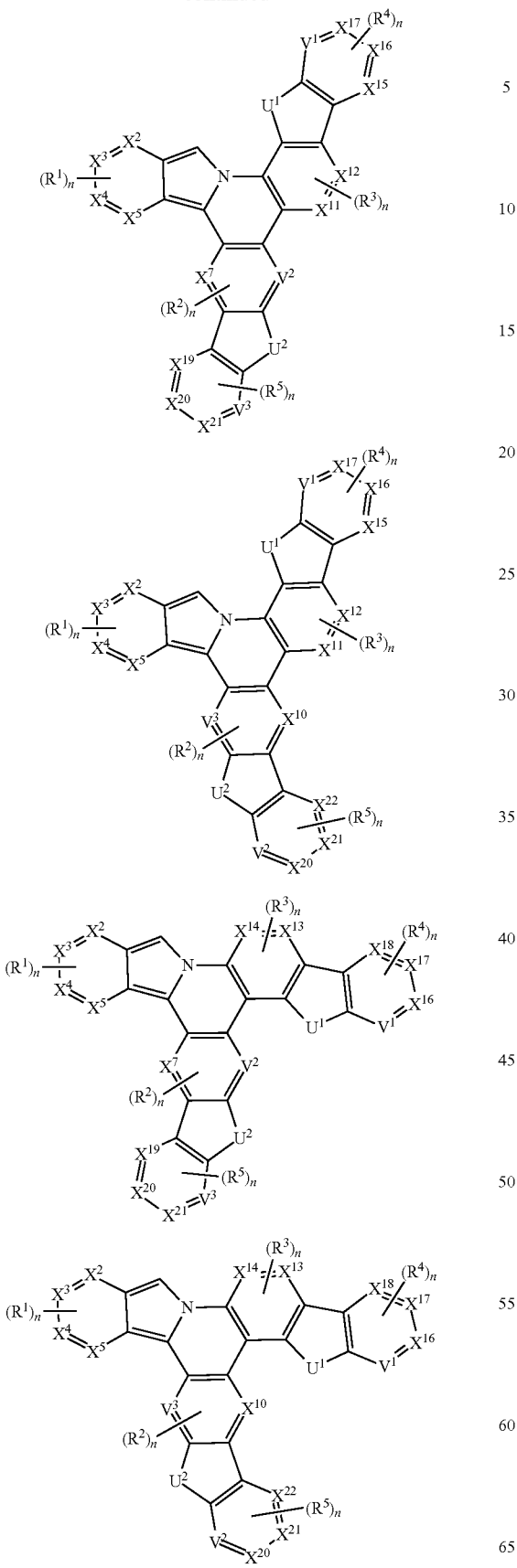
314
-continued
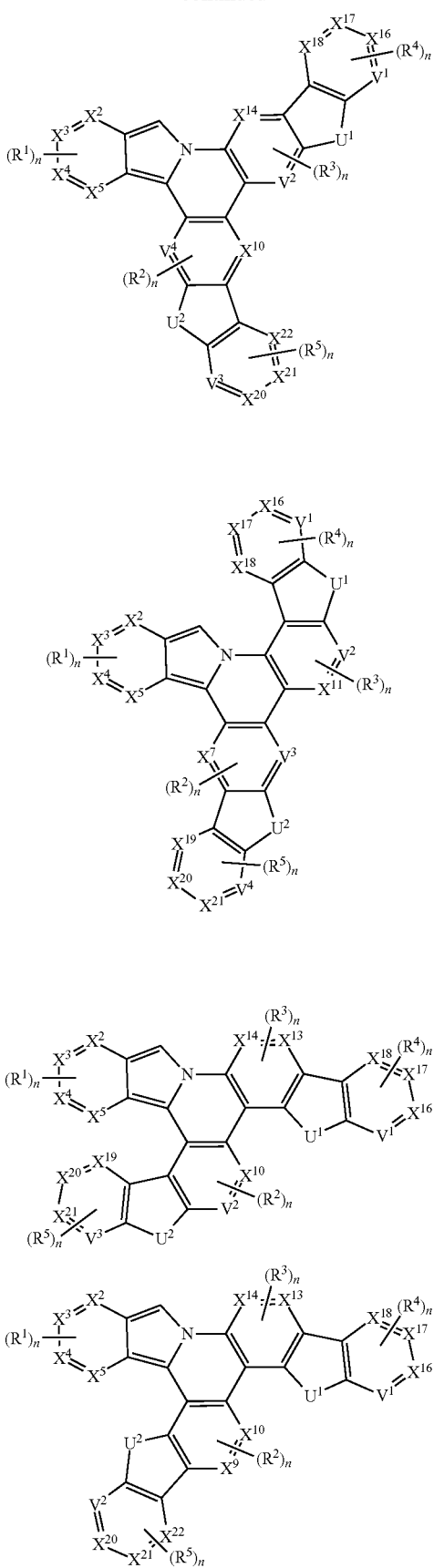

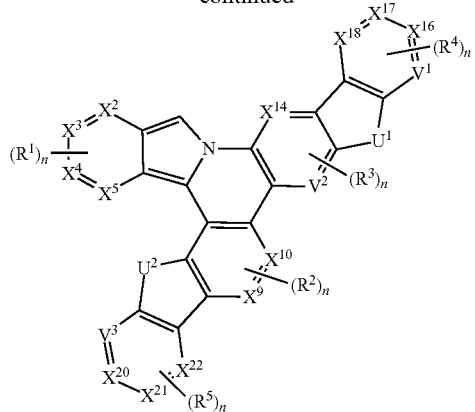
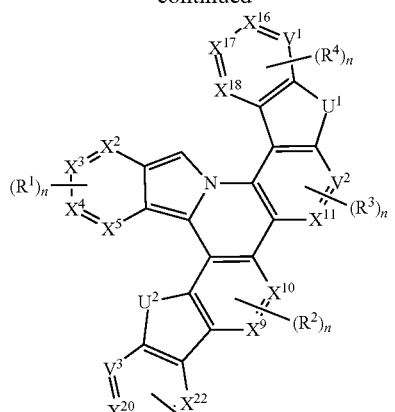
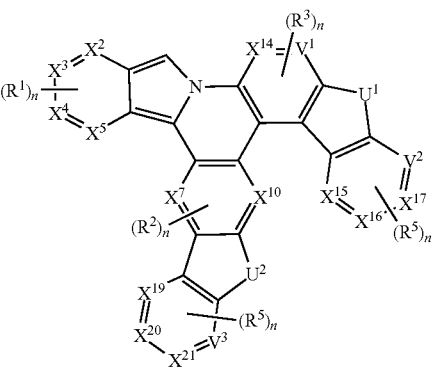
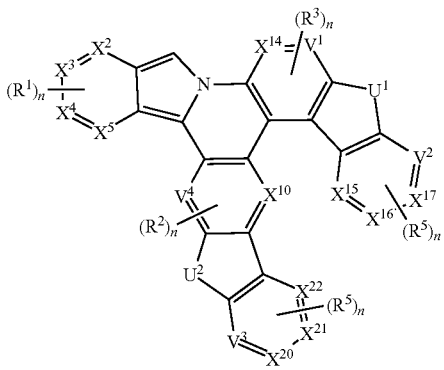

-continued
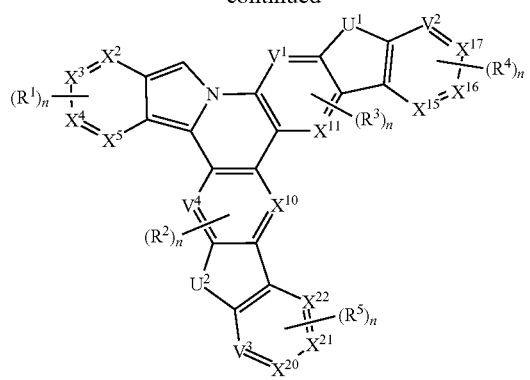
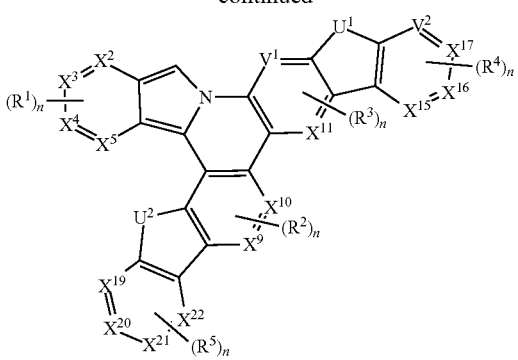
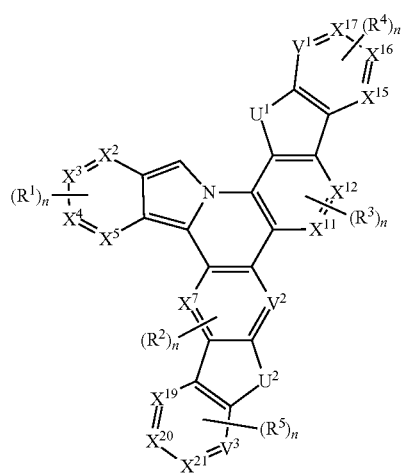
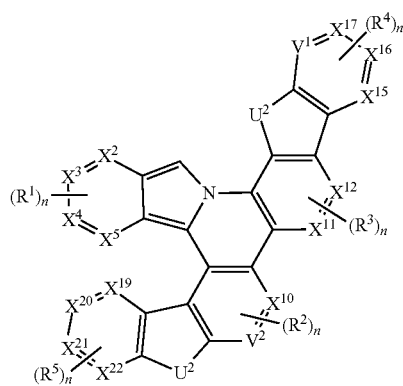
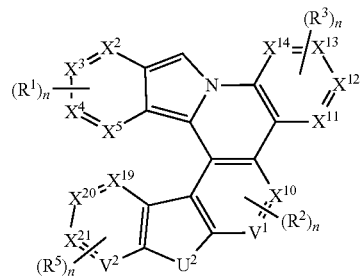
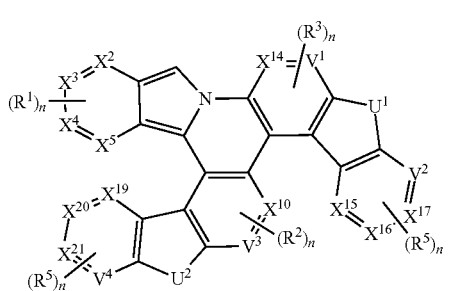
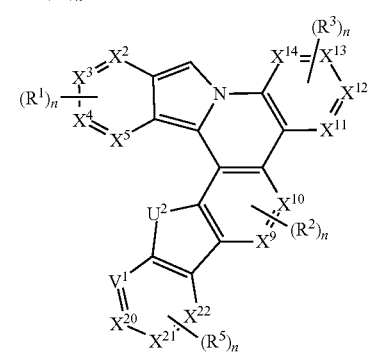
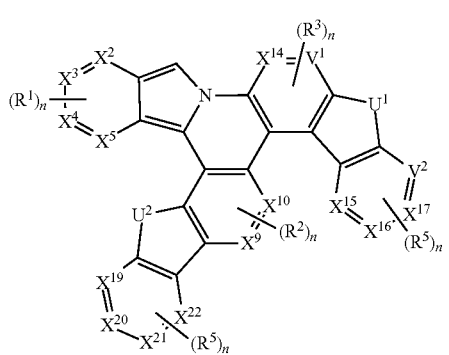
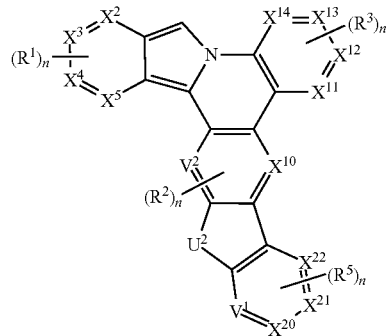

-continued

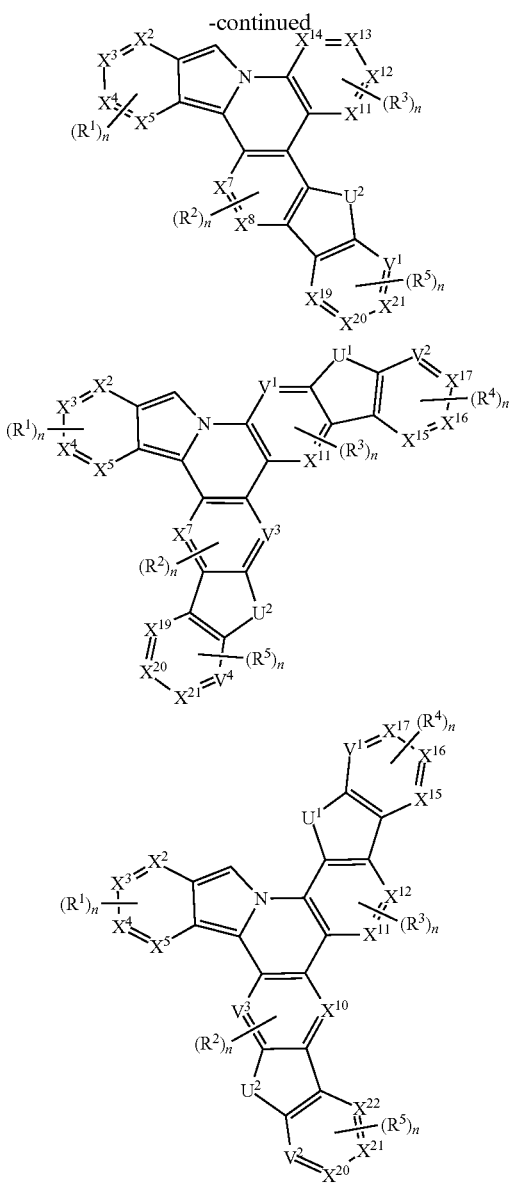

wherein:
R$^1$, R$^2$, R$^3$, R$^4$, and R$^5$ each independently represents hydrogen, cyanide, halogen, hydroxy, amino, nitro, thiol, or substituted or unsubstituted C$_1$-C$_4$ alkyl, alkoxy, or aryl,
X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$, X$^{17}$, X$^{18}$, X$^{19}$, X$^{20}$, X$^{21}$, and X$^{22}$ each independently represents substituted or unsubstituted C, N, Si, O, or S, valency permitting,
V$^1$, V$^2$, V$^3$, and V$^4$ each independently represents substituted or unsubstituted C or N, valency permitting,
U$^1$ and U$^2$ each independently represents O, S, CRR', SiRR', or NAr*, where R and R' each independently represents hydrogen, cyanide, halogen, hydroxy, amino, nitro, thiol, or optionally substituted C$_1$-C$_4$ alkyl, alkoxy, or aryl, and Ar* represents a substituted phenyl, pyridyl, naphthyl, pyrimidyl, pyridazinyl, pyrazinyl, pyrazolyl, imidazolyl, oxazolyl, or thiazolyl ring, and Ar* is optionally covalently bonded to V$^1$, V$^2$, V$^3$, or V$^4$ to form one or more 5-membered or 6-membered rings,
U$^3$ and U$^4$ each independently represents CR, SiR, or N, where R represents optionally substituted C$_1$-C$_4$ alkyl, alkoxy, aryl or heteroaryl, and
each n is independently an integer as permitted by valence.

3. The compound of claim 1, wherein the compound is represented by one of the following structures:

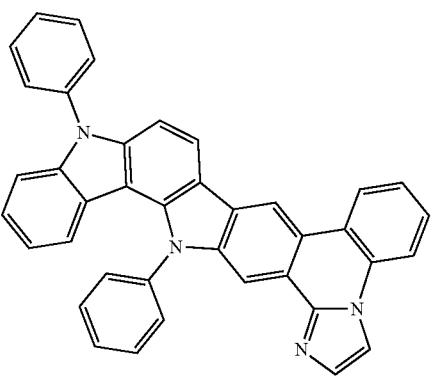

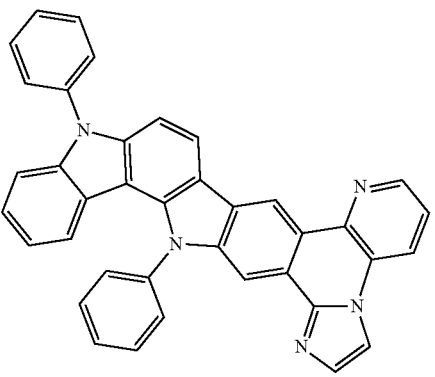

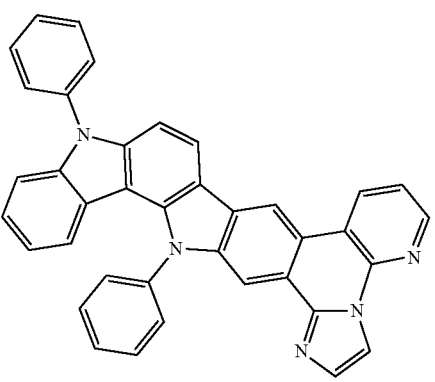

321
-continued
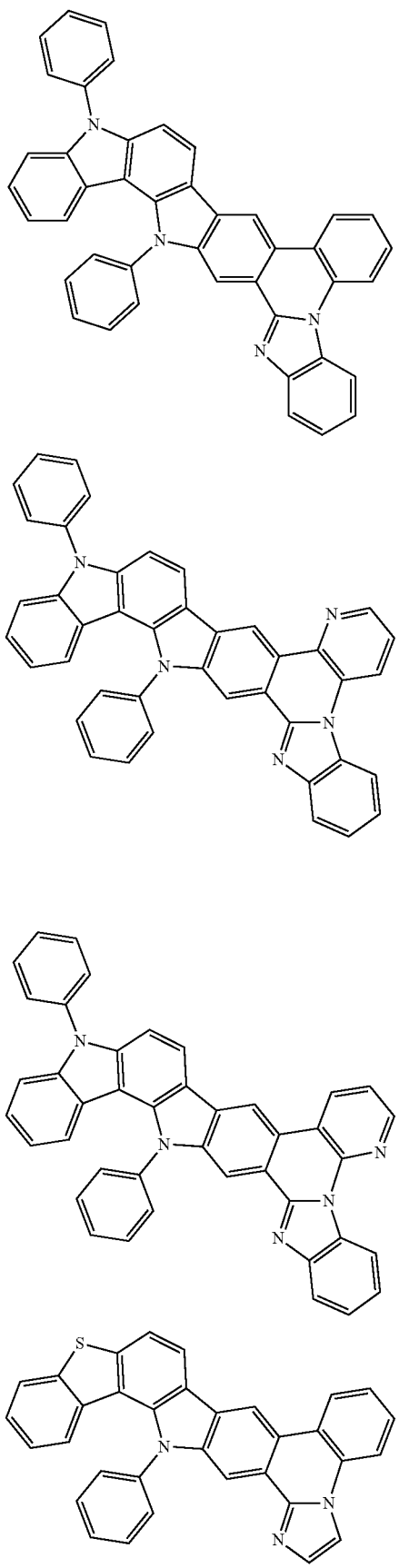
322
-continued
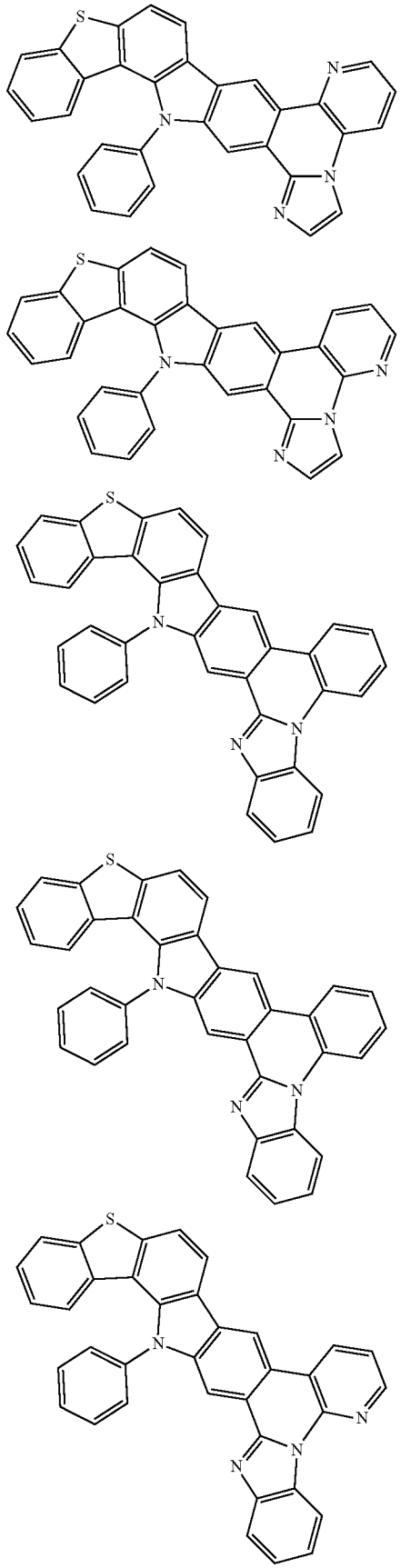

323
-continued
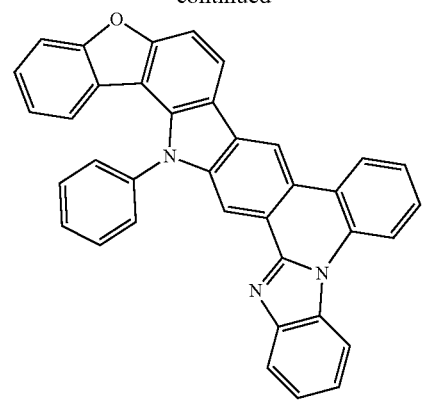
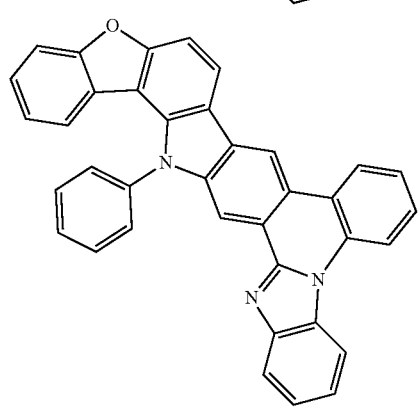
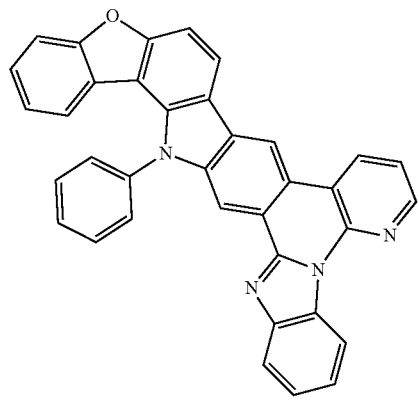
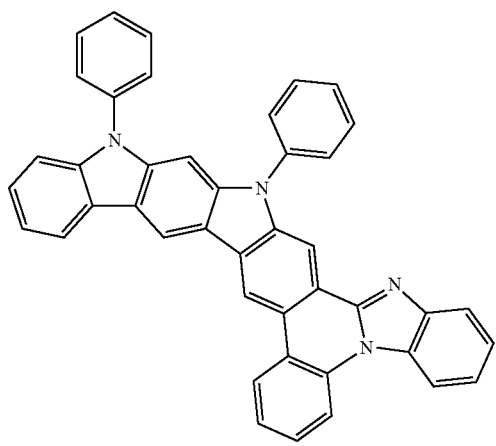
324
-continued
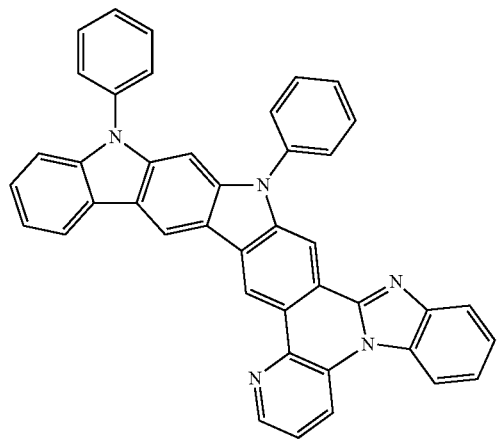
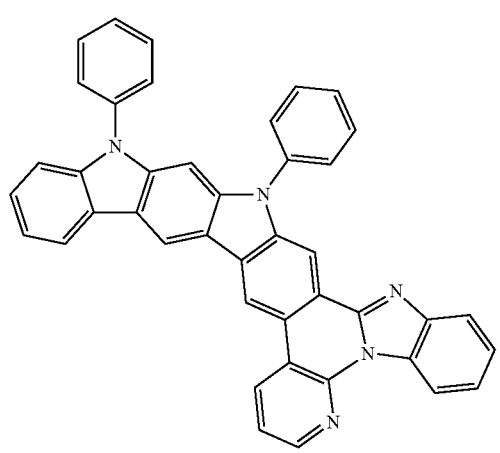
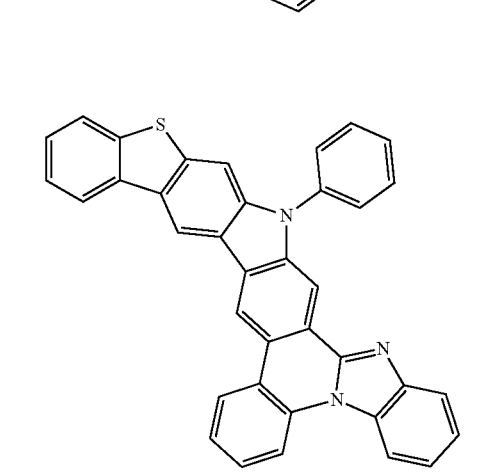
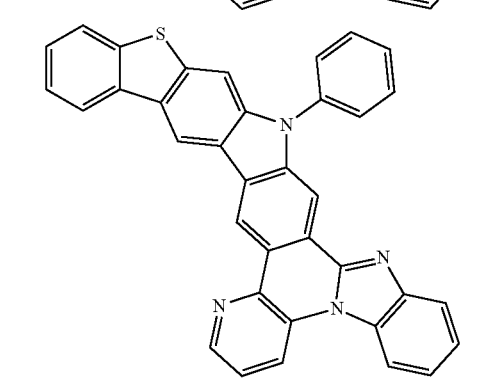

325
-continued
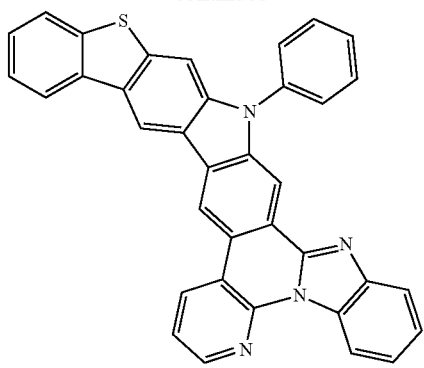
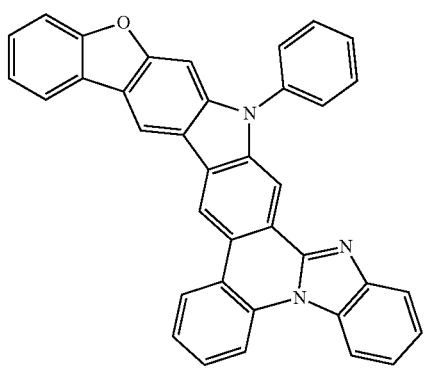
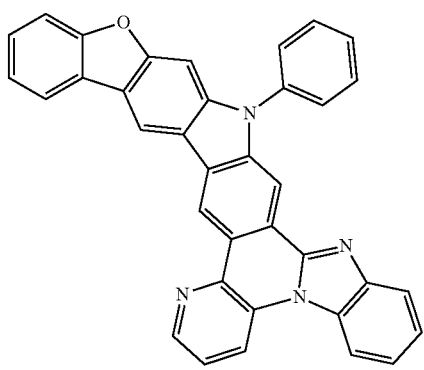
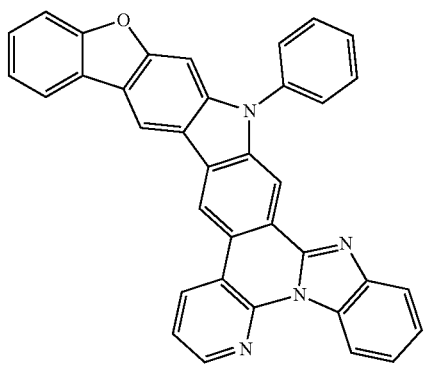
326
-continued
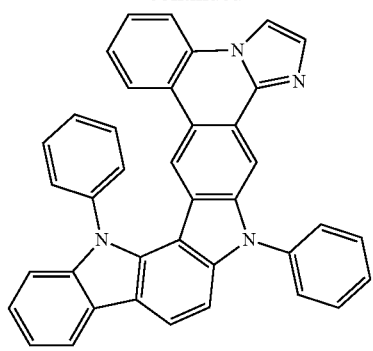
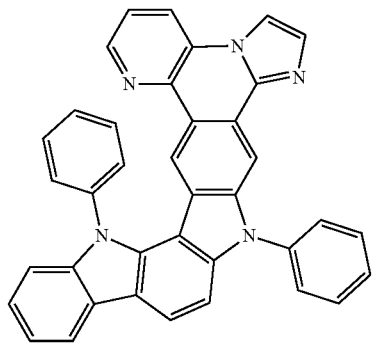
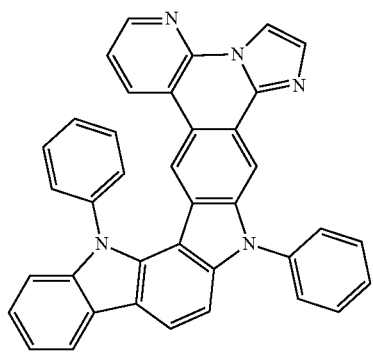
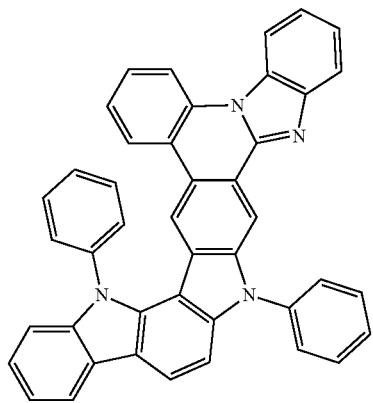

327
-continued
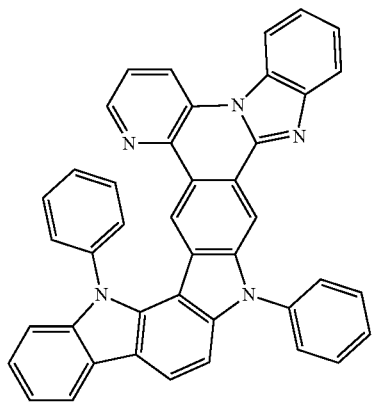
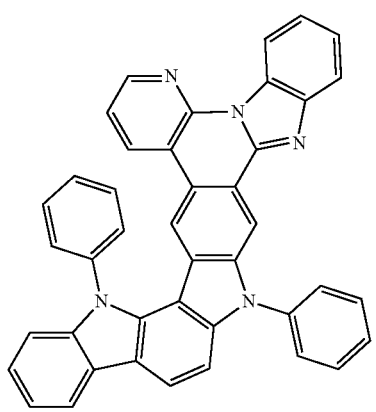
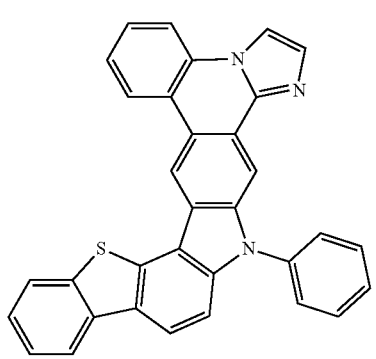
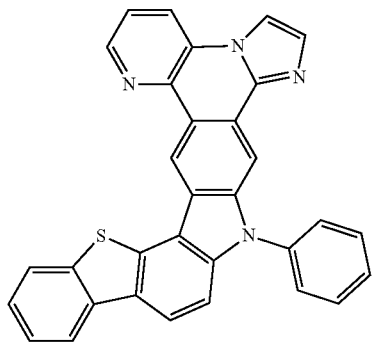
328
-continued
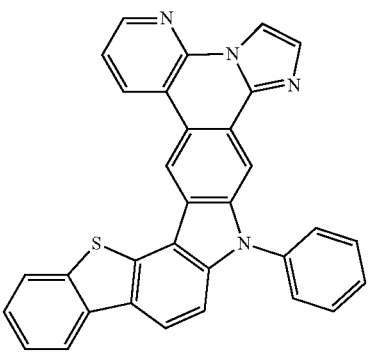
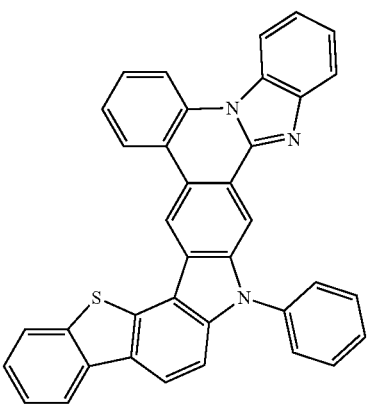
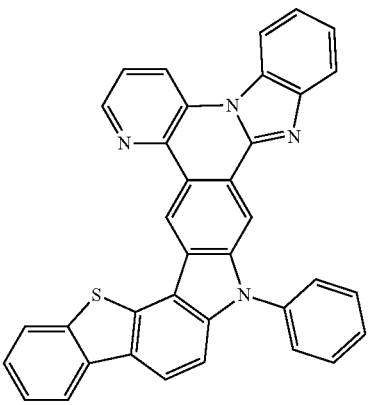
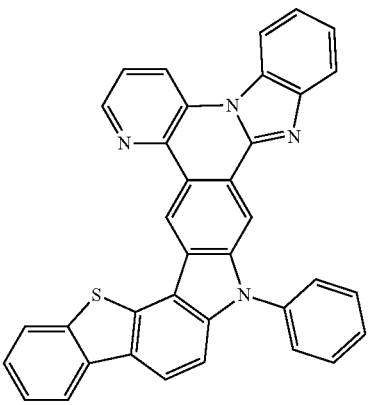

329
-continued
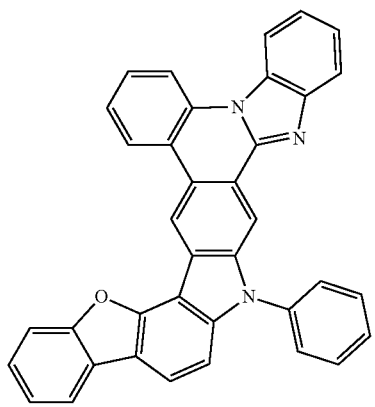
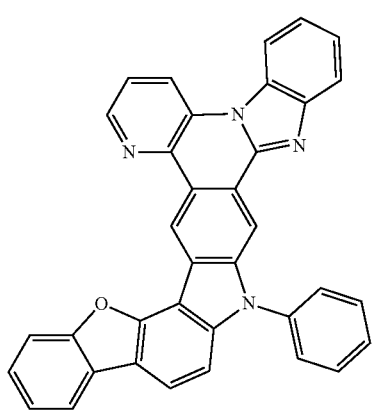
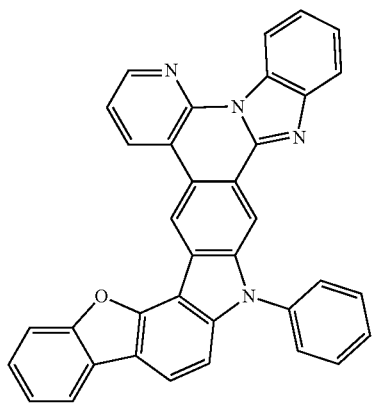
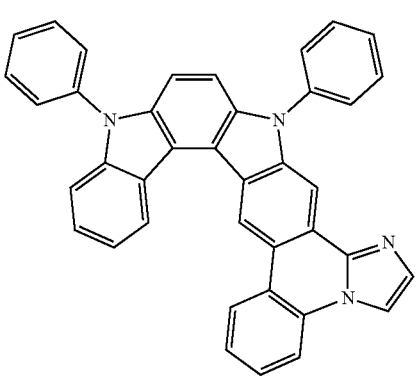
330
-continued
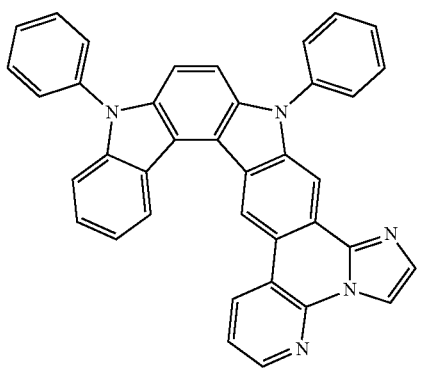
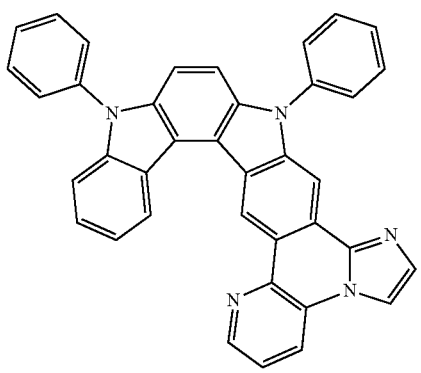
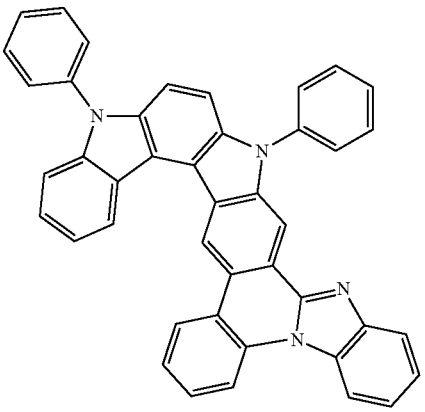
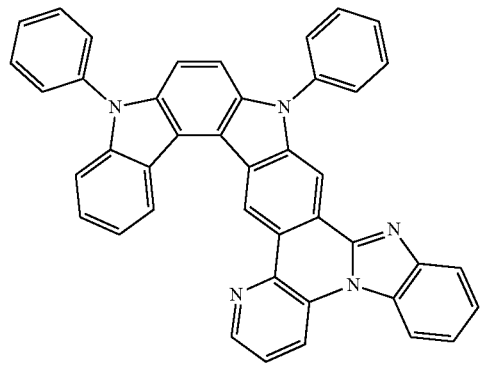

331
-continued
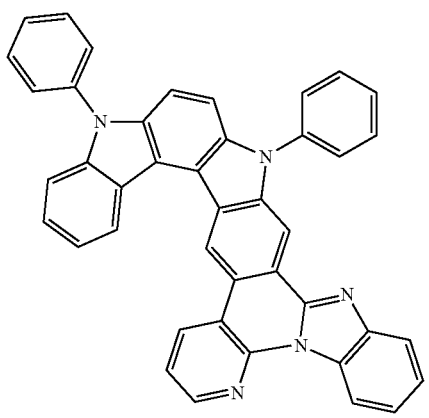
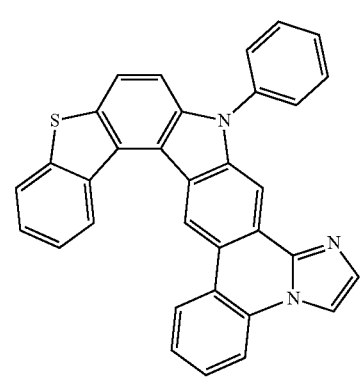
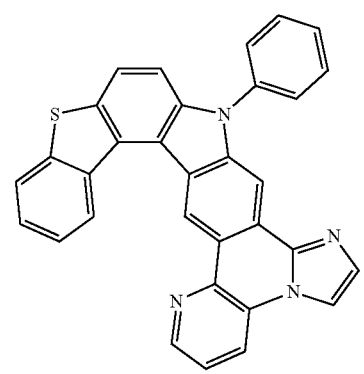
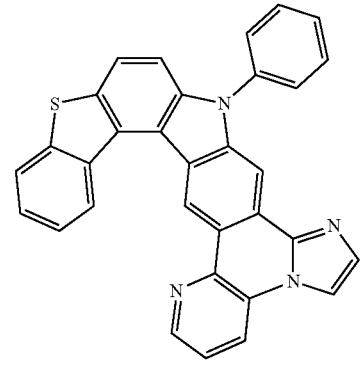
332
-continued
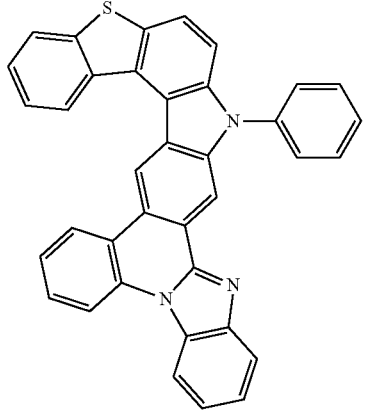
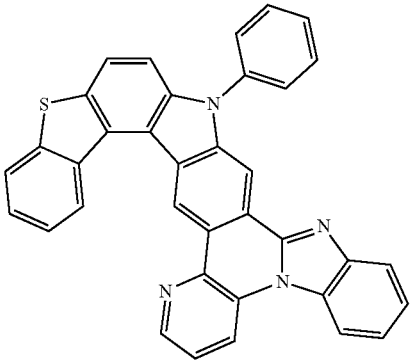
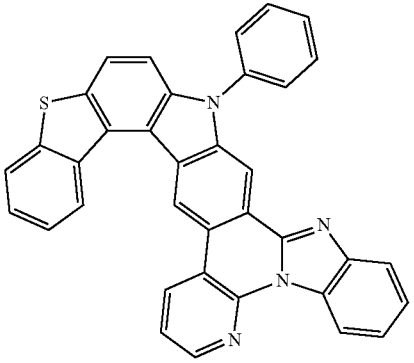
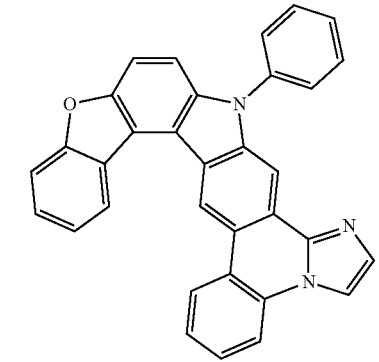

333
-continued
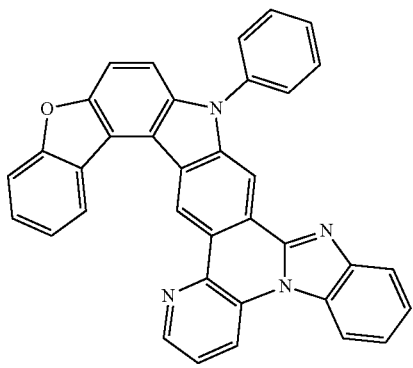
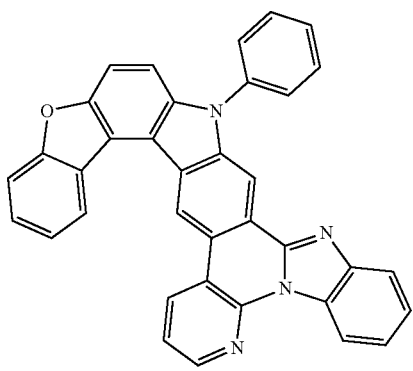
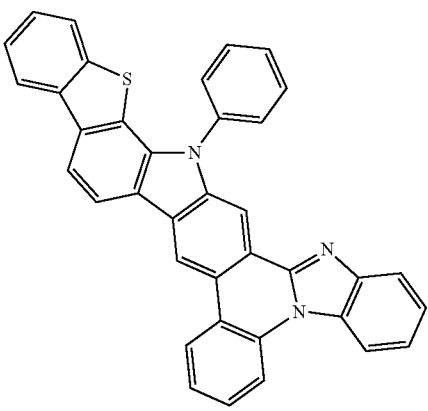
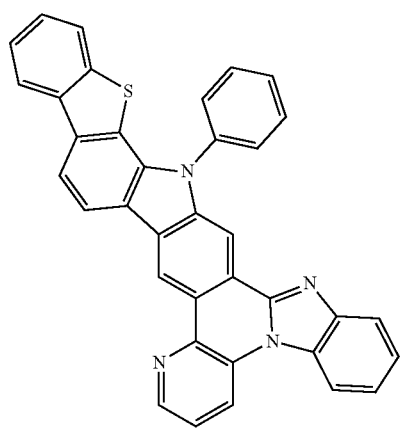
334
-continued
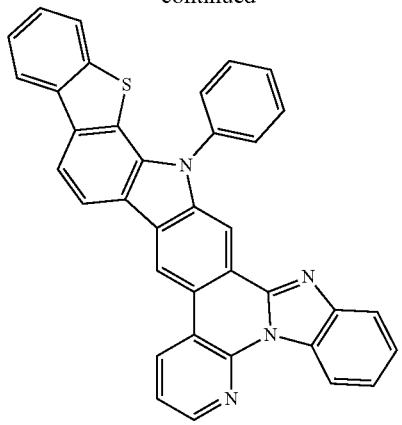
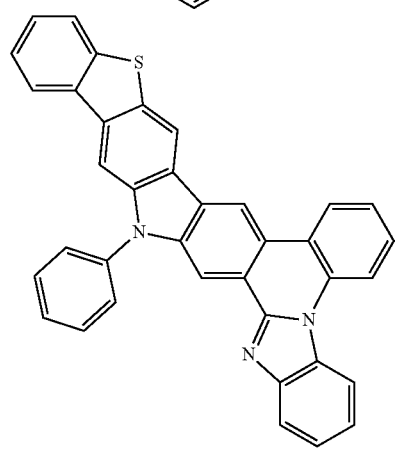
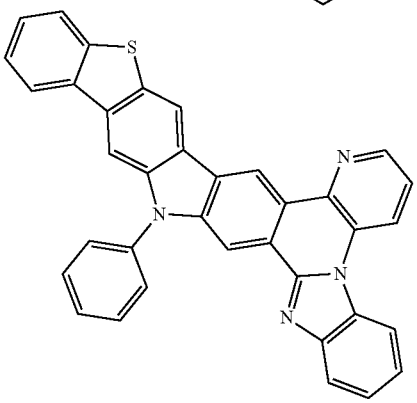
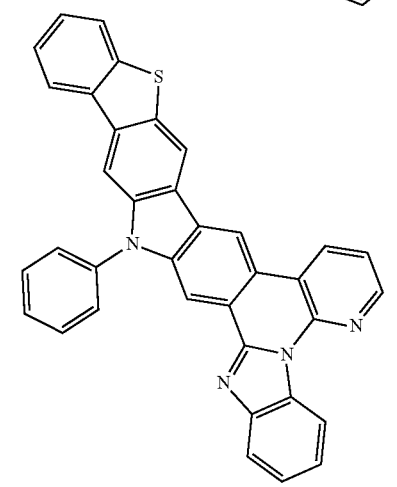

335
-continued
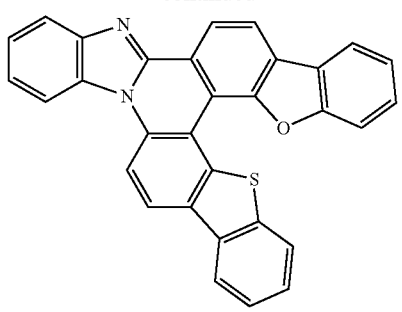
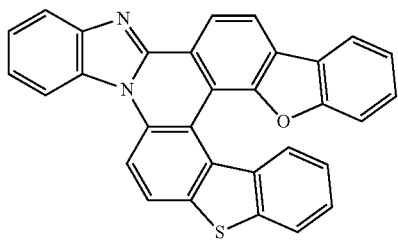
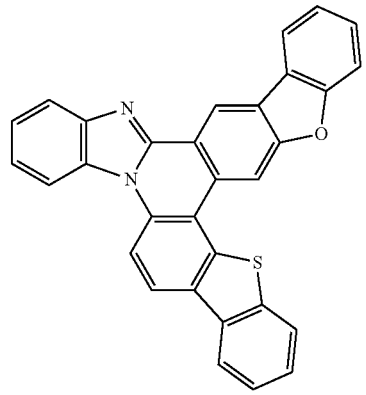
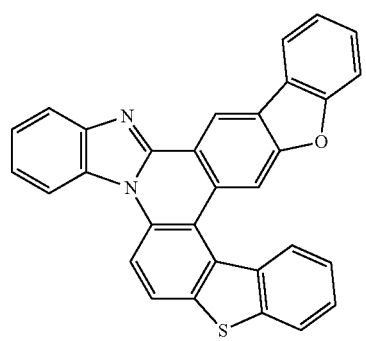
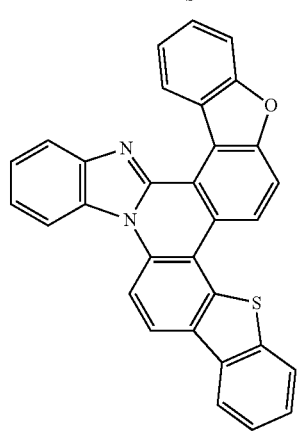
336
-continued
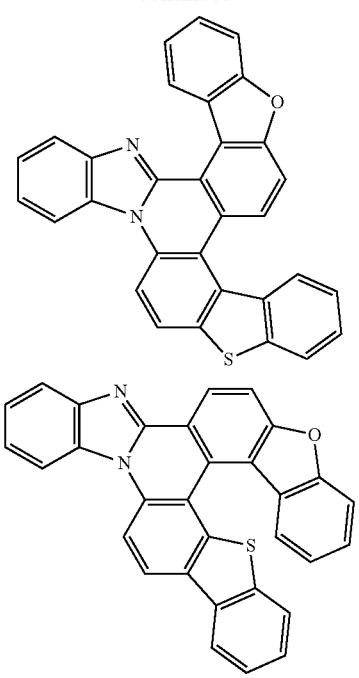
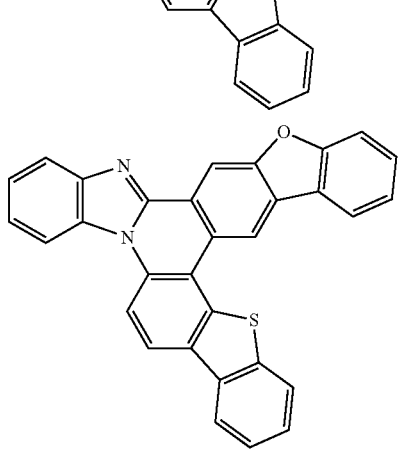
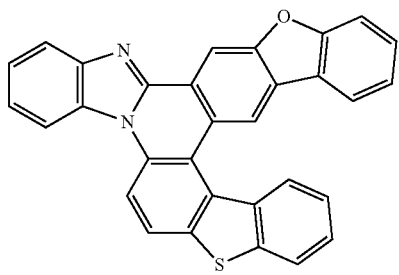
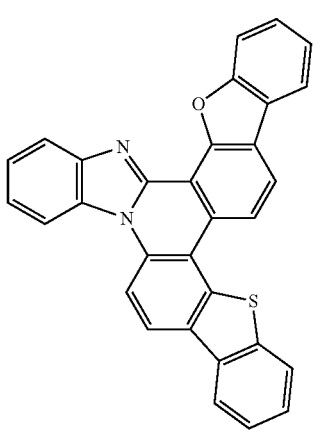

337
-continued
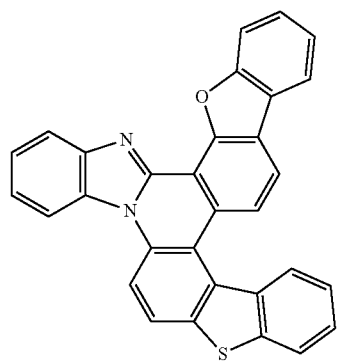
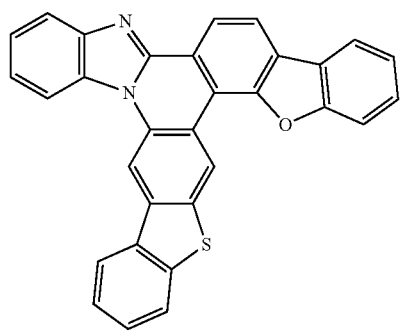
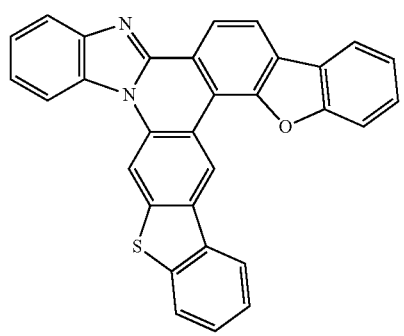
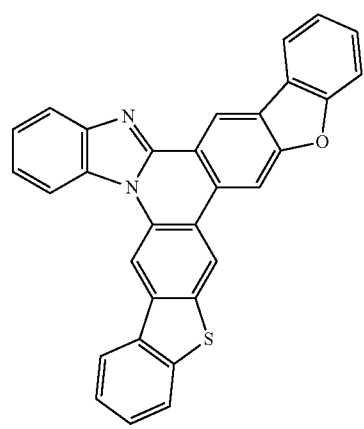
338
-continued
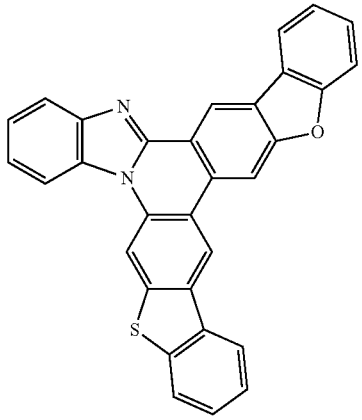
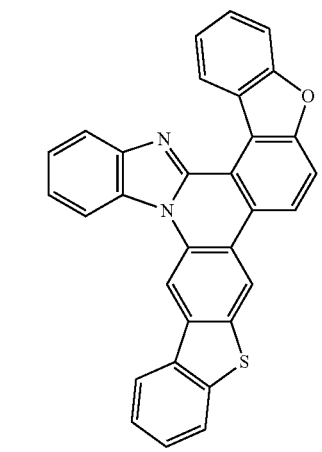
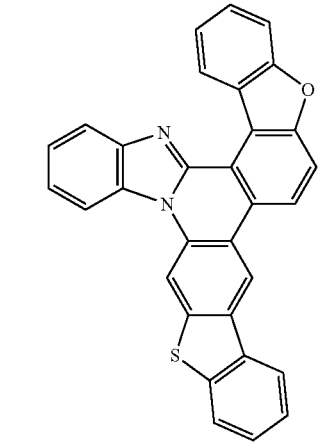
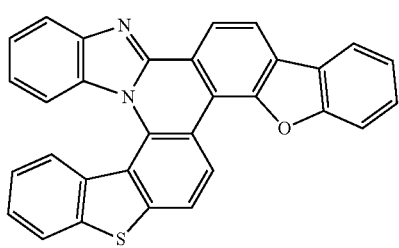

339
-continued
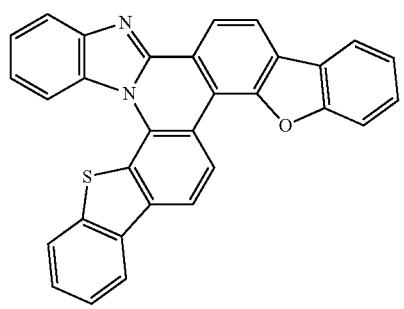
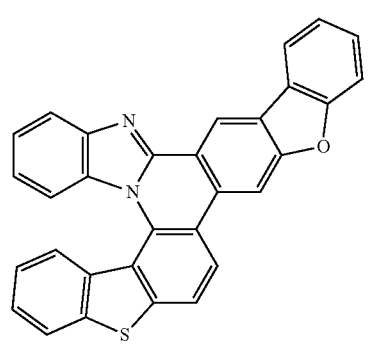
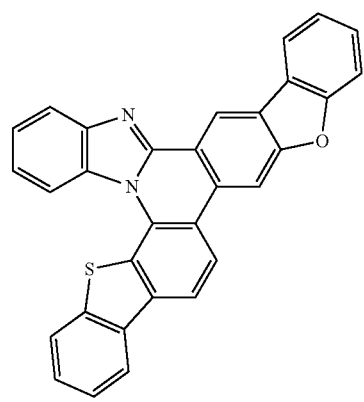
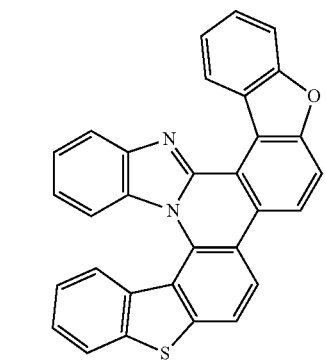
340
-continued
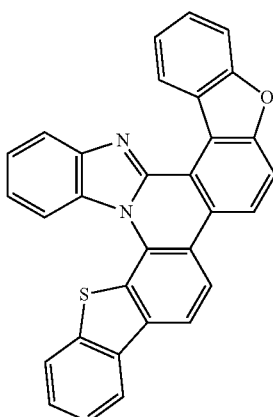
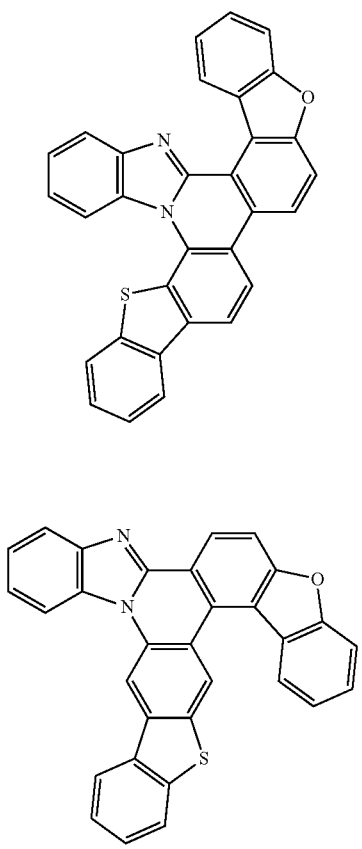
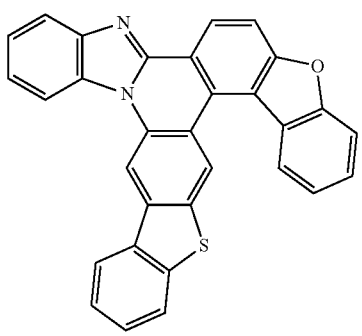
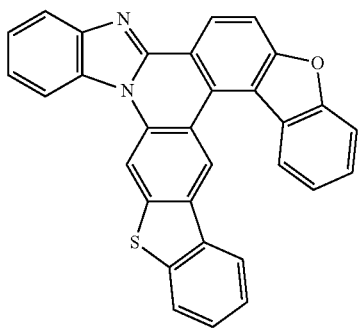

341
-continued
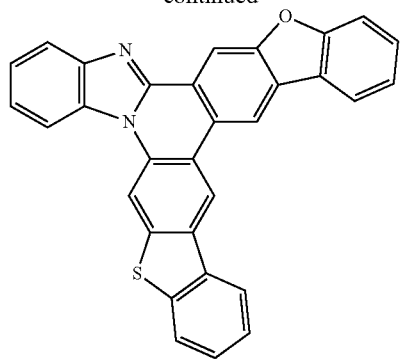
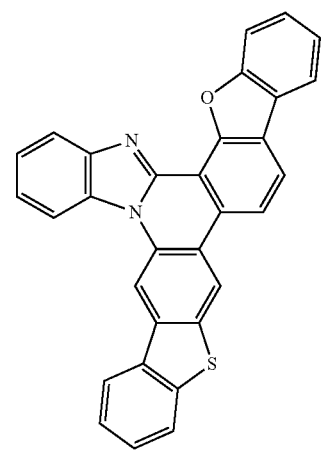
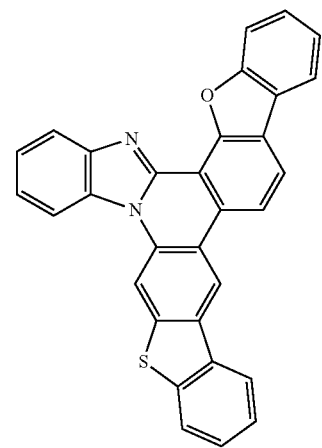
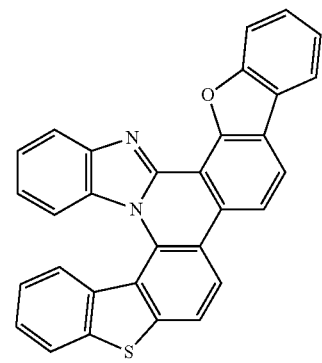
342
-continued
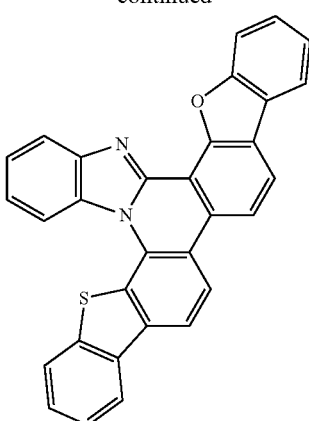
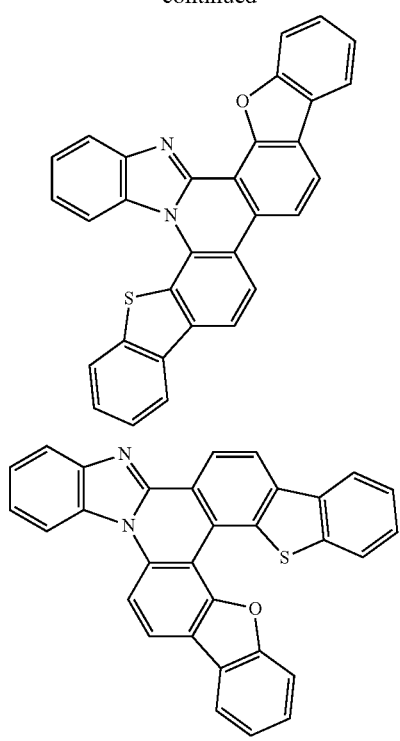
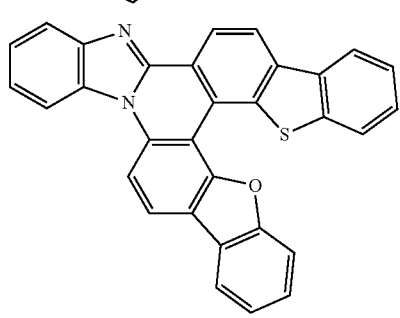
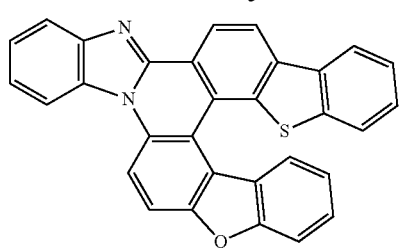
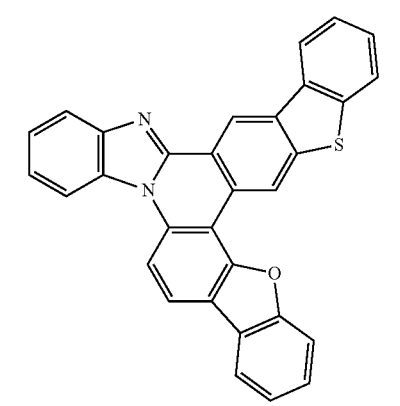
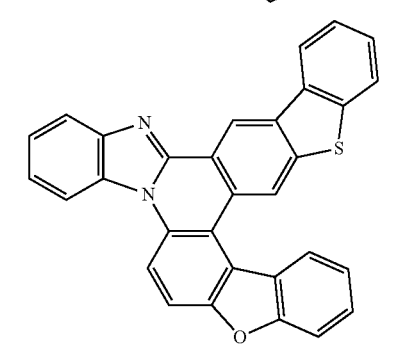

343
-continued
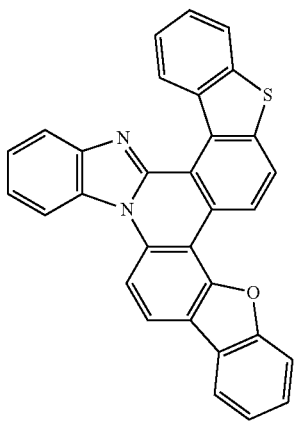
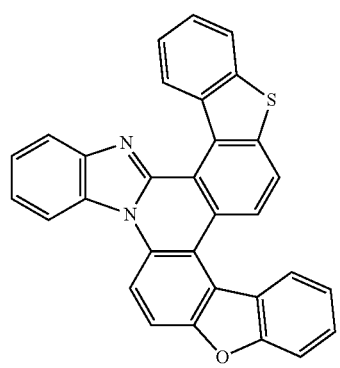
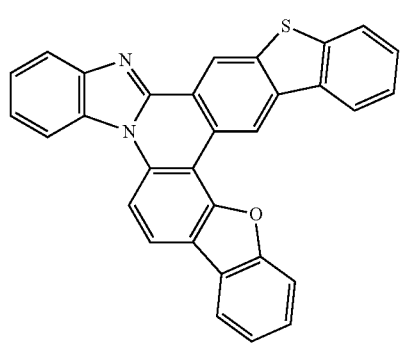
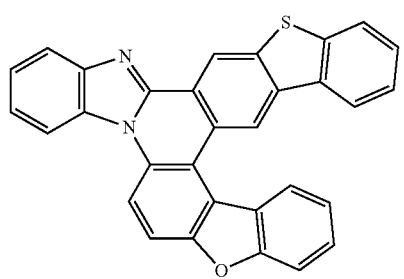
344
-continued
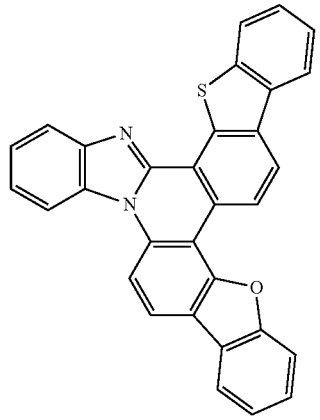
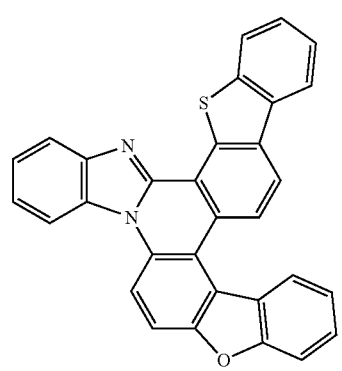
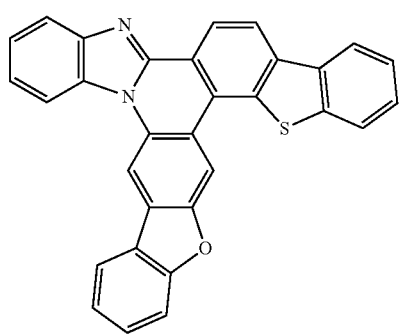
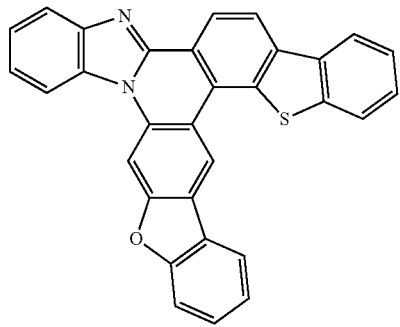

345
-continued
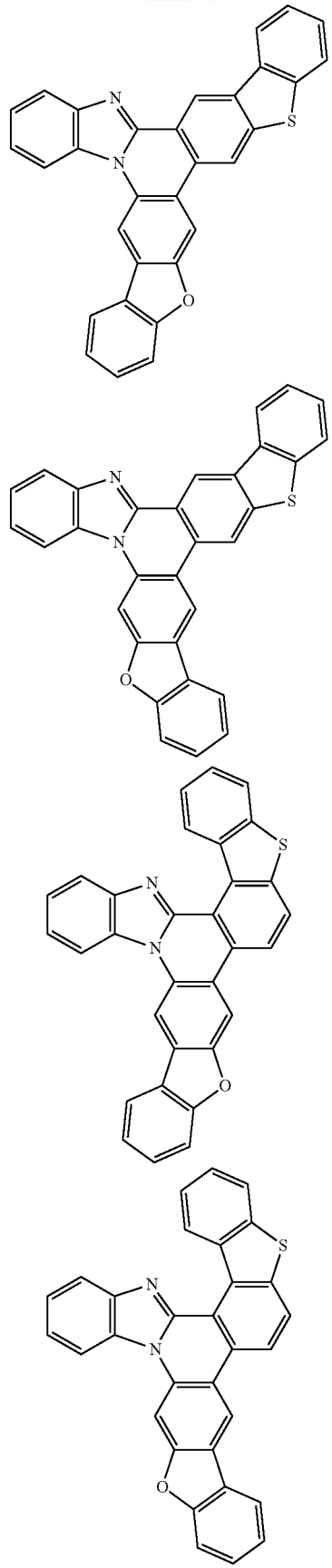
346
-continued
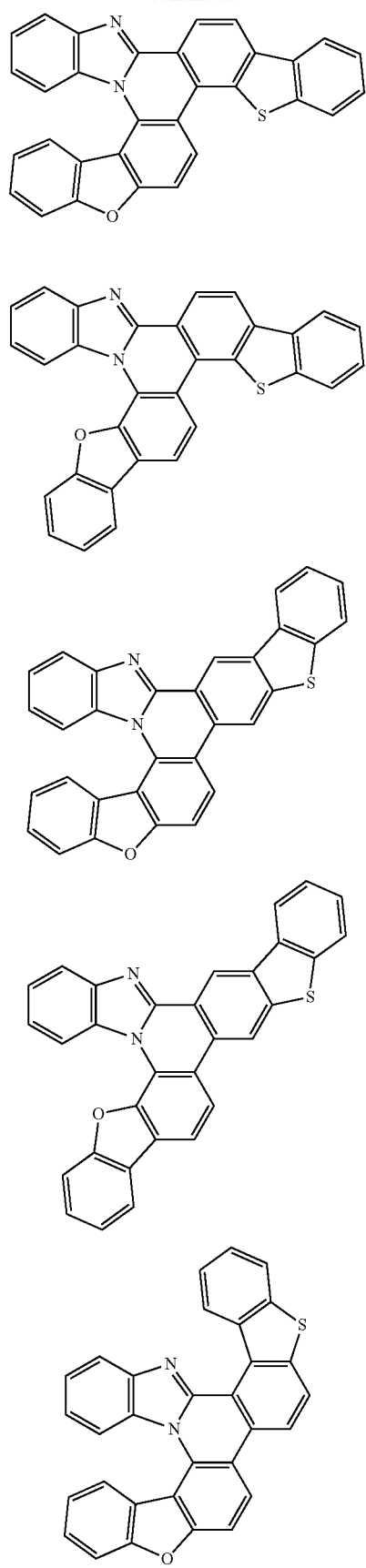

347
-continued
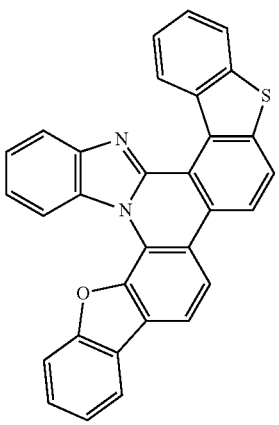
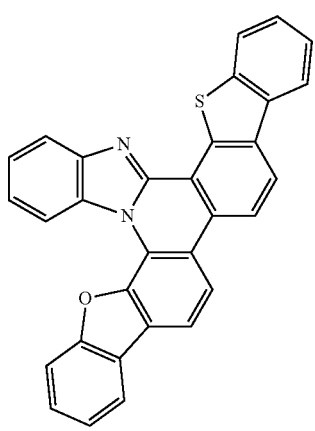
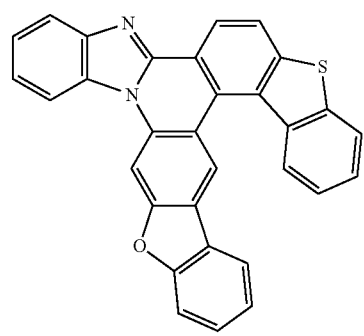
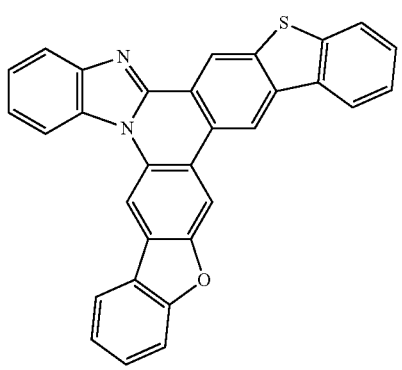
348
-continued
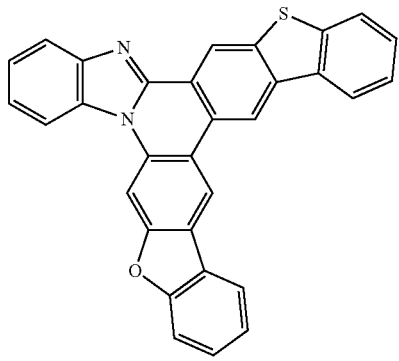
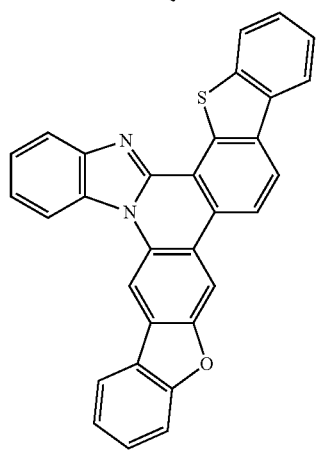
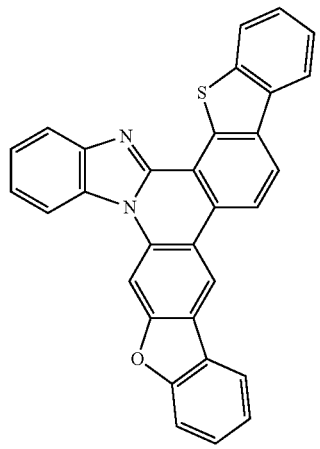
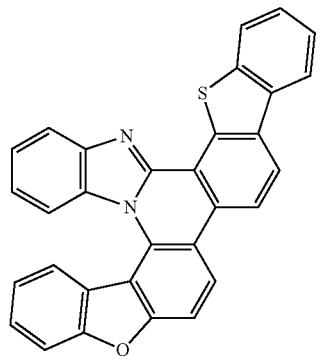

349
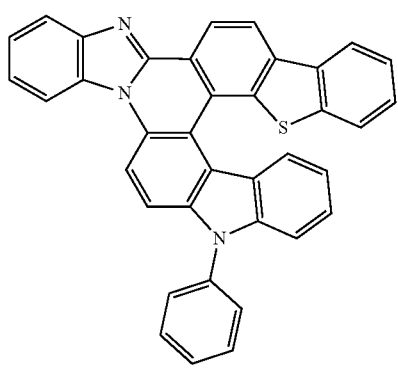
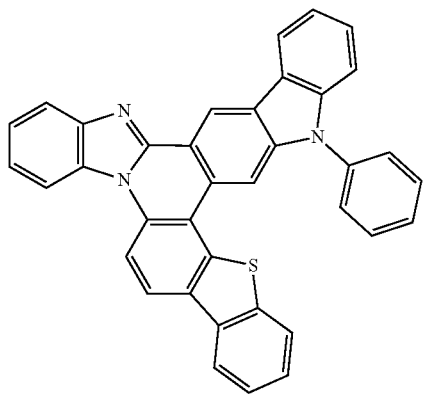
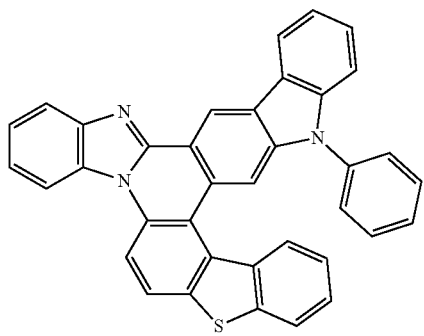
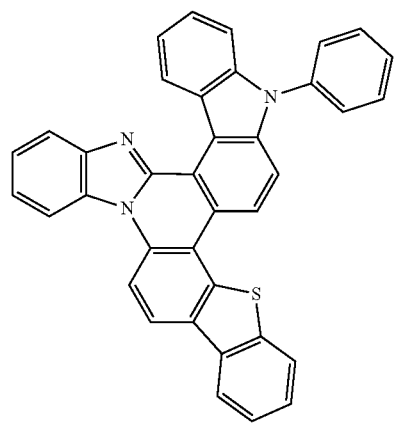
350
-continued
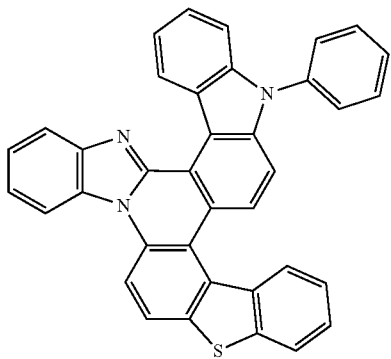
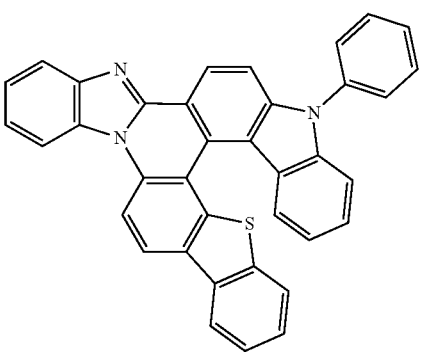
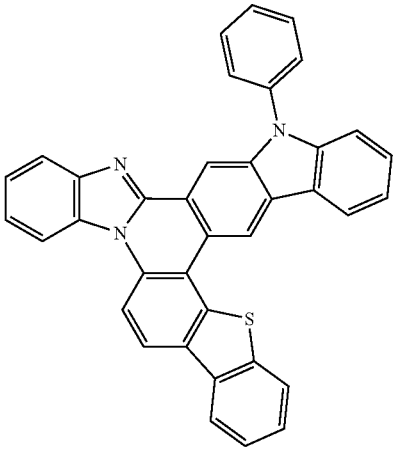
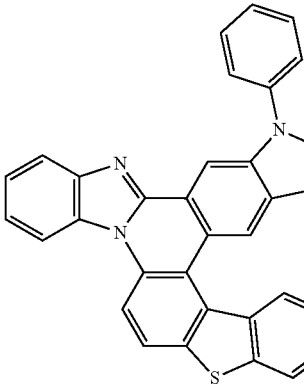

351
-continued
352
-continued
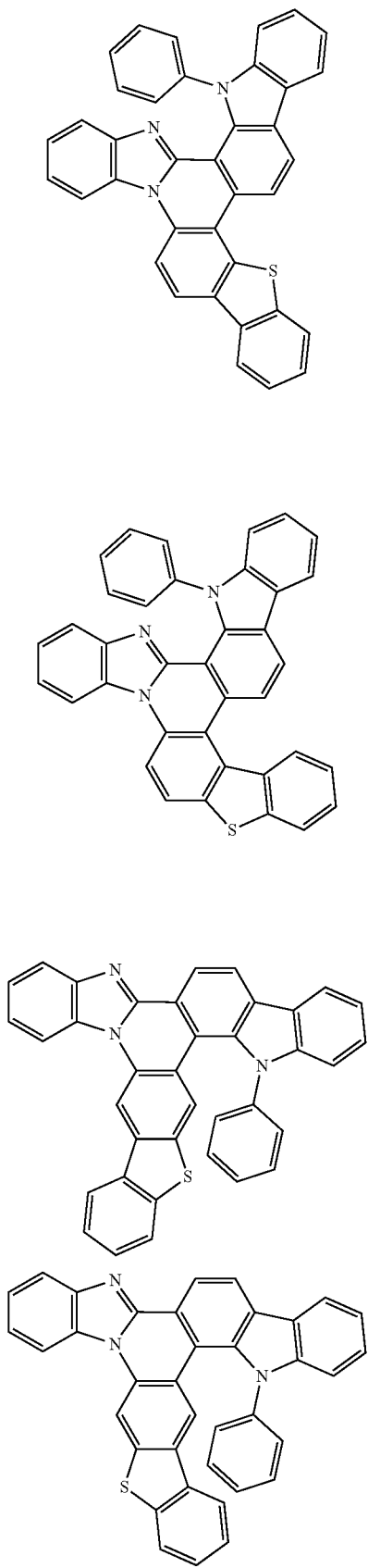
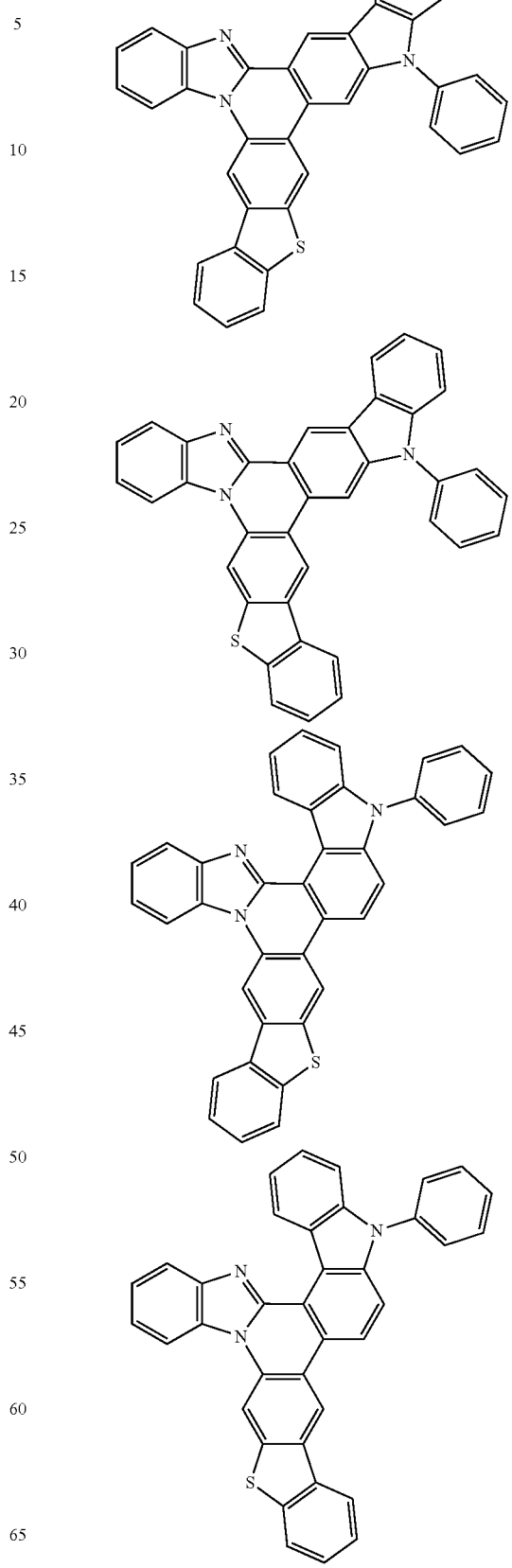

353
-continued
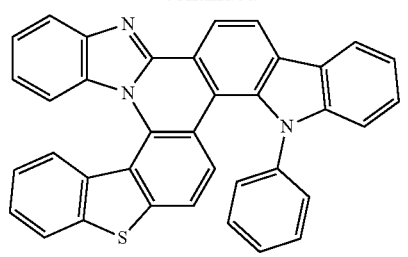
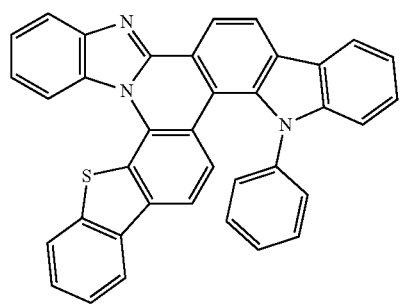
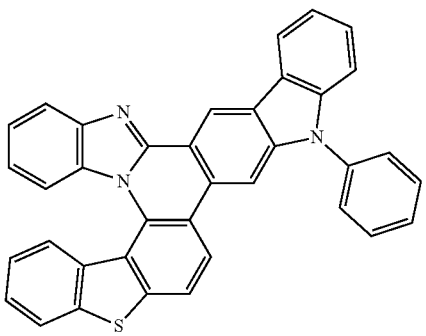
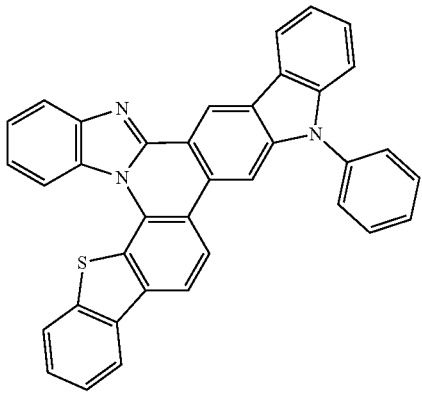
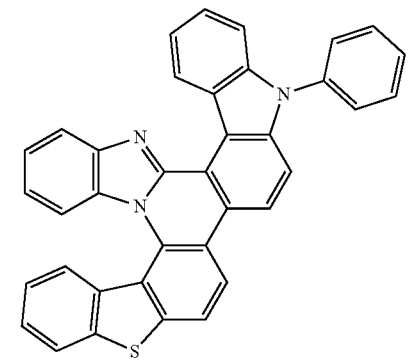
354
-continued
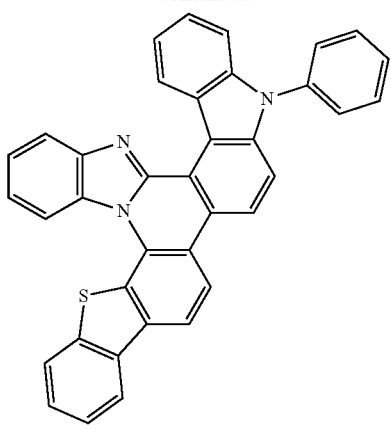
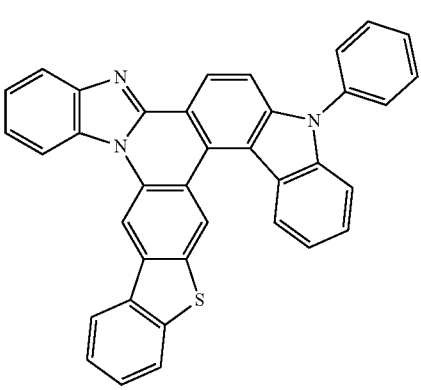
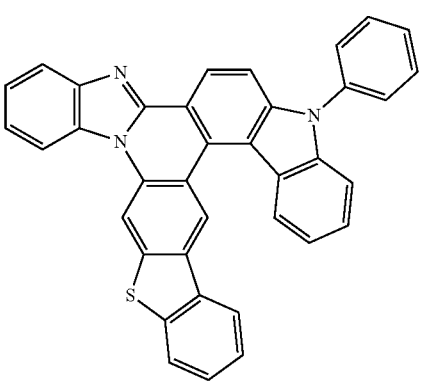
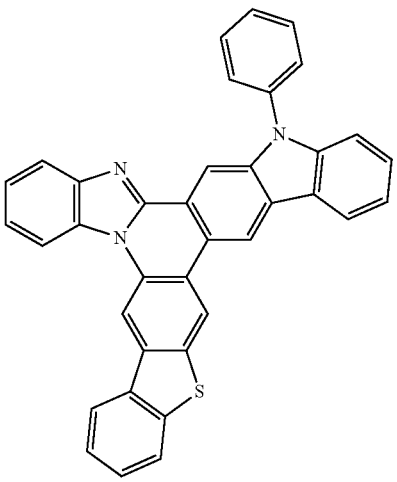

355
-continued
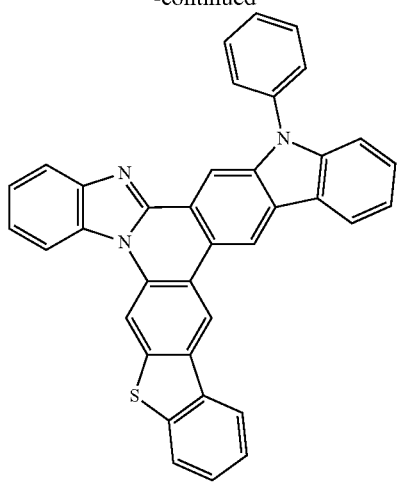
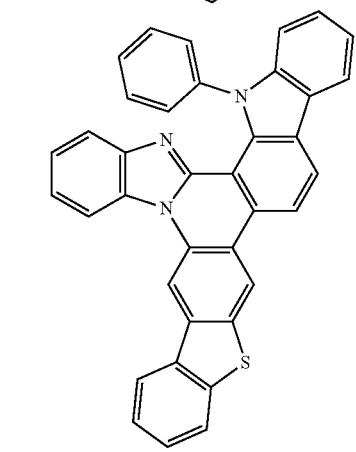
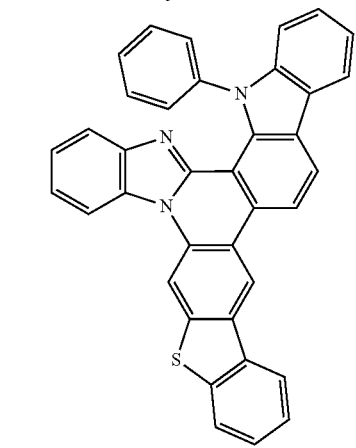
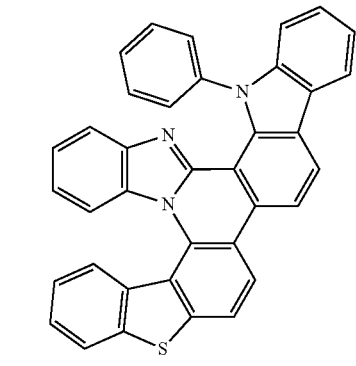
356
-continued
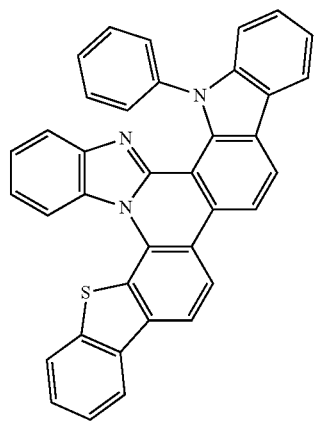
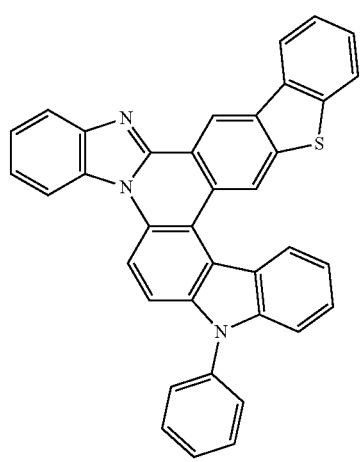
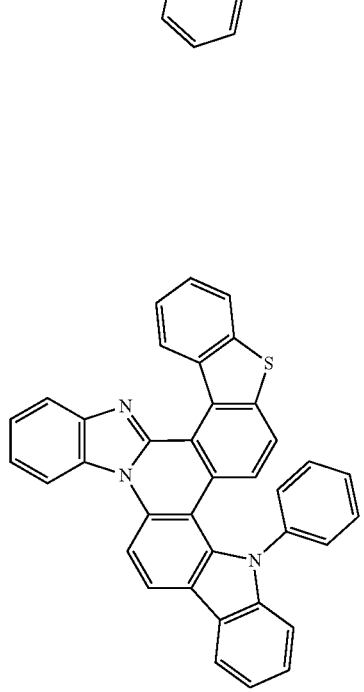

357
-continued
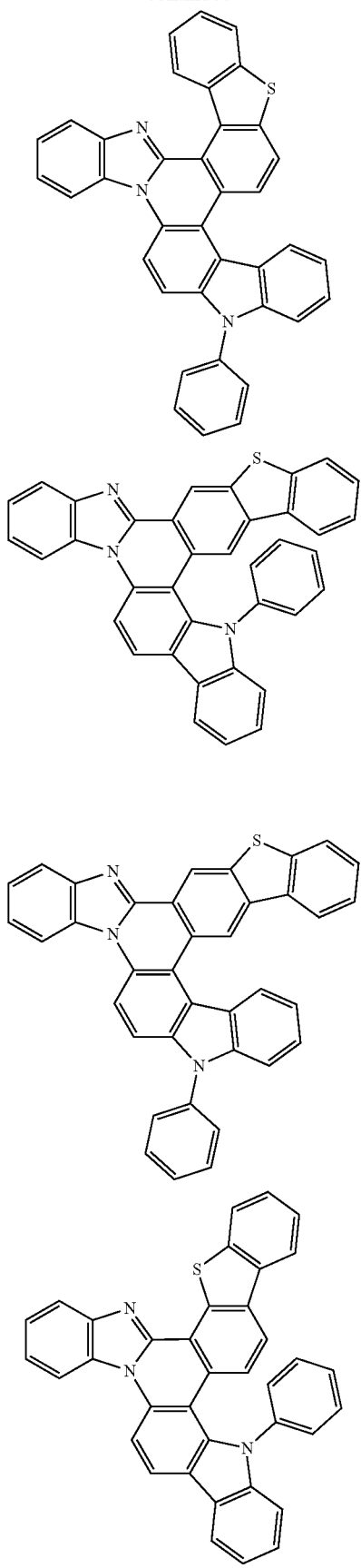
358
-continued
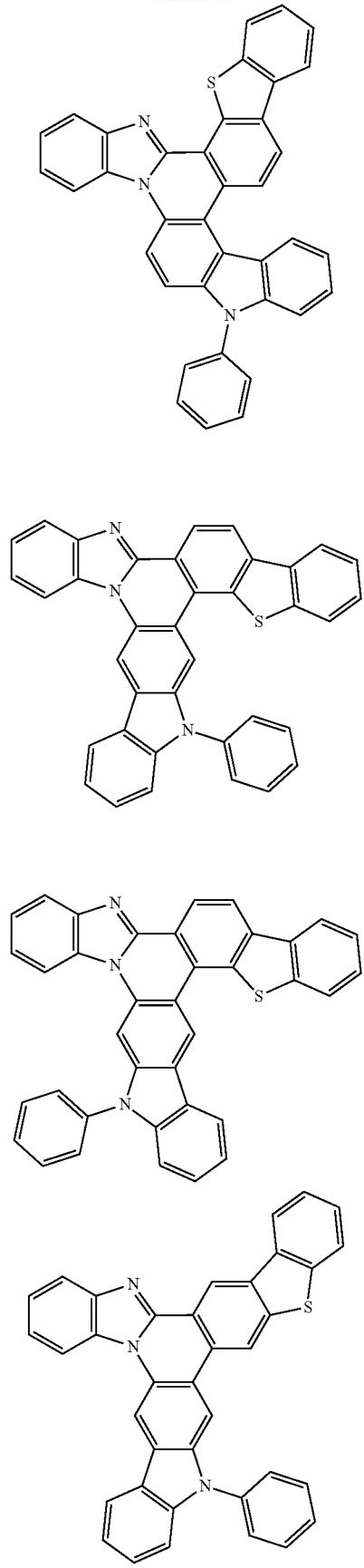

359
-continued
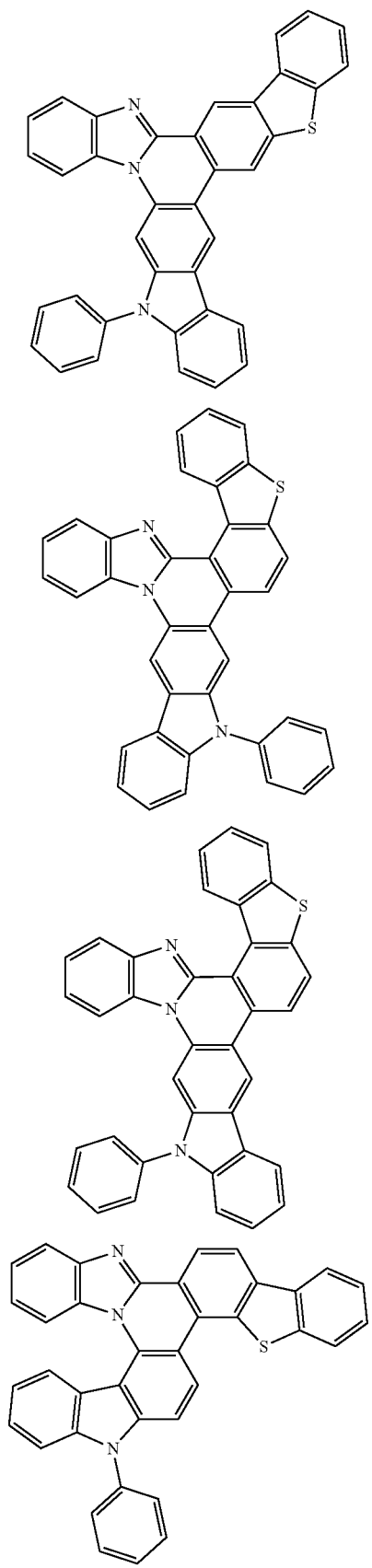
360
-continued
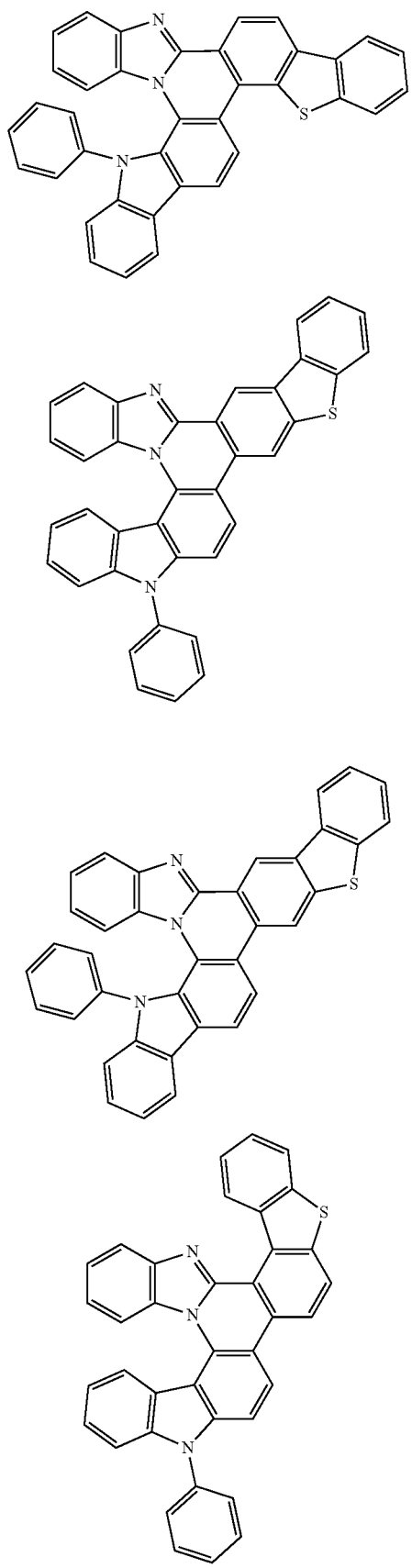

361
-continued
362
-continued
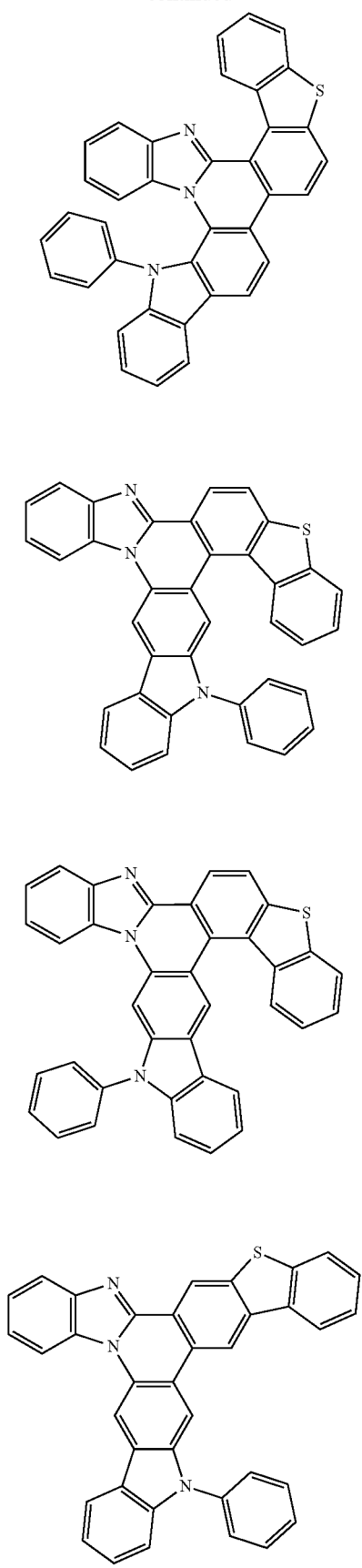
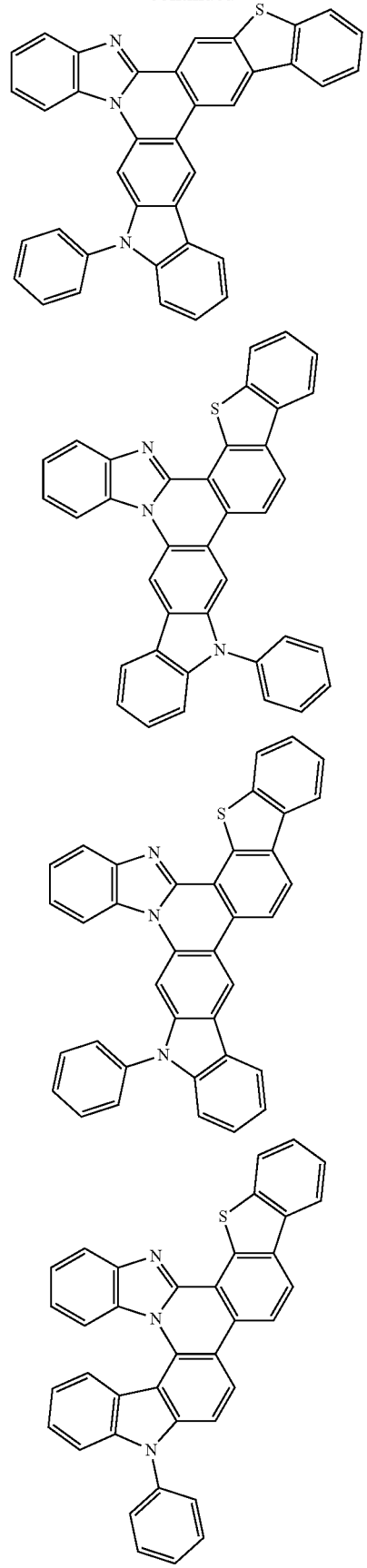

363
-continued
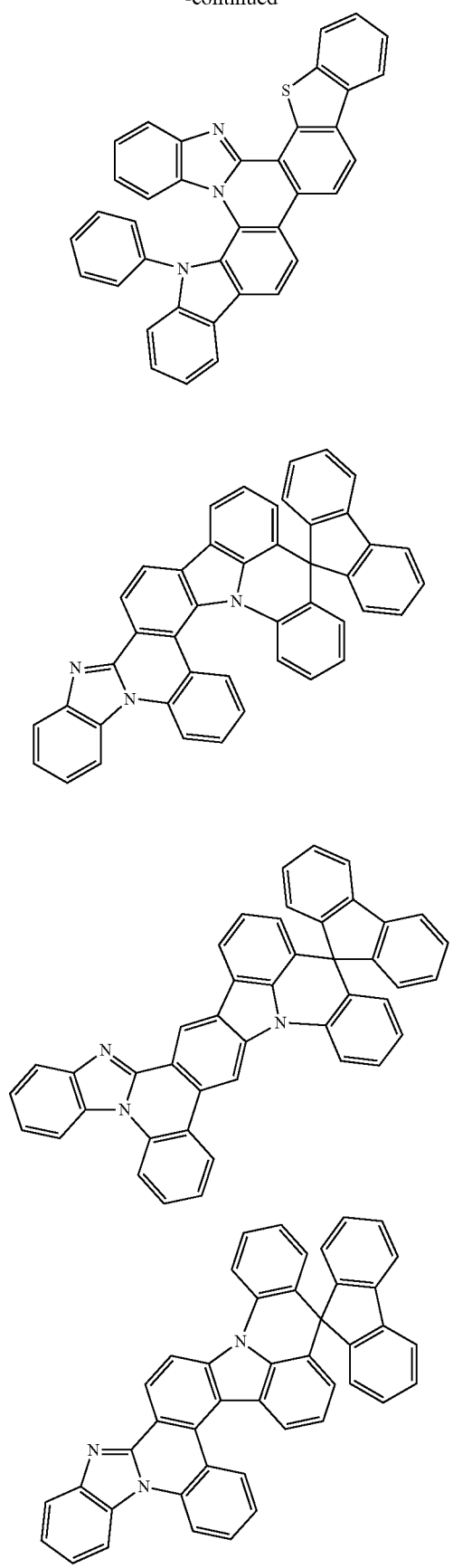
364
-continued
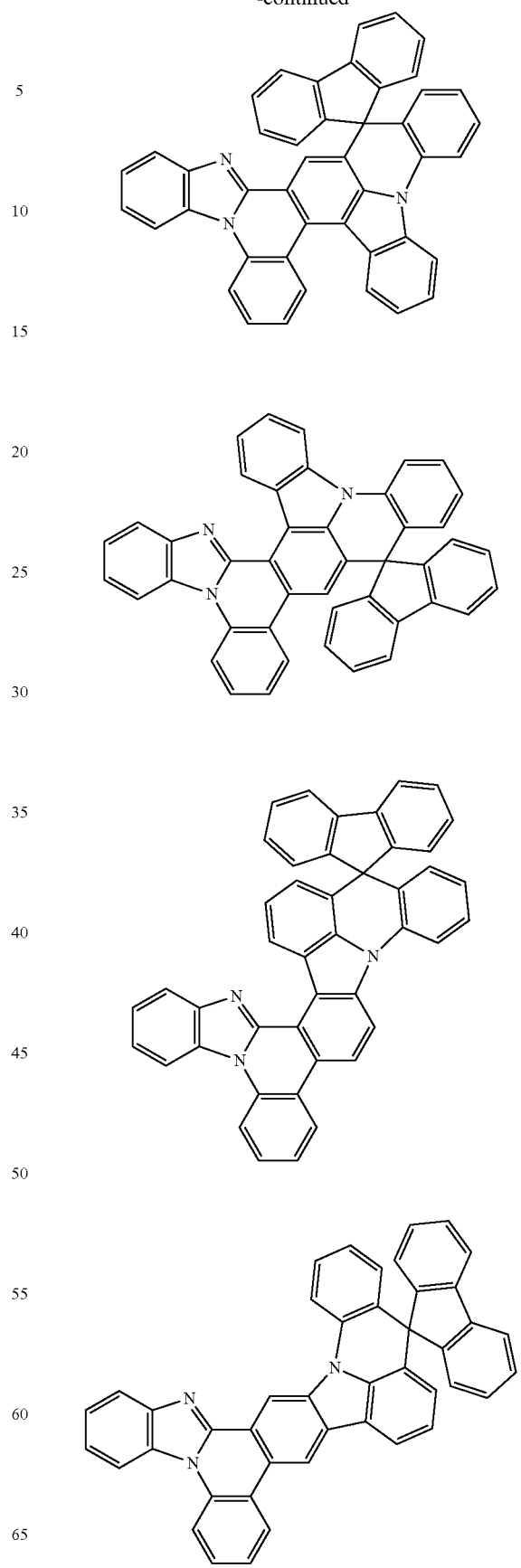

365
-continued
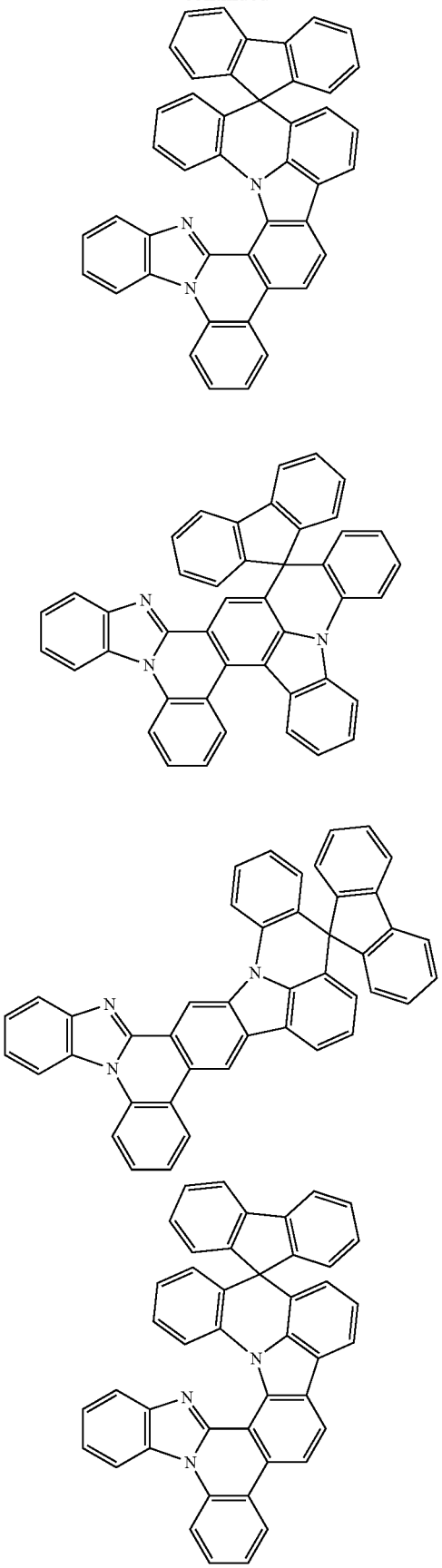
366
-continued
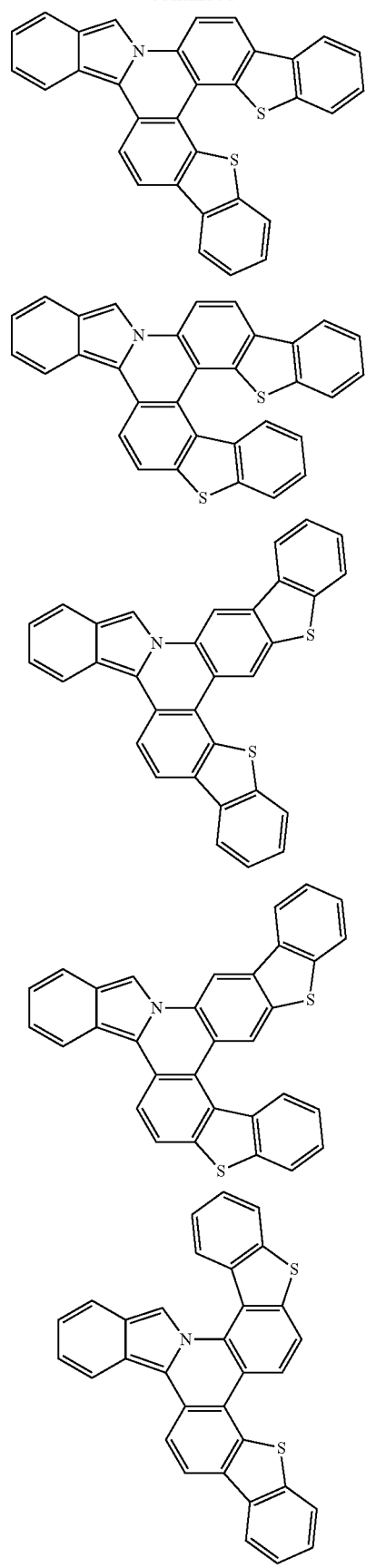

367
-continued
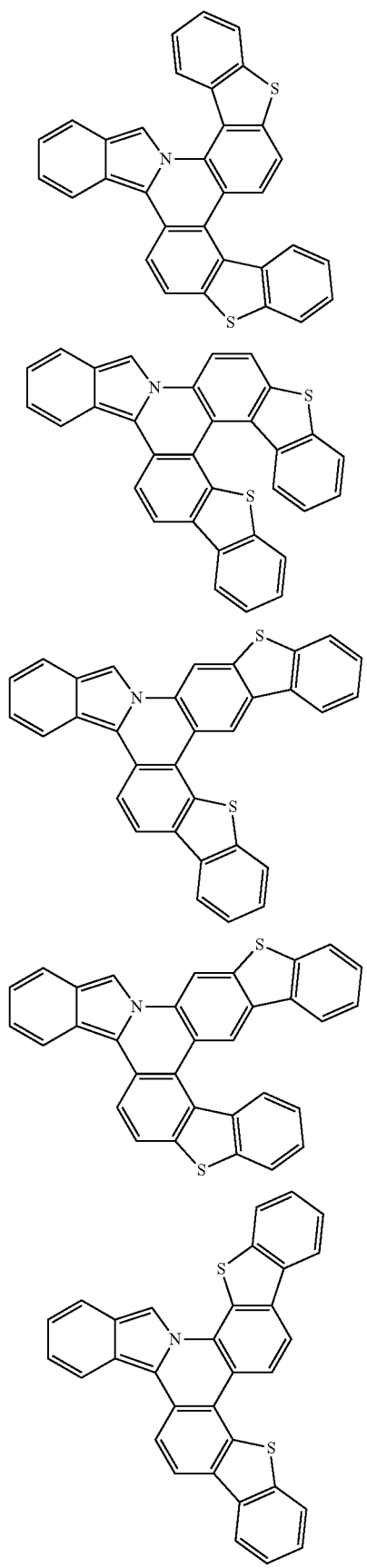
368
-continued
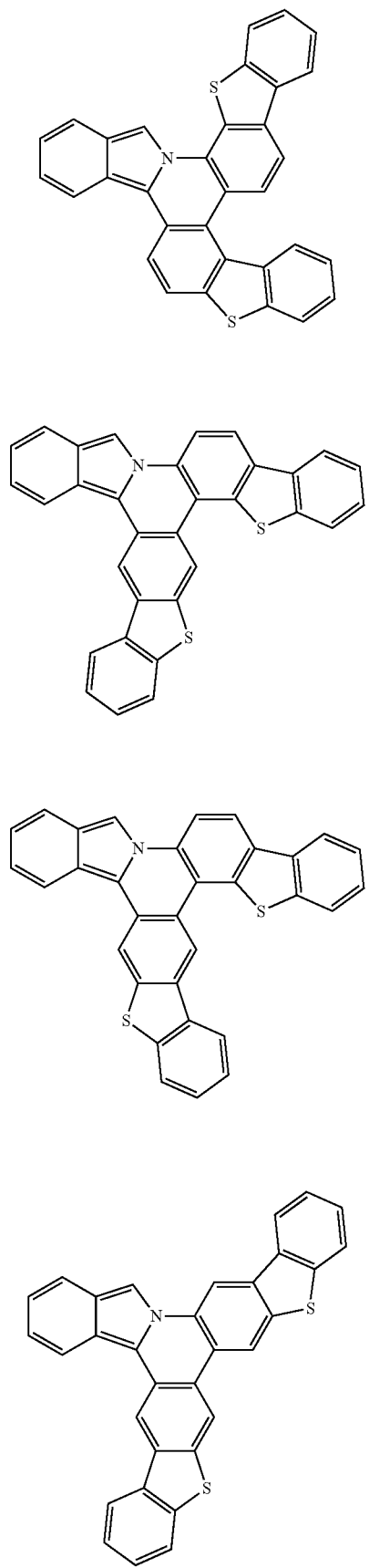

369
-continued
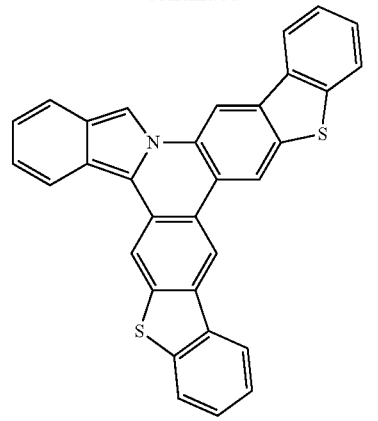
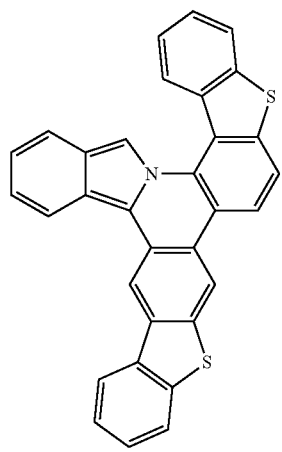
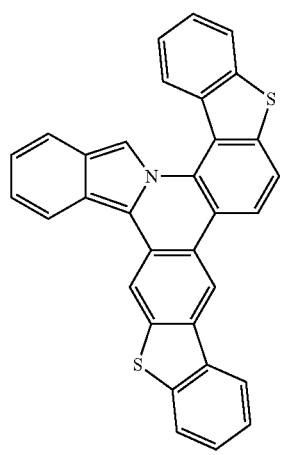
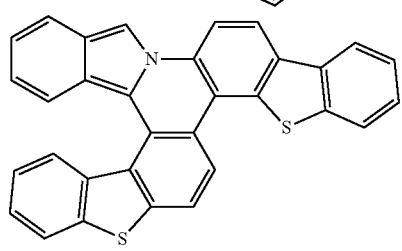
370
-continued
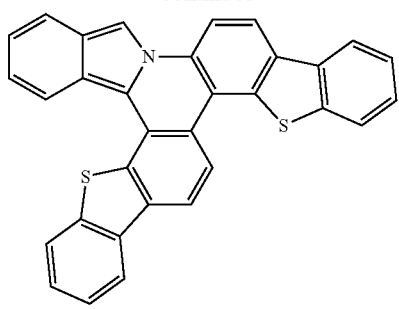
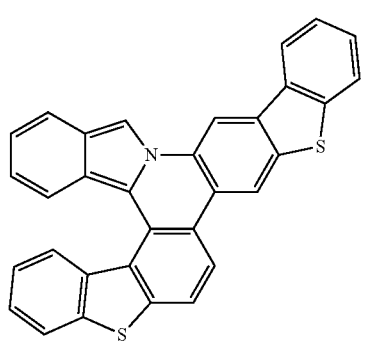
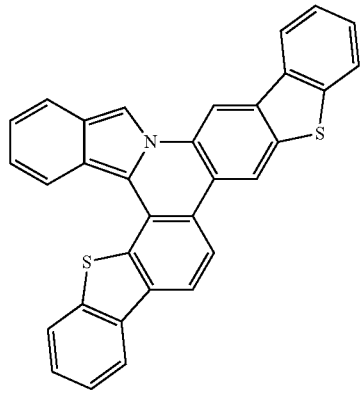
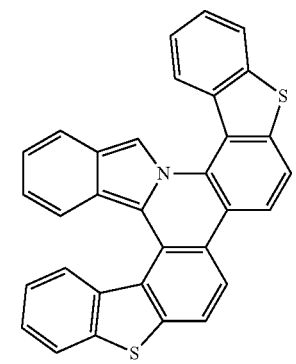

371
-continued
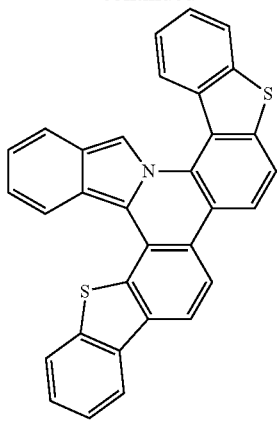
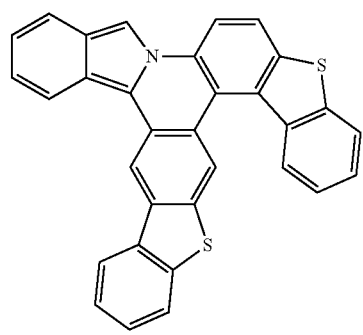
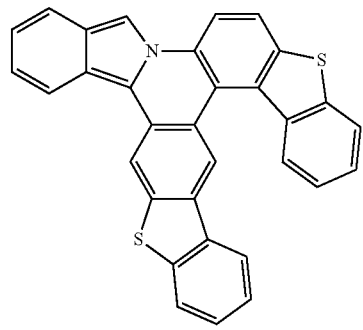
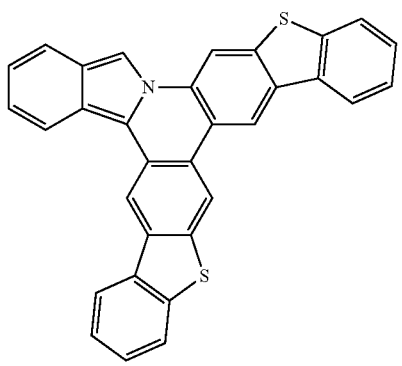
372
-continued
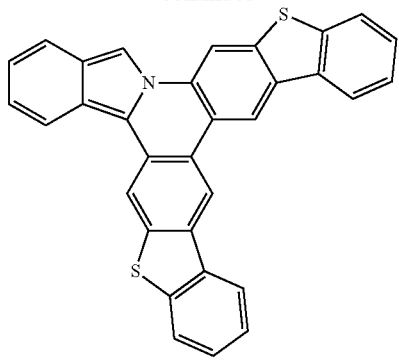
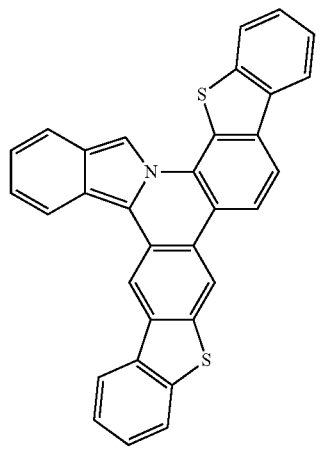
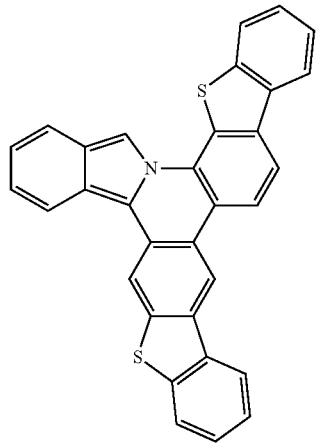
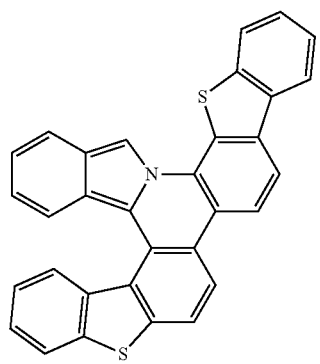

373
-continued
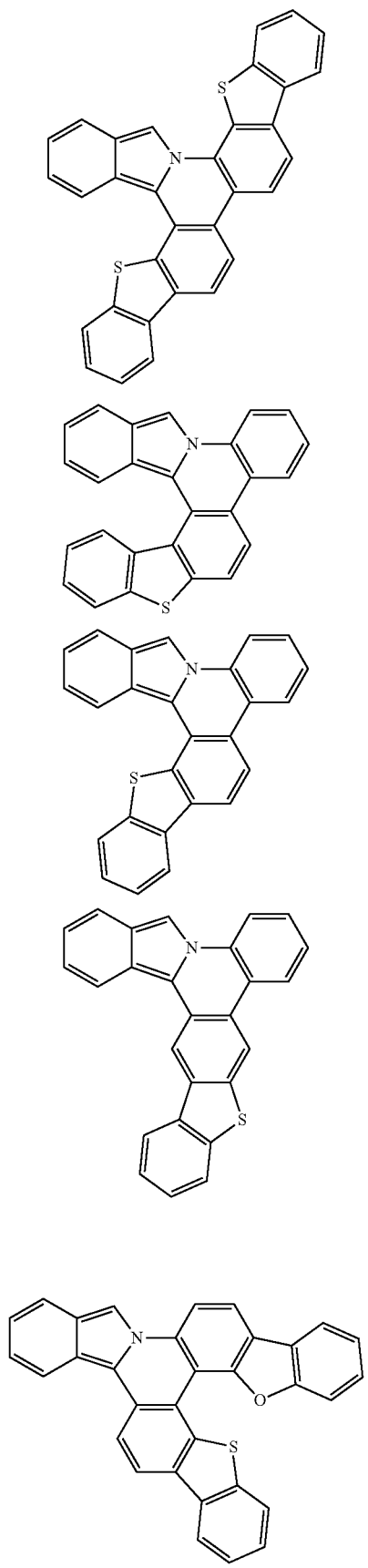
374
-continued
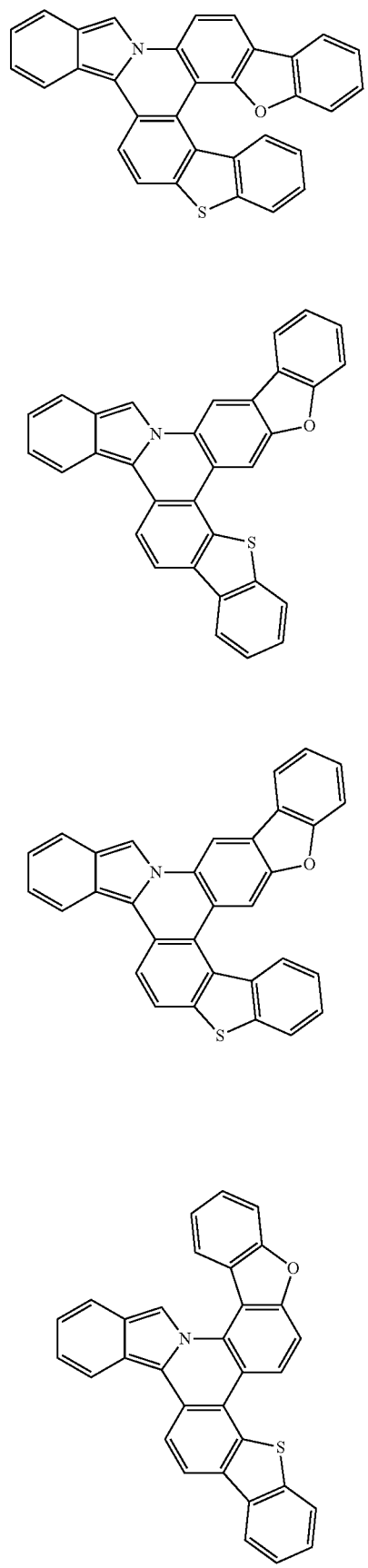

375
-continued
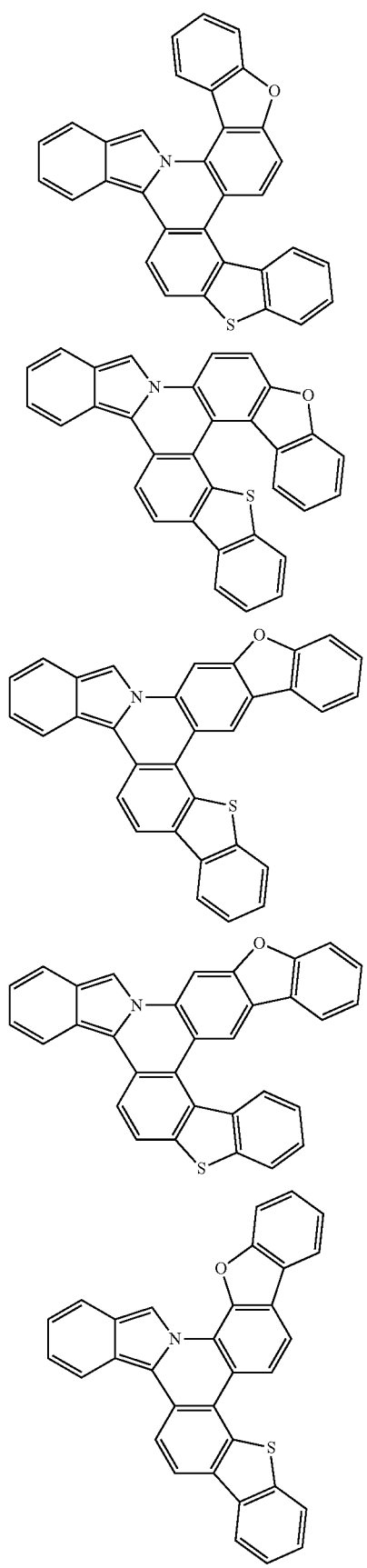
376
-continued
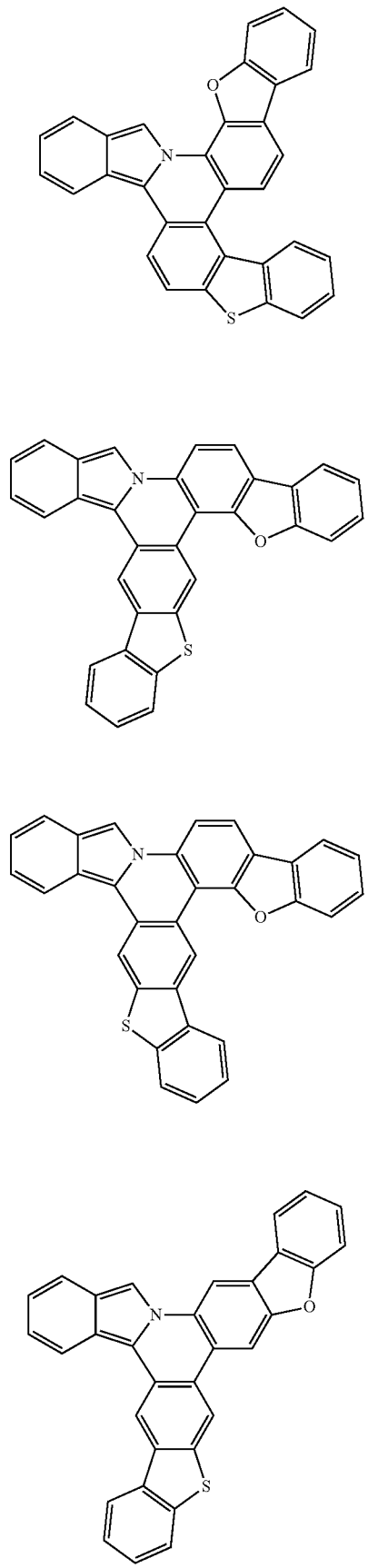

377
-continued
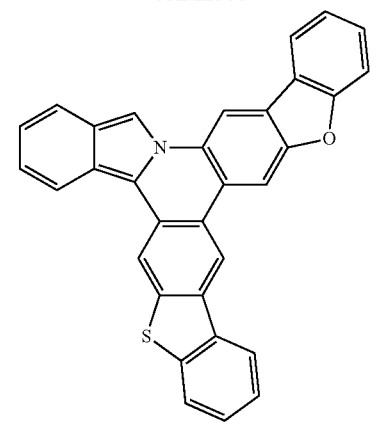
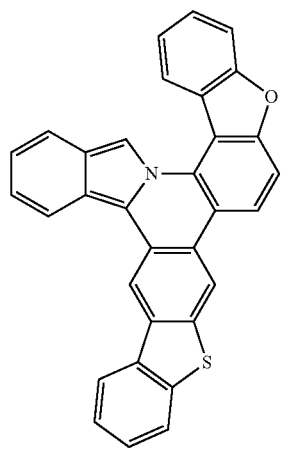
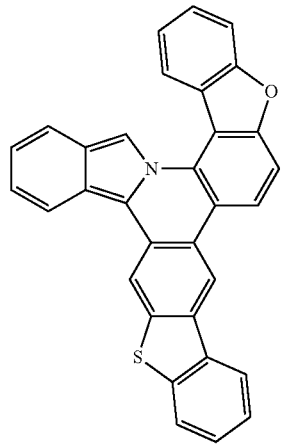
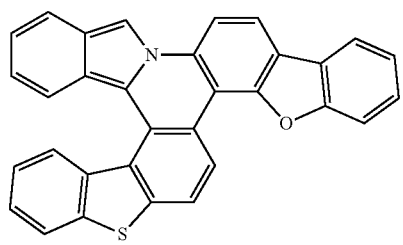
378
-continued
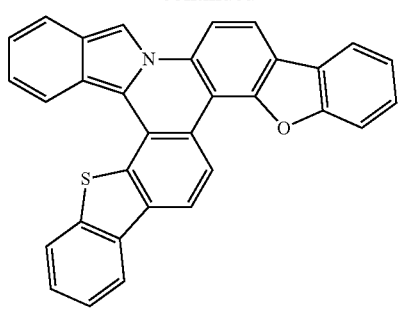
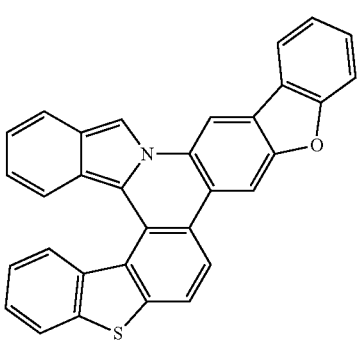
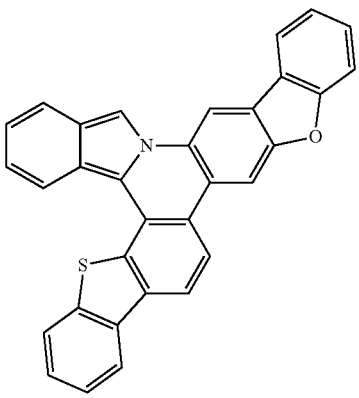
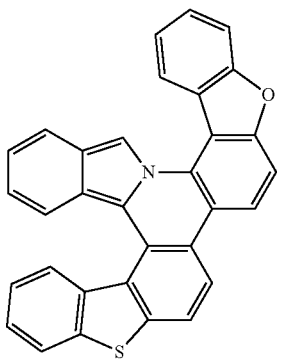

379
-continued
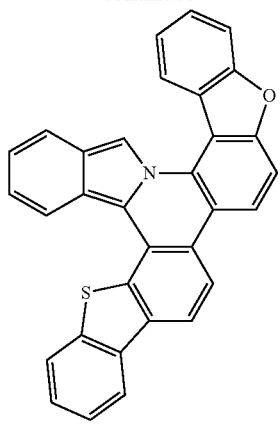
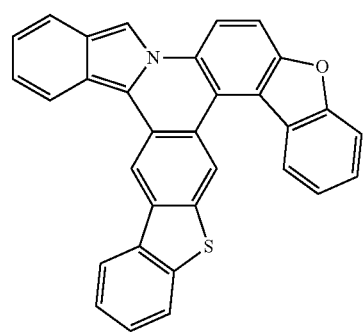
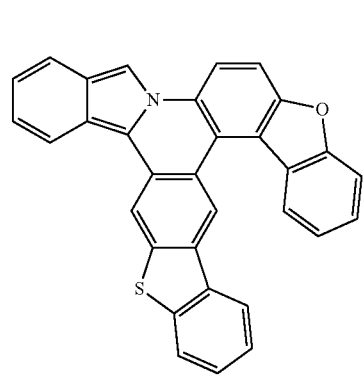
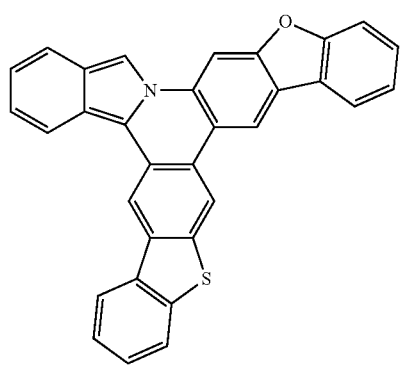
380
-continued
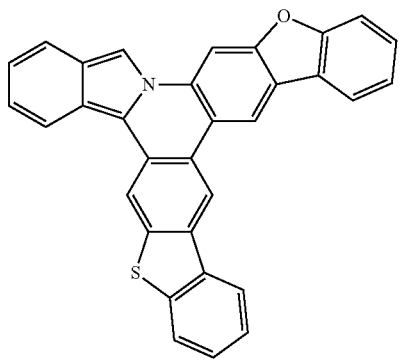
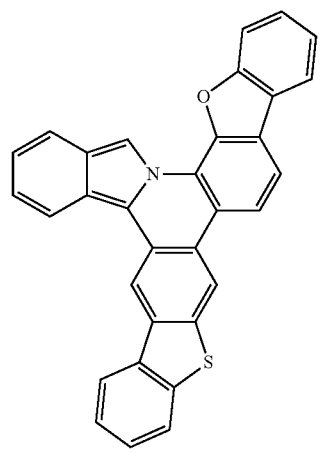
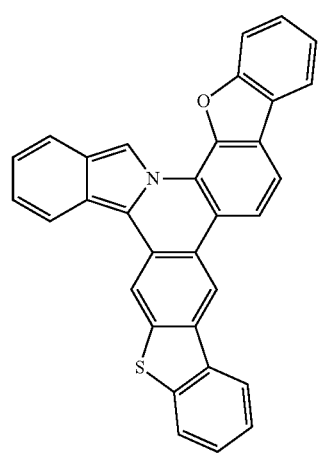
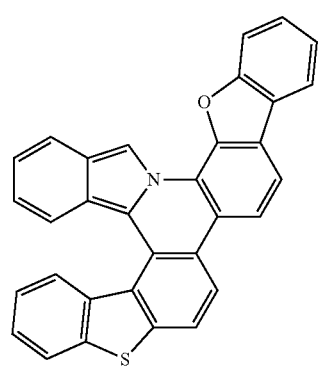

381
-continued
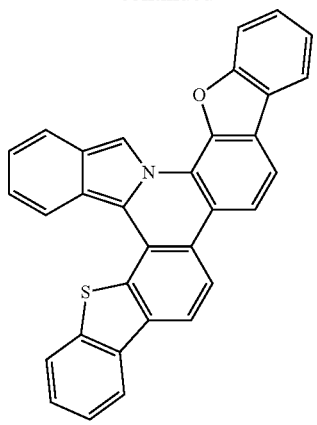
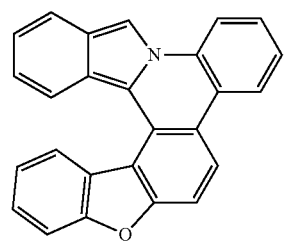
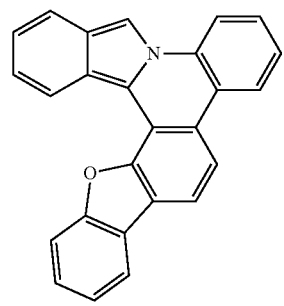
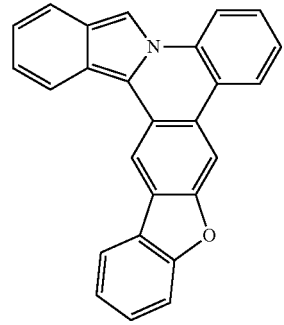
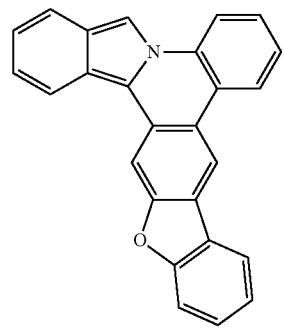
382
-continued
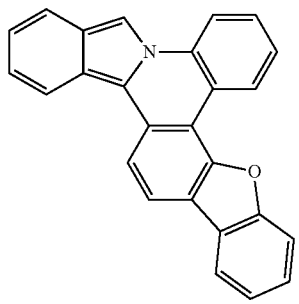
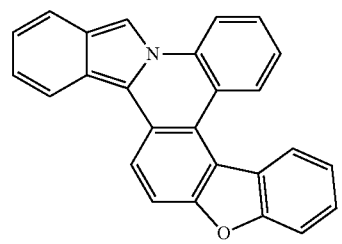
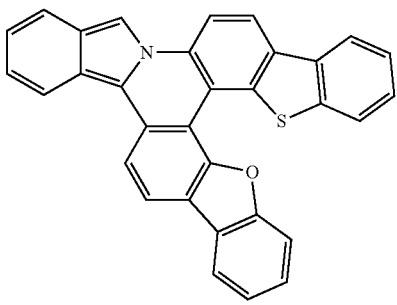
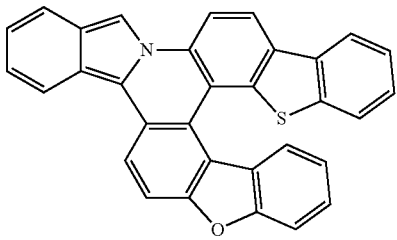
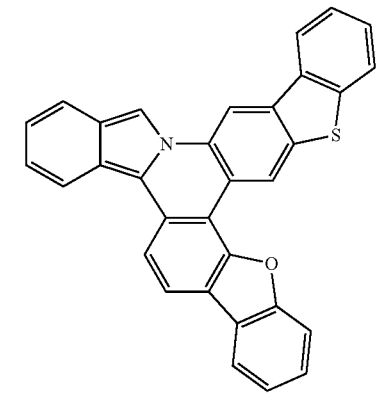

383
-continued
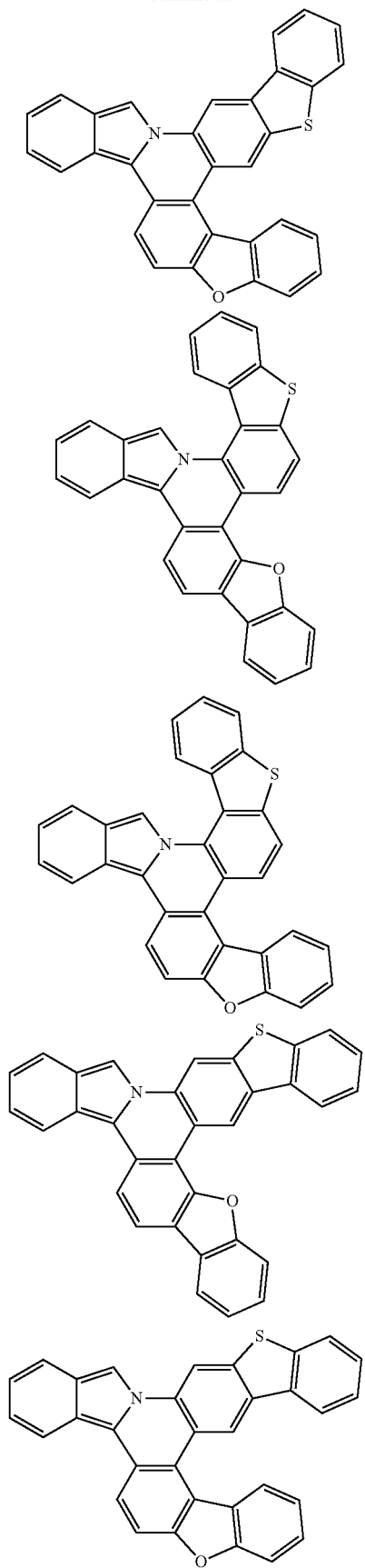
384
-continued
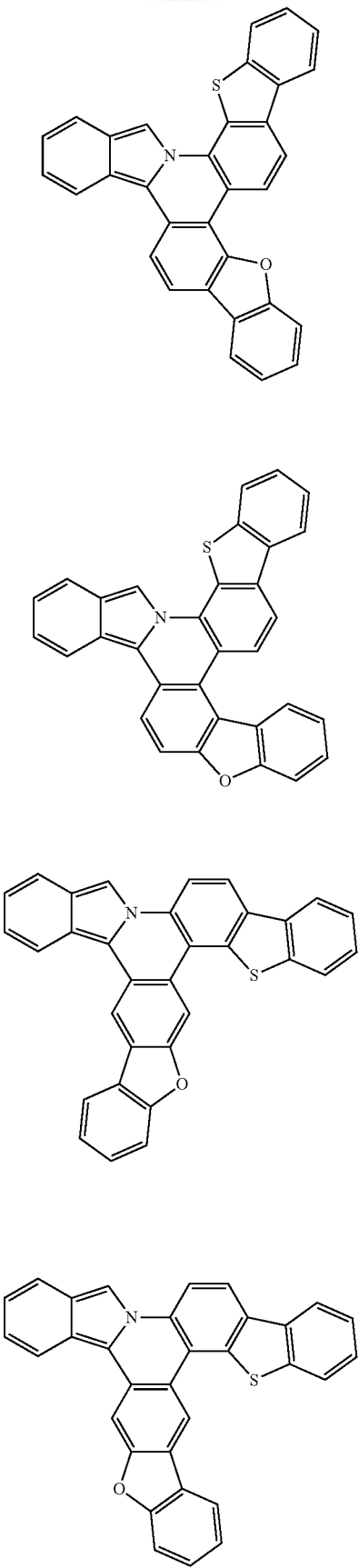

385
-continued
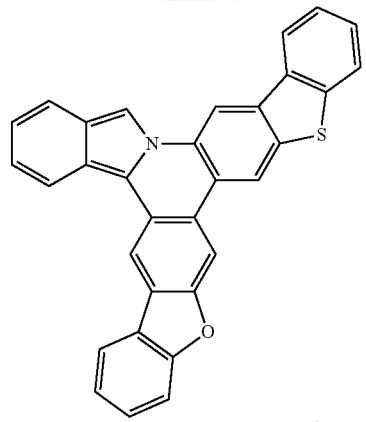
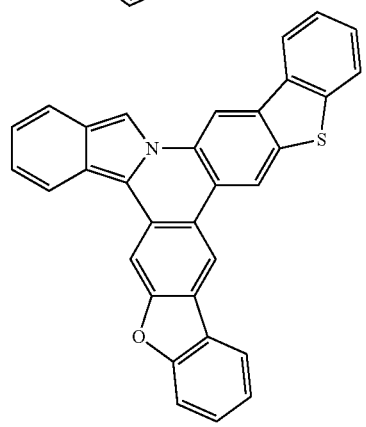
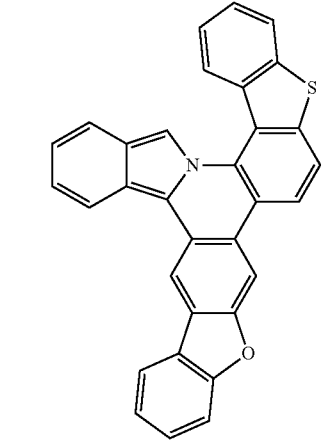
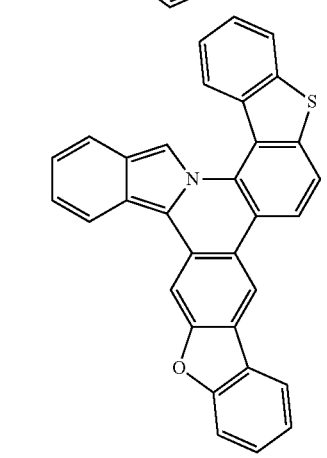
386
-continued
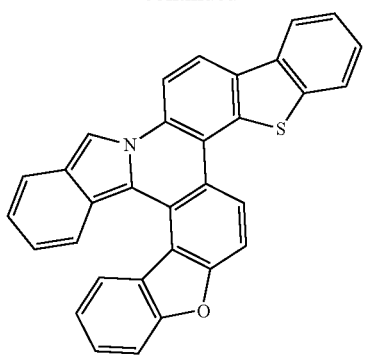
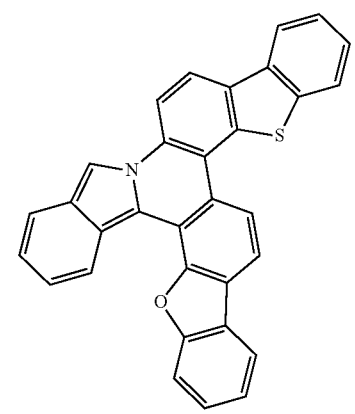
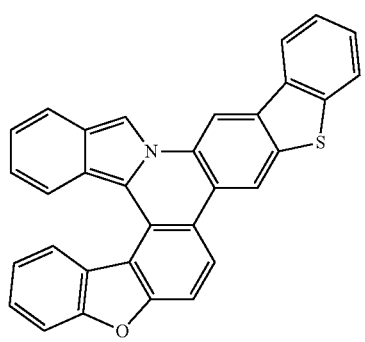
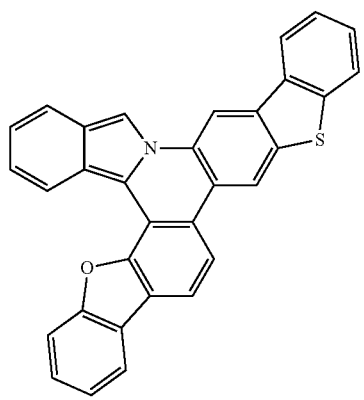

387
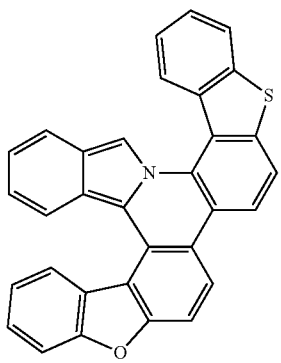
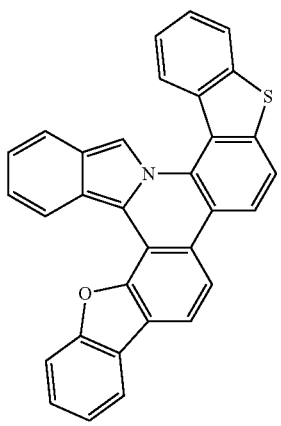
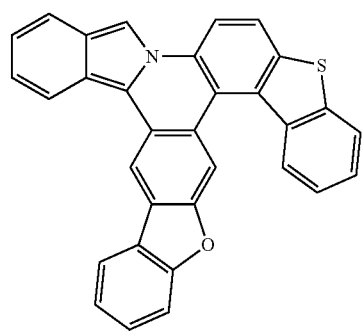
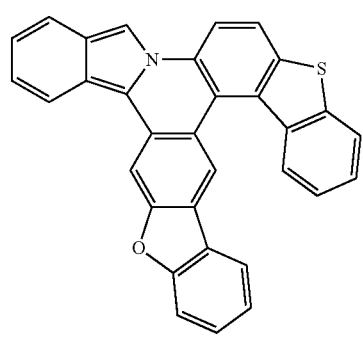
388
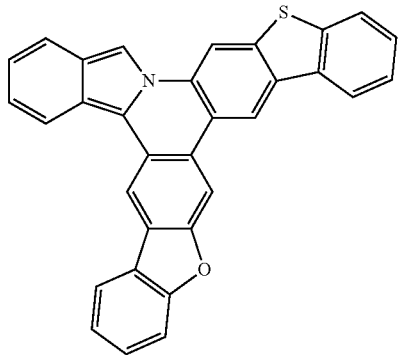
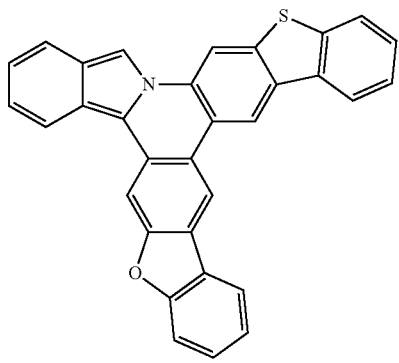
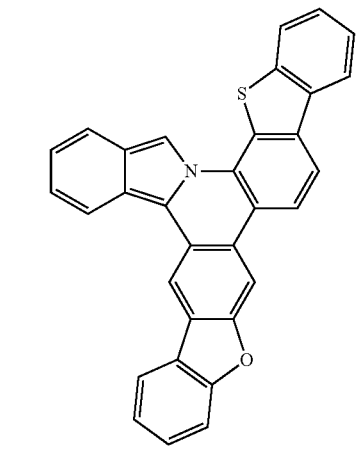
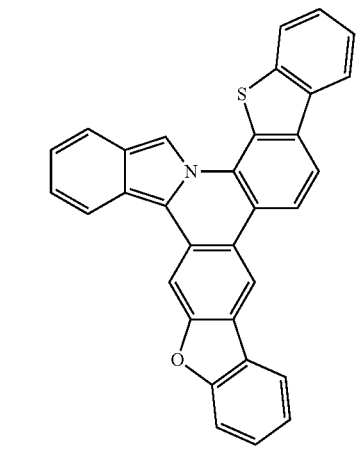

389
-continued
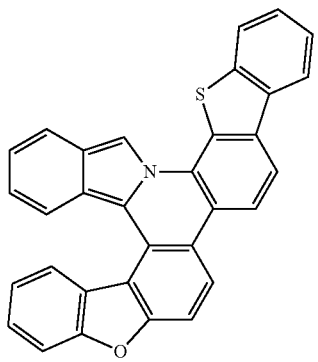
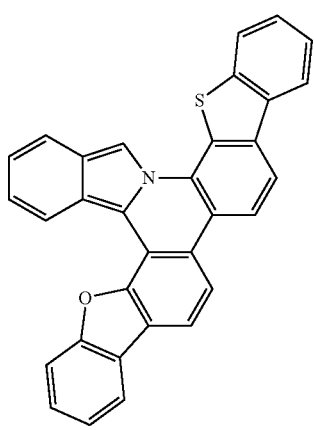
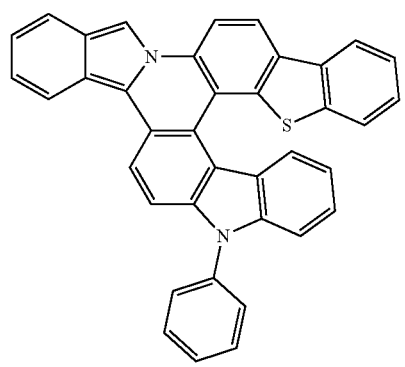
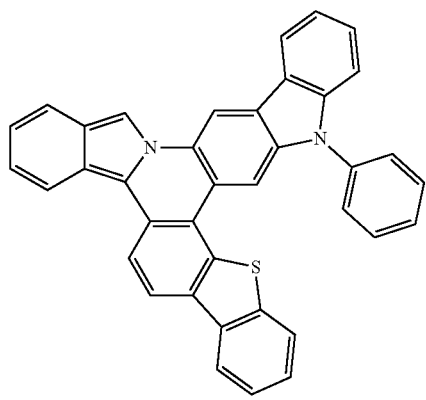
390
-continued
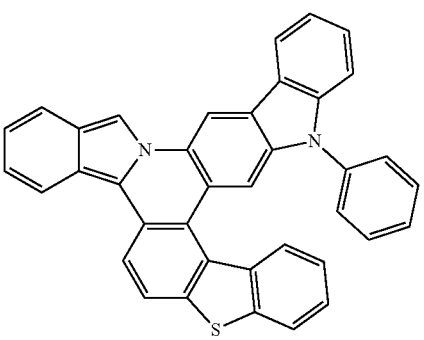
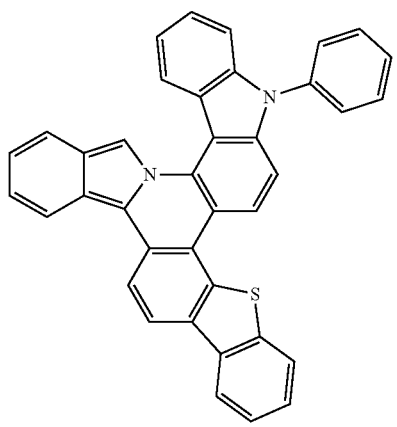
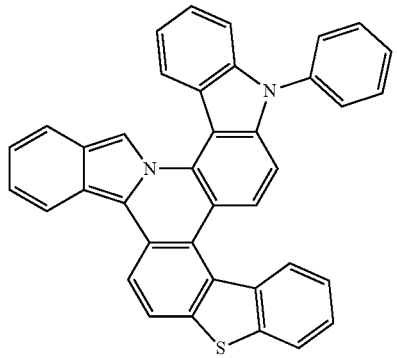
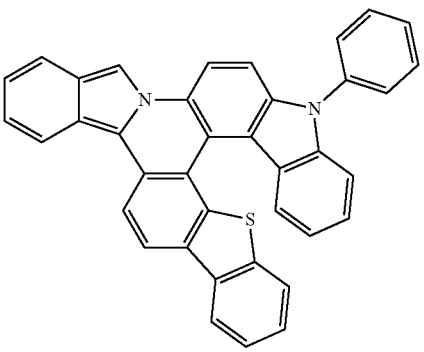

391
-continued
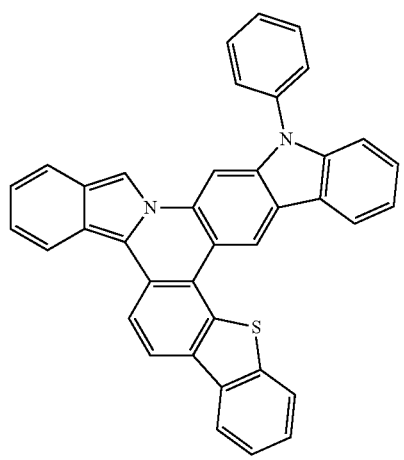
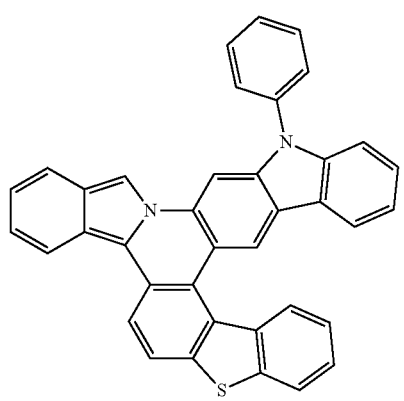
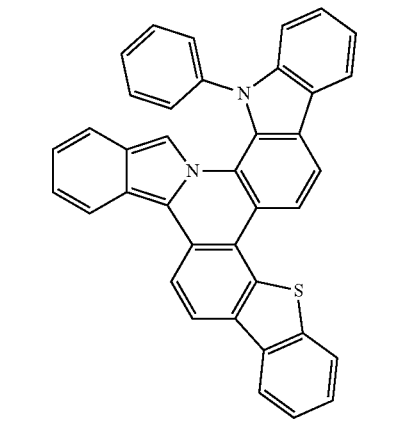
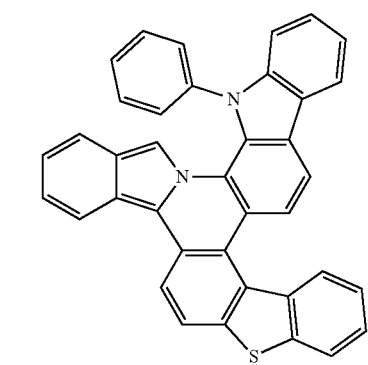
392
-continued
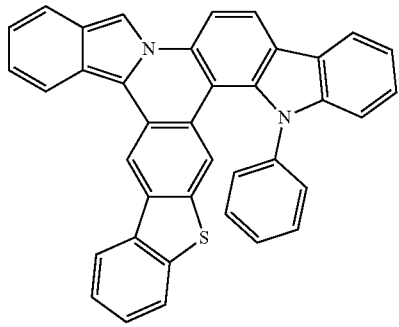
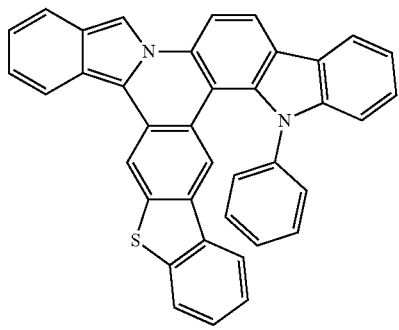
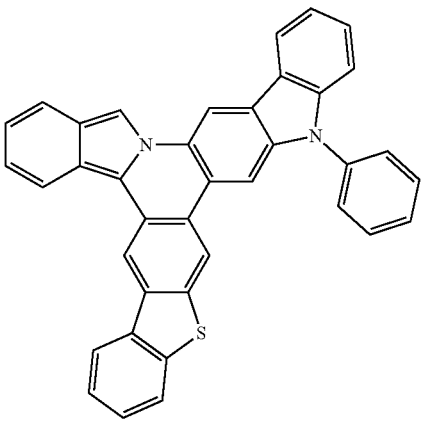
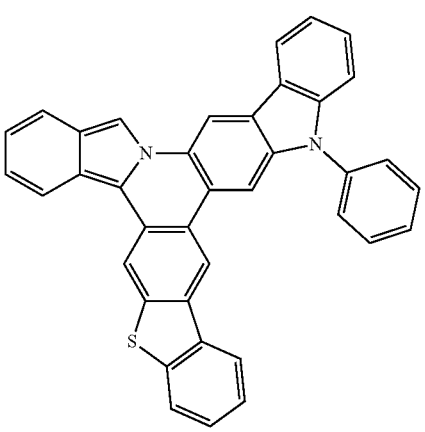

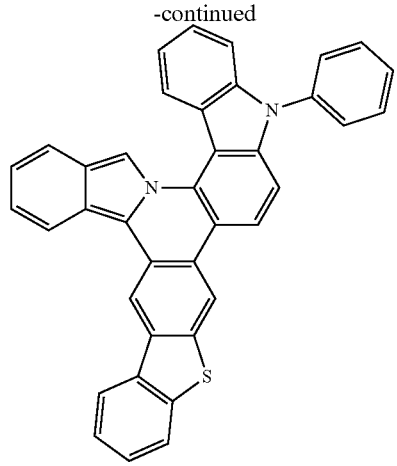
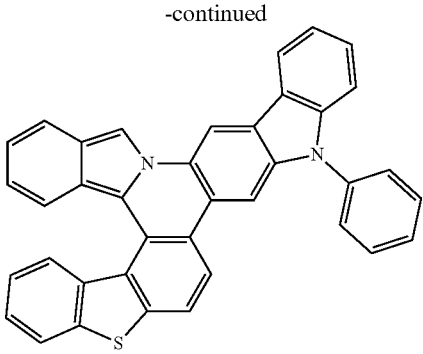
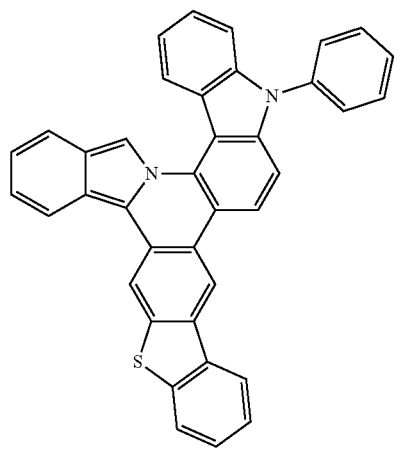
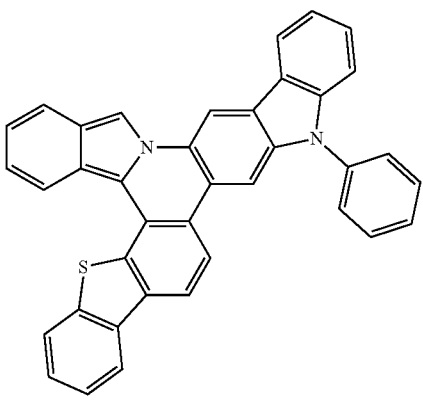
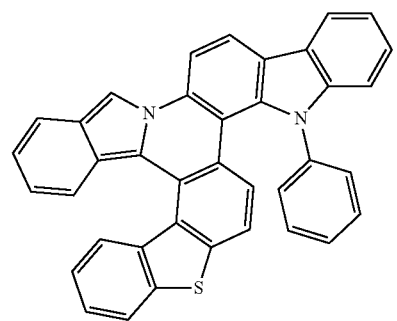
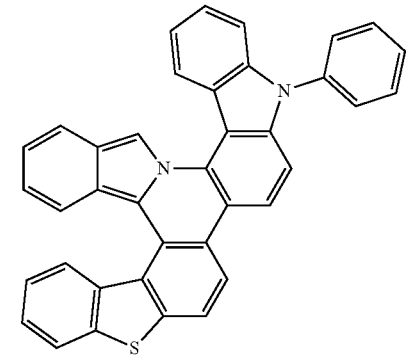
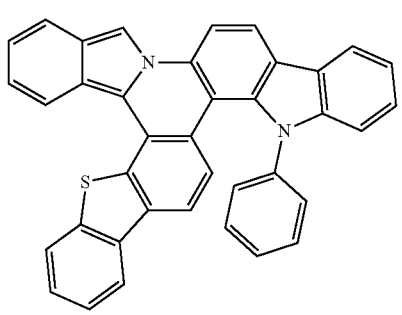
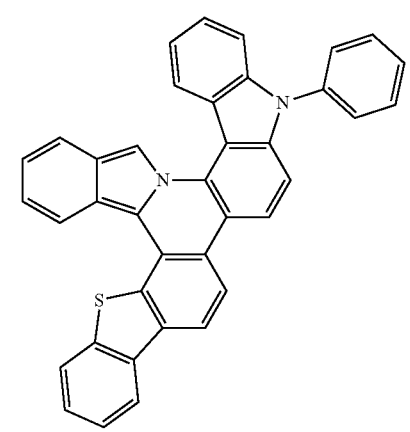

395
-continued
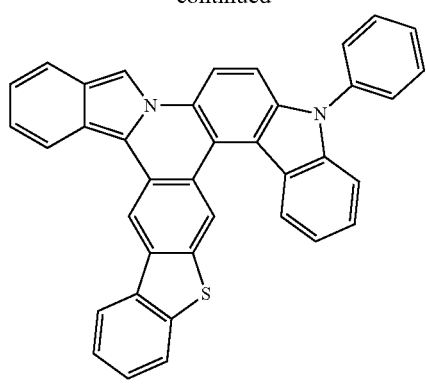
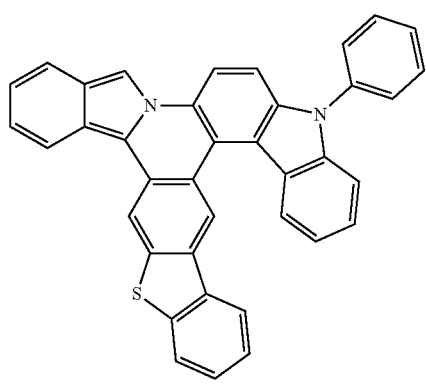
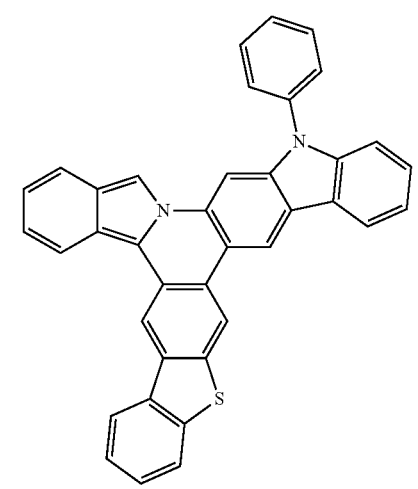
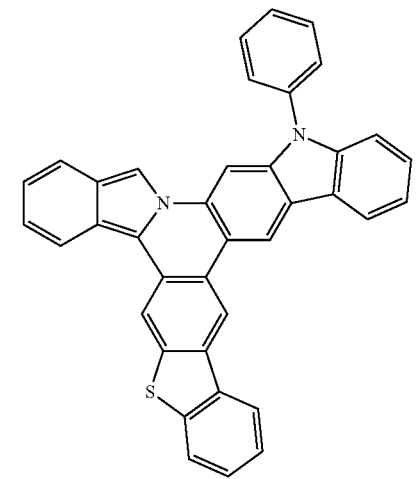
396
-continued
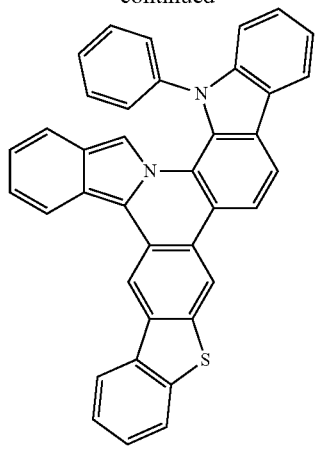
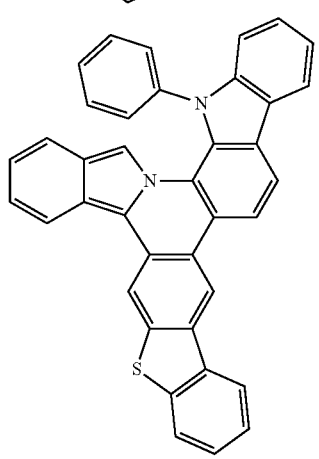
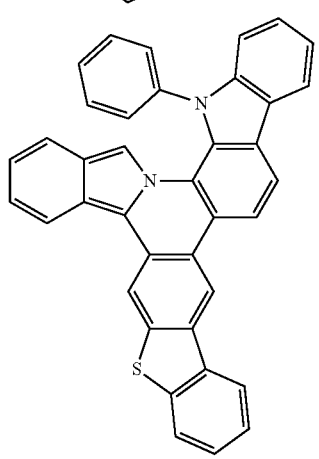
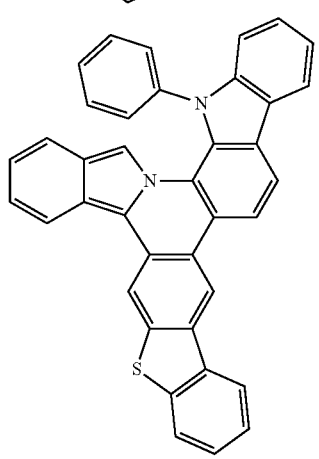

397
-continued
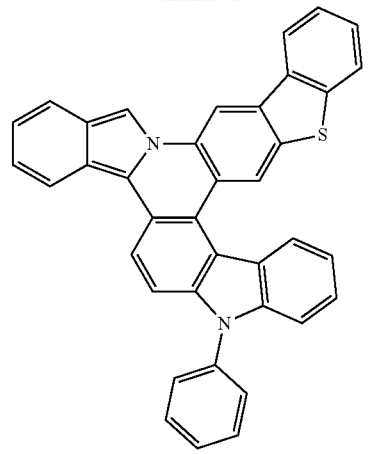
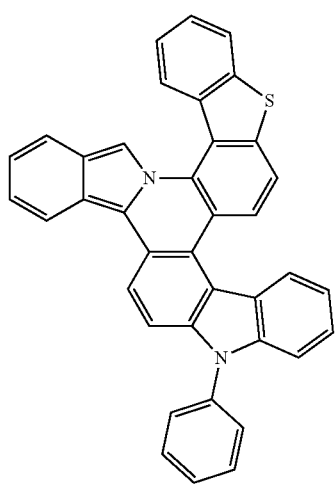
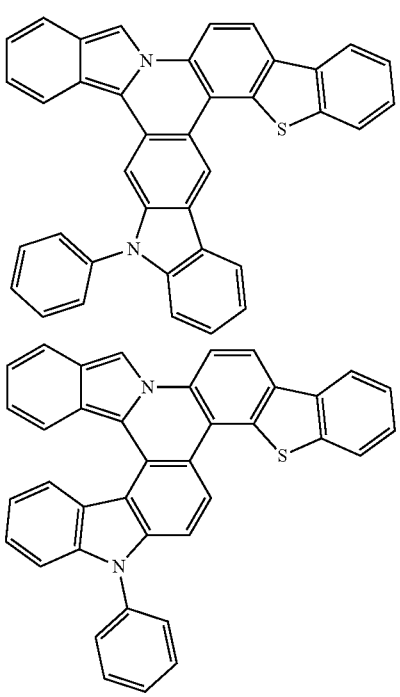
398
-continued
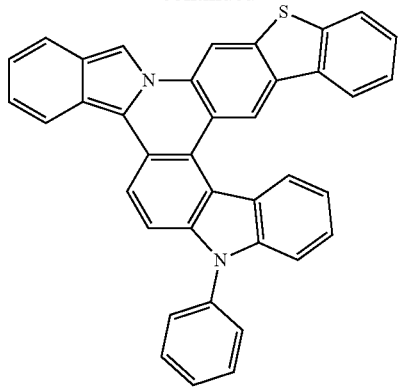
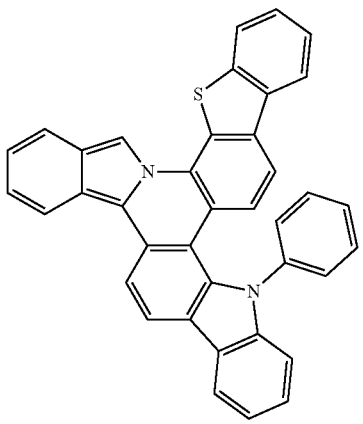
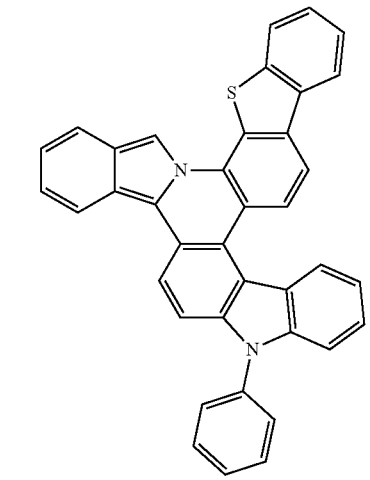
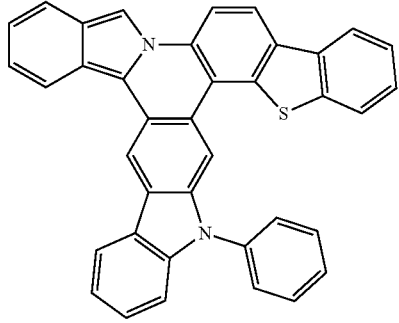

399
-continued
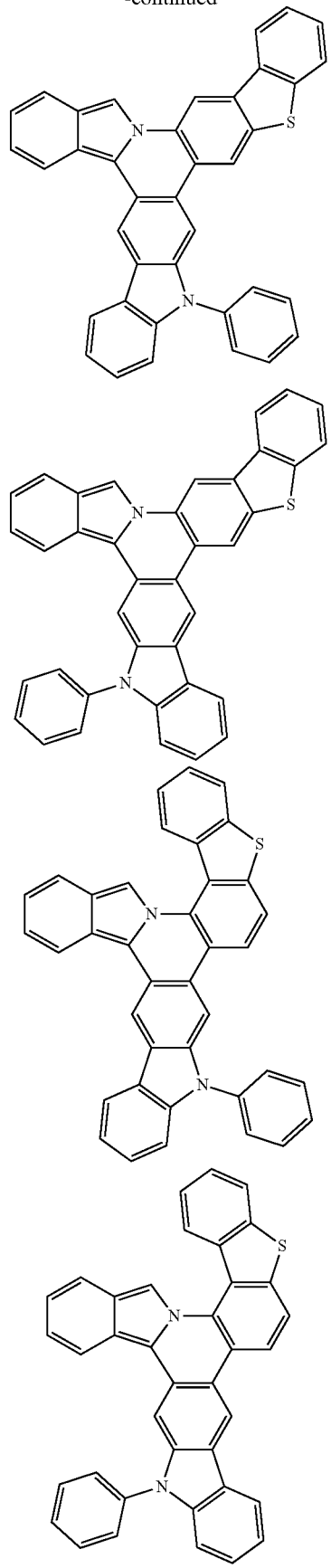
400
-continued
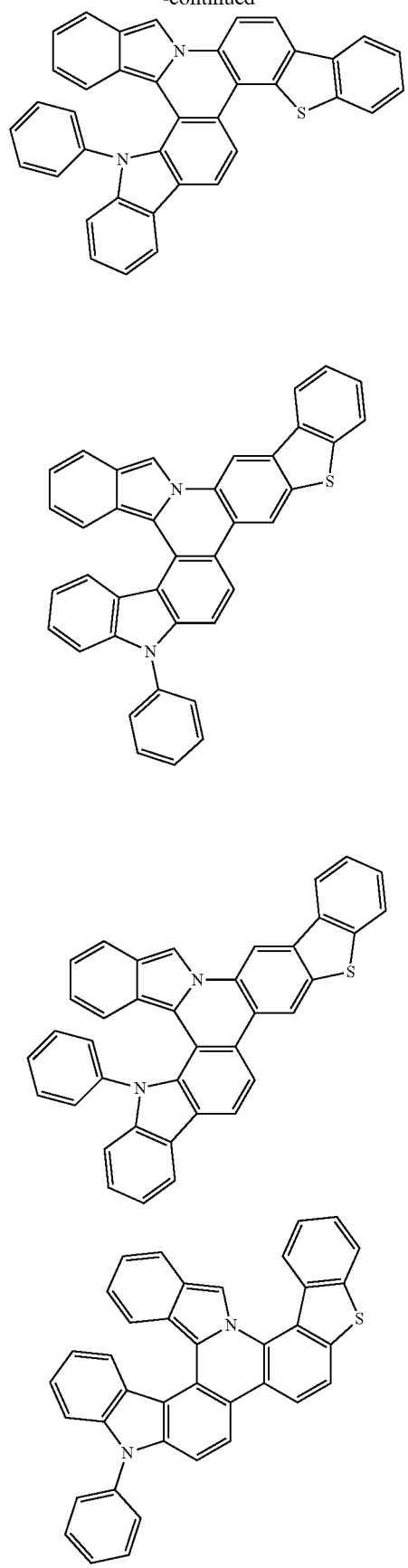

401
-continued
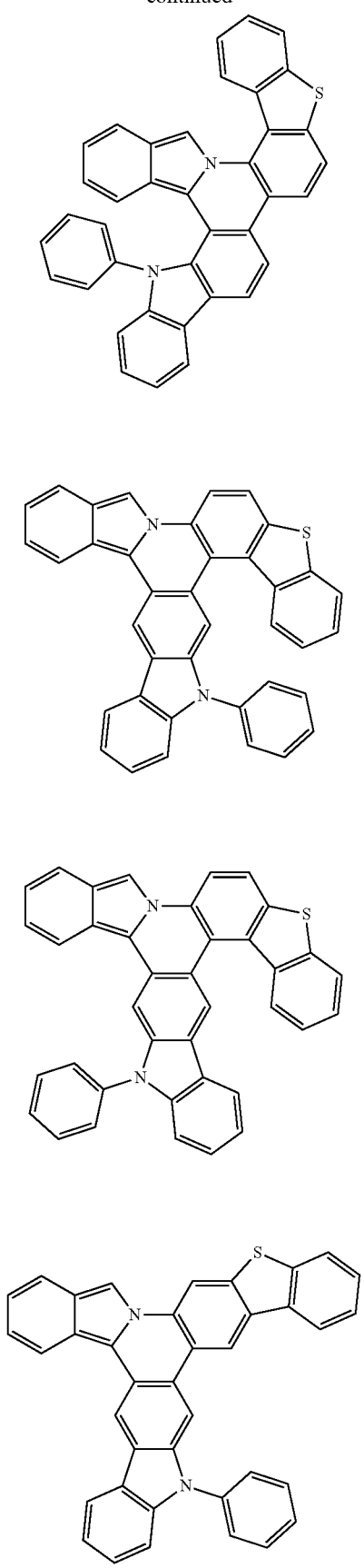
402
-continued
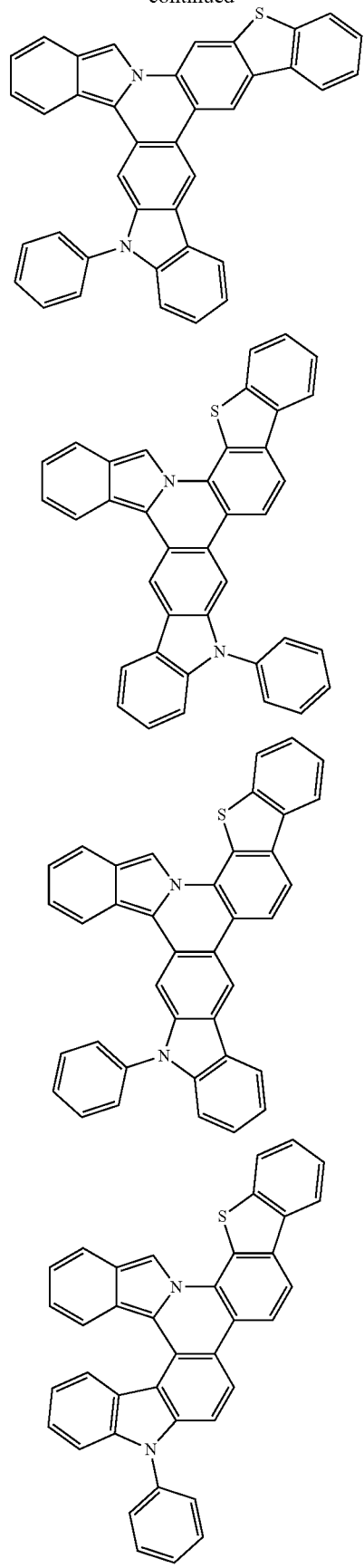

-continued

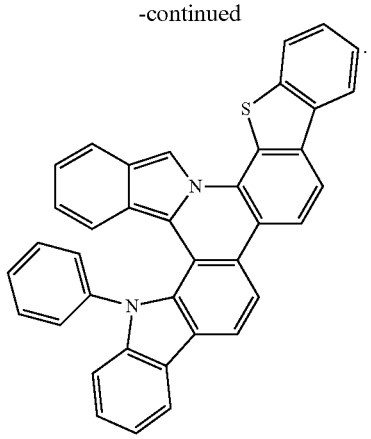

4. An organic light emitting diode comprising the compound of claim 1.

5. A light emitting device comprising the light emitting diode of claim 4.

6. An organic light emitting diode comprising the compound of claim 2.

7. A light emitting device comprising the light emitting diode of claim 6.

8. An organic light emitting diode comprising the compound of claim 3.

9. A light emitting device comprising the light emitting diode of claim 8.

* * * * *